(12) United States Patent
Mengel et al.

(10) Patent No.: US 10,350,206 B2
(45) Date of Patent: Jul. 16, 2019

(54) BENZYL SUBSTITUTED INDAZOLES AS BUB1 INHIBITORS

(71) Applicant: Bayer Pharma Aktiengesellschaft, Berlin (DE)

(72) Inventors: Anne Mengel, Berlin (DE); Hans-Georg Lerchen, Leverkusen (DE); Manfred Möwes, Berlin (DE); Thomas Müller, Frankfurt (DE); Lars Bärfacker, Düsseldorf (DE); Marion Hitchcock, Brookline, MA (US); Arwed Cleve, Berlin (DE); Joachim Kuhnke, Potsdam (DE); Hans Briem, Berlin (DE); Gerhard Siemeister, Berlin (DE); Wilhelm Bone, Berlin (DE); Amaury Ernesto Fernandez-Montalvan, Berlin (DE); Jens Schröder, Berlin (DE); Ursula Mönning, Woltersdorf (DE); Simon Holton, Berlin (DE)

(73) Assignee: Bayer Pharma Aktiengesellschaft, Berlin (DE)

(*) Notice: Subject to any disclaimer, the term of this patent is extended or adjusted under 35 U.S.C. 154(b) by 0 days.

(21) Appl. No.: 15/512,494

(22) PCT Filed: Sep. 17, 2015

(86) PCT No.: PCT/EP2015/071340
§ 371 (c)(1),
(2) Date: Mar. 17, 2017

(87) PCT Pub. No.: WO2016/042084
PCT Pub. Date: Mar. 24, 2016

(65) Prior Publication Data
US 2017/0273980 A1  Sep. 28, 2017

(30) Foreign Application Priority Data

Sep. 19, 2014 (EP) .................................... 14185604
Jul. 15, 2015 (EP) .................................... 15176903

(51) Int. Cl.
*A61K 31/506* (2006.01)
*C07D 401/14* (2006.01)
*C07D 403/14* (2006.01)

(52) U.S. Cl.
CPC .......... *A61K 31/506* (2013.01); *C07D 401/14* (2013.01); *C07D 403/14* (2013.01)

(58) Field of Classification Search
CPC ... A61K 31/506; C07D 403/14; C07D 401/14
See application file for complete search history.

(56) References Cited

U.S. PATENT DOCUMENTS

| 5,470,862 | A  | 11/1995 | Lin et al. |
|---|---|---|---|
| 6,462,068 | B1 | 10/2002 | Straub et al. |
| 6,833,364 | B1 | 12/2004 | Straub et al. |
| 9,643,953 | B2 | 5/2017 | Hitchcock et al. |
| 9,682,974 | B2 | 6/2017 | Mengel et al. |
| 9,745,285 | B2 | 8/2017 | Mengel et al. |
| 9,765,058 | B2 | 9/2017 | Hitchcock et al. |
| 2011/0130410 | A1 | 6/2011 | Mais et al. |
| 2014/0249133 | A1 | 9/2014 | Hitchcock et al. |
| 2015/0141372 | A1 | 5/2015 | Hitchcock et al. |
| 2016/0046604 | A1 | 2/2016 | Hitchcock et al. |
| 2016/0046610 | A1 | 2/2016 | Hitchcock et al. |
| 2016/0052912 | A1 | 2/2016 | Hilger et al. |
| 2016/0145238 | A1 | 5/2016 | Mengel et al. |
| 2016/0145239 | A1 | 5/2016 | Hitchcock et al. |
| 2016/0145267 | A1 | 5/2016 | Hitchcock et al. |
| 2016/0151370 | A1 | 6/2016 | Hitchcock et al. |
| 2016/0168130 | A1 | 6/2016 | Hitchcock et al. |
| 2016/0326159 | A1 | 11/2016 | Mengel et al. |

(Continued)

FOREIGN PATENT DOCUMENTS

| CA | 2663297 A1 | 3/2008 |
|---|---|---|
| CL | 2017000578 | 9/2017 |

(Continued)

OTHER PUBLICATIONS

U.S. Appl. No. 14/778,975, filed Sep. 21, 2015, Hitchcock et al.
U.S. Appl. No. 14/899,418, filed Dec. 17, 2015, Hitchcock et al.
U.S. Appl. No. 14/899,469, filed Dec. 17, 2015, Hitchcock et al.

(Continued)

*Primary Examiner* — Erich A Leeser
(74) *Attorney, Agent, or Firm* — Morrison & Foerster LLP

(57) ABSTRACT

Compounds of formula (I) as defined herein and their use as pharmaceuticals.

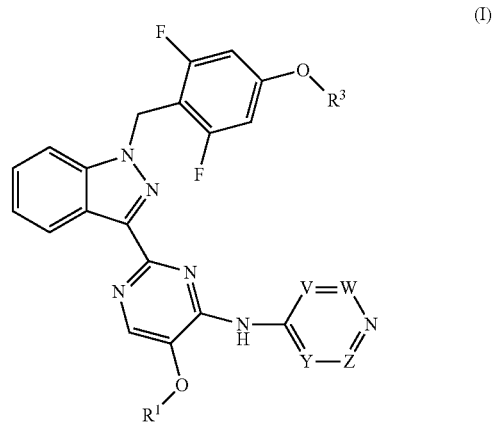

28 Claims, 1 Drawing Sheet
Specification includes a Sequence Listing.

(56) References Cited

U.S. PATENT DOCUMENTS

| | | | |
|---|---|---|---|
| 2017/0260198 A1 | 9/2017 | Hitchcock et al. | |
| 2017/0275269 A1 | 9/2017 | Mengel et al. | |
| 2017/0275270 A1 | 9/2017 | Barfacker et al. | |
| 2017/0305882 A1 | 10/2017 | Mengel et al. | |

FOREIGN PATENT DOCUMENTS

| | | | | |
|---|---|---|---|---|
| CL | 2017000640 | | 10/2017 | |
| CL | 2017000658 | | 12/2017 | |
| JP | 2010111624 | A | 5/2010 | |
| WO | WO-2000021954 | | 4/2000 | |
| WO | WO-2003051833 | | 6/2003 | |
| WO | WO-2003082274 | | 10/2003 | |
| WO | WO-2004024159 | | 3/2004 | |
| WO | WO-2004031186 | | 4/2004 | |
| WO | WO-2005070900 | | 8/2005 | |
| WO | WO-2007038613 | | 4/2007 | |
| WO | WO-2007065010 | | 6/2007 | |
| WO | WO2008141731 | A3 | 3/2009 | |
| WO | WO2010069966 | A1 | 6/2010 | |
| WO | WO-2011049988 | | 4/2011 | |
| WO | WO-2011115804 | | 9/2011 | |
| WO | WO-2011126903 | | 10/2011 | |
| WO | WO-2012003405 | | 1/2012 | |
| WO | WO 2013/050438 | * | 4/2013 | ........... C07D 401/14 |
| WO | WO-2013050438 | | 4/2013 | |
| WO | WO-2013092512 | | 6/2013 | |
| WO | WO-2013101830 | | 7/2013 | |
| WO | WO-2013167698 | | 11/2013 | |
| WO | WO-2014047111 | | 3/2014 | |
| WO | WO-2014047325 | | 3/2014 | |
| WO | WO-2014047662 | | 3/2014 | |
| WO | WO-2014147144 | | 9/2014 | |
| WO | WO-2014147203 | | 9/2014 | |
| WO | WO-2014147204 | | 9/2014 | |
| WO | WO 2014-202584 | | 12/2014 | |
| WO | WO-2014202583 | | 12/2014 | |
| WO | WO-2014202586 | | 12/2014 | |
| WO | WO-2014202588 | | 12/2014 | |
| WO | WO-2014202590 | | 12/2014 | |
| WO | WO-2015063003 | | 5/2015 | |
| WO | WO-2016041925 | | 3/2016 | |
| WO | WO-2016042080 | | 3/2016 | |
| WO | WO-2016042081 | | 3/2016 | |
| WO | WO-2016042084 | | 3/2016 | |
| WO | WO2016042518 | A1 | 3/2016 | |
| WO | WO2016042536 | A1 | 3/2016 | |
| WO | WO2016044789 | A1 | 3/2016 | |
| WO | WO-2017/148995 | A1 | 9/2017 | |
| WO | WO-2017/157991 | A1 | 9/2017 | |
| WO | WO-2017/157992 | A1 | 9/2017 | |
| WO | WO-2018122168 | | 7/2018 | |
| WO | WO-2018158175 | | 9/2018 | |
| WO | WO2018206547 | A1 | 11/2018 | |
| WO | WO2018215282 | A1 | 11/2018 | |

OTHER PUBLICATIONS

U.S. Appl. No. 14/900,548, filed Dec. 21, 2015, Mengel et al.
U.S. Appl. No. 14/900,575, filed Dec. 21, 2015, Hitchcock et al.
U.S. Appl. No. 14/900,599, filed Dec. 21, 2015, Hitchcock et al.
U.S. Appl. No. 15/438,254, filed Feb. 21, 2017, Hitchcock et al.
U.S. Appl. No. 15/453,679, filed Mar. 8, 2017, Hitchcock et al.
U.S. Appl. No. 15/456,239, filed Mar. 10, 2017, Hitchcock et al.
U.S. Appl. No. 15/471,885, filed Mar. 28, 2017, Hilger et al.
U.S. Appl. No. 15/512,473, filed Mar. 17, 2017, Mengel et al.
U.S. Appl. No. 15/512,474, filed Mar. 17, 2017, Mengel et al.
U.S. Appl. No. 15/512,517, filed Mar. 17, 2017, Barfacker et al.
International Search Report dated Nov. 10, 2015 for PCT Application No. PCT/EP2015/071340 filed Sep. 17, 2015, 5 pages.
U.S. Appl. No. 14/350,160, filed Apr. 7, 2014 for Hitchcock et al. (Also published as US-20140249133, cited herewith).
U.S. Appl. No. 14/400,315, filed Nov. 10, 2014 for Hitchcock et al. (Also published as US-20150141372, cited herewith).
U.S. Appl. No. 14/778,604, filed Sep. 20, 2015 for Hilger et al. (Also published as US-20160052912, cited herewith).
U.S. Appl. No. 14/778,733, filed Sep. 21, 2015 for Hitchcock et al. (Also published as US-20160046604, cited herewith).
U.S. Appl. No. 15/032,957, filed Apr. 28, 2016 for Mengel et al. (Also published as US-20160326159, cited herewith).
Final Office Action dated May 11, 2018, for U.S. Appl. No. 15/438,254, filed Feb. 21, 2017, 15 pages.
Bolanos-Garcia et al. (Mar. 2011). "BUB1 and BUBR1: multifaceted kinases of the cell cycle," Trends in Biochem. Sciences 36(3): 141-150.
Elowe, S. (Aug. 2011). "Bub1 and BubR1: at the Interface between Chromosome Attachment and the Spindle Checkpoint," Molecular and Cellular Biology 31(15): 3085-3093.
EPO Communication per Rule 161/162 dated May 2, 2017, for EP Application No. 15763619.2 filed on Sep. 17, 2015, 2 pages.
EPO Communication per Article 94(3) and Annex dated Sep. 11, 2018, for EP Application No. 15763619.2 filed on Sep. 17, 2015, 5 pages.
Final Office Action dated Jun. 4, 2015 for U.S. Appl. No. 14/350,160, filed Oct. 4, 2012, by Hitchcock et al., 14 pages.
Gura, T. (Nov. 7, 1997). "Cancer Models: Systems for Identifying New Drugs Are Often Faulty," Science 278(5340): 1041-1042.
Hanahan et al. (Mar. 4, 2011). "Hallmarks of Cancer: The Next Generation," Cell 144: 646-674.
Hanahan et al. (Jan. 7, 2000). "The Hallmarks of Cancer," Cell 100: 57-70.
International Search Report and Written Opinion dated Oct. 30, 2012 for PCT Application No. PCT/EP2012/069562, filed Oct. 4, 2012, 11 pages.
Johnson, J. et al. (2001). "Relationships between drug activity in NCI preclinical in vitro and in vivo models and early clinical trials," British Journal of Cancer 84(10): 1424-1431.
Kang, J. et al. (Nov. 7, 2008). "Structure and Substrate Recruitment of the Human Spindle Checkpoint Kinase Bub1," Molecular Cell 32: 394-405.
Kawashima et al. (Jan. 8, 2010). "Phosphorylation of H2A by Bub1 Prevents Chromosomal Instability Through Localizing Shugoshin," Science 327: 172-177.
King, R. W. (2008). "When 2+2=5: The origins and fates of aneuploidy and tetraploid cells," Biochimica et Biophys Acta 1786: 4-14.
Kops, G.J.P.L. et al. (Oct. 2005). "On the Road to Cancer: Aneuploidy and the Mitotic Checkpoint," Nature Reviews 5: 773-785.
Krenn, V. et al. (Feb. 13, 2012). "Structural analysis reveals features of the spindle checkpoint kinase Bub1-kinetochore subunit Knl1 interaction," J Cell Biol. 196(4): 451-467.
Musacchio et al. (May 2007). "The spindle-assembly checkpoint in space and time," Nature Reviews/Molecular Cell Biology 8:379-393.
Non-final Office Action dated Sep. 18, 2014 for U.S. Appl. No. 14/350,160, filed Oct. 4, 2012, by Hitchcock et al., 15 pages.
Non-final Office Action dated Apr. 21, 2016 for U.S. Appl. No. 14/350,160, filed Oct. 4, 2012, by Hitchcock et al., 15 pages.
Nyati, S. et al. (2015). "The kinase activity of the Ser/Thr kinase BUB1 promotes TGF-β signaling," Science Signaling 8(356): 1-12.
Pearce, H.L. et al. (2008). Cancer Drug Design and Discovery Chapter 18 "Failure modes in anticancer drug discovery and development," Edited by Stephen Neidle, pp. 424-435.
Response to EPO Communication per Rule 161/162 dated Nov. 2, 2017, for EP Application No. 15763619.2 filed on Sep. 17, 2015, 41 pages.
Ricke, R.M. et al. (Dec. 3, 2012). "Bub1 kinase activity drives error correction and mitotic checkpoint control but not tumor suppression," J. Cell Biol. (199(6): 931-949.
Rieder et al. (Nov. 2004). "Stuck in Division or Passing through: Review What Happens When Cells Cannot Satisfy the Spindle Assembly Checkpoint," Developmental Cell 7:637-651.
Roberts et al. (Dec. 1994). "The *Saccharomyces cerevisiae* Checkpoint gene BUB1 Encodes a Novel Protein Kinase," Molecular and Cellular Biology 14(12): 8282-8291.

(56) References Cited

OTHER PUBLICATIONS

Schmidt et al. (Jan. 16, 2006). "Exploiting the Compromised Spindle Assembly Checkpoint Function of Tumor Cells" Cell Cycle 5(2): 159-163.
Schmidt et al. (2007). "Mitotic drug targets and the development of novel anti-mitotic anticancer drugs," Drug Resistance Updates 10: 162-181.
Simone (1996). Textbook of Medicine 20th Edition, Edited by Bennett, J.C. and Plum, F., Introduction, 1: 1004-1101.
Suijkerbuijk et al. (Acta 1786). "Preventing aneuploidy: The contribution of mitotic checkpoint proteins," Biochimica et Biophysica 2008: 24-31.
Watanabe, Y., "Temporal and Spatial Regulation of Targeting Aurora B to the Inner Centromere," Cold Springs Harbor Symp. On Quantitative Biol. 75, 2010 Pub. Cold Spg. Harbor Lab Press, 419-423.
Weaver, B.A.A. et al. (Nov. 1, 2007). "Aneuploidy: Instigator and inhibitor of Tumorigenesis," *Cancer Res.* 67(21): 10103-10105.
Written Opinion dated Nov. 10, 2015 for PCT Application No. PCT/EP2015/071340, filed Sep. 17, 2015, 9 pages.
Yuan et al. (Jan. 15, 2006). "Increased Expression of Mitotic Checkpoint Genes in Breast Cancer Cells with Chromosomal Instability," Clin. Cancer Res. 12(2): 405-410.
European Office Action dated Apr. 26, 2019 for EP Application No. 15763619.2 filed on Sep. 17, 2015, 6 pages.

\* cited by examiner

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Val Leu Leu Pro Lys Lys Ser Phe Ala Glu Pro Gly
1               5                   10

BENZYL SUBSTITUTED INDAZOLES AS BUB1 INHIBITORS

CROSS REFERENCE TO RELATED APPLICATIONS

This application is the national stage of International Application No. PCT/EP2015/071340, filed internationally on Sep. 17, 2015, which claims the benefit of European Application No. 14185604.7, filed Sep. 19, 2014, and European Application No. 15176903.1, filed Jul. 15, 2015, the disclosures of which are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052014800SEQLIST.txt, date recorded: Mar. 14, 2017, size: 1 KB).

FIELD OF APPLICATION OF THE INVENTION

The invention relates to substituted Benzyl Substituted Indazole compounds, a process for their production and the use thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The eukaryotic cell division cycle (or cell cycle) ensures the duplication of the genome and its distribution to the daughter cells by passing through a coordinated and regulated sequence of events. The cell cycle is divided into four successive phases:
1. The G1 phase represents the time before the DNA replication, in which the cell grows and is sensitive to external stimuli.
2. In the S phase the cell replicates its DNA, and
3. in the G2 phase preparations are made for entry into mitosis.
4. In mitosis (M phase), the duplicated chromosomes get separated supported by a spindle device built from microtubules, and cell division into two daughter cells is completed.

To ensure the extraordinary high fidelity required for an accurate distribution of the chromosomes to the daughter cells, the passage through the cell cycle is strictly regulated and controlled. The enzymes that are necessary for the progression through the cycle must be activated at the correct time and are also turned off again as soon as the corresponding phase is passed. Corresponding control points ("checkpoints") stop or delay the progression through the cell cycle if DNA damage is detected, or the DNA replication or the creation of the spindle device is not yet completed. The mitotic checkpoint (also known as spindle checkpoint or spindle assembly checkpoint) controls the accurate attachment of mircrotubules of the spindle device to the kinetochors (the attachment site for microtubules) of the duplicated chromosomes. The mitotic checkpoint is active as long as unattached kinetochores are present and generates a wait-signal to give the dividing cell the time to ensure that each kinetochore is attached to a spindle pole, and to correct attachment errors. Thus the mitotic checkpoint prevents a mitotic cell from completing cell division with unattached or erroneously attached chromosomes [Suijkerbuijk S J and Kops G J, Biochem. Biophys. Acta 1786, 24, 2008; Musacchio A and Salmon E D, Nat. Rev. Mol. Cell. Biol. 8, 379, 2007]. Once all kinetochores are attached with the mitotic spindle poles in a correct bipolar (amphitelic) fashion, the checkpoint is satisfied and the cell enters anaphase and proceeds through mitosis.

The mitotic checkpoint is established by a complex network of a number of essential proteins, including members of the MAD (mitotic arrest deficient, MAD 1-3) and Bub (Budding uninhibited by benzimidazole, Bub 1-3) families, Mps1 kinase, cdc20, as well as other components [reviewed in Bolanos-Garcia V M and Blundell T L, Trends Biochem. Sci. 36, 141, 2010], many of these being over-expressed in proliferating cells (e.g. cancer cells) and tissues [Yuan B et al., Clin. Cancer Res. 12, 405, 2006]. The major function of an unsatisfied mitotic checkpoint is to keep the anaphase-promoting complex/cyclosome (APC/C) in an inactive state. As soon as the checkpoint gets satisfied the APC/C ubiquitin-ligase targets cyclin B and securin for proteolytic degradation leading to separation of the paired chromosomes and exit from mitosis.

Inactive mutations of the Ser/Thr kinase Bub1 prevented the delay in progression through mitosis upon treatment of cells of the yeast *S. cerevisiae* with microtubule-destabilizing drugs, which led to the identification of Bub1 as a mitotic checkpoint protein [Roberts B T et al., Mol. Cell Biol., 14, 8282, 1994]. A number of recent publications provide evidence that Bub1 plays multiple roles during mitosis which, have been reviewed by Elowe [Elowe S, Mol. Cell. Biol. 31, 3085, 2011]. In particular, Bub1 is one of the first mitotic checkpoint proteins that binds to the kinetochores of duplicated chromosomes and probably acts as a scaffolding protein to constitute the mitotic checkpoint complex. Furthermore, via phosphorylation of histone H2A, Bub1 localizes the protein shugoshin to the centromeric region of the chromosomes to prevent premature segregation of the paired chromosomes [Kawashima et al. Science 327, 172, 2010]. In addition, together with a Thr-3 phosphorylated Histone H3 the shugoshin protein functions as a binding site for the chromosomal passenger complex which includes the proteins survivin, borealin, INCENP and Aurora B. The chromosomal passenger complex is seen as a tension sensor within the mitotic checkpoint mechanism, which dissolves erroneously formed microtubule-kinetochor attachments such as syntelic (both sister kinetochors are attached to one spindle pole) or merotelic (one kinetochor is attached to two spindle poles) attachments [Watanabe Y, Cold Spring Harb. Symp. Quant. Biol. 75, 419, 2010]. Recent data suggest that the phosphorylation of histone H2A at Thr 121 by Bub1 kinase is sufficient to localize AuroraB kinase to fulfill the attachment error correction checkpoint [Ricke et al. J. Cell Biol. 199, 931-949, 2012].

Incomplete mitotic checkpoint function has been linked with aneuploidy and tumourigenesis [Weaver B A and Cleveland D W, Cancer Res. 67, 10103, 2007; King R W, Biochim Biophys Acta 1786, 4, 2008]. In contrast, complete inhibition of the mitotic checkpoint has been recognised to result in severe chromosome missegregation and induction of apoptosis in tumour cells [Kops G J et al., Nature Rev. Cancer 5, 773, 2005; Schmidt M and Medema R H, Cell Cycle 5, 159, 2006; Schmidt M and Bastians H, Drug Res. Updates 10, 162, 2007]. Thus, mitotic checkpoint abrogation through pharmacological inhibition of components of the mitotic checkpoint, such as Bub1 kinase, represents a new approach for the treatment of proliferative disorders, including solid tumours such as carcinomas, sarcomas, leukaemias and lymphoid malignancies or other disorders, associated with uncontrolled cellular proliferation.

The present invention relates to chemical compounds that inhibit Bub1 kinase.

Established anti-mitotic drugs such as *vinca* alkaloids, taxanes or epothilones activate the mitotic checkpoint, inducing a mitotic arrest either by stabilising or destabilising microtubule dynamics. This arrest prevents separation of the duplicated chromosomes to form the two daughter cells. Prolonged arrest in mitosis forces a cell either into mitotic exit without cytokinesis (mitotic slippage or adaption) or into mitotic catastrophe leading to cell death [Rieder C L and Maiato H, Dev. Cell 7, 637, 2004]. In contrast, inhibitors of Bub1 prevent the establishment and/or functionality of the mitotic checkpoint and/or microtubule-kinetochor attachment error correction mechanisms, which finally results in severe chromosomal missegregation, induction of apoptosis and cell death.

These findings suggest that Bub1 inhibitors should be of therapeutic value for the treatment of proliferative disorders associated with enhanced uncontrolled proliferative cellular processes such as, for example, cancer, inflammation, arthritis, viral diseases, cardiovascular diseases, or fungal diseases in a warm-blooded animal such as man.

WO 2013/050438, WO 2013/092512, WO 2013/167698 disclose substituted benzylindazoles, substituted benzylpyrazoles and substituted benzylcycloalkylpyrazoles, respectively, which are Bub1 kinase inhibitors.

Furthermore, WO 2014/147203, WO 2014/147204, WO2014202590, WO2014202588, WO2014202584, WO2014202583, and WO2015/063003, disclose substituted indazoles, substituted pyrazoles, and substituted cycloalkylpyrazoles, which are Bub1 kinase inhibitors.

Due to the fact that especially cancer disease as being expressed by uncontrolled proliferative cellular processes in tissues of different organs of the human- or animal body still is not considered to be a controlled disease in that sufficient drug therapies already exist, there is a strong need to provide further new therapeutically useful drugs, preferably inhibiting new targets and providing new therapeutic options (e.g. drugs with improved pharmacological properties, such as improved target Bub1 inhibition potency, more potent proliferation inhibition and/or reduced drug-drug interactions when used in combination with other drugs).

DESCRIPTION OF THE INVENTION

Therefore, inhibitors of Bub1 represent valuable compounds that should complement therapeutic options either as single agents or in combination with other drugs.

In accordance with a first aspect, the invention relates to compounds of formula (I), in which

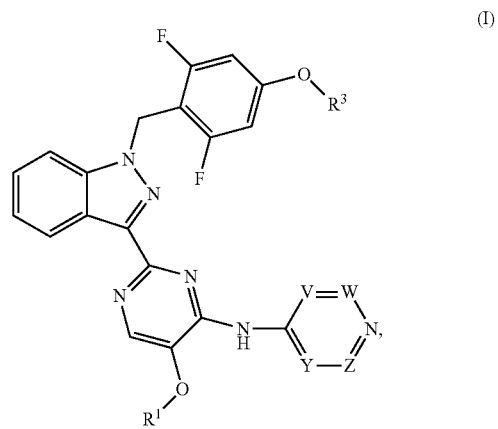

V, W, Y and Z independently of each other represent CH or $CR^2$, wherein one of V, W, Y and Z represents $CR^2$ or, V represents N, and W, Y and Z independently of each other represent CH or $CR^2$, or, V and Y represent N, and W and Z independently of each other represent CH or $CR^2$, $R^1$ represents a group selected from:
$C_1$-$C_6$-alkyl, $C_1$-$C_6$-haloalkyl, $C_3$-$C_6$-cycloalkyl, ($C_1$-$C_3$-alkoxy)-($C_2$-$C_3$-alkyl)-, and ($C_3$-$C_6$-cycloalkyl)-($C_1$-$C_3$-alkyl)-, $R^2$ represents, independently of each other, halogen or a group selected from:
$C_1$-$C_3$-alkyl, $C_3$-$C_4$-cycloalkyl, $C_1$-$C_3$-haloalkyl, $C_1$-$C_3$-alkoxy,
$C_1$-$C_3$-haloalkoxy, —N(H)C(=O)—($C_1$-$C_3$-alkyl), —N(H)C(=O)H,
—N(H)C(=O)—($C_1$-$C_3$-hydroxyalkyl),
—N(H)C(=O)—($C_1$-$C_3$-alkyl)-($C_1$-$C_3$-alkoxy), —N(H)C(=O)-phenyl,
—N(H)C(=O)—($C_3$-$C_4$-cycloalkyl),
—N(H)C(=O)—($C_1$-$C_3$-alkyl)-($C_3$-$C_4$-cycloalkyl), and
—N(H)C(=O)N(H)$R^8$,
said —N(H)C(=O)-phenyl being optionally substituted at the phenyl ring, one, two or three times, identically or differently, with a substituent selected from:
halogen, hydroxy, cyano, $C_1$-$C_4$-alkyl, $C_1$-$C_4$-haloalkyl, $C_1$-$C_4$-alkoxy, $C_1$-$C_4$-haloalkoxy, $C_3$-$C_4$-cycloalkyl, and $C_3$-$C_4$-cycloalkyloxy,
said —N(H)C(=O)—($C_3$-$C_4$-cycloalkyl) being optionally substituted at the $C_3$-$C_4$-cycloalkyl ring with a substituent selected from:
fluorine, chlorine, trifluoromethyl, and methoxy, $R^3$ represents a group selected from:
$C_2$-$C_6$-hydroxyalkyl, and $R^4$,
said $C_2$-$C_6$-hydroxyalkyl groups being optionally substituted with one, two or three halogen atoms selected from:
fluorine, and chlorine, $R^4$ represents —($C_2$-$C_6$-alkyl)-OC(=O)—C(H)($R^5$)—N(H)C(=O)—C(H)($R^7$)—$NH_2$,
in which $C_2$-$C_6$-alkyl is optionally substituted with one, two or three halogen atoms selected from:
fluorine, and chlorine, $R^5$ and $R^7$ independently of each other represent hydrogen (glycine) or a group selected from:

—CH$_3$ (alanine), —C(H)(CH$_3$)$_2$ (valine), —(CH$_2$)$_2$CH$_3$ (norvaline), —CH$_2$C(H)(CH$_3$)$_2$ (leucine), —C(H)(CH$_3$)CH$_2$CH$_3$ (isoleucine), —(CH$_2$)$_3$CH$_3$ (norleucine), —C(CH$_3$)$_3$ (2-tert-butylglycine), benzyl (phenylalanine), 4-hydroxybenzyl (tyrosine), —(CH$_2$)$_3$NH$_2$ (ornithine), —(CH$_2$)$_4$NH$_2$ (lysine), —(CH$_2$)$_2$C(H)(OH)CH$_2$NH$_2$ (hydroxylysine), —CH$_2$OH (serine), —(CH$_2$)$_2$OH (homoserine), —C(H)(OH)CH$_3$ (threonine), —(CH$_2$)$_3$N(H)C(=NH)NH$_2$ (arginine), —(CH$_2$)$_3$N(H)C(=O)NH$_2$ (citrulline), —CH$_2$C(=O)NH$_2$ (asparagine), —CH$_2$C(=O)OH (aspartic acid), —(CH$_2$)$_2$C(=O)OH (glutamic acid), —(CH$_2$)$_2$C(=O)NH$_2$ (glutamine), —CH$_2$SH (cysteine), —(CH$_2$)$_2$SH (homocysteine), —(CH$_2$)$_2$SCH$_3$ (methionine), —CH$_2$SCH$_3$ (S-methylcysteine), (1H-imidazol-4-yl)methyl-(histidine), (1H-indol-3-yl)methyl-(thryptophan), —CH$_2$NH$_2$ (2,3-diaminopropanoic acid), and —(CH$_2$)$_2$NH$_2$ (2,4-diaminobutanoic acid), R$^8$ represents hydrogen or a group selected from:
C$_1$-C$_3$-alkyl, C$_1$-C$_3$-haloalkyl, C$_2$-C$_3$-hydroxyalkyl, C$_3$-C$_4$-cycloalkyl, (C$_3$-C$_4$-cycloalkyl)-(C$_1$-C$_3$-alkyl)-, and (C$_1$-C$_3$-alkoxy)-(C$_2$-C$_3$-alkyl)-, or an N-oxide, a salt, a tautomer or a stereoisomer of said compound, or a salt of said N-oxide, tautomer or stereoisomer.

Another aspect of the invention are compounds of formula (I) as defined herein,
wherein
V, W, Y and Z independently of each other represent CH or CR$^2$, wherein one of V, W, Y and Z represents CR$^2$ or,
V represents N, and W, Y and Z independently of each other represent CH or CR$^2$,
R$^1$ represents a group selected from:
C$_1$-C$_3$-alkyl, C$_1$-C$_3$-haloalkyl, C$_3$-C$_4$-cycloalkyl, (C$_1$-C$_3$-alkoxy)-(C$_2$-C$_3$-alkyl)-, and (C$_3$-C$_4$-cycloalkyl)-(C$_1$-C$_3$-alkyl)-,
R$^2$ represents, independently of each other, halogen or a group selected from:
C$_1$-C$_3$-alkyl, C$_3$-C$_4$-cycloalkyl, C$_1$-C$_3$-haloalkyl, C$_1$-C$_3$-alkoxy,
C$_1$-C$_3$-haloalkoxy, —N(H)C(=O)—(C$_1$-C$_3$-alkyl), —N(H)C(=O)H,
—N(H)C(=O)—(C$_1$-C$_3$-hydroxyalkyl),
—N(H)C(=O)—(C$_1$-C$_3$-alkyl)-(C$_1$-C$_3$-alkoxy), —N(H)C(=O)-phenyl,
—N(H)C(=O)—(C$_3$-C$_4$-cycloalkyl),
—N(H)C(=O)—(C$_1$-C$_3$-alkyl)-(C$_3$-C$_4$-cycloalkyl), and —N(H)C(=O)N(H)R$^8$,
said —N(H)C(=O)-phenyl being optionally substituted at the phenyl ring, one, two or three times, identically or differently, with a substituent selected from:
halogen, hydroxy, cyano, C$_1$-C$_4$-alkyl, C$_1$-C$_4$-haloalkyl,
C$_1$-C$_4$-alkoxy, C$_1$-C$_4$-haloalkoxy, C$_3$-C$_4$-cycloalkyl, and
C$_3$-C$_4$-cycloalkyloxy,
said —N(H)C(=O)—(C$_3$-C$_4$-cycloalkyl) being optionally substituted at the C$_3$-C$_4$-cycloalkyl ring with a substituent selected from:
fluorine, chlorine, trifluoromethyl, and methoxy,
R$^3$ represents a group selected from:
C$_2$-C$_6$-hydroxyalkyl, and R$^4$,
said C$_2$-C$_6$-hydroxyalkyl groups being optionally substituted with one, two or three halogen atoms selected from:
fluorine, and chlorine,
R$^4$ represents —(C$_2$-C$_6$-alkyl)-OC(=O)—C(H)(R$^5$)—N(H)C(=O)—C(H)(R$^7$)—NH$_2$,
in which C$_2$-C$_6$-alkyl is optionally substituted with one, two or three halogen atoms selected from:
fluorine, and chlorine,
R$^5$ and R$^7$ independently of each other represent hydrogen (glycine) or a group selected from:
—CH$_3$ (alanine), —C(H)(CH$_3$)$_2$ (valine), —(CH$_2$)$_2$CH$_3$ (norvaline), —CH$_2$C(H)(CH$_3$)$_2$ (leucine), —C(H)(CH$_3$)CH$_2$CH$_3$ (isoleucine), —(CH$_2$)$_3$CH$_3$ (norleucine), —C(CH$_3$)$_3$ (2-tert-butylglycine), benzyl (phenylalanine), 4-hydroxybenzyl (tyrosine), —(CH$_2$)$_3$NH$_2$ (ornithine), —(CH$_2$)$_4$NH$_2$ (lysine), —(CH$_2$)$_2$C(H)(OH)CH$_2$NH$_2$ (hydroxylysine), —CH$_2$OH (serine), —(CH$_2$)$_2$OH (homoserine), —C(H)(OH)CH$_3$ (threonine), —(CH$_2$)$_3$N(H)C(=NH)NH$_2$ (arginine), —(CH$_2$)$_3$N(H)C(=O)NH$_2$ (citrulline), —CH$_2$C(=O)NH$_2$ (asparagine), —CH$_2$C(=O)OH (aspartic acid), —(CH$_2$)$_2$C(=O)OH (glutamic acid), —(CH$_2$)$_2$C(=O)NH$_2$ (glutamine), —CH$_2$SH (cysteine), —(CH$_2$)$_2$SH (homocysteine), —(CH$_2$)$_2$SCH$_3$ (methionine), —CH$_2$SCH$_3$ (S-methylcysteine), (1H-imidazol-4-yl)methyl-(histidine), (1H-indol-3-yl)methyl-(thryptophan), —CH$_2$NH$_2$ (2,3-diaminopropanoic acid), and —(CH$_2$)$_2$NH$_2$ (2,4-diaminobutanoic acid), R$^8$ represents hydrogen or a group selected from:
C$_1$-C$_3$-alkyl, C$_1$-C$_3$-haloalkyl, C$_2$-C$_3$-hydroxyalkyl, C$_3$-C$_4$-cycloalkyl,
(C$_3$-C$_4$-cycloalkyl)-(C$_1$-C$_3$-alkyl)-, and (C$_1$-C$_3$-alkoxy)-(C$_2$-C$_3$-alkyl)-, or an N-oxide, a salt, a tautomer or a stereoisomer of said compound, or a salt of said N-oxide, tautomer or stereoisomer.

Another aspect of the invention are compounds of formula (I) as defined herein, wherein
V, W, Y and Z independently of each other represent CH or CR$^2$, wherein one of V, W, Y and Z represents CR$^2$ or,
V represents N, and W, Y and Z independently of each other represent CH or CR$^2$,
R$^1$ represents a group selected from:
C$_1$-C$_3$-alkyl, C$_1$-C$_3$-haloalkyl, and C$_3$-C$_4$-cycloalkyl,
R$^2$ represents, independently of each other, halogen or a group selected from:
C$_1$-C$_3$-alkyl, C$_3$-C$_4$-cycloalkyl, C$_1$-C$_3$-haloalkyl, C$_1$-C$_3$-alkoxy,
C$_1$-C$_3$-haloalkoxy, —N(H)C(=O)—(C$_1$-C$_3$-alkyl), —N(H)C(=O)H,
—N(H)C(=O)—(C$_1$-C$_3$-hydroxyalkyl),
—N(H)C(=O)—(C$_1$-C$_3$-alkyl)-(C$_1$-C$_3$-alkoxy), —N(H)C(=O)-phenyl,
—N(H)C(=O)—(C$_3$-C$_4$-cycloalkyl),
—N(H)C(=O)—(C$_1$-C$_3$-alkyl)-(C$_3$-C$_4$-cycloalkyl), and —N(H)C(=O)N(H)R$^8$,
said —N(H)C(=O)-phenyl being optionally substituted at the phenyl ring, one, two or three times, identically or differently, with a substituent selected from:
halogen, hydroxy, cyano, C$_1$-C$_4$-alkyl, C$_1$-C$_4$-haloalkyl,
C$_1$-C$_4$-alkoxy, C$_1$-C$_4$-haloalkoxy, C$_3$-C$_4$-cycloalkyl, and
C$_3$-C$_4$-cycloalkyloxy,
said —N(H)C(=O)—(C$_3$-C$_4$-cycloalkyl) being optionally substituted at the C$_3$-C$_4$-cycloalkyl ring with a substituent selected from:

fluorine, chlorine, trifluoromethyl, and methoxy,
$R^3$ represents a group selected from:
$C_2$-$C_6$-hydroxyalkyl, and $R^4$,
said $C_2$-$C_6$-hydroxyalkyl group being optionally substituted with one, two or three halogen atoms selected from:
fluorine, and chlorine,
$R^4$ represents —($C_2$-$C_6$-alkyl)-OC(=O)—C(H)($R^5$)—N(H)C(=O)—C(H)($R^7$)—NH$_2$,
in which $C_2$-$C_6$-alkyl is optionally substituted with one, two or three halogen atoms selected from:
fluorine, and chlorine,
$R^5$ and $R^7$ independently of each other represent a group selected from:
—CH$_3$ (alanine), —C(H)(CH$_3$)$_2$ (valine), —(CH$_2$)$_2$CH$_3$ (norvaline), —(CH$_2$)$_3$NH$_2$ (ornithine), —(CH$_2$)$_4$NH$_2$ (lysine), and —(CH$_2$)$_3$N(H)C(=NH)NH$_2$ (arginine),
$R^8$ represents hydrogen or a group selected from:
$C_1$-$C_3$-alkyl, $C_1$-$C_3$-haloalkyl, $C_2$-$C_3$-hydroxyalkyl, $C_3$-$C_4$-cycloalkyl,
($C_3$-$C_4$-cycloalkyl)-($C_1$-$C_3$-alkyl)-, and ($C_1$-$C_3$-alkoxy)-($C_2$-$C_3$-alkyl)-,
or an N-oxide, a salt, a tautomer or a stereoisomer of said compound, or a salt of said N-oxide, tautomer or stereoisomer.

Another aspect of the invention are compounds of formula (I) as defined herein, wherein
V, W, Y and Z independently of each other represent CH or CR$^2$, wherein one of V, W, Y and Z represents CR$^2$
or,
V represents N, and W, Y and Z independently of each other represent CH or CR$^2$,
$R^1$ represents a $C_1$-$C_3$-alkyl group,
$R^2$ represents, independently of each other, halogen or a group selected from:
$C_1$-$C_3$-alkyl, $C_3$-$C_4$-cycloalkyl, $C_1$-$C_3$-haloalkyl, $C_1$-$C_3$-alkoxy,
and —N(H)C(=O)—($C_1$-$C_3$-alkyl),
$R^3$ represents a group selected from:
$C_2$-$C_6$-hydroxyalkyl, and $R^4$,
$R^4$ represents —($C_2$-$C_6$-alkyl)-OC(=O)—C(H)($R^5$)—N(H)C(=O)—C(H)($R^7$)—NH$_2$,
$R^5$ and $R^7$ independently of each other represent a group selected from:
—CH$_3$ (alanine), and —(CH$_2$)$_4$NH$_2$ (lysine),
or an N-oxide, a salt, a tautomer or a stereoisomer of said compound, or a salt of said N-oxide, tautomer or stereoisomer.

Another aspect of the invention are compounds of formula (I) as defined herein, wherein
V, W, Y and Z independently of each other represent CH or CR$^2$, wherein one of V, W, Y and Z represents CR$^2$
or,
V represents N, and W, Y and Z independently of each other represent CH or CR$^2$,
$R^1$ represents a methyl group,
$R^2$ represents, independently of each other, fluorine, chlorine or a group selected from:
methyl, cyclopropyl, difluoromethyl, methoxy, and —N(H)C(=O)—CH$_3$,
$R^3$ represents a group selected from:
—(CH$_2$)$_2$OH, and $R^4$,
$R^4$ represents —(CH$_2$)$_2$—OC(=O)—C(H)($R^5$)—N(H)C(=O)—C(H)($R^7$)—NH$_2$,
$R^5$ represents —CH$_3$ (alanine),
$R^7$ represents —(CH$_2$)$_4$NH$_2$ (lysine),
or an N-oxide, a salt, a tautomer or a stereoisomer of said compound, or a salt of said N-oxide, tautomer or stereoisomer.

Another aspect of the invention are compounds of formula (I) as defined herein, wherein
V, W, Y and Z independently of each other represent CH or CR$^2$, wherein one of V, W, Y and Z represents CR$^2$
or,
V represents N, and W, Y and Z independently of each other represent CH or CR$^2$,
$R^1$ represents a methyl group,
$R^2$ represents, independently of each other, fluorine, chlorine or a group selected from:
methyl, cyclopropyl, difluoromethyl, methoxy, —N(H)C(=O)—CH$_3$,
—N(H)C(=O)-cyclopropyl, and —N(H)C(=O)N(H)-cyclopropyl,
$R^3$ represents a —(CH$_2$)$_2$OH group,
or an N-oxide, a salt, a tautomer or a stereoisomer of said compound, or a salt of said N-oxide, tautomer or stereoisomer.

Another aspect of the invention are compounds of formula (I) as defined herein, wherein
V, W, Y and Z independently of each other represent CH or CR$^2$, wherein one of V, W, Y and Z represents CR$^2$
or,
V represents N, and W, Y and Z independently of each other represent CH or CR$^2$,
$R^1$ represents a methyl group,
$R^2$ represents, independently of each other, fluorine, chlorine or a group selected from:
methyl, methoxy, —N(H)C(=O)—CH$_3$, and —N(H)C(=O)-cyclopropyl,
$R^3$ represents a —(CH$_2$)$_2$OH group,
or an N-oxide, a salt, a tautomer or a stereoisomer of said compound, or a salt of said N-oxide, tautomer or stereoisomer.

Another aspect of the invention are compounds of formula (I) as defined herein, wherein
V, W and Z each represent CH, and Y represents CR$^2$,
or
V, W and Y each represent CH, and Z represents CR$^2$,
or
V and W each represent CH, and Y and Z independently of each other represent CR$^2$,
or,
V represents N, and W represents CH or CR$^2$, and Y and Z each represent CH,
$R^1$ represents a methyl group,
$R^2$ represents, independently of each other, fluorine, chlorine or a group selected from:
methyl, methoxy, —N(H)C(=O)—CH$_3$, and —N(H)C(=O)-cyclopropyl,
$R^3$ represents a —(CH$_2$)$_2$OH group,
or an N-oxide, a salt, a tautomer or a stereoisomer of said compound, or a salt of said N-oxide, tautomer or stereoisomer.

In a further aspect of the invention compounds of formula (I) as described above are selected from the group consisting of:
2-{4-[(3-{4-[(3-chloropyridin-4-yl)amino]-5-methoxypyrimidin-2-yl}-1H-indazol-1-yl)methyl]-3,5-difluorophenoxy}ethanol,
2-{3,5-difluoro-4-[(3-{5-methoxy-4-[(2-methylpyridin-4-yl)amino]pyrimidin-2-yl}-1H-indazol-1-yl)methyl]phenoxy}ethanol, 2-{3,5-difluoro-4-[(3-{5-methoxy-4-[(3-methoxypyridin-4-yl)amino]pyrimidin-2-yl}-1H-indazol-1-yl)methyl]phenoxy}ethanol,
N-{4-[(2-{1-[2,6-difluoro-4-(2-hydroxyethoxy)benzyl]-1H-indazol-3-yl}-5-methoxypyrimidin-4-yl)amino]pyridin-2-yl}acetamide,
2-{3,5-difluoro-4-[(3-{5-methoxy-4-[(3-methylpyridin-4-yl)amino]pyrimidin-2-yl}-1H-indazol-1-yl)methyl]phenoxy}ethanol,
2-{3,5-difluoro-4-[(3-{4-[(3-fluoropyridin-4-yl)amino]-5-methoxypyrimidin-2-yl}-1H-indazol-1-yl)methyl]phenoxy}ethanol,
2-(4-{[3-(4-{[2-(difluoromethyl)pyridin-4-yl]amino}-5-methoxypyrimidin-2-yl)-1H-indazol-1-yl]methyl}-3,5-difluorophenoxy)ethanol,
2-{4-[(3-{4-[(2,5-dimethylpyridin-4-yl)amino]-5-methoxypyrimidin-2-yl}-1H-indazol-1-yl)methyl]-3,5-difluorophenoxy}ethanol,
2-{4-[(3-{4-[(3-cyclopropylpyridin-4-yl)amino]-5-methoxypyrimidin-2-yl}-1H-indazol-1-yl)methyl]-3,5-difluorophenoxy}ethanol,
2-{1-[2,6-difluoro-4-(2-hydroxyethoxy)benzyl]-1H-indazol-3-yl}-4-[(2-methylpyrimidin-4-yl)amino]pyrimidin-5-ol
2-{3,5-difluoro-4-[(3-{4-[(2-fluoropyridin-4-yl)amino]-5-methoxypyrimidin-2-yl}-1H-indazol-1-yl)methyl]phenoxy}ethanol,
2-{3,5-difluoro-4-[(3-{4-[(5-fluoro-2-methylpyridin-4-yl)amino]-5-methoxypyrimidin-2-yl}-1H-indazol-1-yl)methyl]phenoxy}ethanol,
2-[3,5-difluoro-4-({3-[5-methoxy-4-(pyrimidin-4-ylamino)pyrimidin-2-yl]-1H-indazol-1-yl}methyl)phenoxy]ethanol
N-{4-[(2-{1-[2,6-difluoro-4-(2-hydroxyethoxy)benzyl]-1H-indazol-3-yl}-5-methoxypyrimidin-4-yl)amino]-5-methylpyridin-2-yl}acetamide,
2-{3,5-difluoro-4-[(3-{5-methoxy-4-[(2-methylpyridin-4-yl)amino]pyrimidin-2-yl}-1H-indazol-1-yl)methyl]phenoxy}ethyl L-lysyl-L-alaninate, salt with trifluoroacetic acid,
2-{3,5-difluoro-4-[(3-{5-methoxy-4-[(2-methylpyridin-4-yl)amino]pyrimidin-2-yl}-1H-indazol-1-yl)methyl]phenoxy}ethyl L-lysyl-L-alaninate,
2-{3,5-difluoro-4-[(3-{5-methoxy-4-[(3-methoxypyridin-4-yl)amino]pyrimidin-2-yl}-1H-indazol-1-yl)methyl]phenoxy}ethyl L-lysyl-L-alaninate, salt with trifluoroacetic acid,
2-{3,5-difluoro-4-[(3-{5-methoxy-4-[(3-methoxypyridin-4-yl)amino]pyrimidin-2-yl}-1H-indazol-1-yl)methyl]phenoxy}ethyl L-lysyl-L-alaninate,
N-{4-[(2-{1-[2,6-difluoro-4-(2-hydroxyethoxy)benzyl]-1H-indazol-3-yl}-5-methoxy-pyrimidin-4-yl)amino]pyridin-2-yl}cyclopropanecarboxamide,
1-cyclopropyl-3-{4-[(2-{1-[2,6-difluoro-4-(2-hydroxyethoxy)benzyl]-1H-indazol-3-yl}-5-methoxypyrimidin-4-yl)amino]pyridin-2-yl}urea,
2-{3,5-difluoro-4-[(3-{5-methoxy-4-[(3-methoxy-2-methylpyridin-4-yl)amino]pyrimidin-2-yl}-1H-indazol-1-yl)methyl]phenoxy}ethanol,
2-{3,5-difluoro-4-[(3-{5-methoxy-4-[(5-methoxy-2-methylpyridin-4-yl)amino]pyrimidin-2-yl}-1H-indazol-1-yl)methyl]phenoxy}ethanol,
3-{4-[(3-{4-[(2,5-dimethylpyridin-4-yl)amino]-5-methoxypyrimidin-2-yl}-1H-indazol-1-yl)methyl]-3,5-difluorophenoxy}propan-1-ol,
3-{3,5-difluoro-4-[(3-{5-methoxy-4-[(3-methoxypyridin-4-yl)amino]pyrimidin-2-yl}-1H-indazol-1-yl)methyl]phenoxy}propan-1-ol,
3-{3,5-difluoro-4-[(3-{5-methoxy-4-[(2-methylpyrimidin-4-yl)amino]pyrimidin-2-yl}-1H-indazol-1-yl)methyl]phenoxy}propan-1-ol,
(2R)-3-{3,5-difluoro-4-[(3-{5-methoxy-4-[(2-methylpyrimidin-4-yl)amino]pyrimidin-2-yl}-1H-indazol-1-yl)methyl]phenoxy}-2-methylpropan-1-ol,
(2R)-3-{4-[(3-{4-[(2,5-dimethylpyridin-4-yl)amino]-5-methoxypyrimidin-2-yl}-1H-indazol-1-yl)methyl]-3,5-difluorophenoxy}-2-methylpropan-1-ol,
N-[4-({2-[1-(2,6-difluoro-4-{[(2R)-3-hydroxy-2-methylpropyl]oxy}benzyl)-1H-indazol-3-yl]-5-methoxypyrimidin-4-yl}amino)pyridin-2-yl]acetamide,
(2R)-3-{3,5-difluoro-4-[(3-{5-methoxy-4-[(3-methoxypyridin-4-yl)amino]pyrimidin-2-yl}-1H-indazol-1-yl)methyl]phenoxy}-2-methylpropan-1-ol,
3-{3,5-difluoro-4-[(3-{5-methoxy-4-[(2-methylpyridin-4-yl)amino]pyrimidin-2-yl}-1H-indazol-1-yl)methyl]phenoxy}propan-1-ol,
2-{4-[(3-{4-[(2,6-dimethylpyrimidin-4-yl)amino]-5-methoxypyrimidin-2-yl}-1H-indazol-1-yl)methyl]-3,5-difluorophenoxy}ethanol,
2-{3,5-difluoro-4-[(3-{4-[(2-fluoropyridin-4-yl)amino]-5-methoxypyrimidin-2-yl}-1H-indazol-1-yl)methyl]phenoxy}ethyl D-lysyl-L-alaninate, salt with trifluoroacetic acid,
2-{3,5-difluoro-4-[(3-{4-[(2-fluoropyridin-4-yl)amino]-5-methoxypyrimidin-2-yl}-1H-indazol-1-yl)methyl]phenoxy}ethyl D-lysyl-L-alaninate,
2-{3,5-difluoro-4-[(3-{4-[(2-fluoropyridin-4-yl)amino]-5-methoxypyrimidin-2-yl}-1H-indazol-1-yl)methyl]phenoxy}ethyl L-lysyl-L-alaninate, salt with trifluoroacetic acid, and
2-{3,5-difluoro-4-[(3-{4-[(2-fluoropyridin-4-yl)amino]-5-methoxypyrimidin-2-yl}-1H-indazol-1-yl)methyl]phenoxy}ethyl L-lysyl-L-alaninate with trifluoroacetic acid,
or an N-oxide, a salt, a tautomer or a stereoisomer of said compound, or a salt of said N-oxide, tautomer or stereoisomer.

In a further aspect of the invention compounds of formula (I) as described above are selected from the group consisting of:
2-{4-[(3-{4-[(3-chloropyridin-4-yl)amino]-5-methoxypyrimidin-2-yl}-1H-indazol-1-yl)methyl]-3,5-difluorophenoxy}ethanol,
2-{3,5-difluoro-4-[(3-{5-methoxy-4-[(2-methylpyridin-4-yl)amino]pyrimidin-2-yl}-1H-indazol-1-yl)methyl]phenoxy}ethanol,
2-{3,5-difluoro-4-[(3-{5-methoxy-4-[(3-methoxypyridin-4-yl)amino]pyrimidin-2-yl}-1H-indazol-1-yl)methyl]phenoxy}ethanol,
N-{4-[(2-{1-[2,6-difluoro-4-(2-hydroxyethoxy)benzyl]-1H-indazol-3-yl}-5-methoxypyrimidin-4-yl)amino]pyridin-2-yl}acetamide,
2-{3,5-difluoro-4-[(3-{5-methoxy-4-[(3-methylpyridin-4-yl)amino]pyrimidin-2-yl}-1H-indazol-1-yl)methyl]phenoxy}ethanol,
2-{3,5-difluoro-4-[(3-{4-[(3-fluoropyridin-4-yl)amino]-5-methoxypyrimidin-2-yl}-1H-indazol-1-yl)methyl]phenoxy}ethanol,
2-(4-{[3-(4-{[2-(difluoromethyl)pyridin-4-yl]amino}-5-methoxypyrimidin-2-yl)-1H-indazol-1-yl]methyl}-3,5-difluorophenoxy)ethanol, 2-{4-[(3-{4-[(2,5-dimethylpyridin-4-yl)amino]-5-methoxy-pyrimidin-2-yl}-1H-indazol-1-yl)methyl]-3,5-difluorophenoxy}ethanol, 2-{4-[(3-{4-[(3-cyclopropylpyridin-4-yl)amino]-5-methoxypyrimidin-2-yl}-1H-indazol-1-yl)methyl]-3,5-difluorophenoxy}ethanol, 2-{1-[2,6-difluoro-4-(2-hydroxyethoxy)benzyl]-1H-indazol-3-yl}-4-[(2-methylpyrimidin-4-yl)amino]pyrimidin-5-ol 2-{3,5-difluoro-4-[(3-{4-[(2-fluoropyridin-4-yl)amino]-5-methoxypyrimidin-2-yl}-1H-indazol-1-yl)methyl]phenoxy}ethanol, 2-{3,5-difluoro-4-[(3-{4-[(5-fluoro-2-methylpyridin-4-yl)amino]-5-methoxypyrimidin-2-yl}-1H-indazol-1-yl)methyl]phenoxy}ethanol, 2-[3,5-difluoro-4-({3-[5-methoxy-4-(pyrimidin-4-ylamino)pyrimidin-2-yl]-1H-indazol-1-yl}methyl)phenoxy]ethanol N-{4-[(2-{1-[2,6-difluoro-4-(2-hydroxyethoxy)benzyl]-1H-indazol-3-yl}-5-methoxypyrimidin-4-yl)amino]-5-methylpyridin-2-yl}acetamide, 2-{3,5-difluoro-4-[(3-{5-methoxy-4-[(2-methylpyridin-4-yl)amino]pyrimidin-2-yl}-1H-indazol-1-yl)methyl]phenoxy}ethyl L-lysyl-L-alaninate, salt with trifluoroacetic acid, and 2-{3,5-difluoro-4-[(3-{5-methoxy-4-[(3-methoxypyridin-4-yl)amino]pyrimidin-2-yl}-1H-indazol-1-yl)methyl]phenoxy}ethyl L-lysyl-L-alaninate, salt with trifluoroacetic acid, N-{4-[(2-{1-[2,6-difluoro-4-(2-hydroxyethoxy)benzyl]-1H-indazol-3-yl}-5-methoxypyrimidin-4-yl)amino]pyridin-2-yl}cyclopropanecarboxamide, 1-cyclopropyl-3-{4-[(2-{1-[2,6-difluoro-4-(2-hydroxyethoxy)benzyl]-1H-indazol-3-yl}-5-methoxypyrimidin-4-yl)amino]pyridin-2-yl}urea, 2-{3,5-difluoro-4-[(3-{5-methoxy-4-[(3-methoxy-2-methylpyridin-4-yl)amino]pyrimidin-2-yl}-1H-indazol-1-yl)methyl]phenoxy}ethanol, 2-{3,5-difluoro-4-[(3-{5-methoxy-4-[(5-methoxy-2-methylpyridin-4-yl)amino]pyrimidin-2-yl}-1H-indazol-1-yl)methyl]phenoxy}ethanol, 3-{4-[(3-{4-[(2,5-dimethylpyridin-4-yl)amino]-5-methoxy-pyrimidin-2-yl}-1H-indazol-1-yl)methyl]-3,5-difluorophenoxy}propan-1-ol, 3-{3,5-difluoro-4-[(3-{5-methoxy-4-[(3-methoxypyridin-4-yl)amino]pyrimidin-2-yl}-1H-indazol-1-yl)methyl]phenoxy}propan-1-ol, 3-{3,5-difluoro-4-[(3-{5-methoxy-4-[(2-methylpyrimidin-4-yl)amino]pyrimidin-2-yl}-1H-indazol-1-yl)methyl]phenoxy}propan-1-ol, (2R)-3-{3,5-difluoro-4-[(3-{5-methoxy-4-[(2-methylpyrimidin-4-yl)amino]pyrimidin-2-yl}-1H-indazol-1-yl)methyl]phenoxy}-2-methylpropan-1-ol, (2R)-3-{4-[(3-{4-[(2,5-dimethylpyridin-4-yl)amino]-5-methoxypyrimidin-2-yl}-1H-indazol-1-yl)methyl]-3,5-difluorophenoxy}-2-methylpropan-1-ol, N-[4-({2-[1-(2,6-difluoro-4-{[(2R)-3-hydroxy-2-methylpropyl]oxy}benzyl)-1H-indazol-3-yl]-5-methoxypyrimidin-4-yl}amino)pyridin-2-yl]acetamide, (2R)-3-{3,5-difluoro-4-[(3-{5-methoxy-4-[(3-methoxypyridin-4-yl)amino]pyrimidin-2-yl}-1H-indazol-1-yl)methyl]phenoxy}-2-methylpropan-1-ol, 3-{3,5-difluoro-4-[(3-{5-methoxy-4-[(2-methylpyridin-4-yl)amino]pyrimidin-2-yl}-1H-indazol-1-yl)methyl]phenoxy}propan-1-ol, 2-{4-[(3-{4-[(2,6-dimethylpyrimidin-4-yl)amino]-5-methoxypyrimidin-2-yl}-1H-indazol-1-yl)methyl]-3,5-difluorophenoxy}ethanol, 2-{3,5-difluoro-4-[(3-{4-[(2-fluoropyridin-4-yl)amino]-5-methoxypyrimidin-2-yl}-1H-indazol-1-yl)methyl]phenoxy}ethyl D-lysyl-L-alaninate, salt with trifluoroacetic acid, and 2-{3,5-difluoro-4-[(3-{4-[(2-fluoropyridin-4-yl)amino]-5-methoxypyrimidin-2-yl}-1H-indazol-1-yl)methyl]phenoxy}ethyl L-lysyl-L-alaninate, salt with trifluoroacetic acid, or an N-oxide, a salt, a tautomer or a stereoisomer of said compound, or a salt of said N-oxide, tautomer or stereoisomer.

A further aspect of the invention are compounds of formula (I) supra, wherein

V, W, Y and Z independently of each other represent CH or $CR^2$, wherein one of V, W, Y and Z represents $CR^2$ or, V represents N, and W, Y and Z independently of each other represent CH or $CR^2$, or, V and Y represent N, and W and Z independently of each other represent CH or $CR^2$.

Yet another aspect of the invention are compounds of formula (I) supra in which, V, W, Y and Z independently of each other represent CH or $CR^2$, wherein one of V, W, Y and Z represents $CR^2$.

Yet another aspect of the invention are compounds of formula (I) supra in which, V represents N, and W, Y and Z independently of each other represent CH or $CR^2$.

Yet another aspect of the invention are compounds of formula (I) supra in which, V and Y represent N, and W and Z independently of each other represent CH or $CR^2$.

Yet another aspect of the invention are compounds of formula (I) supra in which, V, W and Z each represent CH, and Y represents $CR^2$, or V, W and Y each represent CH, and Z represents $CR^2$, or V and W each represent CH, and Y and Z independently of each other represent $CR^2$, or, V represents N, and W represents CH or $CR^2$, and Y and Z each represent CH.

Yet another aspect of the invention are compounds of formula (I) supra in which, V, W and Z each represent CH, and Y represents $CR^2$, or V, W and Y each represent CH, and Z represents $CR^2$, or V and W each represent CH, and Y and Z independently of each other represent $CR^2$.

Yet another aspect of the invention are compounds of formula (I) supra in which, V, W and Z each represent CH, and Y represents $CR^2$.

Yet another aspect of the invention are compounds of formula (I) supra in which, V, W and Y each represent CH, and Z represents $CR^2$.

Yet another aspect of the invention are compounds of formula (I) supra in which, V and W each represent CH, and Y and Z independently of each other represent $CR^2$.

Yet another aspect of the invention are compounds of formula (I) supra in which, V represents N, and W represents CH or $CR^2$, and Y and Z each represent CH.

A further aspect of the invention are compounds of formula (I) supra, wherein
$R^1$ represents a group selected from:
$C_1$-$C_6$-alkyl, $C_1$-$C_6$-haloalkyl, $C_3$-$C_6$-cycloalkyl, ($C_1$-$C_3$-alkoxy)-($C_2$-$C_3$-alkyl)-, and ($C_3$-$C_6$-cycloalkyl)-($C_1$-$C_3$-alkyl)-.

Yet another aspect of the invention are compounds of formula (I) supra in which,
$R^1$ represents a group selected from:
$C_1$-$C_6$-alkyl.

Yet another aspect of the invention are compounds of formula (I) supra in which,
$R^1$ represents a group selected from:
$C_1$-$C_3$-alkyl, $C_1$-$C_3$-haloalkyl, and $C_3$-$C_4$-cycloalkyl.

Yet another aspect of the invention are compounds of formula (I) supra in which,
$R^1$ represents a $C_1$-$C_3$-alkyl group, preferably methyl.

A further aspect of the invention are compounds of formula (I) supra, wherein
$R^2$ represents, independently of each other, halogen or a group selected from:
$C_1$-$C_3$-alkyl, $C_3$-$C_4$-cycloalkyl, $C_1$-$C_3$-haloalkyl, $C_1$-$C_3$-alkoxy,
$C_1$-$C_3$-haloalkoxy, —N(H)C(=O)—($C_1$-$C_3$-alkyl), —N(H)C(=O)H,
—N(H)C(=O)—($C_1$-$C_3$-hydroxyalkyl),
—N(H)C(=O)—($C_1$-$C_3$-alkyl)-($C_1$-$C_3$-alkoxy), —N(H)C(=O)-phenyl,
—N(H)C(=O)—($C_3$-$C_4$-cycloalkyl),
—N(H)C(=O)—($C_1$-$C_3$-alkyl)-($C_3$-$C_4$-cycloalkyl), and
—N(H)C(=O)N(H)$R^8$,
said —N(H)C(=O)-phenyl being optionally substituted at the phenyl ring, one, two or three times, identically or differently, with a substituent selected from:
halogen, hydroxy, cyano, $C_1$-$C_4$-alkyl, $C_1$-$C_4$-haloalkyl,
$C_1$-$C_4$-alkoxy, $C_1$-$C_4$-haloalkoxy, $C_3$-$C_4$-cycloalkyl, and
$C_3$-$C_4$-cycloalkyloxy,
said —N(H)C(=O)—($C_3$-$C_4$-cycloalkyl) being optionally substituted at the $C_3$-$C_4$-cycloalkyl ring with a substituent selected from:
fluorine, chlorine, trifluoromethyl, and methoxy.

Yet another aspect of the invention are compounds of formula (I) supra in which,
$R^2$ represents, independently of each other, halogen or a group selected from:
$C_1$-$C_3$-alkyl, $C_3$-$C_4$-cycloalkyl, $C_1$-$C_3$-haloalkyl, $C_1$-$C_3$-alkoxy,
—N(H)C(=O)—($C_1$-$C_3$-alkyl).

Yet another aspect of the invention are compounds of formula (I) supra in which,
$R^2$ represents, independently of each other, fluorine, chlorine or a group selected from:
methyl, cyclopropyl, difluoromethyl, methoxy, and —N(H)C(=O)—$CH_3$.

Yet another aspect of the invention are compounds of formula (I) supra in which,
$R^2$ represents, independently of each other, fluorine, chlorine or a group selected from:
methyl, cyclopropyl, difluoromethyl, methoxy, —N(H)C(=O)—$CH_3$,
—N(H)C(=O)-cyclopropyl, and —N(H)C(=O)N(H)-cyclopropyl.

Yet another aspect of the invention are compounds of formula (I) supra in which,
$R^2$ represents, independently of each other, fluorine, chlorine or a group selected from:
methyl, methoxy, —N(H)C(=O)—$CH_3$, and —N(H)C(=O)-cyclopropyl.

A further aspect of the invention are compounds of formula (I) supra, wherein
$R^3$ represents a group selected from:
$C_2$-$C_6$-hydroxyalkyl, and $R^4$,
said $C_2$-$C_6$-hydroxyalkyl groups being optionally substituted with one, two or three halogen atoms selected from:
fluorine, and chlorine.

Yet another aspect of the invention are compounds of formula (I) supra in which,
$R^3$ represents a group selected from:
$C_2$-$C_6$-hydroxyalkyl, and $R^4$.

Yet another aspect of the invention are compounds of formula (I) supra in which,
$R^3$ represents a group selected from:
$C_2$-$C_6$-hydroxyalkyl,
said $C_2$-$C_6$-hydroxyalkyl groups being optionally substituted with one, two or three halogen atoms selected from:
fluorine, and chlorine.

Yet another aspect of the invention are compounds of formula (I) supra in which,
$R^3$ represents a group selected from $R^4$.

Yet another aspect of the invention are compounds of formula (I) supra in which,
$R^3$ represents a group selected from:
—$(CH_2)_2$OH, and $R^4$.

Yet another aspect of the invention are compounds of formula (I) supra in which,
$R^3$ represents —$(CH_2)_2$OH.

Yet another aspect of the invention are compounds of formula (I) supra in which,
$R^3$ represents $C_2$-$C_6$-hydroxyalkyl, A further aspect of the invention are compounds of formula (I) supra, wherein
$R^4$ represents —($C_2$-$C_6$-alkyl)-OC(=O)—C(H)($R^5$)—N(H)C(=O)—C(H)($R^7$)—$NH_2$,
in which $C_2$-$C_6$-alkyl is optionally substituted with one, two or three halogen atoms selected from:
fluorine, and chlorine.

Yet another aspect of the invention are compounds of formula (I) supra in which,
$R^4$ represents —($C_2$-$C_6$-alkyl)-OC(=O)—C(H)($R^5$)—N(H)C(=O)—C(H)($R^7$)—$NH_2$.

Yet another aspect of the invention are compounds of formula (I) supra in which,
$R^4$ represents —$(CH_2)_2$—OC(=O)—C(H)($R^5$)—N(H)C(=O)—C(H)($R^7$)—$NH_2$.

A further aspect of the invention are compounds of formula (I) supra, wherein
$R^5$ and $R^7$ independently of each other represent hydrogen (glycine) or a group selected from:
—$CH_3$ (alanine), —C(H)($CH_3$)$_2$ (valine), —$(CH_2)_2CH_3$ (norvaline), —$CH_2$C(H)($CH_3$)$_2$ (leucine), —C(H)($CH_3$)$CH_2CH_3$ (isoleucine), —$(CH_2)_3CH_3$ (norleucine), —C($CH_3$)$_3$ (2-tert-butylglycine), benzyl (phenylalanine), 4-hydroxybenzyl (tyrosine), —$(CH_2)_3NH_2$ (ornithine), —$(CH_2)_4NH_2$ (lysine), —$(CH_2)_2$C(H)(OH)$CH_2NH_2$ (hydroxylysine), —$CH_2$OH (serine), —$(CH_2)_2$OH (homoserine), —C(H)(OH)$CH_3$ (threonine), —$(CH_2)_3$N(H)C(=NH)$NH_2$ (arginine), —(CH$_2$)$_3$N(H)C(=O)NH$_2$ (citrulline), —CH$_2$C(=O)NH$_2$ (asparagine), —CH$_2$C(=O)OH (aspartic acid), —(CH$_2$)$_2$C(=O)OH (glutamic acid), —(CH$_2$)$_2$C(=O)NH$_2$ (glutamine), —CH$_2$SH (cysteine), —(CH$_2$)$_2$SH (homocysteine), —(CH$_2$)$_2$SCH$_3$ (methionine), —CH$_2$SCH$_3$ (S-methylcysteine), (1H-imidazol-4-yl)methyl-(histidine), (1H-indol-3-yl)methyl-(thryptophan), —CH$_2$NH$_2$ (2,3-diaminopropanoic acid), and —(CH$_2$)$_2$NH$_2$ (2,4-diaminobutanoic acid).

Yet another aspect of the invention are compounds of formula (I) supra in which,
R$^5$ and R$^7$ independently of each other represent a group selected from:
—CH$_3$ (alanine), —C(H)(CH$_3$)$_2$ (valine), —(CH$_2$)$_2$CH$_3$ (norvaline), —(CH$_2$)$_3$NH$_2$ (ornithine), —(CH$_2$)$_4$NH$_2$ (lysine), and —(CH$_2$)$_3$N(H)C(=NH)NH$_2$ (arginine).

Yet another aspect of the invention are compounds of formula (I) supra in which,
R$^5$ and R$^7$ independently of each other represent a group selected from:
—CH$_3$ (alanine), and —(CH$_2$)$_4$NH$_2$ (lysine).

Yet another aspect of the invention are compounds of formula (I) supra in which,
R$^5$ represents —CH$_3$ (alanine), and
R$^7$ represents —(CH$_2$)$_4$NH$_2$ (lysine).

A further aspect of the invention are compounds of formula (I) supra, wherein
R$^8$ represents hydrogen or a group selected from:
C$_1$-C$_3$-alkyl, C$_1$-C$_3$-haloalkyl, C$_2$-C$_3$-hydroxyalkyl, C$_3$-C$_4$-cycloalkyl,
(C$_3$-C$_4$-cycloalkyl)-(C$_1$-C$_3$-alkyl)-, and (C$_1$-C$_3$-alkoxy)-(C$_2$-C$_3$-alkyl)-.

One aspect of the invention are compounds of formula (I) as described in the examples, as characterized by their names in the title, as claimed in claim 6 or 7, and their structures as well as the subcombinations of all residues specifically disclosed in the compounds of the examples.

Another aspect of the present invention are the intermediates as used for their synthesis.

A further aspect of the invention are compounds of formula (I), which are present as their salts.

Yet another aspect of the invention are compounds of formula (I) in which the salt is a pharmaceutically acceptable salt.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

Another embodiment of the invention are compounds according to the claims as disclosed in the Claims section wherein the definitions are limited according to the preferred or more preferred definitions as disclosed below or specifically disclosed residues of the exemplified compounds and subcombinations thereof.

In accordance with a further aspect, the present invention relates to intermediate compounds which are useful in the preparation of compounds of the present invention of general formula (I), particularly in the method described herein.

In particular, the present invention relates to a compound of general formula (1-34):

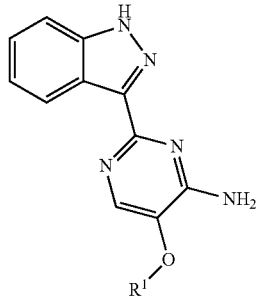

(1-34)

in which R$^1$ is as defined herein.

In accordance with yet another aspect, the present invention relates to the use of an intermediate compound of general formula (1-34):

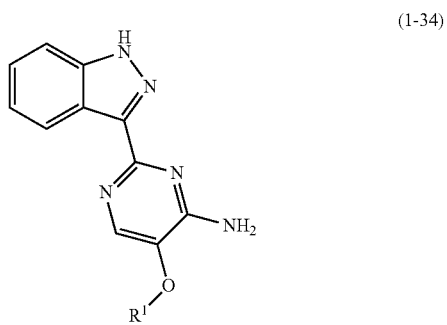

(1-34)

in which R$^1$ is as defined herein, for the preparation of a compound of general formula (Ia) as defined infra.

In accordance with yet another aspect, the present invention relates to a compound of formula (1-9):

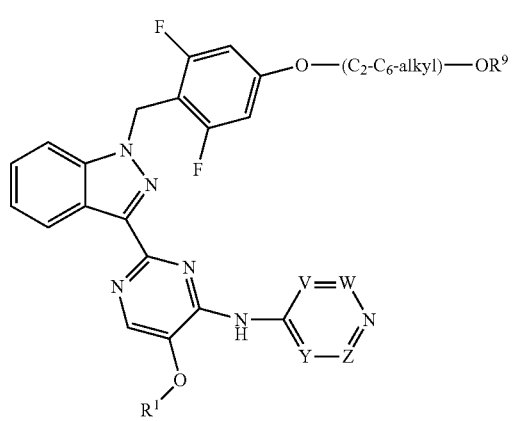

1-9 in which R$^1$, V, W, Y and Z are as defined herein, and R$^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl.

In accordance with yet another aspect, the present invention relates to the use of a compound of formula (1-9):

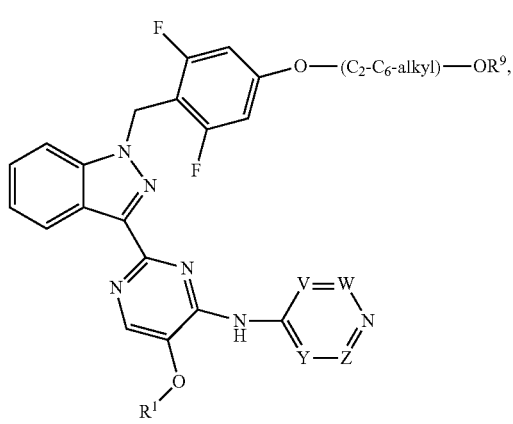

in which $R^1$, V, W, Y and Z are as defined herein and $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl, for the preparation of a compound of general formula (I) or (Ia) as defined herein.

In accordance with yet another aspect, the present invention relates to a compound of formula (1-9a):

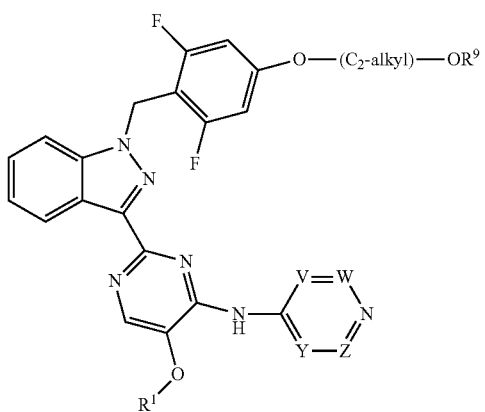

in which $R^1$, V, W, Y and Z are as defined herein, and $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl.

In accordance with yet another aspect, the present invention relates to the use of a compound of formula (1-9a):

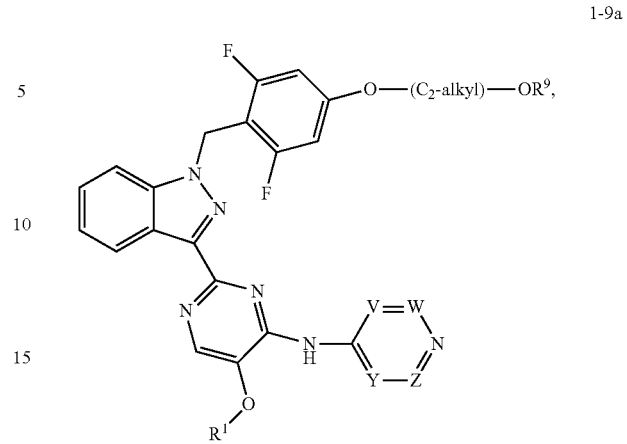

in which $R^1$, V, W, Y and Z are as defined herein and $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl, for the preparation of a compound of general formula (I) as defined herein or a compound (Ia-1):

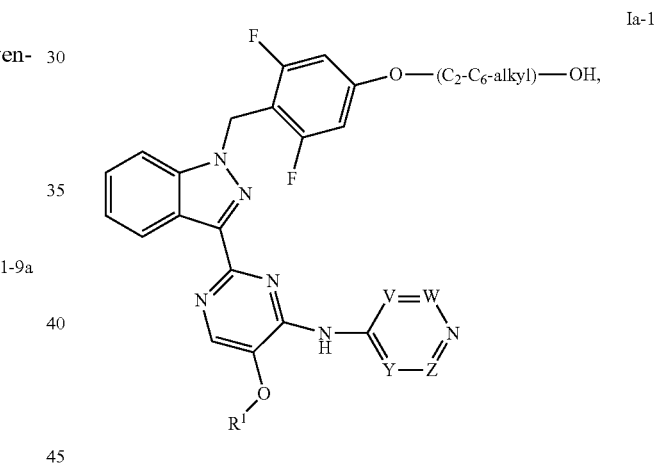

in which $R^1$, V, W, Y and Z are as defined herein.

In accordance with yet another aspect, the present invention relates to a compound of formula (1-20):

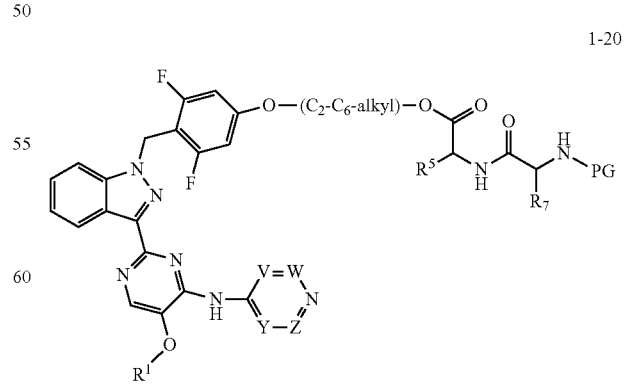

in which $R^1$, $R^5$, $R^7$, V, W, Y and Z are as defined herein for the compound of formula (I), and PG represents an amino protecting group, such as, for example fluorenylmethyloxycarbonyl, benzyloxycarbonyl, allyloxycarbonyl or tert-butyloxycarbonyl.

In accordance with yet another aspect, the present invention relates to the use of a compound of formula (1-20):

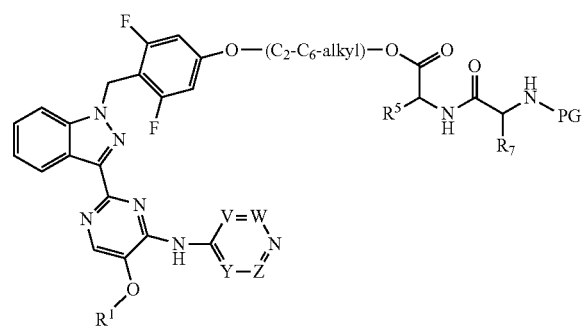

(1-20)

in which $R^1$, $R^5$, $R^7$, V, W, Y and Z are as defined herein for the compound of formula (I), and PG represents an amino protecting group, such as, for example fluorenylmethyloxycarbonyl, benzyloxycarbonyl, allyloxycarbonyl or tert-butyloxycarbonyl, for the preparation of a compound of general formula (I) or (Ib) as defined herein.

In accordance with yet another aspect, the present invention relates to a method of preparing a compound of general formula (Ia) as defined infra, said method comprising the step of allowing an intermediate compound of general formula (1-34):

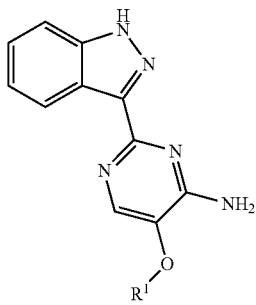

(1-34)

in which $R^1$ is as defined herein for the compound of formula (I), to react with a compound of general formula (1-3):

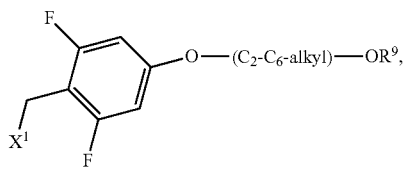

(1-3)

in which $R^9$ represents a methyl- or an ethyl group or an alcohol protecting group, such as tert-butyldimethylsilyl, tert-butyldiphenylsilyl, triethylsilyl, triisopropylsilyl or tetrahydropyranyl, and $X^1$ represents F, Cl, Br, I or a sulfonate, such as, trifluormethylsulfonate or p-toluolsulfonate, thereby giving a compound of general formula (1-7):

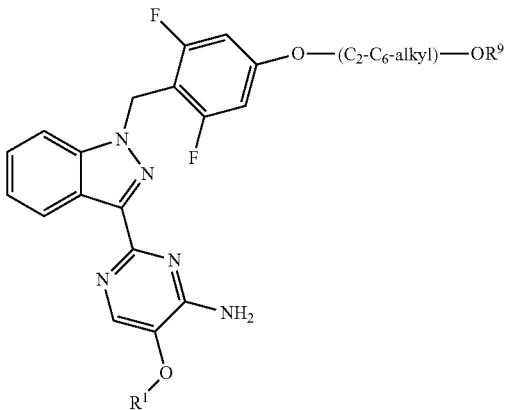

(1-7)

in which $R^1$ is as defined herein for the compound of formula (I), and $R^9$ represents a methyl- or an ethyl group or an alcohol protecting group, such as tert-butyldimethylsilyl, tert-butyldiphenylsilyl, triethylsilyl, triisopropylsilyl or tetrahydropyranyl.

In accordance with yet another aspect, the present invention relates to a method of preparing a compound of general formula (Ia) as defined infra, said method comprising the step of allowing an intermediate compound of general formula (1-7):

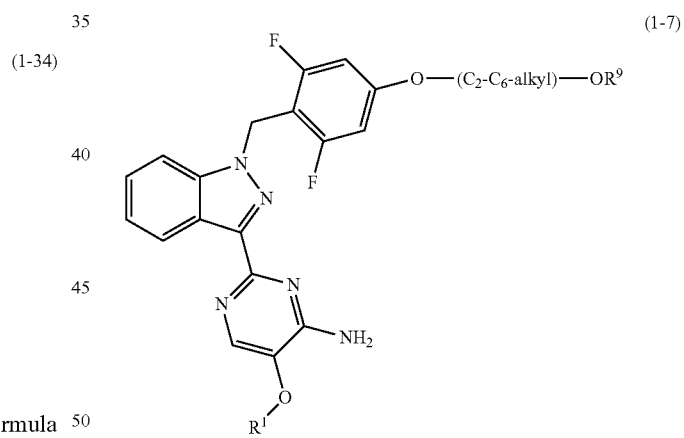

(1-7)

in which $R^1$ is as defined herein, and $R^9$ represents a methyl- or an ethyl group or an alcohol protecting group, such as tert-butyldimethylsilyl, tert-butyldiphenylsilyl, triethylsilyl, triisopropylsilyl or tetrahydropyranyl, to react with a compound of general formula (1-8):

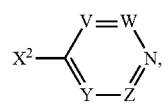

(1-8)

in which V, W, Y and Z are as defined for the compound of general formula (I), supra, and $X^2$ represents F, Cl, Br, I, boronic acid or a boronic acid ester, such as 4,4,5,5-tetramethyl-2-phenyl-1,3,2-dioxaborolane (boronic acid pinacole ester), thereby giving a compound of general formula (1-9):

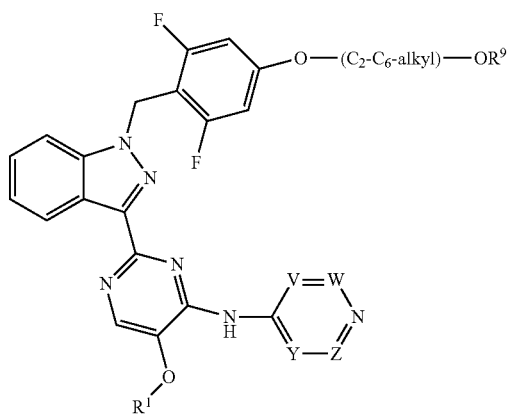

(1-9)

in which $R^1$, V, W, Y and Z are as defined herein for the compound of formula (I), and $R^9$ represents a methyl- or an ethyl group or an alcohol protecting group, such as tert-butyldimethylsilyl, tert-butyldiphenylsilyl, triethylsilyl, triisopropylsilyl or tetrahydropyranyl.

In accordance with yet another aspect, the present invention relates to a method of preparing a compound of general formula (Ia) as defined infra, said method comprising the step of allowing an intermediate compound of general formula (1-9):

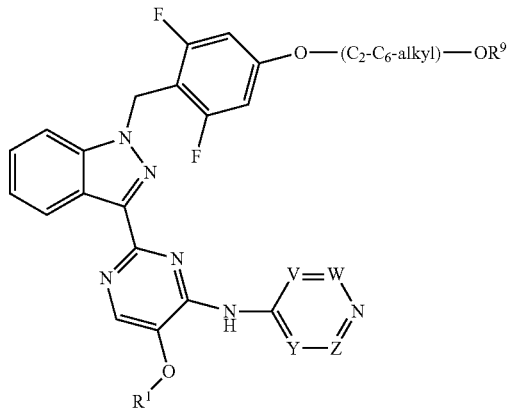

(1-9)

in which $R^1$, V, W, Y and Z are as defined herein for the compound of formula (I), and $R^9$ represents a methyl- or an ethyl group or an alcohol protecting group, such as tert-butyldimethylsilyl, tert-butyldiphenylsilyl, triethylsilyl, triisopropylsilyl or tetrahydropyranyl, to react with a deprotection agent, such as a dealkylating agent, for example, boron 5 trichloride, thereby giving a compound of general formula (Ia):

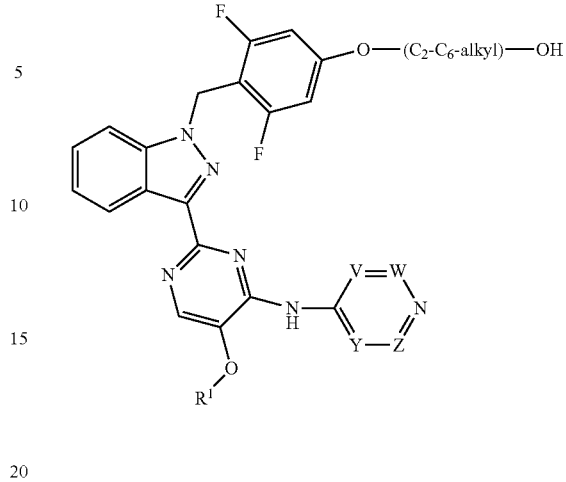

(Ia)

in which $R^1$, V, W, Y and Z are as defined herein for the compound of formula (I).

In accordance with yet another aspect, the present invention relates to a method of preparing a compound of general formula (Ib) as defined infra, said method comprising the step of allowing an intermediate compound of general formula (1-20):

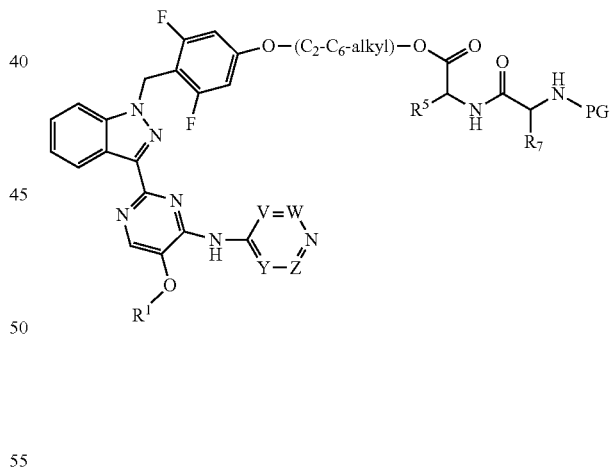

1-20 in which $R^1$, $R^5$, $R^7$, V, W, Y and Z are as defined herein for the compound of formula (I), and PG represents an amino protecting group, such as, for example fluorenylmethyloxycarbonyl, benzyloxycarbonyl, allyloxycarbonyl or tert-butyloxycarbonyl, to react with a with Broensted acid, such as, for example trifluoroacetic acid, thereby giving a compound of general formula (Ib):

(Ib)

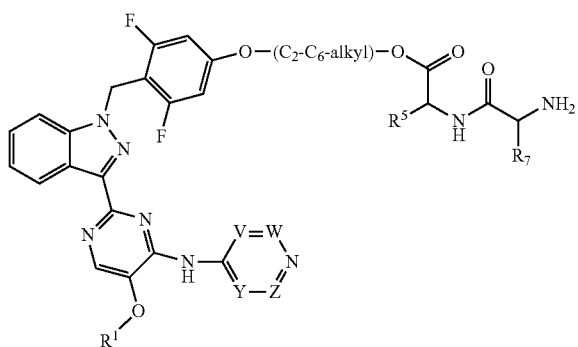

in which R¹, R⁵, R⁷, V, W, Y and Z are as defined herein for the compound of formula (I).

DEFINITIONS

Figure 1:
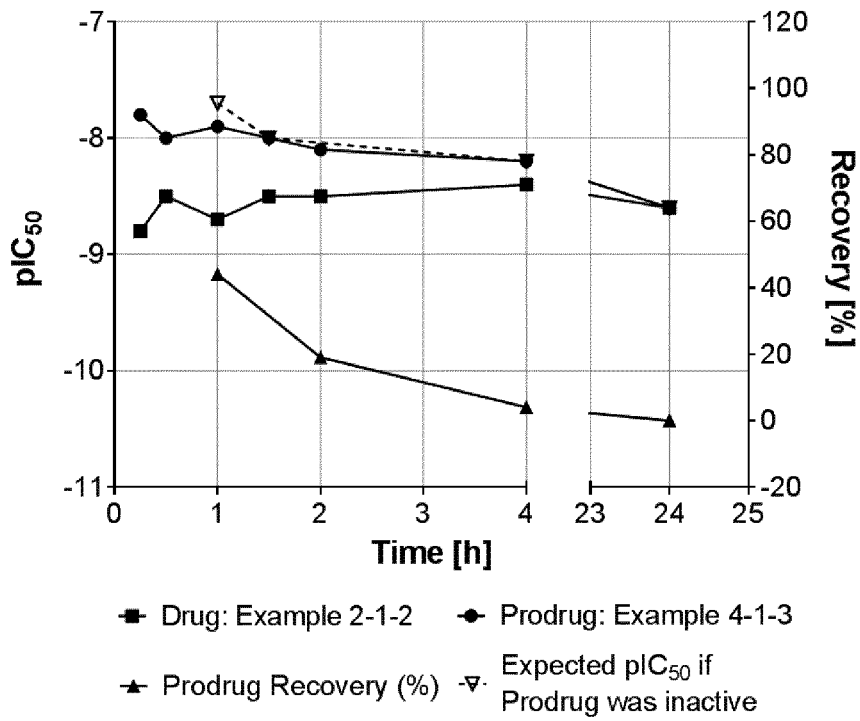
FIG. 1: binding affinities over time of example 2-1-2 and example 4-1-3 (prodrug), together with the prodrug stability and $pIC_{50}$ to be expected if only the drug present.

Constituents which are optionally substituted as stated herein, may be substituted, unless otherwise noted, one or more times, independently from one another at any possible position. When any variable occurs more than one time in any constituent, each definition is independent. For example, whenever $R^1$, $R^2$, $R^3$, $R^4$, $R^5$, $R^7$, $R^8$ V, W, Y and/or Z occur more than one time for any compound of formula (I) each definition of $R^1$, $R^2$, $R^3$, $R^4$, $R^5$, $R^7$, $R^8$, V, W, Y and Z is independent.

Should a constituent be composed of more than one part, e.g. $C_1$-$C_4$-alkoxy-$C_1$-$C_4$-alkyl-, the position of a possible substituent can be at any of these parts at any suitable position. A hyphen at the beginning or at the end of the constituent marks the point of attachment to the rest of the molecule. Should a ring be substituted the substituent could be at any suitable position of the ring, also on a ring nitrogen atom if suitable.

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

The terms as mentioned in the present text have preferably the following meanings:

The term "halogen atom", "halo-" or "Hal-" is to be understood as meaning a fluorine, chlorine, bromine or iodine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "$C_1$-$C_6$-haloalkyl" is to be understood as meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said $C_1$-$C_6$-haloalkyl group is, for example, —$CF_3$, —$CHF_2$, —$CH_2F$, —$CF_2CF_3$, —$CH_2CH_2F$, —$CH_2CHF_2$, —$CH_2CF_3$, —$CH_2CH_2CF_3$, or —$CH(CH_2F)_2$.

The term "$C_1$-$C_6$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof. Particularly preferred is "$C_1$-$C_4$-alkoxy" e.g. a methoxy, ethoxy, n-propoxy, iso-propoxy, n-butoxy, iso-butoxy, tert-butoxy or sec-butoxyor an isomer thereof. More preferred is "$C_1$-alkoxy", i.e. methoxy.

The term "$C_1$-$C_4$-haloalkoxy" is to be understood as meaning a linear or branched, saturated, monovalent $C_1$-$C_4$-alkoxy group, as defined supra, in which one or more of the hydrogen atoms is replaced, in identically or differently, by a halogen atom. Particularly, said halogen atom is F. Said $C_1$-$C_4$-haloalkoxy group is, for example, —$OCF_3$, —$OCHF_2$, —$OCH_2F$, —$OCF_2CF_3$, or —$OCH_2CF_3$.

The term "$C_1$-$C_6$-hydroxyalkyl" is to be understood as preferably meaning a linear or branched, saturated, monovalent hydrocarbon group in which the term "$C_1$-$C_6$-alkyl" is defined supra, and in which one or more hydrogen atoms is replaced by a hydroxy group, e.g. a hydroxymethyl, 1-hydroxyethyl, 2-hydroxyethyl, 1,2-dihydroxyethyl, 3-hydroxypropyl, 2-hydroxypropyl, 2,3-dihydroxypropyl, 1,3-dihydroxypropan-2-yl, 3-hydroxy-2-methyl-propyl, 2-hydroxy-2-methyl-propyl, 1-hydroxy-2-methyl propyl group. Preferred is "$C_1$-$C_3$-hydroxyalkyl", e.g. a hydroxymethyl, 1-hydroxyethyl, 2-hydroxyethyl, 1,2-dihydroxyethyl, 3-hydroxypropyl, 2-hydroxypropyl, 2,3-dihydroxypropyl, 1,3-dihydroxypropan-2-yl.

The term "$C_2$-$C_6$-hydroxyalkyl" is to be understood as meaning a linear or branched, saturated, monovalent hydrocarbon group having 2, 3, 4, 5, or 6 carbon atoms, in which one or more hydrogen atoms is replaced by a hydroxy group, e.g. a 2-hydroxyethyl, 3-hydroxypropyl, 2-hydroxypropyl, 2,3-dihydroxypropyl, 3-hydroxy-2-methyl-propyl, 2-hydroxy-2-methyl-propyl. Preferred is "$C_2$-$C_4$-hydroxyalkyl", more preferred is "$C_2$-hydroxyalkyl", i.e. a 2-hydroxyethyl group.

The term "$C_3$-$C_6$-cycloalkyl" is to be understood as meaning a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl ring.

The term "$C_3$-$C_6$-cycloalkyloxy" is to be understood as meaning a saturated, monovalent, monocyclic hydrocarbon group of formula —O-cycloalkyl, in which the term "cycloalkyl" is defined supra, e.g. a. a cyclopropyloxy, cyclobutyloxy, cyclopentyloxy or cyclohexyloxy group.

The term "$C_1$-$C_6$", as used throughout this text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy", is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

The term "$C_2$-$C_6$", as used throughout this text, e.g. in the context of the definition of "$C_2$-$C_6$-hydroxyalkyl", is to be understood as meaning a hydroxyalkyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_2$-$C_5$, $C_3$-$C_4$, particularly $C_2$-$C_3$, $C_2$-$C_4$, $C_2$-$C_5$, $C_2$-$C_6$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any 5 sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The term "V, W, Y and Z independently of each other represent CH or $CR^2$, wherein one of V, W, Y and Z represents $CR^2$", is to be understood as meaning that at least one of V, W, Y and Z represents $CR^2$, and the remaining, independently from each other, represent CH or $CR^2$, as it is known to a skilled person. For example, according to certain embodiments of the invention, V, W, Y and Z independently of each other represent CH or $CR^2$, wherein one of V, W, Y and Z represents $CR^2$ and the remaining represent CH; according to other embodiments of the invention, V, W, Y and Z independently of each other represent CH or $CR^2$, wherein two of V, W, Y and Z, independently of each other, represent $CR^2$ and the remaining represent CH; still according to other embodiments of the invention, V, W, Y and Z independently of each other represent CH or $CR^2$, wherein three of V, W, Y and Z, independently of each other, represent $CR^2$ and the remaining represents CH, for example.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{35}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence is preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention optionally contain one or more asymmetric centre, depending upon the location and nature of the various substituents desired. Asymmetric carbon atoms is present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention optionally contain sulphur atoms which are asymmetric, such as an asymmetric sulfoxide, of structure:

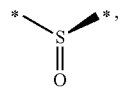

for example,
in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention may exist as tautomers.

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of formula (I) of the present invention with an anti-cancer agent as defined below is an embodiment of the invention.

The term "(chemotherapeutic) anti-cancer agents", includes but is not limited to 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

It has now been found, and this constitutes the basis of the present invention, that said compounds of the present invention have surprising and advantageous properties.

In particular, said compounds of the present invention have surprisingly been found to effectively inhibit Bub1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The intermediates used for the synthesis of the compounds of claims 1 to 8 as described below, as well as their use for the synthesis of the compounds of claims 1 to 8, are one further aspect of the present invention. Preferred intermediates are the Intermediate Examples as disclosed below.

General Procedures

The compounds according to the invention can be prepared according to the following schemes 1 through 13.

The schemes and procedures described below illustrate synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^3$, $R^5$, $R^7$, V, W, Y or Z can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

One route for the preparation of compounds of general formula (Ia) is described in Scheme 1.

Scheme 1

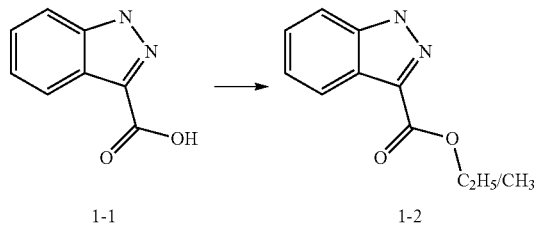
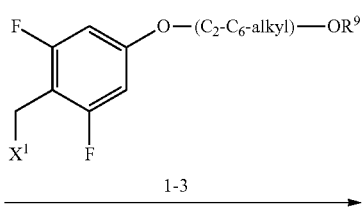

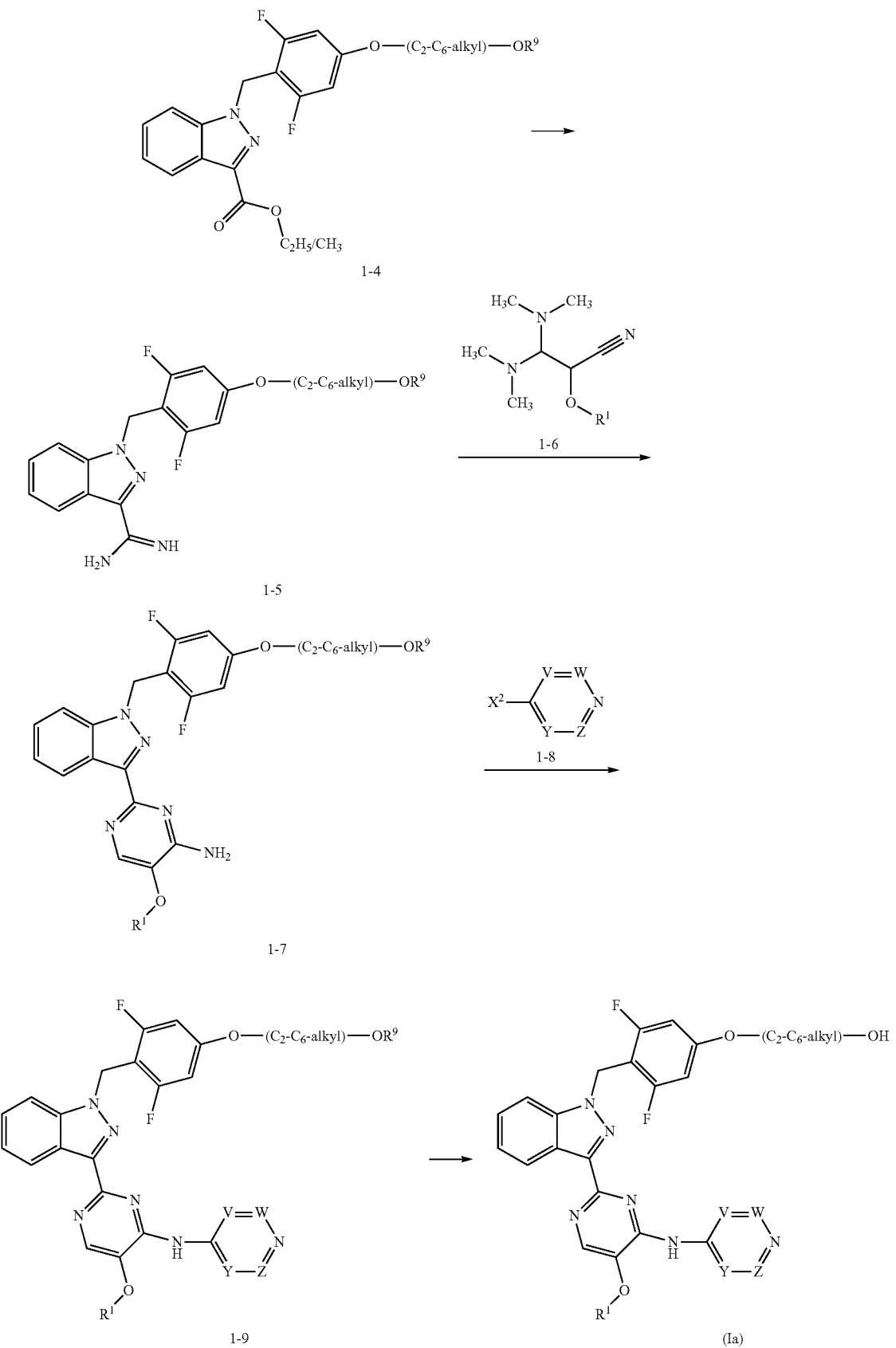

Scheme 1: Route for the preparation of compounds of general formula (Ia), wherein $R^1$, V, W, Y and Z have the meaning as given for general formula (I), supra, $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl, $X^1$ represents F, Cl, Br, I or a sulfonate, e.g. trifluormethylsulfonate or p-toluolsulfonate. $X^2$ represents F, Cl, Br, I, boronic acid or a boronic acid ester, such as for example 4,4,5,5-tetramethyl-2-phenyl-1,3,2-dioxaborolane (boronic acid pinacole ester).

In addition, interconversion of any of the substituents $R^1$, V, W, Y or Z can be achieved before and/or after the exemplified transformations. These modifications can be such as the introduction of protecting groups, cleavage of protecting groups, reduction or oxidation of functional groups, halogenation, metallation, substitution or other reactions 5 known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Compounds of general formulae (1-6) and (1-8) are either commercially available or can be prepared according to procedures available from the public domain, as understandable to the person skilled in the art. Specific examples are described in the subsequent paragraphs.

A suitably substituted 1H-indazole-3-carboxylic acid of the general formula (1-1) can be reacted with methanol or ethanol in the presence of catalytic amounts of a Broensted acid, such as, for example, hydrochloric acid or sulphuric acid, at temperatures ranging from 0°C. to boiling point of the respective alcohol, preferably the reaction is carried out at 85° C., to furnish alkyl 1H-indazole-3-carboxylat e intermediates of general formula (1-2).

Alkyl 1H-indazole-3-carboxylate Intermediates of the general formula (1-2) can be converted to intermediates of general formula (1-4) by reaction with a suitable alkylating agent, such as, for example a substituted benzyl halide (1-3), in the presence of a suitable base, such as, for example sodium hydride, in a suitable solvent system, such as, for example, DMF, at a temperature between −20° C. and boiling point of the respective solvent, preferably the reaction is carried out at 0° C.

Intermediates of general formula (1-4) are treated with the reagent methylchloroaluminiumamide prepared in situ by addition of ammonium chloride to commercially available trimethylaluminium, in a suitable solvent system, such as, for example, toluene, at a temperature between 0° C. and the boiling point of the respective solvent, preferably the reaction is carried out at 80° C. and are quenched with a suitable solvent system, such as, for example, methanol, to form the desired intermediate of general formula (1-5).

Intermediates of general formula (1-5) can be converted to intermediates of general formula (1-7) by reaction with a suitably substituted 3,3-bis-(dimethylamino)propanenitrile of the general formula (1-6), such as, for example 3,3-bis(dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-7) can be reacted with a suitable six membered heterocycle of the general formula (1-8), such as, for example 4-bromo-2-methyl-pyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, such as, for example, DMF, in a temperature range from room temperature to the boiling point of the respective solvent, preferably the reaction is carried out at at 100° C. to furnish compounds of general formula (1-9). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0), chloro(2'-amino-1,1'-biphenyl-2-yl)palladium(II) dimer, (2'-amino-1,1'-biphenyl-2-yl)methanesulfonatopalladium(II) dimer, trans-di(p-acetato)bis[o-(di-o-tolylphosphino)benzyl]dipalladium(II) [cataCXium® C], allylchloro[1,3-bis(2,4,6-trimethylphenyl)imidazol-2-ylidene]palladium(II), allylchloro[1,3-bis(2,6-diisopropylphenyl)imidazol-2-ylidene]palladium(II), chloro[(1,3-dimesitylimidazol-[1,3-bis(2,4,6-trimethylphenyl)-1,3-dihydro-2H-imidazol-2-ylidene](chloro){2-[(dimethylamino)methyl] phenyl}palladium, chloro[(1,2,3-N)-3-phenyl-2-propenyl][1,3-bis(2,6-di-iso-propylphenyl)imidazol-2-ylidene]palladium(II), [2-(acetylamino)phenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]phenyl}palladium, {1,3-bis[2,6-di(propan-2-yl)phenyl]-2,3-dihydro-1H-imidazol-2-yl}(dichloro)(3-chloropyridine-kappaN)palladium, [1,3-bis(2,6-diisopropylphenyl) imidazol-2-ylidene](3-chloropyridyl)palladium(II) dichloride, [2-(acetylamino)-4-methoxyphenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]-3,5-dimethoxyphenyl}palladium, dichloro[1,3-bis(2,6-di-3-pentylphenyl)imidazol-2-ylidene](3-chloropyridyl) palladium(II), dichloro(di-p-chloro)bis[1,3-bis(2,6-di-iso-propylphenyl) imidazol-2-ylidene] dipalladium(II), 2-(2'-di-tert-butylphosphine)biphenylpalladium(II) acetate, chloro[dicyclohexyl(2',6'-dimethoxybiphenyl-2-yl)-lambda5-phosphanyl][2-(phenyl-kappaC2)ethanaminato-kappaN]palladium, [2-(2-aminoethyl)phenyl](chloro)palladium-di-tert-butyl[2',4',6'-tri(propan-2-yl)biphenyl-2-yl]phosphane, {dicyclohexyl[2',4',6'-tri(propan-2-yl)biphenyl-2-yl] phosphane}{2-[2-(methylazanidyl-kappaN)ethyl]phenyl-kappaC1}palladium, chloro(2-dicyclohexylphosphino-2',6'-dimethoxy-1,1'-biphenyl)(2'-amino-1,1'-biphenyl-2-yl) palladium(II), [2',6'-bis(propan-2-yloxy)biphenyl-2-yl](dicyclohexyl)phosphane-[2-(2-aminoethyl)phenyl](chloro)palladium, [2-(2-aminoethyl)phenyl](chloro){dicyclohexyl[2',4',6'-tri(propan-2-yl)biphenyl-2-yl]-lambda5-phosphanylidene}palladium, 2'-(dicyclohexylphosphanyl)-N,N,N',N'-tetramethylbiphenyl-2,6-diamine-(2'-aminobiphenyl-2-yl)(chloro)palladium, chloro(2-dicyclohexylphosphino-2',6'-di-iso-propoxy-1,1'-biphenyl)(2-amino-1,1'-biphenyl-2-yl)palladium(II), [2'-(azanidyl-kappaN) biphenyl-2-yl-kappaC2](chloro){dicyclohexyl[2',4',6'-tri (propan-2-yl)biphenyl-2-yl]-lambda5-phosphanyl}palladium, (2'-aminobi-phenyl-2-yl)(methanesulfonato-kappaO)palladium-di-tert-butyl[2',4',6'-tri(propan-2-yl)biphenyl-2-yl]phosphane, (2'-aminobiphenyl-2-yl)palladium(1+) methanesulfonate-di-tert-butyl[2',4',6'-tri(propan-2-yl)biphenyl-2-yl]phosphane, dicyclohexyl[3,6-dimethoxy-2',4',6'-tri(propan-2-yl)biphenyl-2-yl]phosphane-[2-(2-aminoethyl)phenyl](chloro)palladium, (2'-aminobiphenyl-2-yl)palladium(1+) methanesulfonate-2'-(dicyclohexylphosphanyl)-N,N,N',N'-tetramethylbiphenyl-2,6-diamine, sodium 2'-(dicyclohexylphosphanyl)-2,6-dim ethoxybiphenyl-3-sulfonate-(2'-aminobiphenyl-2-yl)(chloro)palladium, chloro(2-dicyclohexylphosphino-2',4',6'-tri-iso-propyl-1,1'-biphenyl)[2-(2-aminoethyl)phenyl]palladium(II), (2'-aminobiphenyl-2-yl)(methane-sulfonato-kappaO)palladium-[2',6'-bis(propan-2-yloxy)biphenyl-2-yl](dicyclohexyl) phosphane, (2'-aminobiphenyl-2-yl)(methanesulfonato-kappaO)palladium-dicyclohexyl[2',4',6'-tri(propan-2-yl)biphenyl-2-yl]phosphane, (2'-aminobiphenyl-2-yl)palladium(1+) methanesulfonate-dicyclohexyl[2',4',6'-tri(propan-2-yl)biphenyl-2-yl]phosphane, dicyclohexyl[3,6-dimethoxy-2',4',6'-tri(propan-2-yl)biphenyl-2-yl]phosphane-(2'-aminobiphenyl-2-yl)(chloro)palladium, (2'-aminobiphenyl-2-yl)(methanesulfonato-kappaO)palladium-di-tert-butyl[3,6-dimethoxy-2',4',6'-tri(propan-2-yl)biphenyl-2-yl]phosphane, (2'-aminobiphenyl-2-yl)(methanesulfonato-kappaO)palladium-dicyclohexyl[3,6-dimethoxy-2',4',6'-tri(propan-2-yl)biphenyl-2-yl]phosphane or the following ligands:
racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine), dicyclohexyl(2',4',6'-triisopropyl-3,6-dimethoxybiphenyl-2-yl)phosphine, di-tert-butyl (2',4',6'-triisopropyl-3,6-dimethoxybiphenyl-2-yl)phosphine, di-tert-butyl(2',4',6'-triisopropylbiphenyl-2-yl)phosphine, dicyclohexyl(2',4',6'-triisopropylbiphenyl-2-yl) phosphine, di-tert-butyl(2',4',6'-triisopropyl-3-methoxy-6-methylbiphenyl-2-yl)phos-phine, di-tert-butyl (2',4',6'-triisopropyl-3,4,5,6-tetramethylbiphenyl-2-yl)phosphine, adamantan-1-yl(adamantan-2-yl)(2',4',6'-triisopropyl-3,6-dimethoxybiphenyl-2-yl) phosphine, dicyclohexyl(2',6'-dimethoxybiphenyl-2-yl)phosphine, dicyclohexyl(2',6'-diisopropoxybiphenyl-2-yl)phosphine, 2'-(dicyclohexylphosphino)-N,N-dimethylbiphenyl-2-amine, 2'-(di-tert-butylphosphino)-N,N-dimethylbiphenyl-2-amine, 2'-(di-phenylphosphino)-N,N,N',N'-tetramethylbiphenyl-2,6-diamine, di-tert-butyl (2',4',6'-tricyclohexyl-3,6-dimethoxybiphenyl-2-yl)phosphine, bis[3,5-bis(trifluoromethyl)phe-nyl](2',4',6'-triisopropyl-3,6-dimethoxybiphenyl-2-yl)phosphine, biphenyl-2-yl(di-tert-butyl)phosphine, dicyclohexyl(2'-methylbiphenyl-2-yl)phosphine, biphenyl-2-yl (dicyclohexyl)phosphine, 2'-(dicyclohexylphosphino)-N,N-dimethylbiphenyl-2-amine, 2'-(dicyclohexylphosphino)-N,N,N',N'-tetramethylbiphenyl-2,6-diamine, sodium 2'-(dicyclohexylphosphino)-2,6-diisopropylbiphenyl-4-sulfonate, sodium 2'-(dicyclohexylphosphino)-2,6-dimethoxybiphenyl-3-sulfonate, 1,1'-binaphthalen-2-yl(di-tert-butyl)phosphine, 1,3-bis(2,4,6-trimethylphenyl)-1,3-dihydro-2H-imidazol-2-ylidene, 1,3-bis[2,6-di(propan-2-yl)phenyl]-1,3-dihydro-2H-imidazol-2-ylidene.

Alternatively intermediates of general formula (1-7) can be reacted with a suitable boronic acid or boronic acid pinacole ester of general formula (1-8), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (1-9).

Alternatively intermediates of general formula (1-7) can be reacted with a suitable six membered heterocycle of the general formula (1-8), such as for example 4-fluoro-2-methyl-pyridine, in the presence of a suitable base, such as, for example sodium hydride, in a suitable solvent system, such as, for example DMF, in a temperature range from room temperature to the boiling point of the respective solvent, preferably the reaction is carried out at 90° C. to furnish compounds of general formula (1-9).

Compounds of general formula (1-9) are converted to compounds of general formula (Ia) by treatment with a suitable deprotection agent, such as a dealkylating agent, such as for example boron trichloride, in a suitable solvent, such as, for example, dichloromethane, in a temperature range from room temperature to the boiling point of the respective solvent, preferably the reaction is carried out at room temperature.

One route for the preparation of compounds of general formula (1b) is described in Scheme 2.

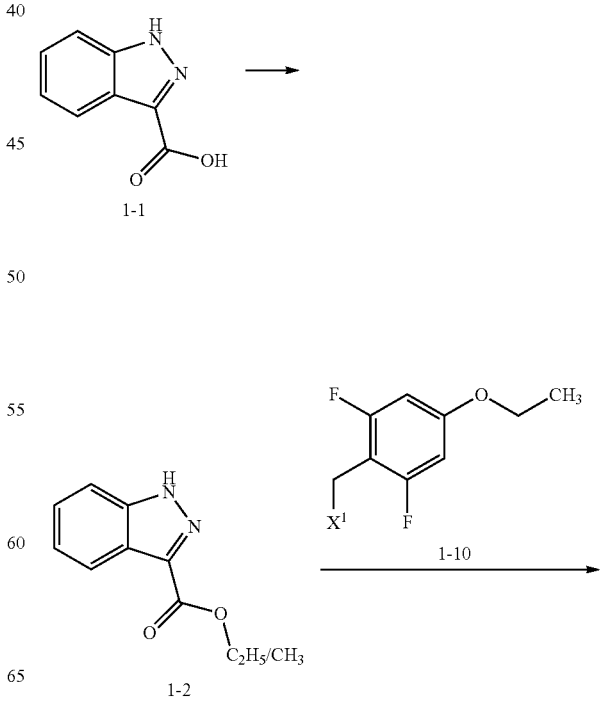

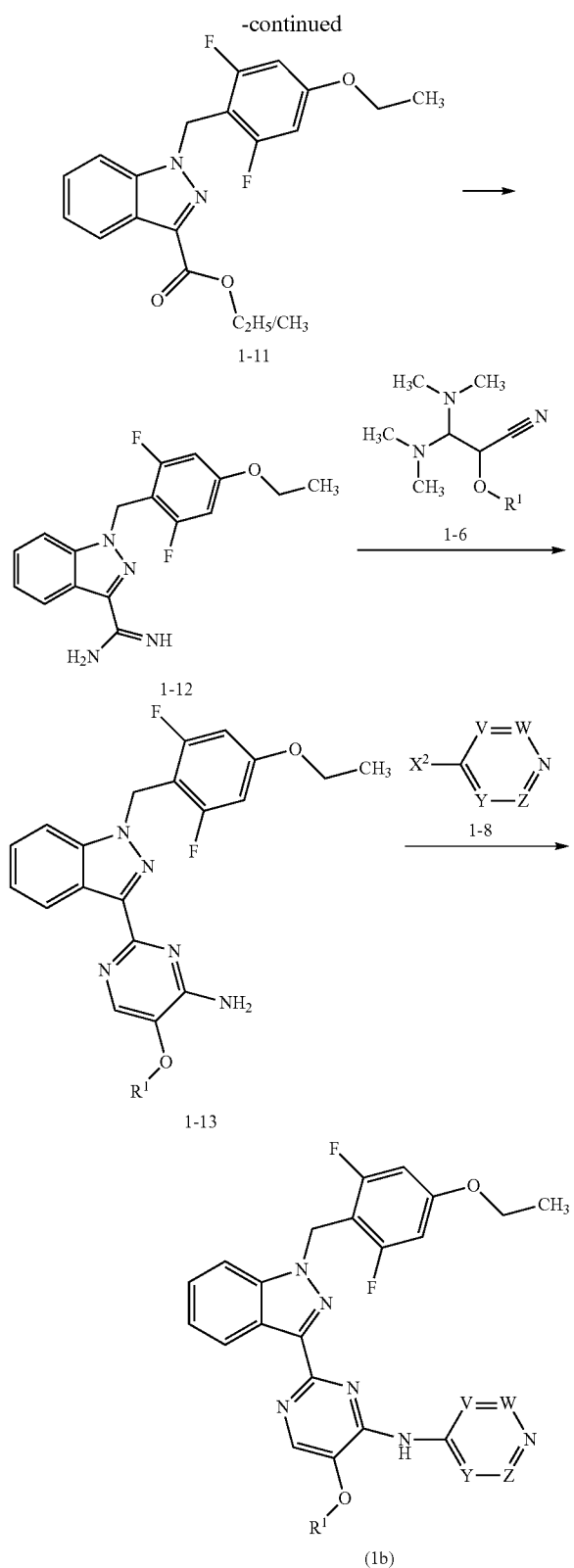

acid or a boronic acid ester, such as for example 4,4,5,5-tetramethyl-2-phenyl-1,3,2-dioxaborolane (boronic acid pinacole ester).

In addition, interconversion of any of the substituents $R^1$, V, W, Y or Z can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

Compounds of general formulae (1-6), (1-8) and (1-10) are either commercially available or can be prepared according to procedures available from the public domain, as understandable to the person skilled in the art. Specific examples are described in the subsequent paragraphs.

A suitably substituted 1H-indazole-3-carboxylic acid of the general formula (1-1) can be reacted with methanol or ethanol in the presence of catalytic amounts of a Broensted acid, such as, for example, hydrochloric acid or sulphuric acid, at temperatures ranging from 0 to boiling point of the respective alcohol, preferably the reaction is carried out at 85° C., to furnish alkyl 1H-indazole-3-carboxylate intermediates of general formula (1-2).

Alkyl 1H-indazole-3-carboxylate Intermediates of the general formula (1-2) can be converted to intermediates of general formula (1-11) by reaction with a suitable alkylating agent, such as, for example a substituted benzyl halide (1-10), in the presence of a suitable base, such as, for example sodium hydride, in a suitable solvent system, such as, for example, DMF, at a temperature between −20° C. and boiling point of the respective solvent, preferably the reaction is carried out at 0° C.

Intermediates of general formula (1-11) are treated with the reagent methylchloroaluminiumamide prepared in situ by addition of ammonium chloride to commercially available trimethylaluminium, in a suitable solvent system, such as, for example, toluene, at a temperature between 0° C. and the boiling point of the respective solvent, preferably the reaction is carried out at 80° C. and are quenched with a suitable solvent system, such as, for example, methanol, to form the desired intermediate of general formula (1-12).

Intermediates of general formula (1-12) can be converted to intermediates of general formula (1-13) by reaction with a suitably substituted 3,3-bis-(dimethylamino)propanenitrile of the general formula (1-6), such as, for example 3,3-bis(dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-13) can be reacted with a suitable six membered heterocycle of the general formula (1-8), such as, for example 4-bromo-2-methylpyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, Scheme 2: Route for the preparation of compounds of general formula (1b), wherein $R^1$, V, W, Y and Z have the meaning as given for general formula (I), supra, $X^1$ represents F, Cl, Br, I or a sulfonate, e.g. trifluormethylsulfonate or p-toluolsulfonate, and $X^2$ represents F, Cl, Br, I, boronic such as, for example, DMF, in a temperature range from room temperature to the boiling point of the respective solvent, preferably the reaction is carried out at at 100° C. to furnish compounds of general formula (1b). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris (dibenzylideneacetone)dipalladium (0), chloro(2'-amino-1,1'-biphenyl-2-yl)palladium(II) dimer, (2'-amino-1,1'-biphenyl-2-yl)methanesulfonatopalladium(II) dimer, trans-di(p-acetato)bis[o-(di-o-tolylphosphino)benzyl]dipalladium(II) [cataCXium® C], allylchloro[1,3-bis(2,4,6-trimethylphenyl)imidazol-2-ylidene]palladium(II), allylchloro[1,3-bis(2,6-diisopropylphenyl)imidazol-2-ylidene]palladium(II), chloro[(1,3-dimesitylimidazol-[1,3-bis(2,4,6-trimethylphenyl)-1,3-dihydro-2H-imidazol-2-ylidene](chloro){2[(dimethylamino)methyl] phenyl}palladium, chloro[(1,2,3-N)-3-phenyl-2-propenyl][1,3-bis(2,6-di-iso-propylphenyl)imidazol-2-ylidene]palladium(II), [2-(acetylamino)phenyl]{1,3-bis[2,6-di(propan-2-yl)phenyl]-1,3-dihydro-2H-imidazol-2-ylidene}chloropalladium, {1,3-bis[2,6-di(propan-2-yl) phenyl]-1,3-dihydro-2H-imidazol-2-ylidene}(chloro){2-[(dimethylamino)methyl]phenyl}palladium, {1,3-bis[2,6-di(propan-2-yl)phenyl]-2,3-dihydro-1H-imidazol-2-yl} (dichloro)(3-chloropyridine-kappaN)palladium, [1,3-bis (2,6-diisopropylphenyl) imidazol-2-ylidene](3-chloropyridyl)palladium(II) dichloride, [2-(acetylamino)-4-methoxyphenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino) methyl]-3,5-dimethoxyphenyl}palladium, dichloro[1,3-bis(2,6-di-3-pentylphenyl)imidazol-2-ylidene](3-chloropyridyl) palladium(II), dichloro(di-p-chloro)bis[1,3-bis(2,6-di-iso-propylphenyl) imidazol-2-ylidene] dipalladium(II), 2-(2'-di-tert-butylphosphine) biphenylpalladium(II) acetate, chloro[dicyclohexyl(2',6'-dimethoxybiphenyl-2-yl)-lambda5-phosphanyl][2-(phenyl-kappaC2)ethanaminato-kappaN]palladium, [2-(2-aminoethyl)phenyl](chloro)palladium-di-tert-butyl[2',4',6'-tri(propan-2-yl)biphenyl-2-yl]phosphane, {dicyclohexyl[2',4',6'-tri(propan-2-yl)biphenyl-2-yl] phosphane}{2-[2-(methylazanidyl-kappaN)ethyl]phenyl-kappaC1}palladium, chloro(2-dicyclohexylphosphino-2',6'-dimethoxy-1,1'-biphenyl)(2'-amino-1,1'-biphenyl-2-yl) palladium(II), [2',6'-bis(propan-2-yloxy)biphenyl-2-yl] (dicyclohexyl)phosphane-[2-(2-aminoethyl)phenyl] (chloro)palladium, [2-(2-aminoethyl)phenyl](chloro){dicyclohexyl[2',4',6'-tri(propan-2-yl)biphenyl-2-yl]-lambda5-phosphanylidene}palladium, 2'-(dicyclohexylphosphanyl)-N,N,N',N'-tetramethylbiphenyl-2,6-diamine-(2'-aminobiphenyl-2-yl)(chloro)palladium, chloro(2-dicyclohexylphosphino-2',6'-di-iso-propoxy-1,1'-biphenyl)(2-amino-1,1'-biphenyl-2-yl)palladium(II), [2'-(azanidyl-kappaN) biphenyl-2-yl-kappaC2](chloro){dicyclohexyl[2',4',6'-tri (propan-2-yl)biphenyl-2-yl]-lambda5-phosphanyl}palladium, (2'-aminobi-phenyl-2-yl) (methanesulfonato-kappaO)palladium-di-tert-butyl[2',4',6'-tri(propan-2-yl)biphenyl-2-yl]phosphane, (2'-aminobiphenyl-2-yl)palladium(1+) methanesulfonate-di-tert-butyl[2',4',6'-tri(propan-2-yl)biphenyl-2-yl] phosphane, dicyclohexyl[3,6-dimethoxy-2',4',6'-tri (propan-2-yl)biphenyl-2-yl]phosphane-[2-(2-aminoethyl) phenyl](chloro)palladium, (2'-aminobiphenyl-2-yl)palladium(1+) methanesulfonate-2'-(dicyclohexylphosphanyl)-N,N,N',N'-tetramethylbiphenyl-2,6-diamine, sodium 2'-(dicyclohexylphosphanyl)-2,6-dim ethoxybiphenyl-3-sulfonate-(2'-aminobiphenyl-2-yl)(chloro)palladium, chloro(2-dicyclohexylphosphino-2',4',6'-tri-iso-propyl-1,1'-biphenyl)[2-(2-aminoethyl)phenyl]palladium(II), (2'-aminobiphenyl-2-yl)(methane-sulfonato-kappaO)palladium-[2',6'-bis(propan-2-yloxy)biphenyl-2-yl] (dicyclohexyl) phosphane, (2'-aminobiphenyl-2-yl) (methanesulfonato-kappaO)palladium-dicyclohexyl[2',4',6'-tri(propan-2-yl)biphenyl-2-yl]phosphane, (2'-aminobiphenyl-2-yl)palladium(1+) methanesulfonate-dicyclohexyl[2',4',6'-tri(propan-2-yl)biphenyl-2-yl] phosphane, dicyclohexyl[3,6-dimethoxy-2',4',6'-tri (propan-2-yl)biphenyl-2-yl]phosphane-(2'-aminobiphenyl-2-yl)(chloro)palladium, (2'-aminobiphenyl-2-yl)(methanesulfonato-kappaO) palladium-di-tert-butyl[3,6-dimethoxy-2',4',6'-tri(propan-2-yl)biphenyl-2-yl]phosphane, (2'-aminobiphenyl-2-yl) (methanesulfonato-kappaO)palladium-dicyclohexyl[3,6-dimethoxy-2',4',6'-tri(propan-2-yl)biphenyl-2-yl] phosphane or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethylphosphonium tetrafluoroborate, 2-(di-tert-butylphosphino) biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine), dicyclohexyl(2',4',6'-triisopropyl-3,6-dimethoxybiphenyl-2-yl)phosphine, di-tert-butyl (2',4',6'-triisopropyl-3,6-dimethoxybiphenyl-2-yl) phosphine, di-tert-butyl(2',4',6'-triiso propylbiphenyl-2-yl)phosphine, dicyclohexyl(2',4',6'-triisopropylbiphenyl-2-yl) phosphine, di-tert-butyl(2',4',6'-triisopropyl-3-methoxy-6-methylbiphenyl-2-yl)phos-phine, di-tert-butyl (2',4',6'-triisopropyl-3,4,5,6-tetramethylbiphenyl-2-yl) phosphine, adamantan-1-yl(adamantan-2-yl)(2',4',6'-triisopropyl-3,6-dimethoxybiphenyl-2-yl) phosphine, dicyclohexyl(2',6'-dimethoxybiphenyl-2-yl)phosphine, dicyclohexyl(2',6'-diisopropoxybiphenyl-2-yl)phosphine, 2'-(dicyclohexylphosphino)-N,N-dimethyl-biphenyl-2-amine, 2'-(di-tert-butylphosphino)-N,N-dimethylbiphenyl-2-amine, 2'-(di-phenylphosphino)-N,N,N',N'-tetramethylbiphenyl-2,6-diamine, di-tert-butyl (2',4',6'-tricyclohexyl-3,6-dimethoxybiphenyl-2-yl) phosphine, bis[3,5-bis(trifluoromethyl)phe-nyl](2',4',6'-triisopropyl-3,6-dimethoxybiphenyl-2-yl)phosphine, biphenyl-2-yl(di-tert-butyl)phosphine, dicyclohexyl(2'-methylbiphenyl-2-yl)phosphine, biphenyl-2-yl (dicyclohexyl)phosphine, 2'-(dicyclohexylphosphino)-N,N-dimethylbiphenyl-2-amine, 2'-(dicyclohexylphosphino)-N,N,N',N'-tetramethylbiphenyl-2,6-diamine, sodium 2'-(dicyclohexylphosphino)-2,6-diisopropylbiphenyl-4-sulfonate, sodium 2'-(dicyclohexylphosphino)-2,6-dimethoxybiphenyl-3-sulfonate, 1,1'-binaphthalen-2-yl (di-tert-butyl)phosphine, 1,3-bis(2,4,6-trimethylphenyl)-1,3-dihydro-2H-imidazol-2-ylidene, 1,3-bis[2,6-di (propan-2-yl)phenyl]-1,3-dihydro-2H-imidazol-2-ylidene.

Alternatively intermediates of general formula (1-13) can be reacted with a suitable boronic acid or boronic acid pinacole ester of general formula (1-8), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (1b).

Alternatively intermediates of general formula (1-13) can be reacted with a suitable six membered heterocycle of the general formula (1-8), such as for example 4-fluoro-2-methyl-pyridine, in the presence of a suitable base, such as, for example sodium hydride, in a suitable solvent system, such as, for example DMF, in a temperature range from room temperature to the boiling point of the respective solvent, preferably the reaction is carried out at 90° C. to furnish compounds of general formula (1b).

Scheme 3

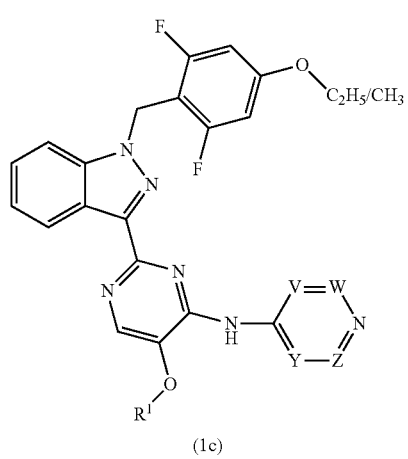

(1c)

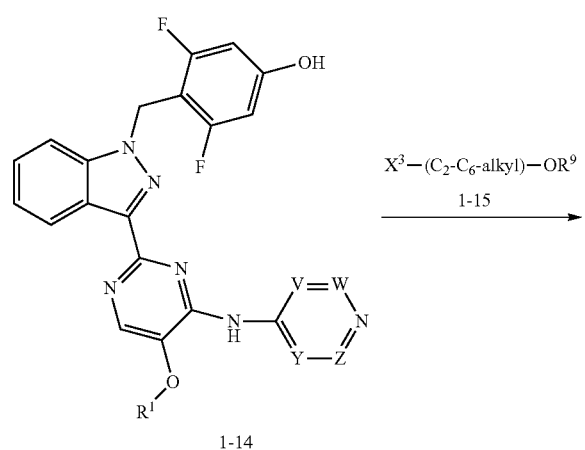

1-14

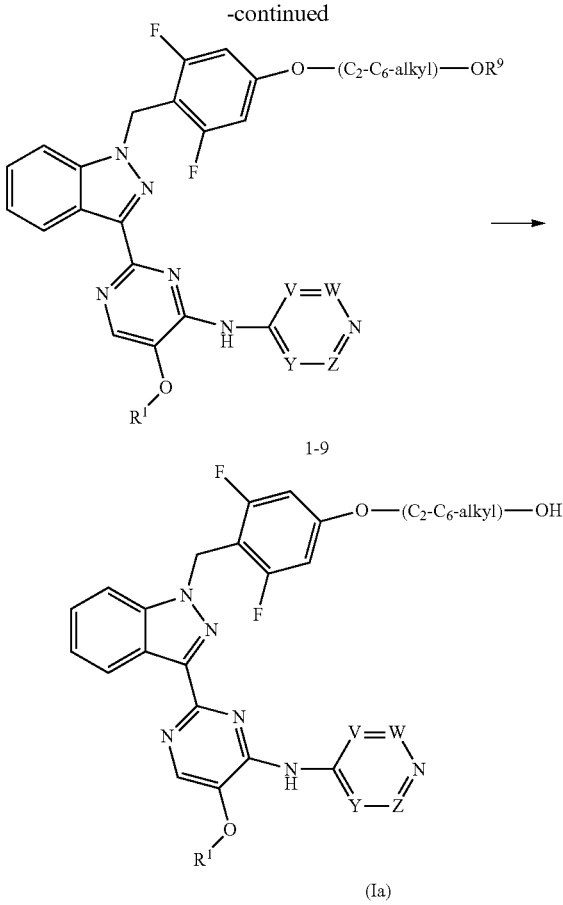

Scheme 3: Process for the preparation of compounds of general formula (Ia) via de-alkylation of compounds of general formula (1c), wherein $R^1$, V, W, Y and Z have the meaning as given for general formula (I), supra, $X^3$ represents F, Cl, Br, I or a sulfonate, e.g. trifluormethylsulfonate or p-toluolsulfonate, and $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl. In addition, interconversion of any of the substituents $R^1$, V, W, Y or Z can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs. Compounds of general formula (1-15) are either commercially available or can be prepared according to procedures available from the public domain, 5 as understandable to the person skilled in the art. Specific examples are described in the subsequent paragraphs.

Compounds of general formula (Ic) are converted to compounds of general formula (1-14) by treatment with a suitable dealkylating agent, such as a suitable demthylating agent, such as for example boron trichloride, in a suitable solvent, such as, for example, dichloromethane, in a temperature range from room temperature to the boiling point of the respective solvent, preferably the reaction is carried out at 40° C.

Compounds of general formula (1-14) are then reacted with a compound of general formula (1-15) as mentioned above, in a suitable solvent, such as, for example, DMF, in the presence of a suitable base, such as, for example, potassium carbonate in a temperature range from room temperature to the boiling point of the respective solvent, preferably the reaction is carried out at room temperature, to furnish compounds of general formula (1-9).

Compounds of general formula (1-9) are converted to compounds of general formula (Ia) by treatment with a suitable deprotection agent, such as a dealkylating agent, such as for example boron trichloride, in a suitable solvent, such as, for example, dichloromethane, in a temperature range from room temperature to the boiling point of the respective solvent, preferably the reaction is carried out at room temperature.

Compounds of general formula (Ia) can be converted into compounds of general formula (Ib) according to the procedure depicted in Scheme 4.

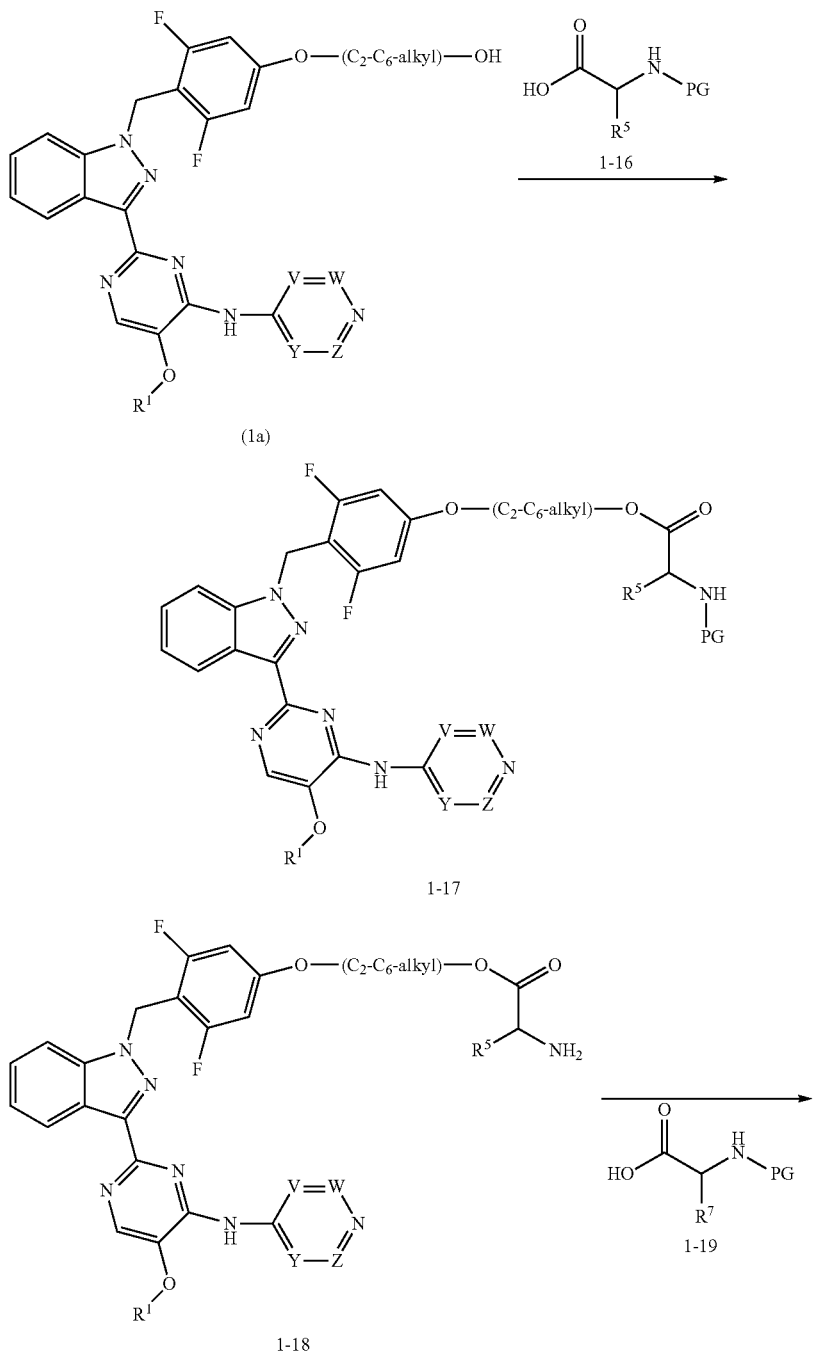

-continued

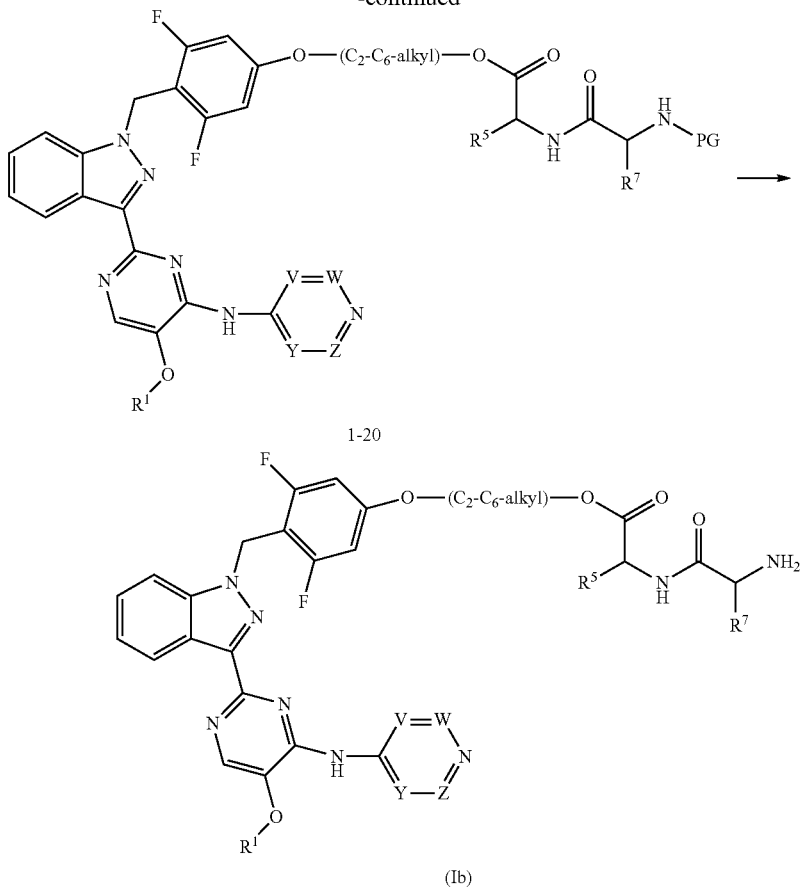

Scheme 4: Route for the preparation of compounds of general formula (Ib), via compounds of general formula (1-18) wherein $R^1$, $R^5$, $R^7$, V, W, Y and Z have the meaning as given for general formula (I), and PG represents an amino protecting group, such as for example fluorenylmethyloxycarbonyl, benzyloxycarbonyl, allyloxycarbonyl or tert-butyloxycarbonyl. In addition, interconversion of any of the substituents $R^1$, $R^5$, $R^7$, V, W, Y op Z can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These 5 transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Compounds of general formula (Ia) are reacted with a compound of general formula (1-16) as mentioned above with a peptide coupling agent, for example N-[(dimethylamino)(3H-[1,2,3]triazolo[4,5-b]pyridin-3-yloxy)methylidene]-N-methylmethanaminium hexafluorophosphate, in a suitable solvent, such as, for example, dichloromethane, in the presence of a suitable base, such as, for example, diisopropylethylamine in a temperature range from −10° C. to the boiling point of the respective solvent, preferably the reaction is carried out at room temperature, to furnish compounds of general formula (1-17).

Appropriate peptide synthesis methods and their applications are well-known to the person skilled in the art (see for example N. Leo Benoitin in *Chemistry of Peptide Synthesis*, CRC Press 2005; John Jones in *Amino Acids and Peptide Synthesis*, Oxford University Press, 2002 and Norbert Sewald and Hans-Dieter Jakubke in Peptides: *Chemistry and Biology*, Wiley-VCH, 2009).

Intermediates of general formula (1-17) can be converted to intermediates of general formula (1-18) by reaction with Broensted acid, such as, for example trifluoroacetic acid, in a suitable solvent system, such as, for example, dichloromethane, in a temperature range from room temperature to the boiling point of the respective solvent, preferably the reaction is carried out at room temperature.

Compounds of general formula (1-18) are then reacted with a compound of general formula (1-19) as mentioned above with a peptide coupling agent, for example N-[(dimethylamino)(3H-[1,2,3]triazolo[4,5-b]pyridin-3-yloxy)methylidene]-N-methylmethanaminium hexafluorophosphate, in a suitable solvent, such as, for example, dichloromethane, in the presence of a suitable base, such as, for example, diisopropylethylamine in a temperature range from −10° C. to the boiling point of the respective solvent, preferably the reaction is carried out at room temperature, to furnish compounds of general formula (1-20).

Intermediates of general formula (1-20) can be converted to compounds of general formula (Ib) by reaction with Broensted acid, such as, for example trifluoroacetic acid, in a suitable solvent system, such as, for example, dichloromethane, in a temperature range from room temperature to the boiling point of the respective solvent, preferably the reaction is carried out at room temperature.

Compound (1-22) can be converted into compounds of general formula (1-6) according to the procedure depicted in Scheme 5.

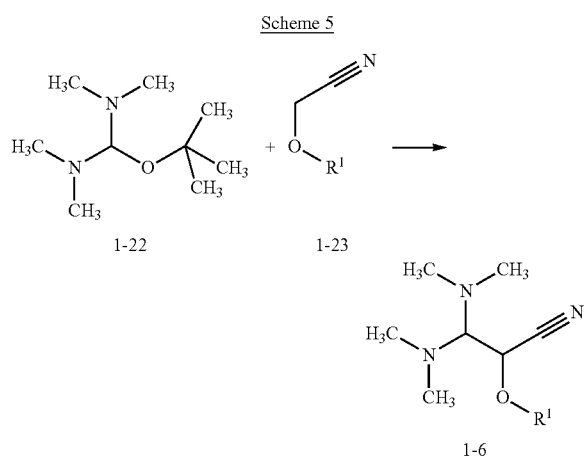

Scheme 5: Process for the transformation of compound (1-22) into compounds of general formula (1-6), wherein $R^1$ has the meaning as given for general formula (I), supra.

Compound (1-22) can be converted into compounds of general formula (1-6) by reaction with a suitable substituted acetonitlrile derivative of the general formula (1-23), such as, for example methoxyacetonitrile, in a temperature range from room temperature to the boiling point of the respective solvent, preferably the reaction is carried out at 80° C.

Compounds of general formula (1-24) can be converted into compounds of general formula (1-3) according to the procedure depicted in Scheme 6.

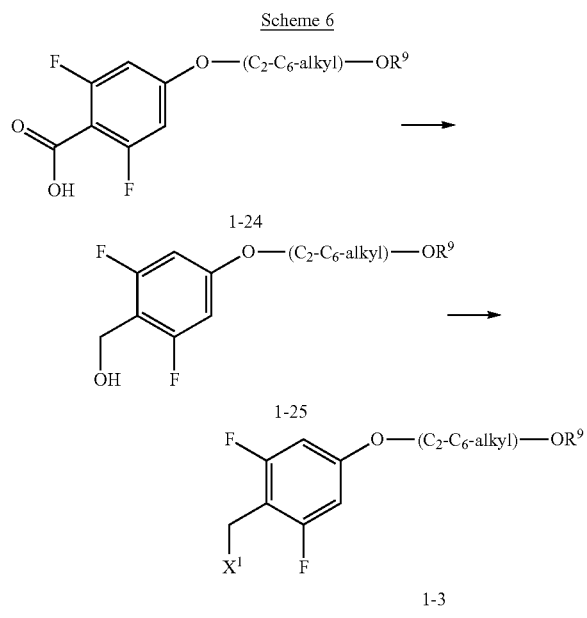

Scheme 6: Process for the transformation of compounds of general formula (1-24) into compounds of general formula (1-3), supra. $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl and $X^1$ represents F, Cl, Br, I or a sulfonate, e.g. trifluormethylsulfonate or p-toluolsulfonate.

Compounds of general formula (1-24) can be converted into compounds of general formula (1-25) by reaction with a suitable reducing agent, such as, for example borane, in a suitable solvent system, such as, for example, tetrahydrofuran, in a temperature range from −78° C. to boiling point of the respective solvent, preferably the reaction is carried out at room temperature.

Compounds of general formula (1-25) can be converted into compounds of general formula (1-3) by reaction with a suitable halogenation or sulfonylation agent, such as for example hydrogen bromide, in a suitable solvent, such as, for example, acetic acid, in a temperature range from 0° C. to the boiling point of the respective solvent, preferably the reaction is carried out at room temperature.

Compounds of general formula (1-26) can be converted into compounds of general formula (1-3) according to the procedure depicted in Scheme 7.

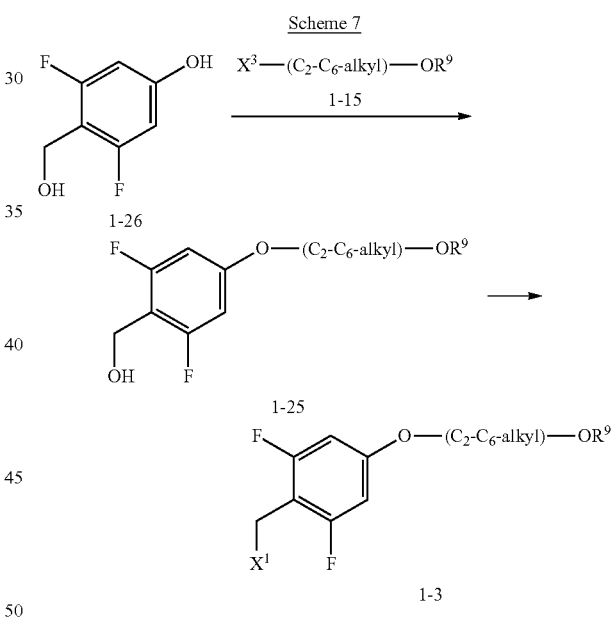

Scheme 7: Process for the transformation of compounds of general formula (1-26) into compounds of general formula (1-3), wherein $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl, $X^1$ and $X^3$ represent F, Cl, Br, I or a sulfonate, e.g. trifluormethylsulfonate or p-toluolsulfonate.

Compounds of general formula (1-26) are reacted with a compound of general formula (1-15) as mentioned above, in a suitable solvent, such as, for example, DMF, in the presence of a suitable base, such as, for example, sodium hydride in a temperature range from room temperature to the boiling point of the respective solvent, preferably the reaction is carried out at room temperature, to furnish compounds of general formula (1-25).

Compounds of general formula (1-25) can be converted into compounds of general formula (1-3) by reaction with a suitable halogenation or sulfonylation agent, such as for example hydrogen bromide, in a suitable solvent, such as, for example, acetic acid, in a temperature range from 0° C. to the boiling point of the respective solvent, preferably the reaction is carried out at room temperature.

Compounds of general formula (1-5) can be converted into compounds of general formula (Ia) according to the procedure depicted in Scheme 8.

rahydropyranyl and $X^2$ represents F, Cl, Br, I, boronic acid or a boronic acid ester, such as for example 4,4,5,5-tetramethyl-2-phenyl-1,3,2-dioxaborolane (boronic acid pinacole ester).

In addition, interconversion of any of the substituents $R^1$, V, W, Y op Z can be achieved before and/or after the exemplified transformations. These modifications can be such as the introduction of protecting groups, cleavage of protecting groups, reduction or oxidation of functional groups, halogenation, metallation, substitution or other reac-

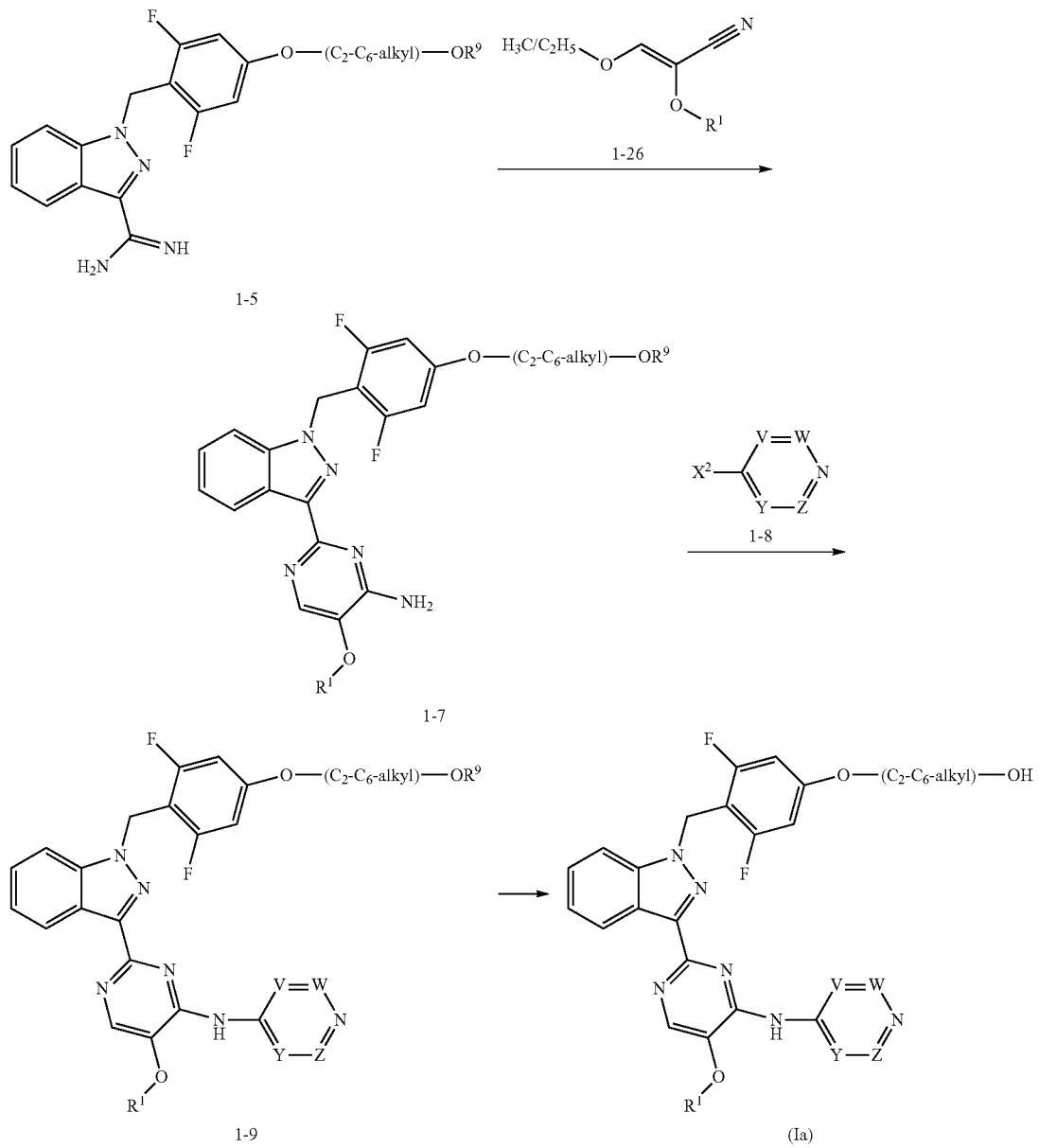

Scheme 8: Alternative route for the preparation of compounds of general formula (Ia), wherein $R^1$, V, W, Y and Z have the meaning as given for general formula (I), supra. $R^9$ represents a methyl- or an ethyl group or an alcohol protecting group, such as for example tert-butyldimethylsilyl, tert-butyldiphenylsilyl, triethylsilyl, triisopropylsilyl or tettions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in*

Organic Synthesis, 3rd edition, Wiley 1999). Specific examples are described in the subsequent para-graphs.

Compounds 1-26 is either commercially available or can be prepared according to procedures available from the public domain, as understandable to the person skilled in the art as referred to below.

Intermediates of general formula (1-5) can be converted to intermediates of general formula (1-7) by reaction with a suitably substituted 3-methoxyacrylonitrile of the general formula (1-26), such as, for example (ethoxymethylene) malononitrile, in the presence of a suitable base, such as, for example sodium methanolate, in a suitable solvent system, such as, for example, methanol, in a temperature range from room temperature to the boiling point of the respective solvent, preferably the reaction is carried out at 65° C.

Intermediates of general formula (1-7) can be reacted with a suitable six membered heterocycle of the general formula (1-8), such as, for example 4-bromo-2-methyl-pyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, such as, for example, DMF, in a temperature range from room temperature to the boiling point of the respective solvent, preferably the reaction is carried out at 100° C. to furnish compounds of general formula (1-9). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0), chloro(2'-amino-1,1'-biphenyl-2-yl)palladium(II) dimer, (2'-amino-1,1'-biphenyl-2-yl)methanesulfonatopalladium(II) dimer, trans-di(p-acetato)bis[o-(di-o-tolylphosphino)benzyl]dipalladium(II) [cataCXium® C], allylchloro[1,3-bis(2,4,6-trimethylphenyl)imidazol-2-ylidene]palladium(II), allylchloro[1,3-bis(2,6-diisopropylphenyl)imidazol-2-ylidene]palladium(II), chloro[(1,3-dimesitylimidazol-[1,3-bis(2,4,6-trimethylphenyl)-1,3-dihydro-2H-imidazol-2-ylidene](chloro){2-[(dimethylamino)methyl]phenyl}palladium, chloro[(1,2,3-N)-3-phenyl-2-propenyl][1,3-bis(2,6-di-iso-propylphenyl)imidazol-2-ylidene]palladium(II), [2-(acetylamino)phenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]phenyl}palladium, {1,3-bis[2,6-di(propan-2-yl)phenyl]-2,3-dihydro-1H-imidazol-2-yl}(dichloro)(3-chloropyridine-kappaN)palladium, [1,3-bis(2,6-diisopropylphenyl) imidazol-2-ylidene](3-chloropyridyl)palladium(II) dichloride, [2-(acetylamino)-4-methoxyphenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]-3,5-dimethoxyphenyl}palladium, dichloro[1,3-bis(2,6-di-3-pentylphenyl)imidazol-2-ylidene](3-chloropyridyl)palladium(II), dichloro(di-p-chloro)bis[1,3-bis(2,6-di-iso-propylphenyl)imidazol-2-ylidene]dipalladium(II), 2-(2'-di-tert-butylphosphine)biphenylpalladium(II) acetate, chloro[dicyclohexyl(2',6'-dimethoxybiphenyl-2-yl)-lambda5-phosphanyl][2-(phenyl-kappaC2)ethanaminato-kappaN]palladium, [2-(2-aminoethyl)phenyl](chloro)palladium-di-tert-butyl[2',4',6'-tri(propan-2-yl)biphenyl-2-yl]phosphane, {dicyclohexyl[2',4',6'-tri(propan-2-yl)biphenyl-2-yl]phosphane}{2-[2-(methylazanidyl-kappaN)ethyl]phenyl-kappaC1}palladium, chloro(2-dicyclohexylphosphino-2',6'-dimethoxy-1,1'-biphenyl)(2'-amino-1,1'-biphenyl-2-yl) palladium(II), [2',6'-bis(propan-2-yloxy)biphenyl-2-yl](dicyclohexyl)phosphane-[2-(2-aminoethyl)phenyl](chloro)palladium, [2-(2-aminoethyl)phenyl](chloro){dicyclohexyl[2',4',6'-tri(propan-2-yl)biphenyl-2-yl]-lambda5-phosphanylidene}palladium, 2'-(dicyclohexylphosphanyl)-N,N,N',N'-tetramethylbiphenyl-2,6-diamine-(2'-aminobiphenyl-2-yl)(chloro)palladium, chloro(2-dicyclohexylphosphino-2',6'-di-iso-propoxy-1,1'-biphenyl)(2-amino-1,1'-biphenyl-2-yl)palladium(II), [2'-(azanidyl-kappaN)biphenyl-2-yl-kappaC2](chloro){dicyclohexyl[2',4',6'-tri(propan-2-yl)biphenyl-2-yl]-lambda5-phosphanyl}palladium, (2'-aminobiphenyl-2-yl)(methanesulfonato-kappaO)palladium-di-tert-butyl[2',4',6'-tri(propan-2-yl)biphenyl-2-yl]phosphane, (2'-aminobiphenyl-2-yl)palladium(1+) methanesulfonate-di-tert-butyl[2',4',6'-tri(propan-2-yl)biphenyl-2-yl] phosphane, dicyclohexyl[3,6-dimethoxy-2',4',6'-tri(propan-2-yl)biphenyl-2-yl]phosphane-[2-(2-aminoethyl)phenyl](chloro)palladium, (2'-aminobiphenyl-2-yl)palladium(1+) methanesulfonate-2'-(dicyclohexylphosphanyl)-N,N,N',N'-tetramethylbiphenyl-2,6-diamine, sodium 2'-(dicyclohexylphosphanyl)-2,6-dim ethoxybiphenyl-3-sulfonate-(2'-aminobiphenyl-2-yl)(chloro)palladium, chloro(2-dicyclohexylphosphino-2',4',6'-tri-iso-propyl-1,1'-biphenyl)[2-(2-aminoethyl)phenyl]palladium(II), (2'-aminobiphenyl-2-yl)(methanesulfonato-kappaO)palladium-[2',6'-bis(propan-2-yloxy)biphenyl-2-yl](dicyclohexyl)phosphane, (2'-aminobiphenyl-2-yl)(methanesulfonato-kappaO)palladium-dicyclohexyl[2',4',6'-tri(propan-2-yl)biphenyl-2-yl]phosphane, (2'-aminobiphenyl-2-yl)palladium(1+) methanesulfonate-dicyclohexyl[2',4',6'-tri(propan-2-yl)biphenyl-2-yl] phosphane, dicyclohexyl[3,6-dimethoxy-2',4',6'-tri(propan-2-yl)biphenyl-2-yl]phosphane-(2'-aminobiphenyl-2-yl)(chloro)palladium, (2'-aminobiphenyl-2-yl)(methanesulfonato-kappaO) palladium-di-tert-butyl[3,6-dimethoxy-2',4',6'-tri(propan-2-yl)biphenyl-2-yl]phosphane, (2'-aminobiphenyl-2-yl)(methanesulfonato-kappaO)palladium-dicyclohexyl[3,6-dimethoxy-2',4',6'-tri(propan-2-yl)biphenyl-2-yl] phosphane or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine), dicyclohexyl(2',4',6'-triisopropyl-3,6-dimethoxybiphenyl-2-yl)phosphine, di-tert-butyl (2',4',6'-triisopropyl-3,6-dimethoxybiphenyl-2-yl) phosphine, di-tert-butyl(2',4',6'-triisopropylbiphenyl-2-yl)phosphine, dicyclohexyl(2',4',6'-triisopropylbiphenyl-2-yl) phosphine, di-tert-butyl(2',4',6'-triisopropyl-3-methoxy-6-methylbiphenyl-2-yl)phos-phine, di-tert-butyl (2',4',6'-triisopropyl-3,4,5,6-tetramethylbiphenyl-2-yl) phosphine, adamantan-1-yl(adamantan-2-yl)(2',4',6'-tri-isopropyl-3,6-dimethoxybiphenyl-2-yl) phosphine, dicyclohexyl(2',6'-dimethoxybiphenyl-2-yl)phosphine, dicyclohexyl(2',6'-diisopropoxybiphenyl-2-yl)phosphine, 2'-(dicyclohexylphosphino)-N,N-dimethylbiphenyl-2- amine, 2'-(di-tert-butylphosphino)-N,N-dimethylbiphenyl-2-amine, 2'-(di-phenylphosphino)-N,N,N',N'-tetramethylbiphenyl-2,6-diamine, di-tert-butyl (2',4',6'-tricyclohexyl-3,6-dimethoxybiphenyl-2-yl) phosphine, bis[3,5-bis(trifluoromethyl)phe-nyl](2',4',6'-triisopropyl-3,6-dimethoxybiphenyl-2-yl)phosphine, biphenyl-2-yl(di-tert-butyl)phosphine, dicyclohexyl(2'-methylbiphenyl-2-yl)phosphine, biphenyl-2-yl (dicyclohexyl)phosphine, 2'-(dicyclohexylphosphino)-N,N-dimethylbiphenyl-2-amine, 2'-(dicyclohexylphosphino)-N,N,N',N'-tetramethylbiphenyl-2,6-diamine, sodium 2'-(dicyclohexylphosphino)-2,6-diisopropylbiphenyl-4-sulfonate, sodium 2'-(dicyclohexylphosphino)-2,6-dimethoxybiphenyl-3-sulfonate, 1,1'-binaphthalen-2-yl (di-tert-butyl)phosphine.

Alternatively intermediates of general formula (1-7) can be reacted with a suitable boronic acid or boronic acid pinacole ester of general formula (1-8), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (1-9).

Alternatively intermediates of general formula (1-7) can be reacted with a suitable six membered heterocycle of the general formula (1-8), such as for example 4-fluoro-2-methyl-pyridine, in the presence of a suitable base, such as, for example sodium hydride, in a suitable solvent system, such as, for example, DMF, in a temperature range from room temperature to the boiling point of the respective solvent, preferably the reaction is carried out at 90° C. to furnish compounds of general formula (1-9).

Compounds of general formula (1-9) are converted to compounds of general formula (Ia) by treatment with a suitable deprotection agent, such as an dealkylating agent, such as for example boron trichloride, in a suitable solvent, such as, for example, dichloromethane, in a temperature range from room temperature to the boiling point of the respective solvent, preferably the reaction is carried out at room temperature.

Compound (1-1) can be converted into compounds of formula (1-2) according to the procedure depicted in Scheme 9.

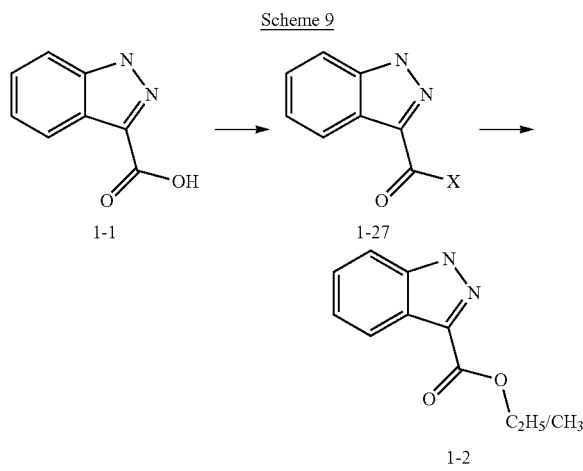

Scheme 9: Route for the preparation of compounds of formula (1-2). X represents Cl and Br.

Alternatively substituted 1H-indazole-3-carboxylic acid (1-1) can be converted to the corresponding substituted 1H-indazole-3-carbonyl halide of the general formula (1-27) by treatment with thionyl halides, for example thionyl chloride in a suitable solvent system, such as, for example, toluene, at a temperature between 0° C. and boiling point of the respective solvent, preferably the reaction is carried out at 120° C. The substituted 1H-indazole-3-carbonyl halide can be reacted with methanol or ethanol in the presence of a base, such as, for example, triethylamine, in an suitable solvent system, such as, for example, dichloromethane, at a temperature between −20° C. and boiling point of the respective solvent, preferably the reaction is carried out at 0° C. to yield the desired alkyl 1H-indazole-3-carboxylate intermediates of formula (1-2).

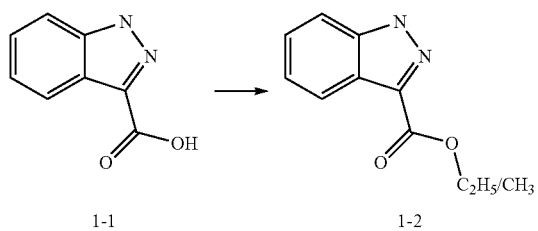

Scheme 10: Route for the preparation of compounds of formula (1-2).

Alternatively compound 1-1 is reacted with methanol or ethanol as mentioned above with a peptide coupling agent, for example N-[(dimethylamino)(3H-[1,2,3]triazolo[4,5-b]pyridin-3-yloxy)methylidene]-N-methylmethanaminium hexafluorophosphate, in a suitable solvent, such as, for example, dichloromethane, in the presence of a suitable base, such as, for example, diisopropylethylamine in a temperature range from −10° C. to the boiling point of the respective solvent, preferably the reaction is carried out at room temperature, to furnish compounds of formula (1-2).

Appropriate peptide synthesis methods and their applications are well-known to the person skilled in the art (see for example N. Leo Benoitin in *Chemistry of Peptide Synthesis*, CRC Press 2005; John Jones in *Amino Acids and Peptide Synthesis*, Oxford University Press, 2002 and Norbert Sewald and Hans-Dieter Jakubke in Peptides: *Chemistry and Biology*, Wiley-VCH, 2009).

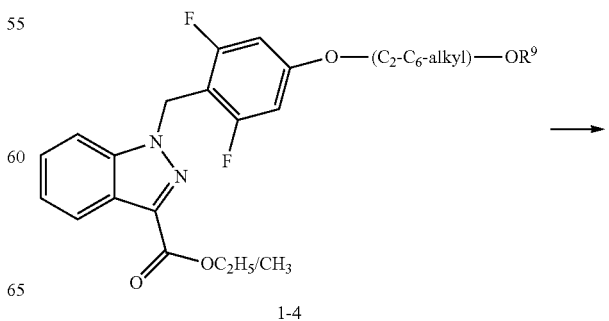

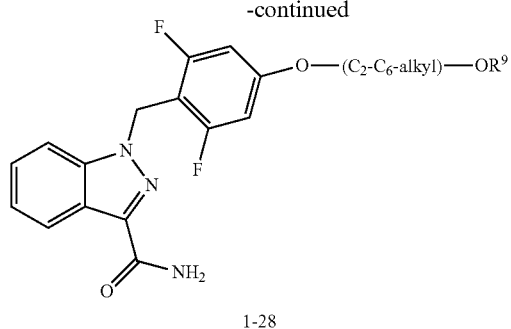

Scheme 11: Route for the preparation of compounds of general formula (1-5), wherein $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl.

Intermediates of general formula (1-4) can be converted to intermediates of general formula (1-28) by reaction with ammonia, in a suitable solvent system, such as, for example, methanol, at a temperature between 0° C. and boiling point of the respective solvent, preferably the reaction is carried out at 50° C., at a pressure between 1 and 10bar, preferably the reaction is carried in a sealed vessel.

Intermediates of general formula (1-28) are treated with triflic anhydride, in a suitable solvent system, such as, for example, tetrahydrofuran, in the presence of a suitable base, such as, for example, pyridine, at a temperature between 0° C. and the boiling point of the respective solvent, preferably the reaction is carried out at room temperature, to form the desired intermediate of general formula (1-29).

Intermediates of general formula (1-29) can be converted to intermediates of general formula (1-5) by reaction with a suitable alcoholate, such as, for example sodium methanolate, in a suitable solvent system, such as, for example, the corresponding alcohol, e.g. methanol, at a temperature between room temperature and the boiling point of the respective solvent, preferably the reaction is carried out at room temperature, and subsequent treatment with a suitable source of ammonium, such as for example, ammonium chloride in the presence of a suitable acid, such as for example acetic acid in a temperature range from room temperature to the boiling point of the respective solvent, preferably the reaction is carried out at 50° C.

An alternative route for the preparation of compounds of general formula (Ia) is described in Scheme 12.

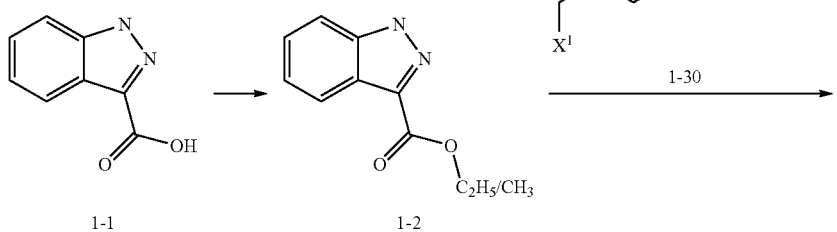

-continued
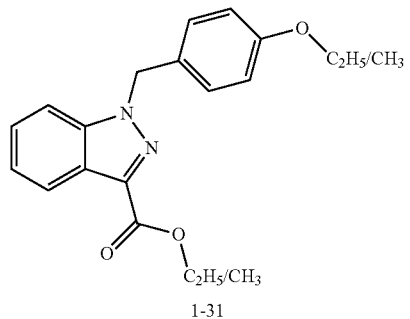 →  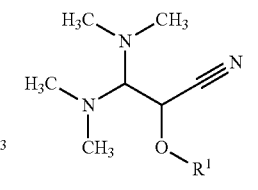 →
1-31     1-32     1-6
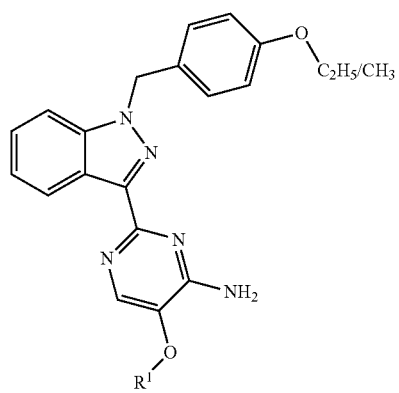 → 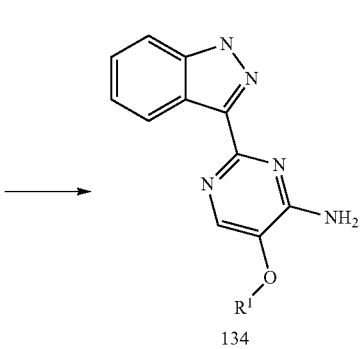 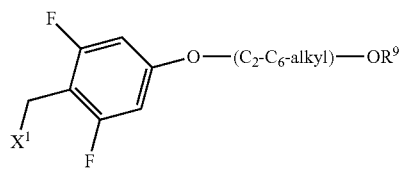 →
1-33     134     1-3
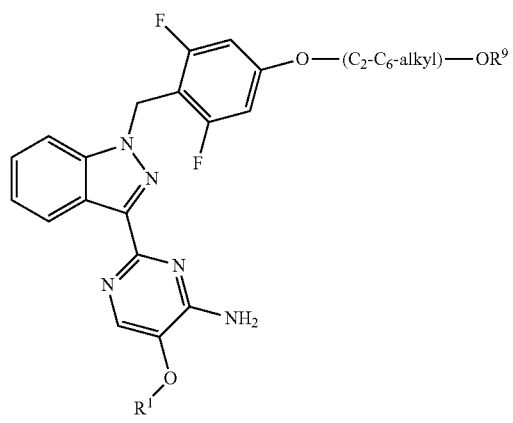 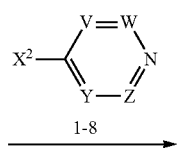 →
1-7     1-8

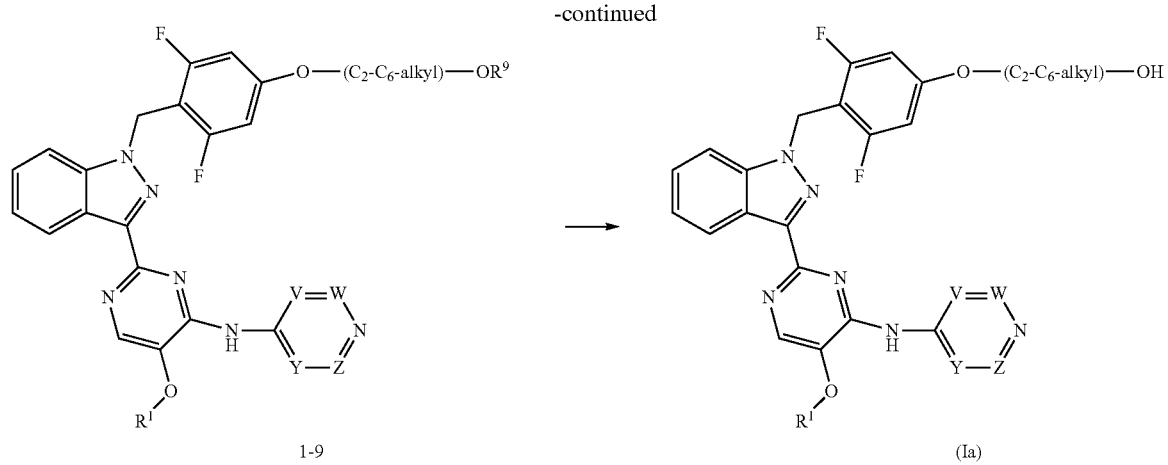

Scheme 12: Route for the preparation of compounds of general formula (Ia), wherein $R^1$, V, W, Y and Z have the meaning as given for general formula (I), supra, $R^9$ represents a methyl- or an ethyl group or an alcohol protecting group, such as for example tert-butyldimethylsilyl, tert-butyldiphenylsilyl, triethylsilyl, triisopropylsilyl or tetrahydropyranyl, $X^1$ represents F, Cl, Br, I or a sulfonate, e.g. trifluormethylsulfonate or p-toluolsulfonate, and $X^2$ represents F, Cl, Br, I, boronic acid or a boronic acid ester, such as for example 4,4,5,5-tetramethyl-2-phenyl-1,3,2-dioxaborolane (boronic acid pinacole ester).

In addition, interconversion of any of the substituents $R^1$, V, W, Y or Z can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Compounds 1-3, 1-6, 1-8 and 1-30 are either commercially available or can be prepared according to procedures available from the public domain, as understandable to the person skilled in the art. Specific examples are described in the subsequent paragraphs.

A suitably substituted 1H-indazole-3-carboxylic acid of the general formula (1-1) can be reacted with methanol or ethanol in the presence of catalytic amounts of a Broensted acid, such as, for example, hydrochloric acid or sulphuric acid, at temperatures ranging from 0° C. to boiling point of the respective alcohol, preferably the reaction is carried out at 85° C., to furnish alkyl 1H-indazole-3-carboxylat e intermediates of general formula (1-2).

Alkyl 1H-indazole-3-carboxylate Intermediates of the general formula (1-2) can be converted to intermediates of general formula (1-31) by reaction with a suitable alkylating agent, such as, for example a substituted benzyl halide (1-30), in the presence of a suitable base, such as, for example sodium hydride, in a suitable solvent system, such as, for example, DMF, at a temperature between −20° C. and boiling point of the respective solvent, preferably the reaction is carried out at 0° C.

Intermediates of general formula (1-31) are treated with the reagent methylchloroaluminiumamide prepared in situ by addition of ammonium chloride to commercially available trimethylaluminium, in a suitable solvent system, such as, for example, toluene, at a temperature between 0° C. and the boiling point of the respective solvent, preferably the reaction is carried out at 80° C. and are quenched with a suitable solvent system, such as, for example, methanol, to form the desired intermediate of general formula (1-32).

Intermediates of general formula (1-32) can be converted to intermediates of general formula (1-33) by reaction with a suitably substituted 3,3-bis-(dimethylamino)propanenitrile of the general formula (1-6), such as, for example 3,3-bis (dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-33) can be converted to intermediates of general formula (1-34) by reaction with a suitably Broensted acid, such as, for example methanesulfonic acid and trifluoroacetic acid, in a suitable solvent system, such as, for example, dichloromethane, in a temperature range from room temperature to the boiling point of the respective solvent, preferably the reaction is carried out at room temperature.

Intermediates of the general formula (1-34) can be converted to intermediates of general formula (1-7) by reaction with a suitable alkylating agent, such as, for example a substituted benzyl halide (1-3), in the presence of a suitable base, such as, for example sodium hydride, in a suitable solvent system, such as, for example, DMF, at a temperature between −20° C. and boiling point of the respective solvent, preferably the reaction is carried out at 0° C.

Intermediates of general formula (1-7) can be reacted with a suitable six membered heterocycle of the general formula (1-8), such as, for example 4-bromo-2-methyl-pyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, such as, for example, DMF, in a temperature range from room temperature to the boiling point of the respective solvent, preferably the reaction is carried out at at 100° C. to furnish compounds of general formula (1-9). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris (dibenzylideneacetone)dipalladium (0), chloro(2'-amino-1,1'-biphenyl-2-yl)palladium(II) dimer, (2'-amino-1,1'-biphenyl-2-yl)methanesulfonatopalladium(II) dimer, trans-di(p-acetato)bis[o-(di-o-tolylphosphino)benzyl]dipalladium(II) [cataCXium® C], allylchloro[1,3-bis(2,4,6-trimethylphenyl)imidazol-2-ylidene]palladium(II), allylchloro[1,3-bis(2,6-diisopropylphenyl)imidazol-2-ylidene]palladium(II), chloro[(1,3-dimesitylimidazol-[1,3-bis(2,4,6-trimethylphenyl)-1,3-dihydro-2H-imidazol-2-ylidene](chloro){2-[(dimethylamino)methyl]phenyl}palladium, chloro[(1,2,3-N)-3-phenyl-2-propenyl][1,3-bis(2,6-di-iso-propylphenyl)imidazol-2-ylidene]palladium(II), [2-(acetylamino)phenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]phenyl}palladium, {1,3-bis[2,6-di(propan-2-yl)phenyl]-2,3-dihydro-1H-imidazol-2-yl}(dichloro)(3-chloropyridine-kappaN)palladium, [1,3-bis(2,6-diisopropylphenyl) imidazol-2-ylidene](3-chloropyridyl)palladium(II) dichloride, [2-(acetylamino)-4-methoxyphenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]-3,5-dimethoxyphenyl}palladium, dichloro[1,3-bis(2,6-di-3-pentylphenyl)imidazol-2-ylidene](3-chloropyridyl) palladium(II), dichloro(di-p-chloro)bis[1,3-bis(2,6-di-iso-propylphenyl) imidazol-2-ylidene] dipalladium(II), 2-(2'-di-tert-butylphosphine) biphenylpalladium(II) acetate, chloro[dicyclohexyl(2',6'-dimethoxybiphenyl-2-yl)-lambda5-phosphanyl][2-(phenyl-kappaC2)ethanaminato-kappaN]palladium, [2-(2-aminoethyl)phenyl](chloro)palladium-di-tert-butyl[2',4',6'-tri(propan-2-yl)biphenyl-2-yl]phosphane, {dicyclohexyl[2',4',6'-tri(propan-2-yl)biphenyl-2-yl]phosphane}{2-[2-(methylazanidyl-kappaN)ethyl]phenyl-kappaC1}palladium, chloro(2-dicyclohexylphosphino-2',6'-dimethoxy-1,1'-biphenyl)(2'-amino-1,1'-biphenyl-2-yl)palladium(II), [2',6'-bis(propan-2-yloxy)biphenyl-2-yl](dicyclohexyl)phosphane-[2-(2-aminoethyl)phenyl](chloro)palladium, [2-(2-aminoethyl)phenyl](chloro){dicyclohexyl[2',4',6'-tri(propan-2-yl)biphenyl-2-yl]-lambda5-phosphanylidene}palladium, 2'-(dicyclohexylphosphanyl)-N,N,N',N'-tetramethylbiphenyl-2,6-diamine-(2'-aminobiphenyl-2-yl)(chloro)palladium, chloro(2-dicyclohexylphosphino-2',6'-di-iso-propoxy-1,1'-biphenyl)(2-amino-1,1'-biphenyl-2-yl)palladium(II), [2'-(azanidyl-kappaN)biphenyl-2-yl-kappaC2](chloro){dicyclohexyl[2',4',6'-tri(propan-2-yl)biphenyl-2-yl]-lambda5-phosphanyl}palladium, (2'-aminobi-phenyl-2-yl)(methanesulfonato-kappaO)palladium-di-tert-butyl[2',4',6'-tri(propan-2-yl)biphenyl-2-yl]phosphane, (2'-aminobiphenyl-2-yl)palladium(1+) methanesulfonate-di-tert-butyl[2',4',6'-tri(propan-2-yl)biphenyl-2-yl]phosphane, dicyclohexyl[3,6-dimethoxy-2',4',6'-tri(propan-2-yl)biphenyl-2-yl]phosphane-[2-(2-aminoethyl)phenyl](chloro)palladium, (2'-aminobiphenyl-2-yl)palladium(1+) methanesulfonate-2'-(dicyclohexylphosphanyl)-N,N,N',N'-tetramethylbiphenyl-2,6-diamine, sodium 2'-(dicyclohexylphosphanyl)-2,6-dim ethoxybiphenyl-3-sulfonate-(2'-aminobiphenyl-2-yl)(chloro)palladium, chloro(2-dicyclohexylphosphino-2',4',6'-tri-iso-propyl-1,1'-biphenyl)[2-(2-aminoethyl)phenyl]palladium(II), (2'-aminobiphenyl-2-yl)(methane-sulfonato-kappaO)palladium-[2',6'-bis(propan-2-yloxy)biphenyl-2-yl](dicyclohexyl) phosphane, (2'-aminobiphenyl-2-yl)(methanesulfonato-kappaO)palladium-dicyclohexyl[2',4',6'-tri(propan-2-yl)biphenyl-2-yl]phosphane, (2'-aminobiphenyl-2-yl)palladium(1+) methanesulfonate-dicyclohexyl[2',4',6'-tri(propan-2-yl)biphenyl-2-yl]phosphane, dicyclohexyl[3,6-dimethoxy-2',4',6'-tri(propan-2-yl)biphenyl-2-yl]phosphane-(2'-aminobiphenyl-2-yl)(chloro)palladium, (2'-aminobiphenyl-2-yl)(methanesulfonato-kappaO)palladium-di-tert-butyl[3,6-dimethoxy-2',4',6'-tri(propan-2-yl)biphenyl-2-yl]phosphane, (2'-aminobiphenyl-2-yl)(methanesulfonato-kappaO)palladium-dicyclohexyl[3,6-dimethoxy-2',4',6'-tri(propan-2-yl)biphenyl-2-yl] phosphane or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethylphosphonium tetrafluoroborate, 2-(di-tert-butylphosphino) biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine), dicyclohexyl(2',4',6'-triisopropyl-3,6-dimethoxybiphenyl-2-yl)phosphine, di-tert-butyl (2',4',6'-triisopropyl-3,6-dimethoxybiphenyl-2-yl) phosphine, di-tert-butyl(2',4',6'-triiso propylbiphenyl-2-yl)phosphine, dicyclohexyl(2',4',6'-triisopropylbiphenyl-2-yl) phosphine, di-tert-butyl(2',4',6'-triisopropyl-3-methoxy-6-methylbiphenyl-2-yl)phos-phine, di-tert-butyl (2',4',6'-triisopropyl-3,4,5,6-tetramethylbiphenyl-2-yl) phosphine, adamantan-1-yl(adamantan-2-yl)(2',4',6'-triisopropyl-3,6-dimethoxybiphenyl-2-yl) phosphine, dicyclohexyl(2',6'-dimethoxybiphenyl-2-yl)phosphine, dicyclohexyl(2',6'-diisopropoxybiphenyl-2-yl)phosphine, 2'-(dicyclohexylphosphino)-N,N-dimethylbiphenyl-2-amine, 2'-(di-tert-butylphosphino)-N,N-dimethylbiphenyl-2-amine, 2'-(di-phenylphosphino)-N,N,N',N'-tetramethylbiphenyl-2,6-diamine, di-tert-butyl (2',4',6'-tricyclohexyl-3,6-dimethoxybiphenyl-2-yl) phosphine, bis[3,5-bis(trifluoromethyl)phe-nyl](2',4',6'-triisopropyl-3,6-dimethoxybiphenyl-2-yl)phosphine, biphenyl-2-yl(di-tert-butyl)phosphine, dicyclohexyl(2'-methylbiphenyl-2-yl)phosphine, biphenyl-2-yl (dicyclohexyl)phosphine, 2'-(dicyclohexylphosphino)-N,N-dimethylbiphenyl-2-amine, 2'-(dicyclohexylphosphino)-N,N,N',N'-tetramethylbiphenyl-2,6-diamine, sodium 2'-(dicyclohexylphosphino)-2,6-diisopropylbiphenyl-4-sulfonate, sodium 2'-(dicyclohexylphosphino)-2,6-dimethoxybiphenyl-3-sulfonate, 1,1'-binaphthalen-2-yl (di-tert-butyl)phosphine, 1,3-bis(2,4,6-trimethylphenyl)-1,3-dihydro-2H-imidazol-2-ylidene, 1,3-bis[2,6-di(propan-2-yl)phenyl]-1,3-dihydro-2H-imidazol-2-ylidene.

Alternatively intermediates of general formula (1-7) can be reacted with a suitable boronic acid or boronic acid pinacole ester of general formula (1-8), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (1-9).

Alternatively intermediates of general formula (1-7) can be reacted with a suitable six membered heterocycle of the general formula (1-8), such as for example 4-fluoro-2-methyl-pyridine, in the presence of a suitable base, such as, for example sodium hydride, in a suitable solvent system, such as, for example DMF, in a temperature range from room temperature to the boiling point of the respective solvent, preferably the reaction is carried out at 90° C. to furnish compounds of general formula (1-9).

Compounds of general formula (1-9) are converted to compounds of general formula (Ia) by treatment with a suitable deprotection agent, such as an dealkylating agent, such as for example boron trichloride, in a suitable solvent, such as, for example, dichloromethane, in a temperature range from room temperature to the boiling point of the respective solvent, preferably the reaction is carried out at room temperature.

Compounds of general formula (1-35) can be converted into compounds of general formula (1-37) according to the procedure depicted in Scheme 13.

Scheme 13 (Z = CNH$_2$)

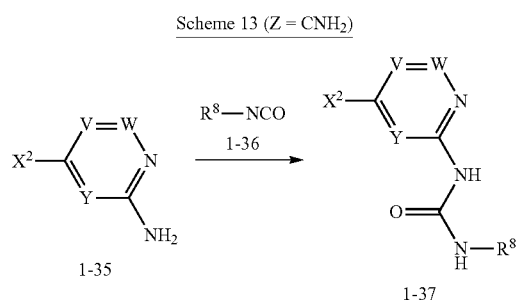

Scheme 13: Route for the preparation of compounds of general formula (1-37), wherein V, W, Y and R$^8$ have the meaning as given for general formula (I), supra. X$^2$ represents F, Cl, Br and I.

Intermediates of general formula (1-35) can be converted to intermediates of general formula (1-37) by reaction with isocyanate derivative (1-36), in a suitable solvent system, such as, for example, THF, in a temperature range from room temperature to the boiling point of the respective solvent, preferably the reaction is carried out at 70° C.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art 5 will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula ( ) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of 5 diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1 to 8 according to the examples, as well as the intermediates used for their preparation.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as meta-chloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

One preferred aspect of the invention is the process for the preparation of the compounds of claims 1 to 8 according to the examples, as well as the intermediates used for their preparation.

Optionally, compounds of the formula (I) can be converted into their salts, or, optionally, salts of the compounds of the formula (I) can be converted into the free compounds. Corresponding processes are customary for the skilled person.

Commercial Utility

As mentioned supra, the compounds of the present invention have surprisingly been found to effectively inhibit Bub1 finally resulting in cell death e.g. apoptosis and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

A further aspect of the invention is the use of the compounds according to formula (I) for the treatment of cervical-, breast-, non-small cell lung-, prostate-, colon- and melanoma tumors and/or metastases thereof, especially preferred for the treatment thereof as well as a method of treatment of cervical-, breast-, non-small cell lung-, prostate-, colon- and melanoma tumors and/or metastases thereof comprising administering an effective amount of a compound of formula (I).

One aspect of the invention is the use of the compounds according to formula (I) for the 5 treatment of cervix tumors as well as a method of treatment of cervix tumors comprising administering an effective amount of a compound of formula (I).

In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of cell death i.e apoptosis.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, especially the treatment, wherein the diseases are haematological tumours, solid tumours and/or metastases thereof.

Another aspect is the use of a compound of formula (I) is for the treatment of cervical-, breast-, non-small cell lung-, prostate-, colon- and melanoma tumors and/or metastases thereof, especially preferred for the treatment thereof. A preferred aspect is the use of a compound of formula (I) for the prophylaxis and/or treatment of cervical tumors especially preferred for the treatment thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g. apoptosis. In an embodiment the disease is a haematological tumour, a solid tumour and/or metastases thereof. In another embodiment the disease is cervical-, breast-, non-small cell lung-, prostate-, colon- and melanoma tumor and/or metastases thereof, in a preferred aspect the disease is cervical tumor.

Method of Treating Hyper-proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited to, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death e.g. apoptosis of such cell types.

Preferably, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)—Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents—examples include but are not limited to nitrogen and argon;

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. solution: A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised powder for i.v. administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

Experimental Part

The following table lists the abbreviations used in this paragraph and in the Intermediate Examples and Examples section as far as they are not explained within the text body.

| Abbreviation | Meaning |
| --- | --- |
| br | broad |
| CI | chemical ionisation |
| d | doublet |
| dd | doublet of doublet |
| DAD | diode array detector |
| DCM | dichloromethane |
| DMF | N,N-dimethylformamide |
| ELSD | Evaporative Light Scattering Detector |
| eq. | equivalent |
| ESI | electrospray (ES) ionisation |
| HPLC | high performance liquid chromatography |
| LC-MS | liquid chromatography mass spectrometry |
| m | multiplet |
| MS | mass spectrometry |
| NMR | nuclear magnetic resonance spectroscopy: chemical shifts (δ) are given in ppm. The chemical shifts were corrected by setting the DMSO signal to 2.50 ppm using unless otherwise stated. |
| PDA | Photo Diode Array |
| PoraPak ™; | a HPLC column obtainable from Waters |
| q | quartet |
| r.t. or rt | room temperature |
| RT | retention time (as measured either with HPLC or UPLC) in minutes |
| s | singlet |
| SM | starting material |
| SQD | Single-Quadrupol-Detector |
| t | triplet |
| THF | tetrahydrofuran |
| UPLC | ultra performance liquid chromatography |

Other abbreviations have their meanings customary per se to the skilled person.

The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash $NH_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

Analytical LC-MS Conditions

LC-MS-data given in the subsequent specific experimental descriptions refer (unless otherwise noted) to the following conditions:

| | |
| --- | --- |
| System: | Waters Acquity UPLC-MS: Binary Solvent Manager, Sample Manager/Organizer, Column Manager, PDA, ELSD, SQD 3001 or ZQ4000 |
| Column: | Acquity UPLC BEH C18 1.7 50 × 2.1 mm |
| Solvent: | A1 = water + 0.1% vol. formic acid (99%) A2 = water + 0.2% vol. ammonia (32%) B1 = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μL |
| Detection: | DAD scan range 210-400 nm -> Peak table ELSD |
| Methods: | MS ESI+, ESI– Switch -> various scan ranges (Report Header) Method 1: A1 + B1 = C:\MassLynx\Mass_100_1000.flp Method 2: A1 + B1 = C:\MassLynx\Mass_160_1000.flp Method 3: A1 + B1 = C:\MassLynx\Mass_160_2000.flp Method 4: A1 + B1 = C:\MassLynx\Mass_160_1000_BasicReport.flp Method 5: A2 + B1 = C:\MassLynx\ |

-continued

```
NH₃_Mass_100_1000.flp
Method 6: A2 + B1 = C:\MassLynx\
NH₃_Mass_160-_1000_BasicReport.flp
```

| System: | Waters ACQUITY SQD UPLC System |
|---|---|
| Column: | Waters Acquity UPLC HSS T3 1.8μ 50 × 1 mm |
| Solvent: | A = water + 0.25% vol. formic acid (99%) |
| | B = acetonitrile + 0.25% vol. formic acid (99%) |
| Gradient: | 0.0 min 90% A → 1.2 min 5% A → 2.0 min 5% |
| Flow: | 0.4 mL/min |
| Temperature: | 50° C. |
| Detection: | DAD scan range 208-400 nm -> Peak table |
| | ELSD |
| Method 7 | |

Preparative HPLC Conditions

"Purification by preparative HPLC" in the subsequent specific experimental descriptions refers to (unless otherwise noted) the following conditions:

Analytics (Pre- and Post-Analytics: Method B):

| System: | Waters Aqcuity UPLC-MS: Binary Solvent Manager, Sample Manager/Organizer, Column Manager, PDA, ELSD, SQD 3001 |
|---|---|
| Column: | Aqcuity BEH C18 1.7 50 × 2.1 mm |
| Solvent: | A1 = water + 0.1% vol. formic acid (99%) |
| | A2 = water + 0.2% vol. ammonia (32%) |
| | B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μL |
| Detection: | DAD scan range 210-400 nm |
| | MS ESI+, ESI−, scan range 160-1000 m/z |
| | ELSD |
| Methods: | Purify_pre.flp |
| | Purify_post.flp |

Preparation:

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A1 = water + 0.1% vol. formic acid (99%) |
| | A2 = water + 0.2% vol. ammonia (32%) |
| | B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm |
| | MS ESI+, ESI−, scan range 160-1000 m/z |

Chiral HPLC Conditions

If not specified otherwise, chiral HPLC-data given in the subsequent specific experimental descriptions refer to the following conditions:

Analytics:

| System: | Dionex: Pump 680, ASI 100, Waters: UV-Detektor 2487 |
|---|---|
| Column: | Chiralpak IC 5 μm 150 × 4.6 mm |
| Solvent: | hexane/ethanol 80:20 + 0.1% diethylamine |
| Flow: | 1.0 mL/min |
| Temperature: | 25° C. |

| Solution: | 1.0 mg/mL ethanol/methanol 1:1 |
|---|---|
| Injection: | 5.0 μl |
| Detection: | UV 280 nm |

Preparation:

| System: | Agilent: Prep 1200, 2 × Prep Pump, DLA, MWD, Prep FC, ESA: Corona |
|---|---|
| Column: | Chiralpak IC 5 μm 250 × 30 mm |
| Solvent: | hexane/ethanol 80:20 + 0.1% diethylamine |
| Flow: | 40 mL/min |
| Temperature: | RT |
| Solution: | 660 mg/5.6 mL ethanol |
| Injection: | 8 × 0.7 mL |
| Detection: | UV 280 nm |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

Determination of Optical Rotation Conditions

Optical rotations were measured in dimethyl sulfoxide at 589 nm wavelength, 20° C., concentration 1.0000 g/100 ml, integration time 10 s, film thickness 100.00 mm.

EXAMPLES

Synthetic Intermediates

Intermediate 1-1-1

Preparation of [2,6-difluoro-4-(2-methoxyethoxy)phenyl]methanol

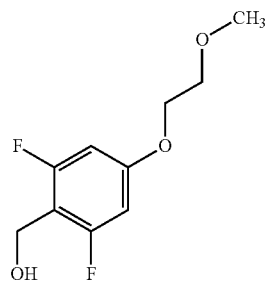

200 mg 3,5-Difluoro-4-(hydroxymethyl)phenol (1.2 mmol, 1.0 eq.) and 0.14 mL 2-bromoethyl methyl ether (1.5 mmol, 1.2 eq.) were dissolved in 16.5 mL DMF. 863 mg potassium carbonate (6.2 mmol, 5.0 eq.), were added and the reaction mixture was stirred overnight at 60° C. The reaction mixture was dissolved in water and ethyl acetate. The aqueous layer was extracted with ethyl acetate twice. The combined organic layers were dried over silicon filter and concentrated in vacuo. The crude product was used without further purification: 269 mg, 90% pure, yield 89%, 1.1 mmol.

¹H-NMR (300 MHz, DMSO-d6): δ [ppm]=3.25 (s, 3H), 3.50-3.65 (m, 2H), 3.99-4.14 (m, 2H), 4.37 (br. s., 2H), 5.07 (br. s., 1H), 6.52-6.75 (m, 2H).

The following intermediate was prepared according to the same procedure from the commercially available starting material or from the indicated starting material (SM)

| | | | |
|---|---|---|---|
| 1-1-2 | 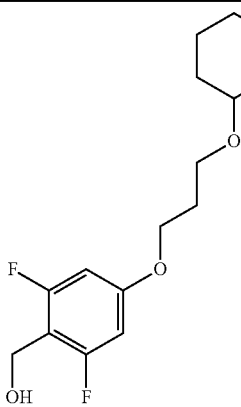 | {2,6-difluoro-4-[3-[(2rac)-tetrahydro-2H-pyran-2-yloxy)propoxy]phenyl}methanol | ¹H NMR (400 MHz, DMSO-d6) δ [ppm] = 1.33-1.54 (m, 4H), 1.56-1.66 (m, 1H), 1.67-1.77 (m, 1H), 1.91-2.01 (m, 2H), 3.37-3.52 (m, 2H), 3.65-3.82 (m, 2H), 3.99-4.12 (m, 2H), 4.41 (d, 2H), 4.53-4.60 (m, 1H), 5.09 (t, 1H), 6.62-6.79 (m, 2H). |
| 1-1-3 SM = 1-18-1 | 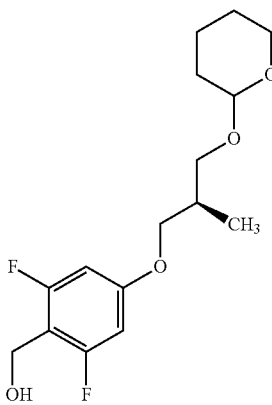 | (2,6-difluoro-4-({(2S)-2-methyl-3-[(2rac)-tetrahydro-2H-pyran-2-yloxy]propyl}oxy)phenyl]methanol | ¹H NMR (400 MHz, DMSO-d6) δ [ppm] = 1.00 (d, 3H), 1.36-1.53 (m, 4H), 1.55-1.79 (m, 2H), 2.09-2.21 (m, 1H), 3.25-3.47 (m, 2H), 3.56-3.74 (m, 2H), 3.85-3.99 (m, 2H), 4.41 (s, 2H), 4.55 (q, 1H), 5.12 (s, 1H), 6.66-6.76 (m, 2H). |

Intermediate 1-2-1

Preparation of 2-(bromomethyl)-1,3-difluoro-5-(2-methoxyethoxy)benzene

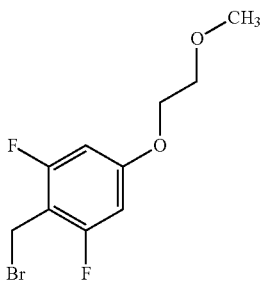

6.0 g [2,6-Difluoro-4-(2-methoxyethoxy)phenyl]methanol 1-1-1 (27.4 mmol, 1.0 eq.) was dissolved in 22 mL dichloromethane. 1.9 mL phosphorous tribromide (20.5 mmol, 0.75 eq.) was dissolved in 22 mL dichloromethane and given to the starting material. The reaction mixture was stirred at room temperature under argon atmosphere for 30 min. The reaction mixture was poured into ice water and the pH was adjusted to 8 by adding saturated sodium hydrogen carbonate solution. It was extracted three times with 5 dichloromethane, washed once with water and brine, filtered through a silicone coated filter and dried under reduced pressure to provide the crude product, which was used without further purification: 8.2 g, 29.2 mmol, 107% yield.

¹H-NMR (300 MHz, DMSO-d6): δ [ppm]=3.28 (s, 3H), 3.58-3.70 (m, 2H), 4.10-4.18 (m, 2H), 4.60 (s, 2H), 6.73-6.90 (m, 2H).

Intermediate 1-3-1

Preparation of methyl 1-(4-methoxybenzyl)-1H-indazole-3-carboxylate

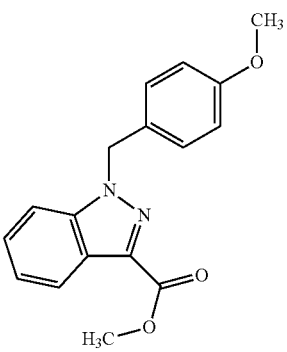 [SMILES: COC(=O)c1nn(Cc2ccc(OC)cc2)c2ccccc12]

20.2 g of Methyl 1 H-indazole-3-carboxylate (114 mmol, 1.0 eq.) were dissolved in 123 mL of dry DMF and cooled to 0° C. 59.7 g of caesium carbonate (183.1 mmol, 1.6 eq.) were added and stirred for 10 min. 23.3 g of 1-(chloromethyl)-4-methoxybenzene (148 mmol, 1.3 eq.) were added dropwise at 0° C. The mixture was stirred at room temperature for 1 hours under nitrogen atmosphere. Then the reaction mixture was partitioned between water and ethyl ester. The organic layer was dried over silicon filter and concentrated in vacuo. The residue was purified by flash chromatography to yield 20.9 g (60 mmol, 52%) of 85% pure target compound.

$^1$H NMR (400 MHz, DMSO-d6) δ [ppm]=3.66 (s, 3H), 3.89 (s, 3H), 5.67 (s, 2H), 6.79-6.90 (m, 2H), 7.20-7.26 (m, 2H), 7.29-7.33 (m, 1H), 7.43-7.47 (m, 1H), 7.84 (d, 1H), 8.05 (dt, 1H).

The following intermediate was prepared according to the same procedure from the commercially available starting material

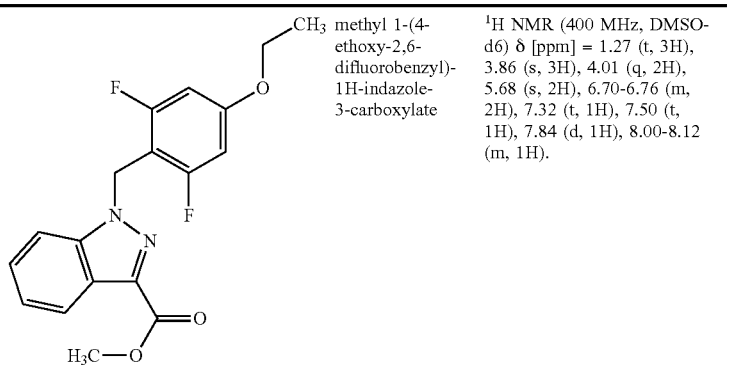

| 1-3-2 | | methyl 1-(4-ethoxy-2,6-difluorobenzyl)-1H-indazole-3-carboxylate | $^1$H NMR (400 MHz, DMSO-d6) δ [ppm] = 1.27 (t, 3H), 3.86 (s, 3H), 4.01 (q, 2H), 5.68 (s, 2H), 6.70-6.76 (m, 2H), 7.32 (t, 1H), 7.50 (t, 1H), 7.84 (d, 1H), 8.00-8.12 (m, 1H). |
|---|---|---|---|

Intermediate 1-4-1

Preparation of 1-(4-methoxybenzyl)-1 H-indazole-3-carboximidamide, salt with hydrochloric acid

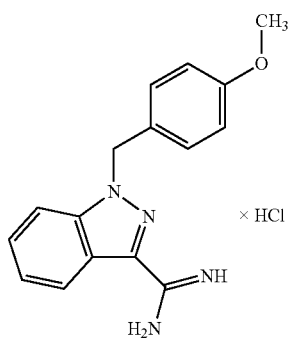 [SMILES: COc1ccc(Cn2nc(C(=N)N)c3ccccc32)cc1]

22.1 g of ammonium chloride (413 mmol, 5.0 eq.) were suspended in 770 mL of dry toluene under nitrogen atmosphere and cooled down to 0° C. bath temperature. 207 mL of 2M trimethylaluminium solution in toluene (413 mmol, 5.0 eq.) were added dropwise. The mixture was stirred at room temperature until disappearance of gassing. 24.5 g of methyl 1-(4-methoxybenzyl)-1 H-indazole-3-carboxylate 1-3-1 (83 mmol, 1.0 eq.) were dissolved in 100 mL of dry toluene and added drop wise to the reaction mixture and stirred for 2 days at 80° C. bath temperature. The mixture was cooled down with an ice bath to 0° C. bath temperature, 100 mL of methanol were added and stirred for one hour at rt. The resulting suspension was filtered off and washed with methanol. The filtrate was concentrated in vacuo and stirred in dichloromethane/methanol. The solid was filtered off and rinsed with dichloromethane twice. The filtrate was concentrated in vacuo. The crude product was used without any further purification: 18.7 g, 67 mmol, 81%.

$^1$H NMR (300 MHz, DMSO-d6) δ [ppm]=3.67 (s, 3H), 5.74 (s, 2H), 6.81-6.89 (m, 2H), 7.23-7.32 (m, 2H), 7.33-7.40 (m, 1H), 7.52 (t, 1H), 7.91 (d, 1H), 7.99 (d, 1H), 9.34 (br. s., 4H).

The following intermediate was prepared according to the same procedure from the indicated starting material (SM=starting material):

| | | | |
|---|---|---|---|
| 1-4-2 SM = 1-3-2 | 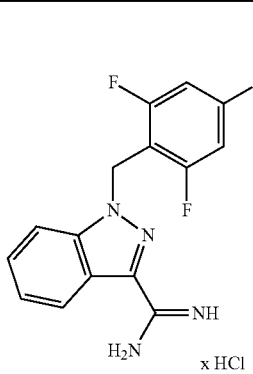 | 1-(4-ethoxy-2,6-difluorobenzyl)-1H-indazole-3-carboximidamide, salt with hydrochloric acid | ¹H NMR (300 MHz, DMSO-d6) δ [ppm] = 1.26 (t, 3H), 4.01 (q, 2H), 5.75 (s, 2H), 6.68-6.78 (m, 2H), 7.34-7.43 (m, 1H), 7.56-7.61 (m, 1H), 7.93 (dd, 2H), 9.29 (br. s, 4H). |

Intermediate 1-5-1

Preparation of 3,3-bis(dimethylamino)-2-methoxypropanenitrile

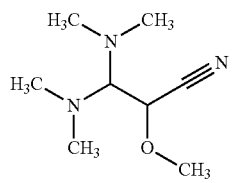

360 g of 1-tert-butoxy-N,N,N',N'-tetramethylmethanediamine (Bredereck's reagent) (2068 mmol, 1 eq.) and 150 g of methoxyacetonitrile (2068 mmol, 1.0 eq.) were stirred for 18 hours at 80° C. The reaction mixture was concentrated in vacuo. The residue was purified by vacuum distillation (0.9 mmbar; bp 60-65° C.) to yield 117 g (683 mmol, 33%) of the analytical pure target compound as a yellowish liquid.

¹H-NMR (400 MHz, DMSO-d6): δ [ppm]=2.23 (s, 6H), 2.29 (s, 6H), 3.23 (d, 1H), 3.39 (s, 3H), 4.73 (d, 1H).

Intermediate 1-6-1

Preparation of 5-methoxy-2-[1-(4-methoxybenzyl)-1H-indazol-3-yl]pyrimidin-4-amine

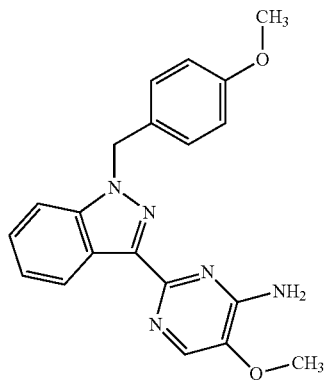 [SMILES: COc1ccc(Cn2nc(-c3ncc(OC)c(N)n3)c3ccccc32)cc1]

6.45 g of 1-(4-Methoxybenzyl)-1H-indazole-3-carboximidamide 1-4-1 (23.0 mmol, 1.0 eq.), 5.40 g of 3,3-bis(dimethylamino)-2-methoxypropanenitrile 1-5-1 (31.5 mmol, 1.4 eq.) and 0.455 mL of piperidine (4.60 mmol, 0.2 eq.) were dissolved in 82.7 mL of dry 3-methylbutan-1-ol, put under a nitrogen atmosphere and stirred at 100° C. for 3 days. The mixture was cooled down at room temperature and stirred for 18 hours for crystallization. The resulting suspension was filtered off. The crystals were washed with cold methanol and dried in vacuo at 50° C. The crystallization was repeated twice with cold methanol to receive 2 further filter cakes and a combined yield of 6.87 g (19 mmol, 82.5%) of the analytically pure target compound.

¹H-NMR (300 MHz, DMSO-d6): δ [ppm]=3.62-3.69 (s, 3H), 3.85 (s, 3H), 5.59 (s, 2H), 6.78-6.90 (m, 4H), 7.11-7.23 (m, 3H), 7.35 (ddd, 1H), 7.68 (d, 1H), 7.95 (s, 1H), 8.53 (d, 1H).

The following intermediate was prepared according to the same procedure from the indicated starting material (SM=starting material):

| | | | |
|---|---|---|---|
| 1-6-2<br>SM1 =<br>1-4-2<br>SM2 =<br>1-5-1<br>110° C.<br>over<br>night | 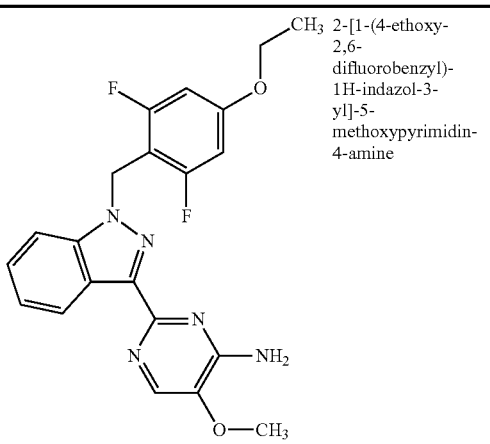 | 2-[1-(4-ethoxy-2,6-difluorobenzyl)-1H-indazol-3-yl]-5-methoxypyrimidin-4-amine | $^1$H-NMR (400 MHz, DMSO-d$_6$): δ [ppm] = 1.26 (t, 3H), 3.84 (s, 3H), 4.00 (q, 2H), 5.60 (s, 2H), 6.66-6.76 (m, 2H), 6.76-6.91 (m, 2H), 7.17 (t, 1H), 7.40 (t, 1H), 7.69 (d, 1H), 7.93 (s, 1H), 8.52 (d, 1H). |

Intermediate 1-7-1

Preparation of 2-(1 H-indazol-3-yl)-5-methoxypyrimidin-4-amine

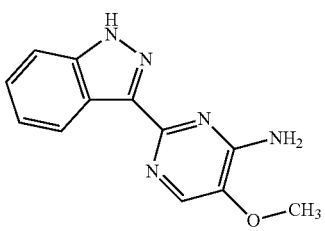 [SMILES: COc1cnc(-c2n[nH]c3ccccc23)nc1N]

7.0 g of 5-Methoxy-2-[1-(4-methoxybenzyl)-1 H-indazol-3-yl]pyrimidin-4-amine 1-6-1 (19.4 mmol, 1.0 eq.) was dissolved in 76 mL 1,2-dichloroethane and 44.8 mL trifluoroacetic acid (581 mmol, 30 eq.) and 17.1 mL trifluoromethanesulfonic acid (194 mmol, 10 eq.) were added drop wise. The reaction mixture was warmed to 75° C. and stirred for 2 h. The reaction mixture was treated with half-sat. sodium carbonate-solution. White material precipitated and was filtered off. To reduce the salt content the filter cake was suspended in water and stirred for 1 h. The water was filtered off and the new filter cake was dried under reduced pressure to provide the analytically pure product: 3.97 g, 16.5 mmol, 85%.

$^1$H-NMR (400 MHz, DMSO-d6): δ [ppm]=3.90 (s, 3H), 6.83 (br. s., 2H), 7.13-7.22 (m, 1H), 7.32-7.39 (m, 1H), 7.56 (d, 1H), 8.00 (s, 1H), 8.56 (d, 1H), 13.20 (br. s, 1H).

Intermediate 1-8-1

Preparation of 2-{1-[2,6-difluoro-4-(2-methoxyethoxy)benzyl]-1 H-indazol-3-yl}-5-methoxypyrimidin-4-amine

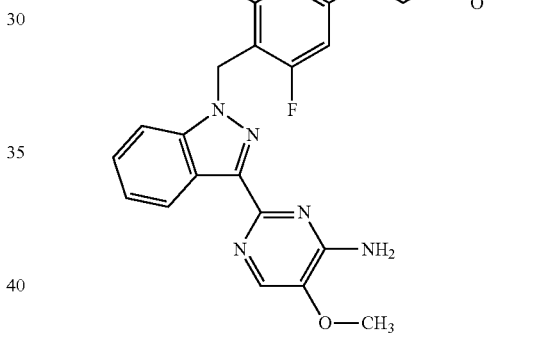

1.0 g 2-(1 H-Indazol-3-yl)-5-methoxypyrimidin-4-amine 1-7-1 (4.1 mmol, 1.0 eq.) was dissolved in 8.0 mL DMF. 182 mg sodium hydride (60%, 4.6 mmol, 1.1 eq.) was added and this mixture was stirred for 15 min at room temperature. Now 153 mg tetra-n-butylammoniumiodide (0.42 mmol, 0.1 eq.) was added and the mixture was cooled to 0° C. with an ice bath. At this temperature 1.3 g 2-(bromomethyl)-1,3-difluoro-5-(2-methoxyethoxy)benzene 1-2-1 (4.6 mmol, 1.1 eq., dissolved in 1 mL DMF) was added drop wise (slowly). At least the ice bath was removed and the mixture was stirred overnight at room temperature. The reaction mixture was diluted with water and dichloromethane. The layers were separated and the aqueous layer was extracted with dichloromethane twice. The combined organic layers were dried using a water resistant filter and the filtrate was dried under reduced pressure. The crude product was treated with Methanol. A white precipitate was filtered off under vacuo and the filter cake was dried in a vacuo drying oven at 50° C. for 2 hours to provide the 95% pure target compound: 1.0 g, 2.2 mmol, 52%.

$^1$H-NMR (400 MHz, DMSO-d6): δ [ppm]=3.26 (s, 3H), 3.54-3.64 (m, 2H), 3.87 (s, 3H), 4.05-4.15 (m, 2H), 5.62 (s, 2H), 6.68-6.95 (m, 4H), 7.15-7.26 (m, 1H), 7.37-7.48 (m, 1H), 7.72 (d, 1H), 7.96 (s, 1H), 8.55 (d, 1H).

The following intermediates were prepared according to the same procedure from the indicated starting material (SM=starting material):

| | | | |
|---|---|---|---|
| 1-8-2<br>SM1 = 1-7-1<br>SM2 = 1-15-1 | 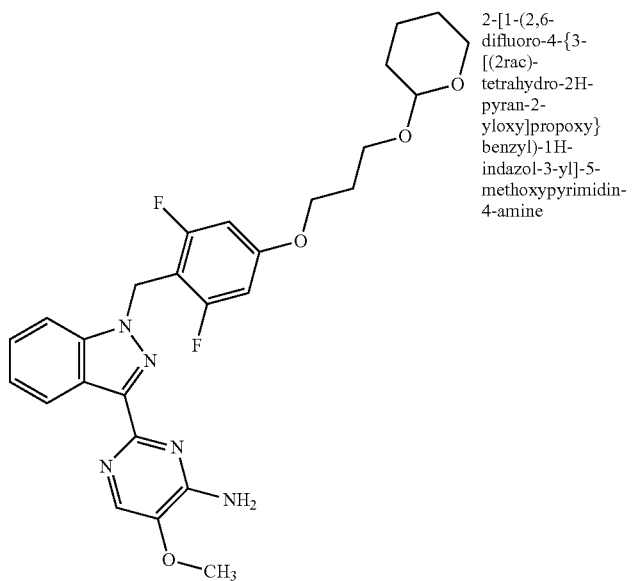 | 2-[1-(2,6-difluoro-4-{3-[(2rac)-tetrahydro-2H-pyran-2-yloxy]propoxy}benzyl)-1H-indazol-3-yl]-5-methoxypyrimidin-4-amine | ¹H-NMR (400 MHz, DMSO-d₆): δ [ppm] = 1.31-1.49 (m, 4H), 1.53-1.74 (m, 2H), 1.92 (t, 2H), 3.34-3.48 (m, 2H), 3.63-3.77 (m, 2H), 3.87 (s, 3H), 4.05 (t, 2H), 4.48-4.56 (m, 1H), 5.62 (s, 2H), 6.70-6.96 (m, 4H), 7.17-7.23 (m, 1H), 7.38-7.46 (m, 1H), 7.71 (d, 1H), 7.96 (s, 1H), 8.54 (d, 1H). |
| 1-8-3<br>SM1 = 1-7-1<br>SM2 = 1-15-2 | 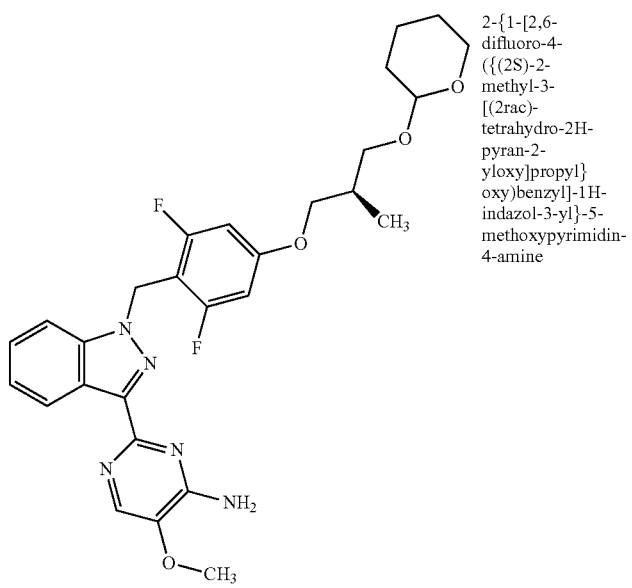 | 2-{1-[2,6-difluoro-4-({(2S)-2-methyl-3-[(2rac)-tetrahydro-2H-pyran-2-yloxy]propyl}oxy)benzyl]-1H-indazol-3-yl}-5-methoxypyrimidin-4-amine | ¹H-NMR (400 MHz, DMSO-d₆): δ [ppm] = 0.97 (d, 3H), 1.33-1.50 (m, 4H), 1.52-1.62 (m, 1H), 1.63-1.75 (m, 1H), 2.07-2.20 (m, 1H), 3.24-3.33 (m, 1H), 3.35-3.43 (m, 1H), 3.53-3.72 (m, 2H), 3.84-3.99 (m, 5H), 4.52 (q, 1H), 5.64 (s, 2H), 6.70-7.05 (m, 4H), 7.22 (t, 1H), 7.40-7.48 (m, 1H), 7.74 (d, 1H), 7.97 (s, 1H), 8.56 (d, 1H). |

Intermediate 1-9-1

Preparation of N-(3-chloropyridin-4-yl)-2-{1-[2,6-difluoro-4-(2-methoxyethoxy)benzyl]-1 H-indazol-3-yl}-5-methoxypyrimidin-4-amine

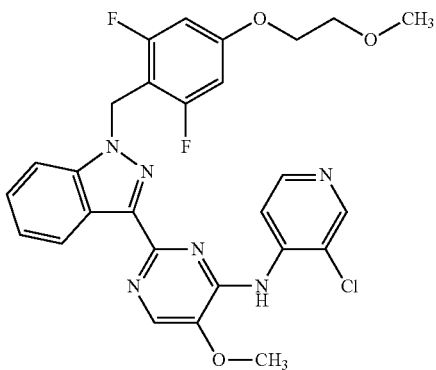 [SMILES: COCCOc1cc(F)c(Cn2nc(-c3ncc(OC)c(Nc4ccncc4Cl)n3)c3ccccc32)c(F)c1]

200 mg of 2-{1-[2,6-Difluoro-4-(2-methoxyethoxy)benzyl]-1 H-indazol-3-yl}-5-methoxypyrimidin-4-amine 1-8-1 (99% pure, 0.45 mmol, 1.0 eq.) was dissolved in 1.7 mL DMF. 118 mg 4-iodo-3-chloropyridine (CAS: 77332-79-7, 0.49 mmol, 1.1 eq.), 438 mg cesium carbonate (1.35 mmol, 3.0 eq.), 10 mg palladium(II)acetate (0.045 mmol, 0.1 eq.) and 39 mg 4,5-Bis(diphenylphosphino)-9,9-dimethylxanthene (0.067 mmol, 0.15 eq.) were added and the mixture was stirred at 105° C. for 16 h. The reaction mixture was diluted with water and dichloromethane. The layers were separated and the aqueous layer was extracted with dichloromethane twice. The combined organic layers were dried using a water resistant filter and the filtrate was concentrated in vacuo.

The crude product was purified by flash chromatography to provide the analytically pure target compound: 177 mg, 0.32 mmol, 71%.

$^1$H-NMR (300 MHz, DMSO-d$_6$): δ [ppm]=3.25 (s, 3H), 3.55-3.66 (m, 2H), 4.00-4.17 (m, 5H), 5.68 (s, 2H), 6.73-6.91 (m, 2H), 7.25 (t, 1H), 7.48 (t, 1H), 7.85 (d, 1H), 8.27 (s, 1H), 8.38 (d, 1H), 8.43-8.51 (m, 2H), 8.64 (s, 1H), 8.96 (d, 1H).

The following intermediate was prepared according to the same procedure from the indicated starting material (SM=starting material):

| | | | |
|---|---|---|---|
| 1-9-2<br>SM1 = 1-8-1<br>SM2 = CAS: 22282-99-1 | 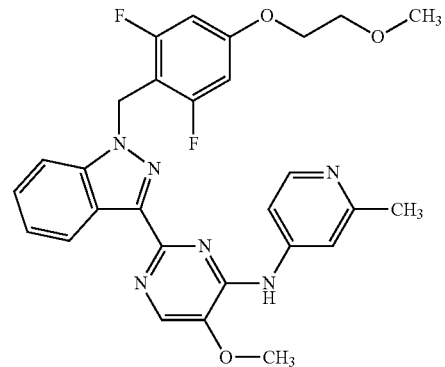 [SMILES: COCCOc1cc(F)c(Cn2nc(-c3ncc(OC)c(Nc4ccnc(C)c4)n3)c3ccccc32)c(F)c1] | 2-{1-[2,6-difluoro-4-(2-methoxyethoxy)benzyl]-1H-indazol-3-yl}-5-methoxy-N-(2-methylpyridin-4-yl)pyrimidin-4-amine | $^1$H-NMR (600 MHz, DMSO-d$_6$): δ [ppm] = 2.46 (s, 3H), 3.27 (s, 3H), 3.59-3.67 (m, 2H), 4.04 (s, 3H), 4.09-4.17 (m, 2H), 5.71 (s, 2H), 6.77-6.86 (m, 2H), 7.28 (t, 1H), 7.47-7.54 (m, 1H), 7.85 (d, 1H), 7.90 (dd, 1H), 8.15 (d, 1H), 8.29 (d, 1H), 8.35 (s, 1H), 8.50 (d, 1H), 9.29 (s, 1H) |
| 1-9-3<br>SM1 = 1-8-1<br>SM2 = CAS: 1209335-53-4 | 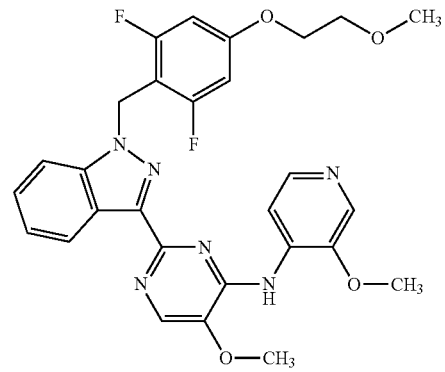 [SMILES: COCCOc1cc(F)c(Cn2nc(-c3ncc(OC)c(Nc4ccncc4OC)n3)c3ccccc32)c(F)c1] | 2-{1-[2,6-difluoro-4-(2-methoxyethoxy)benzyl]-1H-indazol-3-yl}-5-methoxy-N-(3-methoxypyridin-4-yl)pyrimidin-4-amine | $^1$H-NMR (300 MHz, DMSO-d6): δ [ppm] = 3.25 (s, 3H), 3.56-3.65 (m, 2H), 4.02 (s, 3H), 4.05 (s, 3H), 4.07-4.16 (m, 2H), 5.68 (s, 2H), 6.78-6.90 (m, 2H), 7.27 (t, 1H), 7.43-7.54 (m, 1H), 7.85 (d, 1H), 8.07 (s, 1H), 8.20 (d, 1H), 8.36 (d, 2H), 8.45 (d, 1H), 8.95 (d, 1H). |

| | | | |
|---|---|---|---|
| 1-9-4<br>SM1 =<br>1-8-1<br>SM2 =<br>CAS:<br>1026796-81-5 | 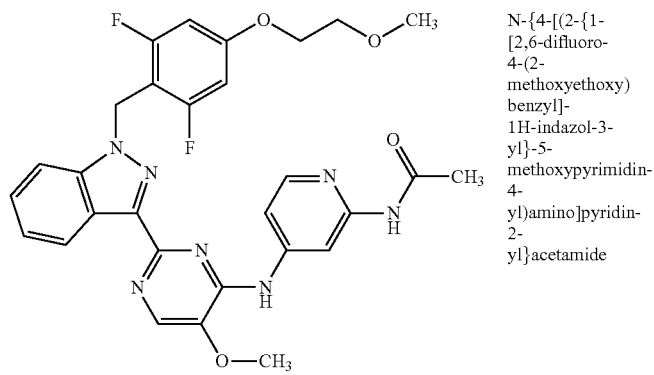 | N-{4-[(2-{1-[2,6-difluoro-4-(2-methoxyethoxy)benzyl]-1H-indazol-3-yl}-5-methoxypyrimidin-4-yl)amino]pyridin-2-yl}acetamide | 1H-NMR (400 MHz, DMSO-d$_6$): δ [ppm] = 2.07 (s, 3H), 3.25 (s, 3H), 3.55-3.65 (m, 2H), 4.00 (s, 3H), 4.07-4.15 (m, 2H), 5.67 (s, 2H), 6.72-6.86 (m, 2H), 7.21 (t, 1H), 7.46 (t, 1H), 7.80 (d, 1H), 8.15 (d, 1H), 8.26-8.38 (m, 3H), 8.44 (d, 1H), 9.46 (s, 1H), 10.27 (s, 1H) |
| 1-9-5<br>SM1 =<br>1-8-1<br>SM2 =<br>CAS:<br>40899-37-4 | 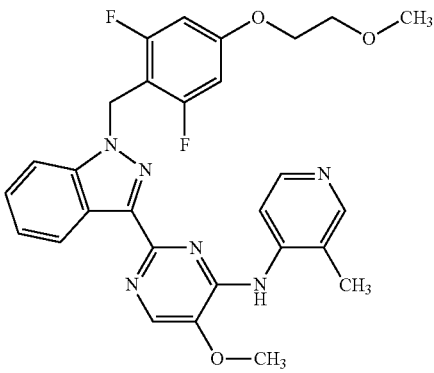 [SMILES: COCCOc1cc(F)c(Cn2nc(-c3ncc(OC)c(Nc4ccncc4C)n3)c3ccccc32)c(F)c1] | 2-{1-[2,6-difluoro-4-(2-methoxyethoxy)benzyl]-1H-indazol-3-yl}-5-methoxy-N-(3-methylpyridin-4-yl)pyrimidin-4-amine | $^1$H-NMR (300 MHz, DMSO-d$_6$): δ [ppm] = 2.25 (s, 3H), 3.25 (s, 3H), 3.57-3.65 (m, 2H), 4.03 (s, 3H), 4.07-4.17 (m, 2H), 5.64 (s, 2H), 6.73-6.87 (m, 2H), 7.10-7.21 (m, 1H), 7.39-7.49 (m, 1H), 7.79 (d, 1H), 8.16-8.44 (m, 6H) |
| 1-9-6<br>SM1 =<br>1-8-1<br>SM2 =<br>CAS:<br>1159811-44-5 | 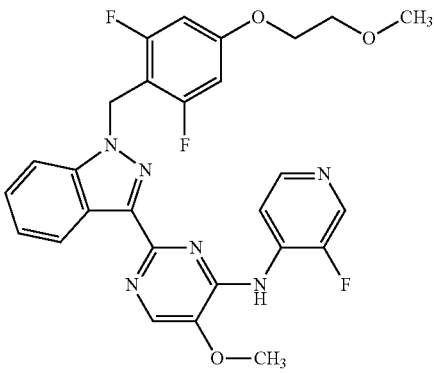 [SMILES: COCCOc1cc(F)c(Cn2nc(-c3ncc(OC)c(Nc4ccncc4F)n3)c3ccccc32)c(F)c1] | 2-{1-[2,6-difluoro-4-(2-methoxyethoxy)benzyl]-1H-indazol-3-yl}-N-(3-fluoropyridin-4-yl)-5-methoxypyrimidin-4-amine | $^1$H-NMR (400 MHz, CHLOROFORM-d): δ [ppm] = 3.43 (s, 3H), 3.67-3.78 (m, 2H), 4.03-4.15 (m, 5H), 5.72 (s, 2H), 6.54 (d, 2H), 7.21-7.34 (m, 1H), 7.40-7.51 (m, 1H), 7.58-7.67 (m, 1H), 7.70-7.79 (m, 1H), 8.27 (s, 1H), 8.48 (br. s., 2H), 8.56 (d, 1H), 9.08-9.20 (m, 1H). |
| 1-9-7<br>SM1 =<br>1-8-1<br>SM2 =<br>CAS:<br>1422766-41-3 | 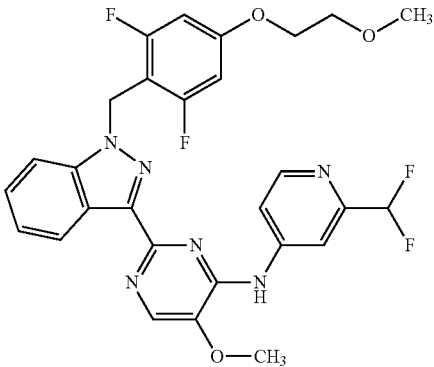 [SMILES: COCCOc1cc(F)c(Cn2nc(-c3ncc(OC)c(Nc4ccnc(C(F)F)c4)n3)c3ccccc32)c(F)c1] | 2-{1-[2,6-difluoro-4-(2-methoxyethoxy)benzyl]-1H-indazol-3-yl}-N-[2-(difluoromethyl)pyridin-4-yl]-5-methoxypyrimidin-4-amine | $^1$H-NMR (400 MHz, DMSO-d$_6$): δ [ppm] = 3.24 (s, 3H), 3.55-3.63 (m, 2H), 4.04 (s, 3H), 4.06-4.14 (m, 2H), 5.69 (s, 2H), 6.69-7.02 (m, 3H), 7.20-7.29 (m, 1H), 7.43-7.52 (m, 1H), 7.77-7.85 (m, 1H), 8.35 (d, 1H), 8.39 (s, 1H), 8.42-8.48 (m, 1H), 8.48-8.56 (m, 2H), 9.72 (s, 1H) |

| | | | |
|---|---|---|---|
| 1-9-8<br>SM1 = 1-8-1<br>SM2 = CAS: 17117-23-6 | 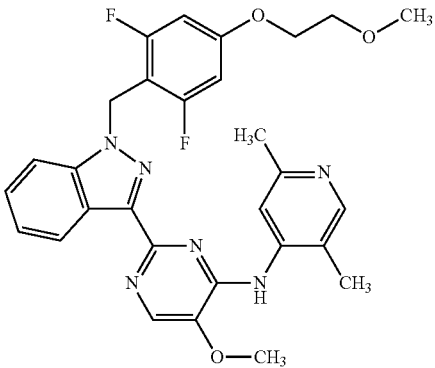 [SMILES: COCCOc1cc(F)c(Cn2nc(-c3ncc(OC)c(Nc4cc(C)ncc4C)n3)c3ccccc32)c(F)c1] | 2-{1-[2,6-difluoro-4-(2-methoxyethoxy)benzyl]-1H-indazol-3-yl}-N-(2,5-dimethylpyridin-4-yl)-5-methoxypyrimidin-4-amine | $^1$H-NMR (400 MHz, DMSO-d$_6$): δ [ppm] = 2.23 (s, 3H), 2.46 (s, 3H), 3.27 (s, 3H), 3.60-3.65 (m, 2H), 4.05 (s, 3H), 4.09-4.16 (m, 2H), 5.67 (s, 2H), 6.75-6.85 (m, 2H), 7.18 (t, 1H), 7.42-7.51 (m, 1H), 7.80 (d, 1H), 8.16 (d, 2H), 8.27 (s, 1H), 8.30-8.36 (m, 2H) |
| 1-9-9<br>SM1 = 1-8-1<br>SM2 = CAS: 1314355-04-8 | 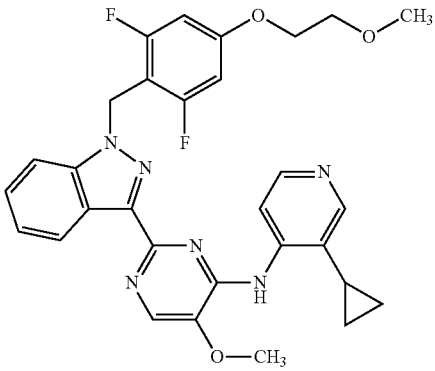 [SMILES: COCCOc1cc(F)c(Cn2nc(-c3ncc(OC)c(Nc4ccncc4C4CC4)n3)c3ccccc32)c(F)c1] | N-(3-cyclopropylpyridin-4-yl)-2-{1-[2,6-difluoro-4-(2-methoxyethoxy)benzyl]-1H-indazol-3-yl}-5-methoxypyrimidin-4-amine | $^1$H-NMR (400 MHz, DMSO-d$_6$): δ [ppm] = 0.65-0.73 (m, 2H), 0.97-1.08 (m, 2H), 1.84-1.98 (m, 1H), 3.25 (s, 3H), 3.57-3.66 (m, 2H), 4.04-4.15 (m, 5H), 5.68 (s, 2H), 6.77-6.88 (m, 2H), 7.21-7.29 (m, 1H), 7.44-7.53 (m, 1H), 7.83 (d, 1H), 8.34 (s, 1H), 8.36-8.47 (m, 4H), 8.76 (d, 1H). |
| 1-9-10<br>SM1 = 1-8-1<br>SM2 = CAS: 4994-86-9 | 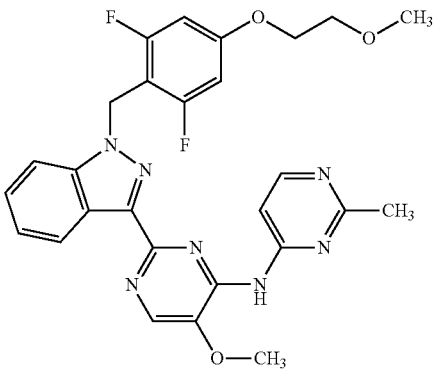 | 2-{1-[2,6-difluoro-4-(2-methoxyethoxy)benzyl]-1H-indazol-3-yl}-5-methoxy-N-(2-methylpyrimidin-4-yl)pyrimidin-4-amine | $^1$H-NMR (400 MHz, DMSO-d$_6$): δ [ppm] = 2.56 (s, 3H), 3.27 (s, 3H), 3.58-3.67 (m, 2H), 4.03 (s, 3H), 4.08-4.17 (m, 2H), 5.70 (s, 2H), 6.82-6.91 (m, 2H), 7.24-7.33 (m, 1H), 7.47-7.54 (m, 1H), 7.87 (d, 1H), 8.45 (s, 1H), 8.49 (d, 1H), 8.53-8.59 (m, 2H), 8.93 (s, 1H). |
| 1-9-12<br>SM1 = 1-8-1<br>SM2 = CAS: 128071-98-7 | 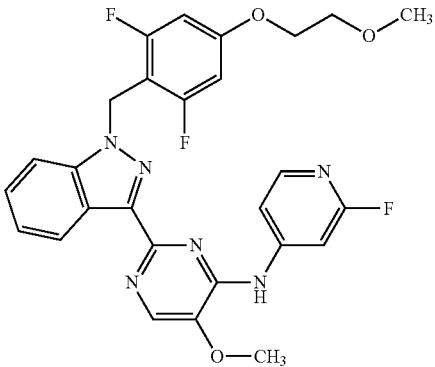 [SMILES: COCCOc1cc(F)c(Cn2nc(-c3ncc(OC)c(Nc4ccnc(F)c4)n3)c3ccccc32)c(F)c1] | 2-{1-[2,6-difluoro-4-(2-methoxyethoxy)benzyl]-1H-indazol-3-yl}-N-(2-fluoropyridin-4-yl)-5-methoxypyrimidin-4-amine | $^1$H-NMR (400 MHz, DMSO-d6): δ [ppm] = 3.25 (s, 3H), 3.57-3.63 (m, 2H), 4.04 (s, 3H), 4.10 (dd, 2H), 5.68 (s, 2H), 6.72-6.83 (m, 2H), 7.26 (t, 1H), 7.46-7.51 (m, 1H), 7.84 (d, 1H), 7.99-8.07 (m, 2H), 8.09 (d, 1H), 8.41 (s, 1H), 8.46 (d, 1H), 9.72 (s, 1H). |

| | | | |
|---|---|---|---|
| 1-9-13<br>SM1 = 1-8-1<br>SM2 =<br>CAS: 1211590-24-7 | 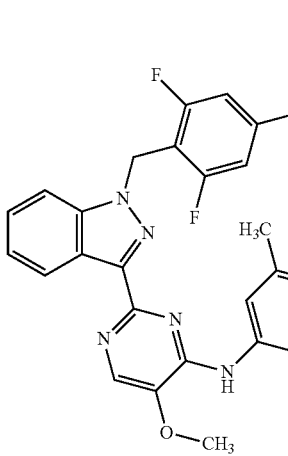 | 2-{1-[2,6-difluoro-4-(2-methoxyethoxy)benzyl]-1H-indazol-3-yl}-N-(5-fluoro-2-methylpyridin-4-yl)-5-methoxypyrimidin-4-amine | ¹H-NMR (400 MHz, DMSO-d6): δ [ppm] = 2.63 (s, 3H), 3.44 (s, 3H), 3.68-3.77 (m, 2H), 4.01-4.13 (m, 5H), 5.75 (s, 2H), 6.42-6.60 (m, 2H), 7.22-7.34 (m, 1H), 7.45 (t, 1H), 7.60 (d, 1H), 7.70 (d, 1H), 8.28 (s, 1H), 8.34 (d, 1H), 8.61 (d, 1H), 8.94 (d, 1H). |
| 1-9-14<br>SM1 = 1-8-1<br>SM2 =<br>CAS: 31462-56-3 | 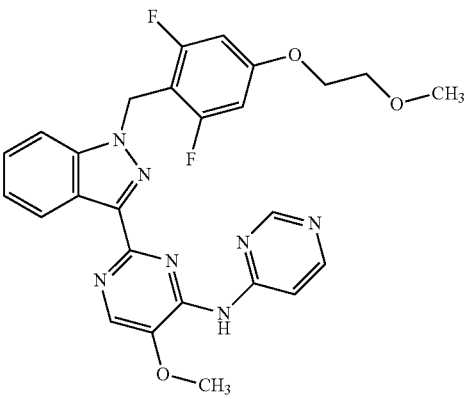 [SMILES: COCCOc1cc(F)c(Cn2nc(-c3ncc(OC)c(Nc4ccncn4)n3)c3ccccc32)c(F)c1] | 2-{1-[2,6-difluoro-4-(2-methoxyethoxy)benzyl]-1H-indazol-3-yl}-5-methoxy-N-(pyrimidin-4-yl)pyrimidin-4-amine | ¹H-NMR (400 MHz, DMSO-d6): δ [ppm] = 3.25 (s, 3H), 3.58-3.64 (m, 2H), 4.02 (s, 3H), 4.08-4.14 (m, 2H), 5.68 (s, 2H), 6.81-6.89 (m, 2H), 7.25-7.31 (m, 1H), 7.44-7.52 (m, 1H), 7.85 (d, 1H), 8.44-8.51 (m, 2H), 8.63 (d, 1H), 8.74 (dd, 1H), 8.87 (d, 1H), 9.10 (s, 1H). |
| 1-9-15<br>SM1 = 1-8-1<br>SM2 =<br>CAS: 1-14-1 | 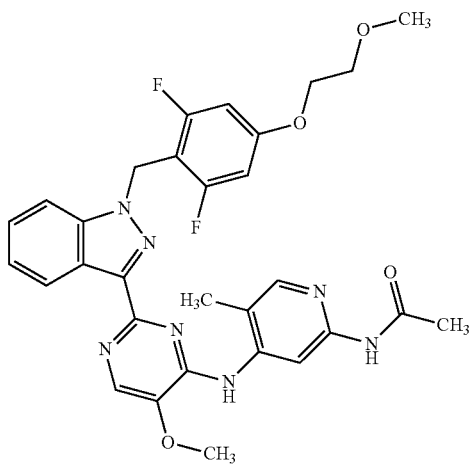 [SMILES: COCCOc1cc(F)c(Cn2nc(-c3ncc(OC)c(Nc4cc(NC(C)=O)ncc4C)n3)c3ccccc32)c(F)c1] | N-{4-[(2-{1-[2,6-difluoro-4-(2-methoxyethoxy)benzyl]-1H-indazol-3-yl}-5-methoxypyrimidin-4-yl)amino]-5-methylpyridin-2-yl}acetamide | ¹H-NMR (400 MHz, DMSO-d6): δ [ppm] = 2.03 (s, 3H), 2.12 (s, 3H), 3.26 (s, 3H), 3.58-3.66 (m, 2H), 4.01 (s, 3H), 4.07-4.14 (m, 2H), 5.60 (s, 2H), 6.72-6.83 (m, 2H), 6.99 (t, 1H), 7.33-7.43 (m, 1H), 7.70 (d, 1H), 8.05 (d, 1H), 8.17 (s, 1H), 8.22 (s, 1H), 8.29 (s, 1H), 8.81 (s, 1H), 10.39 (s, 1H). |

| | | | |
|---|---|---|---|
| 1-9-16<br>SM1 =<br>1-8-2<br>SM2 =<br>CAS:<br>17117-<br>23-6 | 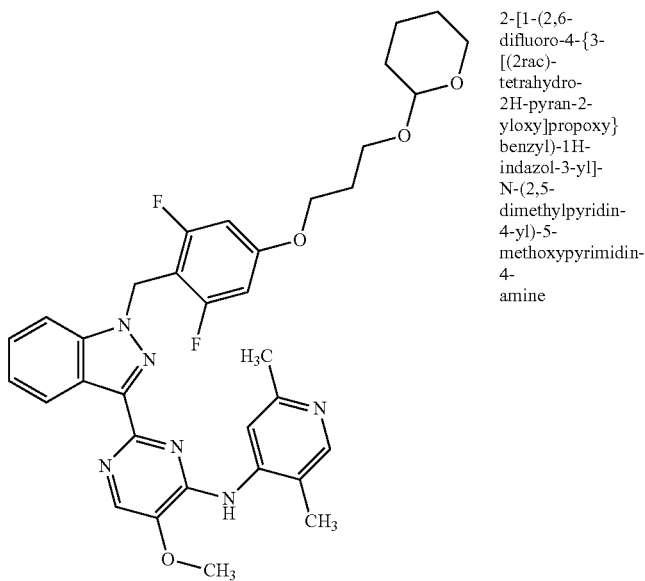 | 2-[1-(2,6-difluoro-4-{3-[(2rac)-tetrahydro-2H-pyran-2-yloxy]propoxy}benzyl)-1H-indazol-3-yl]-N-(2,5-dimethylpyridin-4-yl)-5-methoxypyrimidin-4-amine | ¹H-NMR (400 MHz, DMSO-d6): δ [ppm] = 1.32-1.49 (m, 4H), 1.52-1.74 (m, 2H), 1.94 (quin, 2H), 2.23 (s, 3H), 2.46 (s, 3H), 3.35-3.48 (m, 2H), 3.64-3.77 (m, 2H), 4.02-4.10 (m, 5H), 4.54 (t, 1H), 5.67 (s, 2H), 6.74-6.82 (m, 2H), 7.18 (t, 1H), 7.43-7.49 (m, 1H), 7.81 (d, 1H), 8.16 (s, 1H), 8.27 (s, 1H), 8.30-8.35 (m, 2H). |
| 1-9-17<br>SM1 =<br>1-8-2<br>SM2 =<br>CAS:<br>1209335-<br>53-4 | 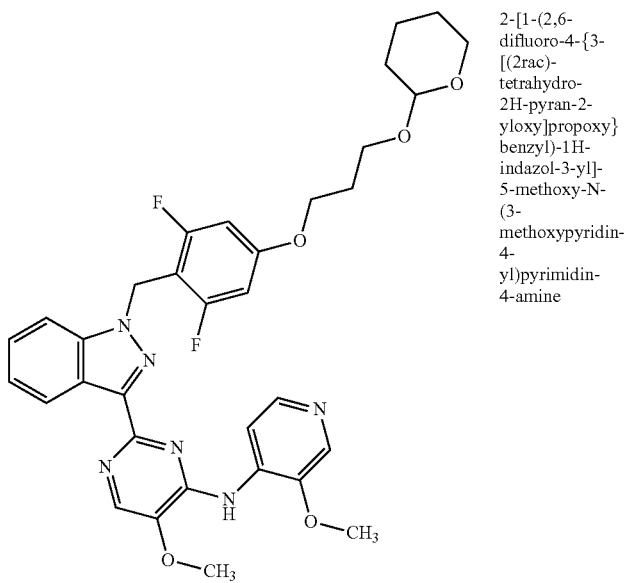 | 2-[1-(2,6-difluoro-4-{3-[(2rac)-tetrahydro-2H-pyran-2-yloxy]propoxy}benzyl)-1H-indazol-3-yl]-5-methoxy-N-(3-methoxypyridin-4-yl)pyrimidin-4-amine | ¹H-NMR (400 MHz, DMSO-d6): δ [ppm] = 1.30-1.47 (m, 4H), 1.50-1.72 (m, 2H), 1.89-1.99 (m, 2H), 3.34-3.48 (m, 2H), 3.62-3.78 (m, 2H), 4.01-4.11 (m, 8H), 4.47-4.56 (m, 1H), 5.70 (s, 2H), 6.79-6.89 (m, 2H), 7.29 (t, 1H), 7.47-7.54 (m, 1H), 7.87 (d, 1H), 8.09 (s, 1H), 8.21 (d, 1H), 8.37 (s, 1H), 8.40 (s, 1H), 8.46 (d, 1H), 8.96 (d, 1H). |

-continued

| | | | |
|---|---|---|---|
| 1-9-18 SM1 = 1-8-2 SM2 = CAS: 4994-86-9 | 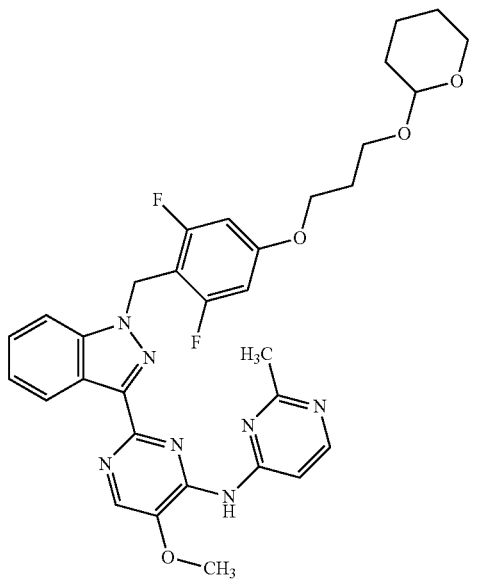 [SMILES: COc1cnc(-c2nn(Cc3c(F)cc(OCCCOC4CCCCO4)cc3F)c3ccccc23)nc1Nc1ccnc(C)n1] | 2-[1-(2,6-difluoro-4-{3-[(2rac)-tetrahydro-2H-pyran-2-yloxy]propoxy}benzyl)-1H-indazol-3-yl]-5-methoxy-N-(2-methylpyrimidin-4-yl)pyrimidin-4-amine | $^1$H-NMR (400 MHz, DMSO-d6): δ [ppm] = 1.29-1.48 (m, 4H), 1.50-1.73 (m, 2H), 1.88-2.00 (m, 2H), 2.56 (s, 3H), 3.36-3.49 (m, 2H), 3.62-3.78 (m, 2H), 4.02 (s, 3H), 4.07 (t, 2H), 4.52 (br. s., 1H), 5.70 (s, 2H), 6.78-6.91 (m, 2H), 7.29 (t, 1H), 7.51 (t, 1H), 7.87 (d, 1H), 8.44 (s, 1H), 8.49 (d, 1H), 8.54 (d, 1H), 8.57 (d, 1H), 8.94 (s, 1H). |
| 1-9-19 SM1 = 1-8-1 SM2 = 1-16-1 | 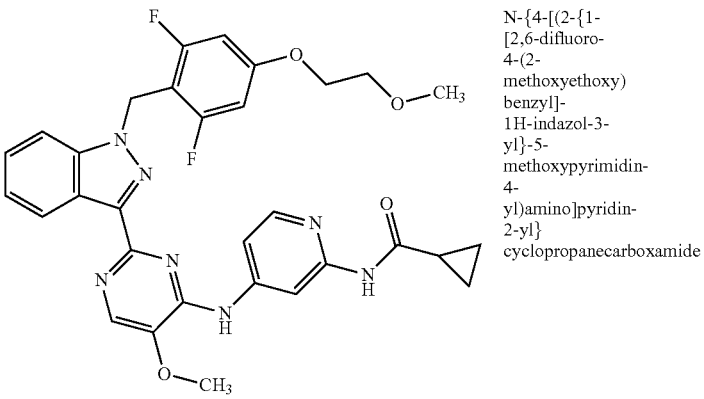 | N-{4-[(2-{1-[2,6-difluoro-4-(2-methoxyethoxy)benzyl]-1H-indazol-3-yl}-5-methoxypyrimidin-4-yl)amino]pyridin-2-yl}cyclopropanecarboxamide | LC-MS: retention time: 1.28 min MS ES+: 602.5 [M + H]+ Method 5 |
| 1-9-20 SM1 = 1-8-1 SM2 = 1-17-1 | 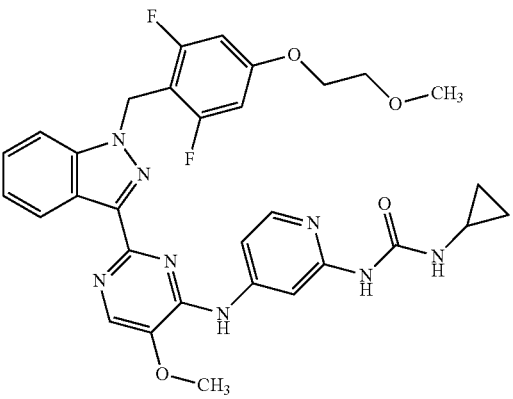 [SMILES: COCCOc1cc(F)c(Cn2nc(-c3ncc(OC)c(Nc4ccnc(NC(=O)NC5CC5)c4)n3)c3ccccc32)c(F)c1] | 1-cyclopropyl-3-{4-[(2-{1-[2,6-difluoro-4-(2-methoxyethoxy)benzyl]-1H-indazol-3-yl}-5-methoxypyrimidin-4-yl)amino]pyridin-2-yl}urea | $^1$H-NMR (400 MHz, DMSO-d6): δ [ppm] = 0.42-0.49 (m, 2H), 0.62-0.71 (m, 2H), 2.58-2.66 (m, 1H), 3.27 (s, 3H), 3.59-3.66 (m, 2H), 4.02 (s, 3H), 4.09-4.17 (m, 2H), 5.68 (s, 2H), 6.77-6.90 (m, 2H), 7.18-7.26 (m, 1H), 7.44-7.52 (m, 1H), 7.56 (br. s, 1H), 7.83 (d, 1H), 8.02-8.07 (m, 1H), 8.07-8.12 (m, 1H), 8.33 (s, 1H), 8.45 (d, 2H), 8.97 (br. s, 1H), 9.43 (s, 1H). |

| | | | |
|---|---|---|---|
| 1-9-22 SM1 = 1-8-1 SM2 = CAS: 1227592-47-3 | 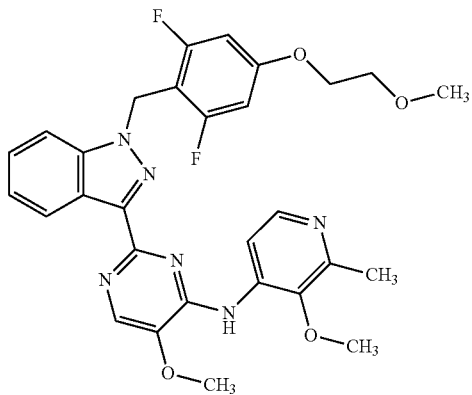 [SMILES: COCCOc1cc(F)c(Cn2nc(-c3ncc(OC)c(Nc4ccnc(C)c4OC)n3)c3ccccc32)c(F)c1] | 2-{1-[2,6-difluoro-4-(2-methoxyethoxy)benzyl]-1H-indazol-3-yl}-5-methoxy-N-(3-methoxy-2-methylpyridin-4-yl)pyrimidin-4-amine | $^1$H-NMR (400 MHz, DMSO-d6): δ [ppm] = 2.48 (s, 3H), 3.26 (s, 3H), 3.56-3.66 (m, 2H), 3.83 (s, 3H), 4.08 (s, 3H), 4.09-4.17 (m, 2H), 5.70 (s, 2H), 6.78-6.90 (m, 2H), 7.24-7.32 (m, 1H), 7.47-7.54 (m, 1H), 7.87 (d, 1H), 8.14 (s, 1H), 8.20 (d, 1H), 8.41 (s, 1H), 8.46 (d, 1H), 8.80 (d, 1H). |
| 1-9-23 SM1 = 1-8-3 SM2 = CAS: 4994-86-9 | 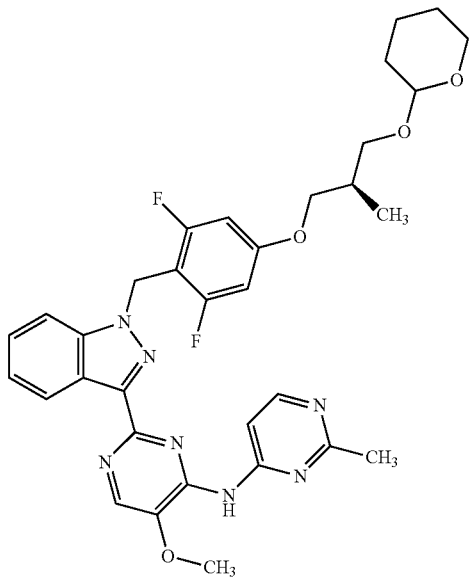 [SMILES: COc1cnc(-c2nn(Cc3c(F)cc(OC[C@H](C)COC4CCCCO4)cc3F)c3ccccc23)nc1Nc1ccnc(C)n1] | 2-{1-[2,6-difluoro-4-({(2S)-2-methyl-3-[(2rac)-tetrahydro-2H-pyran-2-yloxy]propyl}oxy)benzyl]-1H-indazol-3-yl}-5-methoxy-N-(2-methylpyrimidin-4-yl)pyrimidin-4-amine | $^1$H-NMR (400 MHz, DMSO-d6): δ [ppm] = 0.97 (d, 3H), 1.29-1.48 (m, 4H), 1.49-1.70 (m, 2H), 2.07-2.18 (m, 1H), 2.55 (s, 3H), 3.24-3.31 (m, 1H), 3.53-3.70 (m, 2H), 3.86-3.98 (m, 2H), 4.02 (s, 3H), 4.37 (t, 1H), 4.48-4.54 (m, 1H), 5.70 (s, 2H), 6.81-6.89 (m, 2H), 7.25-7.33 (m, 1H), 7.47-7.54 (m, 1H), 7.86 (d, 1H), 8.44 (s, 1H), 8.49 (d, 1H), 8.52-8.60 (m, 2H), 8.94 (s, 1H). |
| 1-9-24 SM1 = 1-8-3 SM2 = CAS: 17117-23-6 | 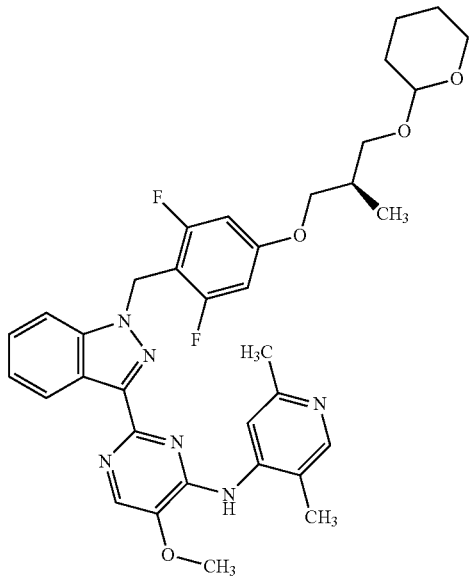 [SMILES: COc1cnc(-c2nn(Cc3c(F)cc(OC[C@H](C)COC4CCCCO4)cc3F)c3ccccc23)nc1Nc1cc(C)ncc1C] | 2-{1-[2,6-difluoro-4-({(2S)-2-methyl-3-[(2rac)-tetrahydro-2H-pyran-2-yloxy]propyl}oxy)benzyl]-1H-indazol-3-yl}-N-(2,5-dimethylpyridin-4-yl)-5-methoxypyrimidin-4-amine | $^1$H-NMR (400 MHz, DMSO-d6): δ [ppm] = 0.97 (d, 3H), 1.31-1.49 (m, 4H), 1.51-1.74 (m, 2H), 2.06-2.18 (m, 1H), 2.23 (s, 3H), 2.46 (s, 3H), 3.24-3.42 (m, 2H), 3.53-3.71 (m, 2H), 3.85-3.99 (m, 2H), 4.05 (s, 3H), 4.49-4.55 (m, 1H), 5.67 (s, 2H), 6.74-6.83 (m, 2H), 7.18 (t, 1H), 7.43-7.50 (m, 1H), 7.81 (d, 1H), 8.16 (d, 2H), 8.27 (s, 1H), 8.30-8.36 (m, 2H). |

| | | | |
|---|---|---|---|
| 1-9-25<br>SM1 = 1-8-3<br>SM2 =<br>CAS: 1026796-81-5 | 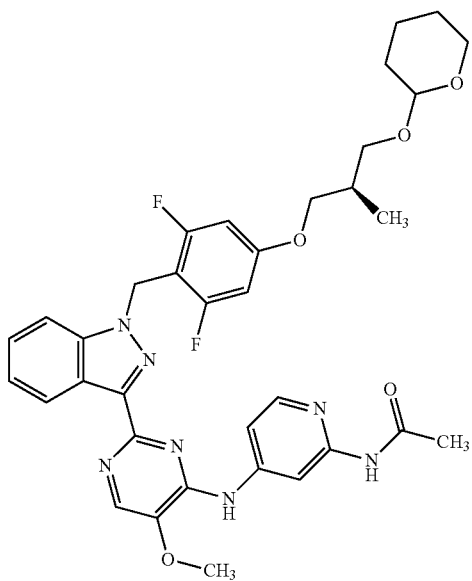 [SMILES: COc1cnc(-c2nn(Cc3c(F)cc(OC[C@H](C)COC4CCCCO4)cc3F)c3ccccc23)nc1Nc1ccnc(NC(C)=O)c1] | N-{4-[(2-{1-[2,6-difluoro-4-({(2S)-2-methyl-3-[(2rac)-tetrahydro-2H-pyran-2-yloxy]propyl}oxy)benzyl]-1H-indazol-3-yl}-5-methoxypyrimidin-4-yl)amino]pyridin-2-yl}acetamide | ¹H-NMR (400 MHz, DMSO-d6): δ [ppm] = 0.96 (d, 3H), 1.30-1.48 (m, 4H), 1.49-1.72 (m, 2H), 2.05-2.18 (m, 4H), 3.24-3.41 (m, 2H), 3.62 (dd, 2H), 3.85-3.98 (m, 2H), 4.01 (s, 3H), 4.46-4.54 (m, 1H), 5.68 (s, 2H), 6.76-6.85 (m, 2H), 7.23 (t, 1H), 7.43-7.52 (m, 1H), 7.83 (d, 1H), 8.17 (d, 1H), 8.29-8.35 (m, 2H), 8.39 (dd, 1H), 8.45 (d, 1H), 9.51 (s, 1H), 10.32 (s, 1H). |
| 1-9-26<br>SM1 = 1-8-3<br>SM2 =<br>CAS: 1209335-53-4 | 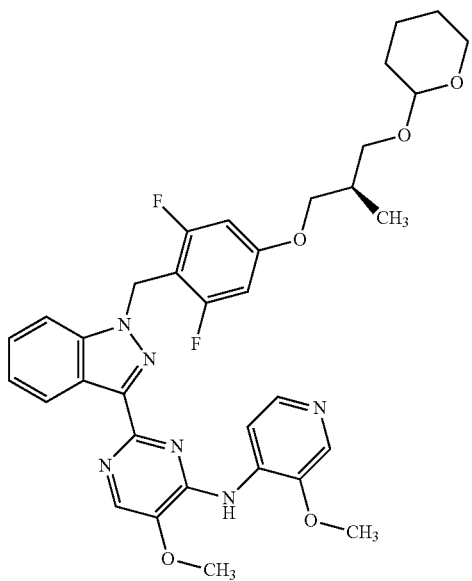 [SMILES: COc1cnccc1Nc1nc(-c2nn(Cc3c(F)cc(OC[C@H](C)COC4CCCCO4)cc3F)c3ccccc23)ncc1OC] | 2-{1-[2,6-difluoro-4-({(2S)-2-methyl-3-[(2rac)-tetrahydro-2H-pyran-2-yloxy]propyl}oxy)benzyl]-1H-indazol-3-yl}-5-methoxy-N-(3-methoxypyridin-4-yl)pyrimidin-4-amine | ¹H-NMR (400 MHz, DMSO-d6): δ [ppm] = 0.96 (d, 3H), 1.29-1.48 (m, 4H), 1.49-1.72 (m, 2H), 2.06-2.18 (m, 1H), 2.07-2.18 (m, 1H), 3.23-3.40 (m, 2H), 3.52-3.70 (m, 2H), 3.85-3.98 (m, 2H), 4.03 (s, 3H), 4.06 (s, 3H), 4.45-4.54 (m, 1H), 5.69 (s, 2H), 6.78-6.89 (m, 2H), 7.25-7.32 (m, 1H), 7.46-7.54 (m, 1H), 7.87 (d, 1H), 8.08 (s, 1H), 8.21 (d, 1H), 8.36 (s, 1H), 8.39 (s, 1H), 8.47 (d, 1H), 8.96 (d, 1H). |

-continued

| | | | |
|---|---|---|---|
| 1-9-27 SM1 = 1-8-1 SM2 = CAS: 1256804-48-4 | 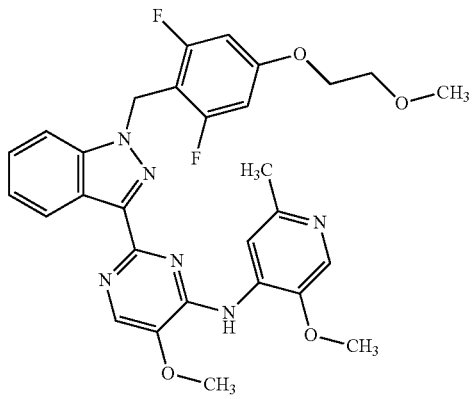 [SMILES: COCCOc1cc(F)c(Cn2nc(-c3ncc(OC)c(Nc4cc(C)ncc4OC)n3)c3ccccc32)c(F)c1] | 2-{1-[2,6-difluoro-4-(2-methoxyethoxy)benzyl]-1H-indazol-3-yl}-5-methoxy-N-(5-methoxy-2-methylpyridin-4-yl)pyrimidin-4-amine | ¹H-NMR (400 MHz, DMSO-d6): δ [ppm] = 2.47 (s, 3H), 3.27 (s, 3H), 3.57-3.66 (m, 2H), 3.99 (s, 3H), 4.06 (s, 3H), 4.08-4.16 (m, 2H), 5.72 (s, 2H), 6.74-6.85 (m, 2H), 7.30 (t, 1H), 7.46-7.55 (m, 1H), 7.86 (d, 1H), 8.05 (s, 1H), 8.19 (s, 1H), 8.39 (s, 1H), 8.51 (d, 1H), 8.80 (s, 1H). |
| 1-9-28 SM1 = 1-8-2 SM2 = CAS: 22282-99-1 | 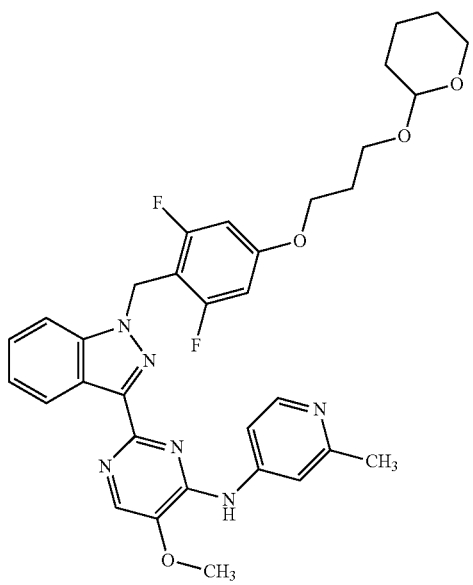 [SMILES: COc1cnc(-c2nn(Cc3c(F)cc(OCCCOC4CCCCO4)cc3F)c3ccccc23)nc1Nc1ccnc(C)c1] | 2-[1-(2,6-difluoro-4-{3-[(2rac)-tetrahydro-2H-pyran-2-yloxy]propoxy}benzyl)-1H-indazol-3-yl]-5-methoxy-N-(2-methylpyridin-4-yl)pyrimidin-4-amine | LC-MS: retention time: 1.45 min MS ES+: 618 [M + H]+ Method 5 |
| 1-9-29 SM1 = 1-8-1 SM2 = CAS: 4472-45-1 | 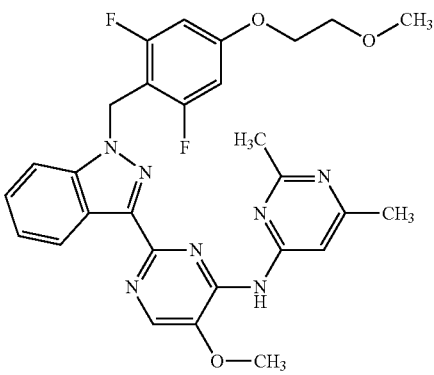 [SMILES: COCCOc1cc(F)c(Cn2nc(-c3ncc(OC)c(Nc4cc(C)nc(C)n4)n3)c3ccccc32)c(F)c1] | 2-{1-[2,6-difluoro-4-(2-methoxyethoxy)benzyl]-1H-indazol-3-yl}-N-(2,6-dimethylpyrimidin-4-yl)-5-methoxypyrimidin-4-amine | ¹H-NMR (400 MHz, CHLOROFORM-d): δ [ppm] = 2.60-2.78 (m, 6H), 3.44 (s, 3H), 3.68-3.76 (m, 2H), 4.01-4.14 (m, 5H), 5.74 (s, 2H), 6.46-6.59 (m, 2H), 7.24-7.33 (m, 1H), 7.40-7.50 (m, 1H), 7.62 (d, 1H), 8.12 (br. s., 1H), 8.29 (s, 1H), 8.60 (d, 1H), 8.68 (br. s., 1H). |

111

Intermediate 1-10-1

Preparation of 4-[(2-{1-[4-(2-{[tert-butyl(dimethyl)silyl]oxy}ethoxy)-2,6-difluorobenzyl]-1 H-indazol-3-yl}-5-methoxypyrimidin-4-yl)amino]pyridine-3-carboxamide

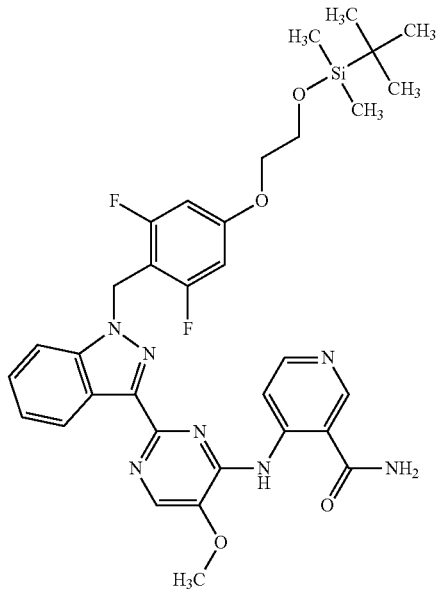 [SMILES: COc1cnc(-c2nn(Cc3c(F)cc(OCCO[Si](C)(C)C(C)(C)C)cc3F)c3ccccc23)nc1Nc1ccncc1C(N)=O]

107 mg of 4-({2-[1-(2,6-Difluoro-4-hydroxybenzyl)-1 H-indazol-3-yl]-5-methoxypyrimidin-4-yl}amino)pyridine-3-carboxamide 1-11-1 (60% pure, 0.13 mmol, 1.0 eq.) was dissolved in 2.9 mL DMF. Then 88 mg potassium carbonte (0.64 mmol, 5.0 eq.) and 0.04 mL of (3-Bromo-ethoxy)-tert-butyldimethylsilane (0.19 mmol, 1.5 eq.) were added. The mixture was stirred over night at 60° C. Again 0.02 mL of 0.04 mL of (3-Bromo-ethoxy)-tert-butyldimethylsilane (0.10 mmol, 0.8 eq.) were added and the reaction mixture was stirred at 60° C. over night. The reaction mixture was diluted with ethyl is acetate and water. The layers were separated and the aqueous layer was extracted with ethyl acetate twice. The combined organic layers were dried using a water resistant filter. The filtrate was concentrated under reduced pressure. The crude product was purified by flash chromatography to provide the 93% pure target compound: 34.6 mg, 0.05 mmol, 38%.

LC-MS:
retention time: 1.63 min
MS ES+: 662.3 [M+H]+
Method 5

112

Intermediate 1-11-1

Preparation of 4-({2-[1-(2,6-difluoro-4-hydroxybenzyl)-1 H-indazol-3-yl]-5-methoxypyrimidin-4-yl}amino)pyridine-3-carboxamide

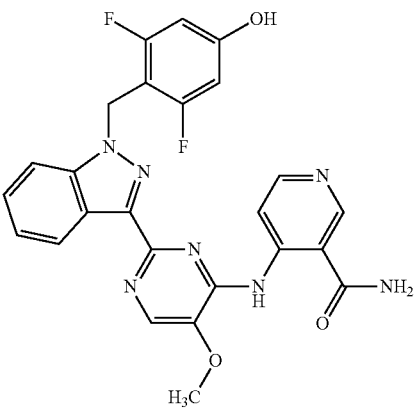 [SMILES: COc1cnc(-c2nn(Cc3c(F)cc(O)cc3F)c3ccccc23)nc1Nc1ccncc1C(N)=O]

620 mg of 4-({2-[1-(4-Ethoxy-2,6-difluorobenzyl)-1 H-indazol-3-yl]-5-methoxypyrimidin-4-yl}amino)pyridine-3-carboxamide 1-12-1 (92% pure, 1.07 mmol, 1.0 eq.) were dissolved in 28 mL dichloromethane and 4.3 mL tribromoborane (1 M in dichloromethane, 4.3 mmol, 4.0 eq.) was added carefully. The mixture was stirred overnight at 50° C. Water and dichloromethane were added to the reaction mixture. Then the pH was adjusted to 11 with sodium hydroxid (2 mol/L). An orange precipitate was filtered off and washed with methanol. The filter cake was purified with flash chromatography to provide the 60% pure target compound which was used without further purification: 107 mg, 0.13 mmol, 12%.

LC-MS:
retention time: 0.76 min
MS ES+: 504.2 [M+H]+
Method 5

Intermediate 1-12-1

Preparation of 4-({2-[1-(4-ethoxy-2,6-difluorobenzyl)-1 H-indazol-3-yl]-5-methoxypyrimidin-4-yl}amino)pyridine-3-carboxamide

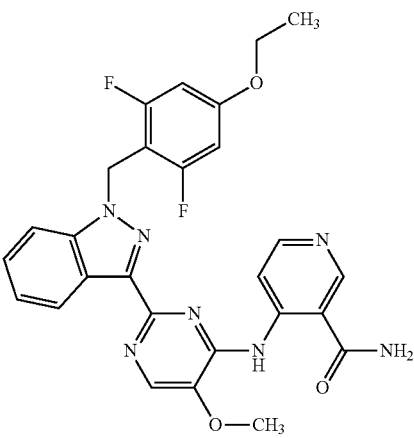 [SMILES: CCOc1cc(F)c(Cn2nc(-c3ncc(OC)c(Nc4ccncc4C(N)=O)n3)c3ccccc32)c(F)c1]

105 mg of 4-({2-[1-(4-Ethoxy-2,6-difluorobenzyl)-1 H-indazol-3-yl]-5-methoxypyrimidin-4-yl}amino)pyridine-3-carbonitrile 1-13-1 (0.204 mmol, 1.0 eq.) was dissolved in 311 µL conc. sulphuric acid (5.83 mmol) and stirred at room temperature for 18 hours. The mixture was poured in ice water and then 2 M sodium hydroxid was added until a basic pH was reached. The aqueous phase was extracted 3 times with dichlorormethane/isopropanol 4:1, dried over magnesium sulphate, filtered off and concentrated in vacuo. The residue was purified by preparative TLC (dichloromethane/methanol 9:1) to yield 6.9 mg (0.01 mmol, 6.3%) of the analytically pure target compound.

$^1$H-NMR (400 MHz, DMSO-d$_6$): δ [ppm]=1.26 (t, 3H), 3.94-4.08 (m, 5H), 5.65 (s, 2H), 6.77 (d, 2H), 7.19-7.32 (m, 1H), 7.40-7.53 (m, 1H), 7.74-7.87 (m, 2H), 8.29-8.55 (m, 4H), 8.92 (s, 1H), 9.20-9.30 (m, 1H), 12.17 (s, 1H).

Intermediate 1-13-1

Preparation of 4-({2-[1-(4-ethoxy-2,6-difluorobenzyl)-1 H-indazol-3-yl]-5-methoxypyrimidin-4-yl}amino)pyridine-3-carbonitrile

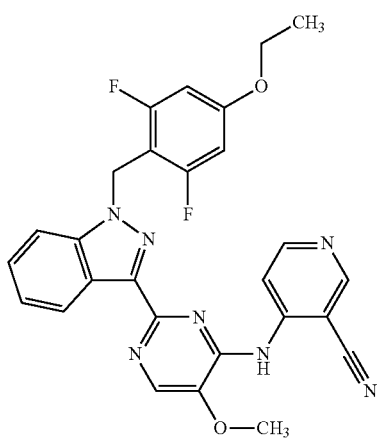 [SMILES: CCOc1cc(F)c(Cn2nc(-c3ncc(OC)c(Nc4ccncc4C#N)n3)c3ccccc32)c(F)c1]

150 mg of 2-[1-(4-Ethoxy-2,6-difluorobenzyl)-1 H-indazol-3-yl]-5-methoxypyrimidin-4-amine 1-6-2 (0.36 mmol, 1.0 eq.), 100 mg of 4-bromopyridine-3-carbonitrile (0.55 mmol, 1.5 eq.), 8.2 mg of palladium(II) acetate (0.036 mmol, 0.1 eq.), 156 mg of 1,1'-binaphthalene-2,2'-diylbis(diphenylphosphane) (0.25 mmol, 0.5 eq), 144 mg of sodium 2-methylpropan-2-olate (97%) (1.503 mmol, 3 eq.) and 52 ml of N,N-dimethylformamide were stirred under nitrogen atmosphere for 30 minutes at 100° C. and 300 W in a CEM microwave. The reaction mixture was washed with half-saturated aqueous sodium chloride solution. The organic layer was extracted twice with ethyl acetate. The combined organic layers were washed with brine and dried over sodium sulfate and concentrated in vacuo. The residue was purified by flash chromatography (hexane/dichloromethane/methanol) and preparative HPLC. A crystallisation from dichloromethane/methanol gave 5.8 mg (0.01 mmol, 2.6%) of the analytically pure target compound.

$^1$H-NMR (500 MHz, DMSO-d6): δ [ppm]=1.30 (t, 3H), 4.05 (q, 2H), 4.07 (s, 3H), 5.67 (s, 2H), 6.80 (m, 2H), 7.22 (t, 1H), 7.48 (t, 1H), 7.83 (d, 1H), 8.32 (d, 1H), 8.45 (br. s, 1H), 8.68 (br. s, 1H), 8.90 (br. s, 1H), 9.15 (br. s, 1H).

Intermediate 1-14-1

Preparation of N-(4-chloro-5-methylpyridin-2-yl)acetamide

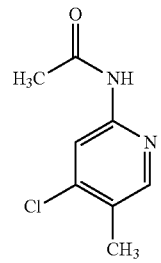

2.0 g 2-Amino-4-chlor-5-methylpyridine (14 mmol, 1.0 eq.) was dissolved in 49 mL acetic anhydride (37 eq.). Then 17 mg 4-dimethylaminopyridine (0.14 mmol, 0.01 eq.) was added. The reaction mixture was stirred for 3 h at 140° C. (reflux). The reaction mixture was diluted with icewater. Now about 95 mL of aqueous ammonia-solution 5 (33%) were added under cooling until pH 10. After 10 min of stirring there was a white solid in the mixture. It was separated by filtration under vacuo. The solid was washed with cold water and it was dried in a vacuo drying oven at 50° C. overnight to provide the analytically pure target compound: 2.3 g, 13 mmol, 90%.

$^1$H-NMR (600 MHz, DMSO-d6): δ [ppm]=2.09 (s, 3H), 2.27 (s, 3H), 8.16 (s, 1H), 8.26 (s, 1H), 10.63 (br. s., 1H).

Intermediate 1-15-1

Preparation of 2-{3-[4-(bromomethyl)-3,5-difluorophenoxy]propoxy}tetra hydro-2H-pyran

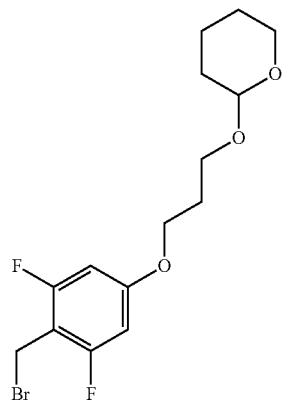 [SMILES: Fc1cc(OCCCOC2CCCCO2)cc(F)c1CBr]

93 mL Lithium bromide-solution (4.0 M in THE, 370 mmol, 6.0 eq.) was treated with 22 mL Triethylamine (160 mmol, 2.6 eq.). Then 18.8 g {2,6-difluoro-4-[3-(tetrahydro-2H-pyran-2-yloxy)propoxy]phenyl}methanol (62.2 mmol, 1.0 eq.), dissolved in 180 mL THF was added dropwise within 10 minutes under argon atmosphere. At 0° C. 10 mL methanesulfonyl chloride (130 mmol, 2.0 eq.) was added dropwise within 15 minutes. It was stirred at 0° C. for 2 hours. The reaction mixture was quenched with saturated sodium hydrogencarbonate solution and extracted three

Intermediate 1-16-1

Preparation of
N-(4-bromopyridin-2-yl)cyclopropanecarboxamide

| 1-15-2<br>SM 1 =<br>1-2-3 | 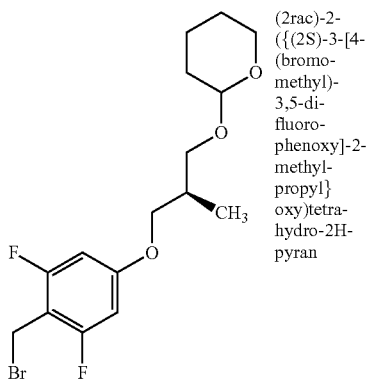 | (2rac)-2-<br>({(2S)-3-[4-<br>(bromo-<br>methyl)-<br>3,5-di-<br>fluoro-<br>phenoxy]-2-<br>methyl-<br>propyl}<br>oxy)tetra-<br>hydro-2H-<br>pyran | The com-<br>pound<br>was used<br>without<br>further<br>purification. |
|---|---|---|---|

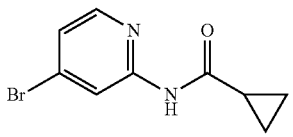 [SMILES: O=C(Nc1cc(Br)ccn1)C1CC1]

250 mg 4-bromopyridin-2-amine (1.44 mmol, 1.0 eq) and 240 μL triethylamine (1.7 mmol, 1.2 eq.) were dissolved in 1.4 mL dichloromethane and cooled to 0° C. Then 160 μL cyclopropanecarbonyl chloride (1.7 mmol, 1.2 eq.) was added dropwise. The icebath was removed and the mixture was stirred at room temperature overnight. The reaction mixture was evaporated under vacuo. The residue was treated with water. The mixture was extracted with ethyl acetate twice. The organic layer was dried using a water resistant filter and the filtrate was concentrated under reduced pressure. The crude product was purified by flash chromatography and HPLC to provide the analytically pure target compound: 113 mg, 0.47 mmol, 33% and 103 mg, 0.43 mmol, 30%.

$^1$H-NMR (500 MHz, DMSO-d6): δ [ppm]=0.77-0.86 (m, 4H), 1.93-2.04 (m, 1H), 7.33 (did, 1H), 8.21 (d, 1H), 8.31 (d, 1H), 11.00 (s, 1H).

Intermediate 1-17-1

Preparation of
1-(4-bromopyridin-2-yl)-3-cyclopropylurea

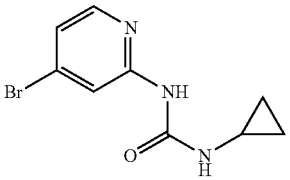 [SMILES: O=C(Nc1cc(Br)ccn1)NC1CC1]

200 mg 4-bromopyridin-2-amine (1.16 mmol, 1.0 eq.) was dissolved in 2.7 mL pyridine and treated with 160 μL isocyanatocyclopropane (2.3 mmol, 2.0 eq.), dissolved in 2.0 mL pyridine. It was stirred at room temperature for 3 days under argon atmosphere. The reaction mixture was concentrated under reduced pressure and the crude product was used without further purification: 334 mg, 1.3 mmol, 113%.

$^1$H-NMR (400 MHz, DMSO-d6): δ [ppm]=0.38-0.49 (m, 2H), 0.60-0.72 (m, 2H), 2.55-2.63 (m, 1H), 7.17 (dd, 1H), 7.69 (br. s., 1H), 7.80 (s, 1H), 8.08 (d, 1H), 9.19 (br. s., 1H).

Intermediate 1-18-1

Preparation of (2rac)-2-{[(2R)-3-bromo-2-methyl-propyl]oxy}tetrahydro-2H-pyran

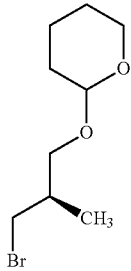

5.0 g 3-bromo-2-methylpropan-1-ol (32.7 mmol, 1.0 eq.) was dissolved in 69 mL dichloromethane and treated with the 3.4 mL 3,4-dihydro-2H-pyran (37.6 mmol, 1.15 eq.) and 34 mg pyridinium p-toluenesulfonate (0.14 mmol, 0.004 eq.). It was stirred at room temperature under argon atmosphere over night. The reaction mixture was treated with 5% sodium hydrogen carbonate solution and the organic layer was washed with this solution twice. The combined organic layers were washed with brine, filtered through a silicone coated filter and dried under reduced pressure to provide the 95% pure target compound, which was used without further purification: 9.3 g, 37 mmol, 114%.

$^1$H-NMR (400 MHz, DMSO-d6): δ [ppm]=0.97 (dd, 3H), 1.37-1.79 (m, 6H), 1.98-2.12 (m, 1H), 3.23-3.30 (m, 1H), 3.39-3.47 (m, 1H), 3.50-3.62 (m, 3H), 3.69-3.79 (m, 1H), 4.52-4.61 (m, 1H).

--- times with ethyl acetate, washed once with water and brine, filtered through a silicone coated filter and dried under reduced pressure. The crude product was used without further purification: 18.8 g, 51 mmol, 83%.

The following intermediate was prepared according to the same procedure from the indicated starting material (SM=starting material):

EXAMPLE COMPOUNDS

Example 2-1-1

Preparation of 2-{4-[(3-{4-[(3-chloropyridin-4-yl)amino]-5-methoxypyrimidin-2-yl}-1H-indazol-1-yl)methyl]-3,5-difluorophenoxy}ethanol

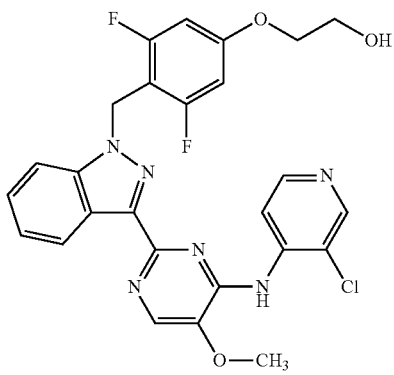 [SMILES: COc1cnc(-c2nn(Cc3c(F)cc(OCCO)cc3F)c3ccccc23)nc1Nc1ccncc1Cl]

177 mg of N-(3-Chloropyridin-4-yl)-2-{1-[2,6-difluoro-4-(2-methoxyethoxy)benzyl]-1 H-indazol-3-yl}-5-methoxypyrimidin-4-amine 1-9-1 (0.32 mmol, 1.0 eq.) were dissolved in 8.2 mL dichloromethane and cooled down to 0° C. 1.0 mL tribromoborane (1 M in dichloromethane, 1.0 mmol, 3.2 eq.) was slowly added at 0° C. When all tribromoborane was added, the icebath was removed and the mixture was stirred at rt for 72 h. The reaction mixture was diluted with icewater and DCM and 2-molar sodiumhydroxide-solution was added until pH12. The layers were separated and the aqueous layer was extracted with dichloromethane twice. The crude product was purified by flash chromatography to provide the 91% pure target compounds: 26 mg, which was further purified py HPLC: 100% pure, 7.9 mg, 15 µmol, 12%

$^1$H-NMR (400 MHz, DMSO-d6): δ [ppm]=3.68 (q, 2H), 4.01 (t, 2H), 4.08 (s, 3H), 4.88 (t, 1H), 5.69 (s, 2H), 6.75-6.90 (m, 2H), 7.27 (t, 1H), 7.50 (t, 1H), 7.85 (d, 1H), 8.26 (s, 1H), 8.40 (d, 1H), 8.43-8.54 (m, 2H), 8.65 (s, 1H), 8.98 (d, 1H).

The following examples were prepared according to the same procedure from the indicated starting materials (SM=starting material):

| | | | |
|---|---|---|---|
| 2-1-2<br>SM =<br>1-9-2 | 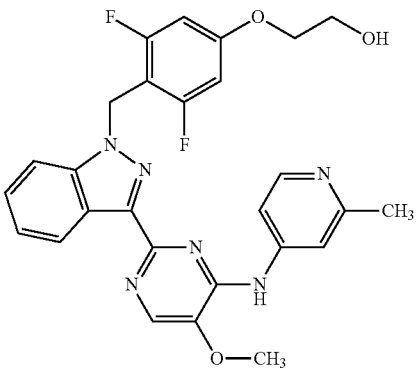 [SMILES: COc1cnc(-c2nn(Cc3c(F)cc(OCCO)cc3F)c3ccccc23)nc1Nc1ccnc(C)c1] | 2-{3,5-difluoro-4-[(3-{5-methoxy-4-[(2-methylpyridin-4-yl)amino]pyrimidin-2-yl}-1H-indazol-1-yl)methyl]phenoxy}ethanol | $^1$H-NMR (400 MHz, DMSO-d$_6$): δ [ppm] = 2.64 (s, 3H), 3.66 (t, 2H), 3.99 (t, 2H), 4.09 (s, 3H), 4.89 (br. s, 1H), 5.72 (s, 2H), 6.71-6.84 (m, 2H), 7.31 (t, 1H), 7.51 (t, 1H), 7.84 (d, 1H), 8.17-8.27 (m, 1H), 8.47 (t, 2H), 8.60 (s, 1H), 8.81 (s, 1H), 10.48 (s, 1H). |
| 2-1-3<br>SM =<br>1-9-3 | 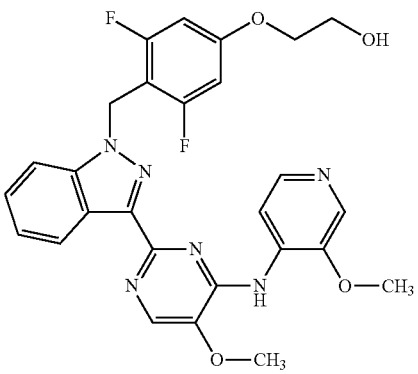 [SMILES: COc1cnccc1Nc1nc(-c2nn(Cc3c(F)cc(OCCO)cc3F)c3ccccc23)ncc1OC] | 2-{3,5-difluoro-4-[(3-{5-methoxy-4-[(3-methoxypyridin-4-yl)amino]pyrimidin-2-yl}-1H-indazol-1-yl)methyl]phenoxy}ethanol | $^1$H-NMR (300 MHz, DMSO-d$_6$): δ [ppm] = 3.66 (q, 2H), 3.93-4.13 (m, 8H), 4.88 (t, 1H), 5.69 (s, 2H), 6.74-6.90 (m, 2H), 7.28 (t, 1H), 7.49 (t, 1H), 7.86 (d, 1H), 8.08 (s, 1H), 8.20 (d, 1H), 8.31-8.50 (m, 3H), 8.95 (d, 1H). |

| | | | |
|---|---|---|---|
| 2-1-4 SM = 1-9-4 | 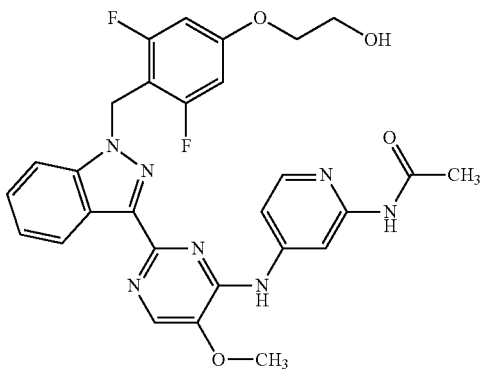 [SMILES: COc1cnc(-c2nn(Cc3c(F)cc(OCCO)cc3F)c3ccccc23)nc1Nc1ccnc(NC(C)=O)c1] | N-{4-[(2-{1-[2,6-difluoro-4-(2-hydroxyethoxy)benzyl]-1H-indazol-3-yl}-5-methoxypyrimidin-4-yl)amino]pyridin-2-yl}acetamide | ¹H-NMR (400 MHz, DMSO-d₆): δ [ppm] = 2.07 (s, 3H), 3.61-3.70 (m, 2H), 3.93-4.06 (m, 5H), 4.86 (t, 1H), 5.67 (s, 2H), 6.70-6.85 (m, 2H), 7.22 (t, 1H), 7.47 (t, 1H), 7.80 (d, 1H), 8.15 (d, 1H), 8.25-8.39 (m, 3H), 8.44 (d, 1H), 9.47 (s, 1H), 10.28 (s, 1H). |
| 2-1-5 SM = 1-9-5 | 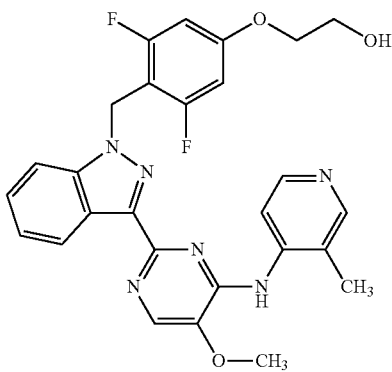 | 2-{3,5-difluoro-4-[(3-{5-methoxy-4-[(3-methylpyridin-4-yl)amino]pyrimidin-2-yl}-1H-indazol-1-yl)methyl]phenoxy}ethanol | ¹H-NMR (400 MHz, DMSO-d₆): δ [ppm] = 2.26 (s, 3H), 3.67 (t, 2H), 4.00 (t, 2H), 4.03 (s, 3H), 4.89 (br. s, 1H), 5.64 (s, 2H), 6.74-6.85 (m, 2H), 7.16 (t, 1H), 7.44 (t, 1H), 7.79 (d, 1H), 8.17-8.27 (m, 2H), 8.32 (s, 2H), 8.35-8.46 (m, 2H). |
| 2-1-6 SM = 1-9-6 | 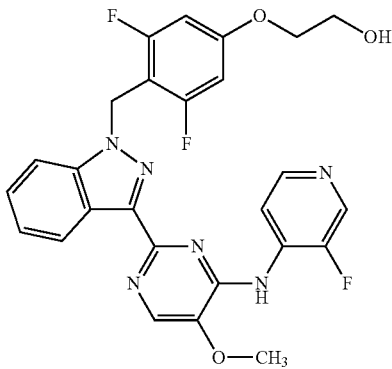 | 2-{3,5-difluoro-4-[(3-{4-[(3-fluoropyridin-4-yl)amino]-5-methoxypyrimidin-2-yl}-1H-indazol-1-yl)methyl]phenoxy}ethanol | ¹H-NMR (400 MHz, DMSO-d₆): δ [ppm] = 3.66 (t, 2H), 3.99 (t, 2H), 4.07 (s, 3H), 5.71 (s, 2H), 6.73-6.87 (m, 2H), 7.23 (t, 1H), 7.49 (t, 1H), 7.83 (d, 1H), 8.13-8.26 (m, 1H), 8.44 (s, 1H), 8.47-8.63 (m, 2H), 8.84 (d, 1H), 9.57 (br. s, 1H). |
| 2-1-7 SM = 1-9-7 | 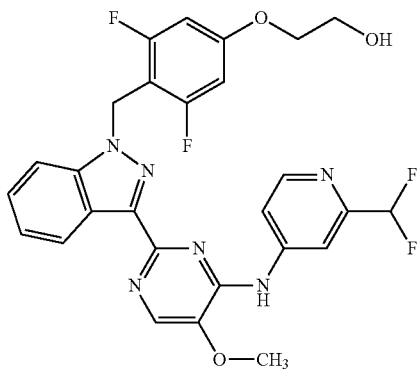 [SMILES: COc1cnc(-c2nn(Cc3c(F)cc(OCCO)cc3F)c3ccccc23)nc1Nc1ccnc(C(F)F)c1] | 2-(4-{[3-(4-{[2-(difluoromethyl)pyridin-4-yl]amino}-5-methoxypyrimidin-2-yl)-1H-indazol-1-yl]methyl}-3,5-difluorophenoxy)ethanol | ¹H-NMR (400 MHz, DMSO-d₆): δ [ppm] = 3.60-3.71 (m, 2H), 3.94-4.12 (m, 5H), 4.85 (t, 1H), 5.69 (s, 2H), 6.68-7.02 (m, 3H), 7.25 (t, 1H), 7.48 (t, 1H), 7.81 (d, 1H), 8.35 (s, 1H), 8.39 (s, 1H), 8.45 (d, 1H), 8.47-8.56 (m, 2H), 9.69 (s, 1H). |

| | | | |
|---|---|---|---|
| 2-1-8 SM = 1-9-8 | 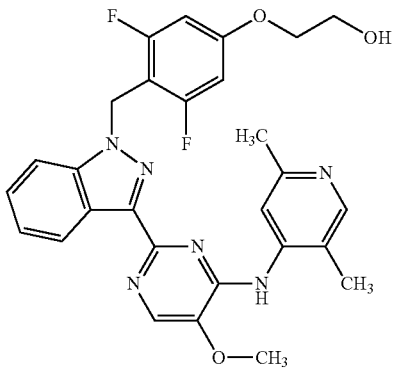 [SMILES: COc1cnc(-c2nn(Cc3c(F)cc(OCCO)cc3F)c3ccccc23)nc1Nc1cc(C)ncc1C] | 2-{4-[(3-{4-[(2,5-dimethylpyridin-4-yl)amino]-5-methoxypyrimidin-2-yl}-1H-indazol-1-yl)methyl]-3,5-difluorophenoxy}ethanol | $^1$H-NMR (400 MHz, DMSO-d$_6$): δ [ppm] = 2.21 (s, 3H), 2.45 (s, 3H), 3.66 (t, 2H), 4.00 (t, 2H), 4.03 (s, 3H), 4.87 (br. s, 1H), 5.66 (s, 2H), 6.71-6.81 (m, 2H), 7.17 (t, 1H), 7.39-7.49 (m, 1H), 7.78 (d, 1H), 8.13 (s, 2H), 8.25 (s, 1H), 8.28-8.36 (m, 2H). |
| 2-1-9 SM = 1-9-9 | 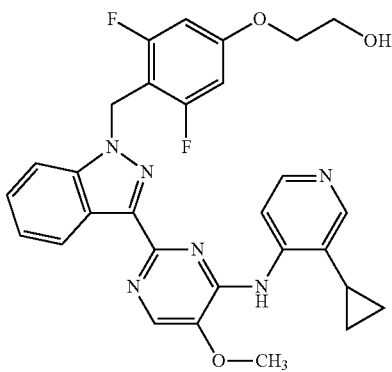 [SMILES: COc1cnc(-c2nn(Cc3c(F)cc(OCCO)cc3F)c3ccccc23)nc1Nc1ccncc1C1CC1] | 2-{4-[(3-{4-[(3-cyclopropylpyridin-4-yl)amino]-5-methoxypyrimidin-2-yl}-1H-indazol-1-yl)methyl]-3,5-difluorophenoxy}ethanol | $^1$H-NMR (400 MHz, DMSO-d$_6$): δ [ppm] = 0.66-0.74 (m, 2H), 0.98-1.07 (m, 2H), 1.87-1.97 (m, 1H), 3.64-3.72 (m, 2H), 4.01 (t, 2H), 4.09 (s, 3H), 4.83-4.94 (m, 1H), 5.69 (s, 2H), 6.77-6.88 (m, 2H), 7.26 (t, 1H), 7.45-7.53 (m, 1H), 7.84 (d, 1H), 8.30-8.48 (m, 5H), 8.79 (d, 1H). |
| 2-1-10 SM = 1-9-10 | 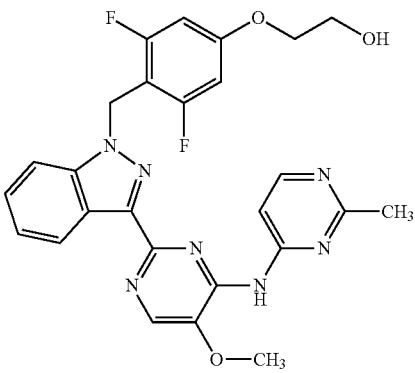 [SMILES: COc1cnc(-c2nn(Cc3c(F)cc(OCCO)cc3F)c3ccccc23)nc1Nc1ccnc(C)n1] | 2-{1-[2,6-difluoro-4-(2-hydroxyethoxy)benzyl]-1H-indazol-3-yl}-4-[(2-methylpyrimidin-4-yl)amino]pyrimidin-5-ol | $^1$H-NMR (400 MHz, DMSO-d$_6$): δ [ppm] = 2.56 (s, 3H), 3.68 (q, 2H), 3.97-4.06 (m, 5H), 4.89 (t, 1H), 5.70 (s, 2H), 6.79-6.88 (m, 2H), 7.25-7.33 (m, 1H), 7.47-7.55 (m, 1H), 7.87 (d, 1H), 8.45 (s, 1H), 8.48 (d, 1H), 8.53-8.60 (m, 2H), 8.93 (s, 1H). |
| 2-1-11 SM = 1-9-11 | 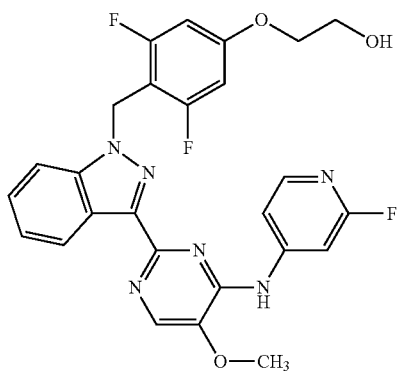 [SMILES: COc1cnc(-c2nn(Cc3c(F)cc(OCCO)cc3F)c3ccccc23)nc1Nc1ccnc(F)c1] | 2-{3,5-difluoro-4-[(3-{4-[(2-fluoropyridin-4-yl)amino]-5-methoxypyrimidin-2-yl}-1H-indazol-1-yl)methyl]phenoxy}ethanol | $^1$H-NMR (400 MHz, DMSO-d$_6$): δ [ppm] = 3.66 (q, 2H), 3.99 (t, 2H), 4.04 (s, 3H), 4.85 (t, 1H), 5.68 (s, 2H), 6.72-6.81 (m, 2H), 7.22-7.30 (m, 1H), 7.45-7.53 (m, 1H), 7.83 (d, 1H), 8.00-8.08 (m, 2H), 8.10 (d, 1H), 8.41 (s, 1H), 8.46 (d, 1H), 9.72 (s, 1H). |

| | | | |
|---|---|---|---|
| 2-1-12 SM = 1-9-13 | 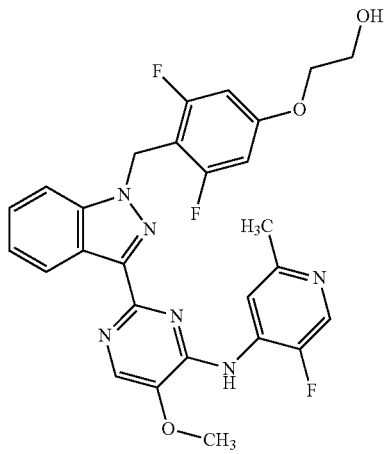 [SMILES: COc1cnc(-c2nn(Cc3c(F)cc(OCCO)cc3F)c3ccccc23)nc1Nc1cc(C)ncc1F] | 2-{3,5-difluoro-4-[(3-{4-[(5-fluoro-2-methylpyridin-4-yl)amino]-5-methoxypyrimidin-2-yl}-1H-indazol-1-yl)methyl]phenoxy}ethanol | $^1$H-NMR (400 MHz, DMSO-d$_6$): δ [ppm]= 2.09 (br. s, 1H), 2.63 (s, 3H), 3.93-3.98 (m, 2H), 4.02-4.07 (m, 2H), 4.09 (s, 3H), 5.75 (s, 2H), 6.46-6.56 (m, 2H), 7.25-7.32 (m, 1H), 7.45 (t, 1H), 7.61 (d, 1H), 7.70 (d, 1H), 8.27 (s, 1H), 8.34 (d, 1H), 8.61 (d, 1H), 8.94 (d, 1H). |
| 2-1-13 SM = 1-9-14 | 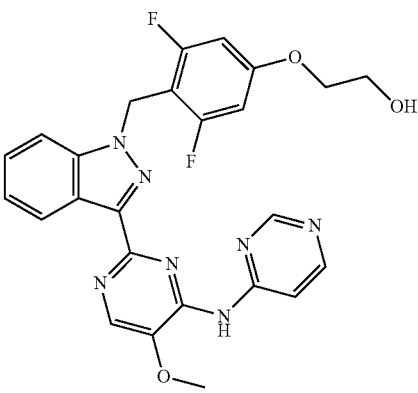 [SMILES: COc1cnc(-c2nn(Cc3c(F)cc(OCCO)cc3F)c3ccccc23)nc1Nc1ccncn1] | 2-[3,5-difluoro-4-({3-[5-methoxy-4-(pyrimidin-4-ylamino)pyrimidin-2-yl]-1H-indazol-1-yl}methyl)phenoxy]ethanol | $^1$H-NMR (400 MHz, DMSO-d$_6$): δ [ppm] = 3.66 (q, 2H), 3.96-4.05 (m, 5H), 4.85 (t, 1H), 5.69 (s, 2H), 6.78-6.87 (m, 2H), 7.28 (t, 1H), 7.46-7.53 (m, 1H), 7.85 (d, 1H), 8.45 (s, 1H), 8.48 (d, 1H), 8.63 (d, 1H), 8.71-8.76 (m, 1H), 8.86 (d, 1H), 9.11 (br. s, 1H). |
| 2-1-14 SM = 1-9-15 | 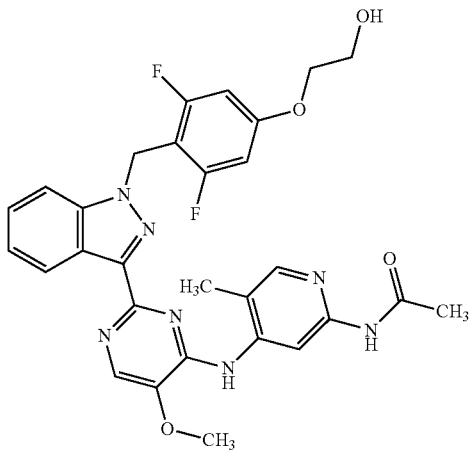 [SMILES: COc1cnc(-c2nn(Cc3c(F)cc(OCCO)cc3F)c3ccccc23)nc1Nc1cc(NC(C)=O)ncc1C] | N-{4-[(2-{1-[2,6-difluoro-4-(2-hydroxyethoxy)benzyl]-1H-indazol-3-yl}-5-methoxypyrimidin-4-yl)amino]-5-methylpyridin-2-yl}acetamide | $^1$H-NMR (400 MHz, DMSO-d$_6$): δ [ppm] = 2.05 (s, 3H), 2.14 (s, 3H), 3.64-3.74 (m, 2H), 3.97-4.08 (m, 5H), 4.89 (t, 1H), 5.62 (s, 2H), 6.70-6.82 (m, 2H), 6.96-7.05 (m, 1H), 7.36-7.45 (m, 1H), 7.72 (d, 1H), 8.06 (d, 1H), 8.19 (s, 1H), 8.23 (s, 1H), 8.30 (s, 1H), 8.84 (s, 1H), 10.43 (s, 1H). |

-continued

| | | | |
|---|---|---|---|
| 2-1-15 SM = 1-9-19 | 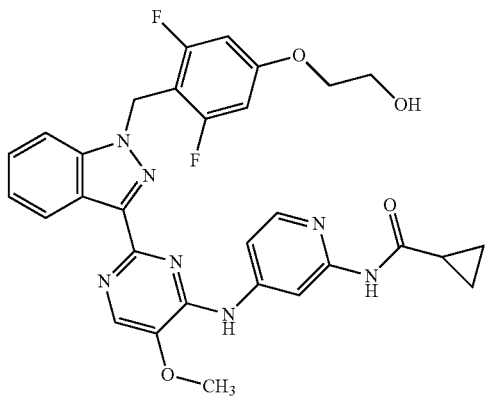 [SMILES: COc1cnc(-c2nn(Cc3c(F)cc(OCCO)cc3F)c3ccccc23)nc1Nc1ccnc(NC(=O)C2CC2)c1] | N-{4-[(2-{1-[2,6-difluoro-4-(2-hydroxyethoxy)benzyl]-1H-indazol-3-yl}-5-methoxy-pyrimidin-4-yl)amino]pyridin-2-yl}cyclopropanecarboxamide | $^1$H-NMR (400 MHz, DMSO-d$_6$): δ [ppm] = 0.69-0.85 (m, 4H), 1.96-2.07 (m, 1H), 3.68 (q, 2H), 3.97-4.06 (m, 5H), 4.90 (t, 1H), 5.69 (s, 2H), 6.77-6.86 (m, 2H), 7.23 (t, 1H), 7.43-7.52 (m, 1H), 7.82 (d, 1H), 8.17 (d, 1H), 8.29-8.37 (m, 3H), 8.44 (d, 1H), 9.46 (s, 1H), 10.63 (s, 1H). |
| 2-1-16 SM = 1-9-20 | 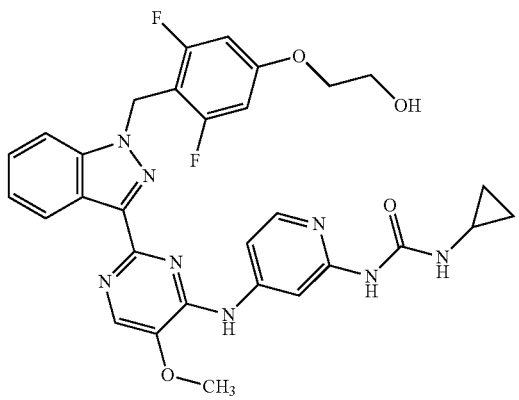 [SMILES: COc1cnc(-c2nn(Cc3c(F)cc(OCCO)cc3F)c3ccccc23)nc1Nc1ccnc(NC(=O)NC2CC2)c1] | 1-cyclopropyl-3-{4-[(2-{1-[2,6-difluoro-4-(2-hydroxyethoxy)benzyl]-1H-indazol-3-yl}-5-methoxy-pyrimidin-4-yl)amino]pyridin-2-yl}urea | $^1$H-NMR (400 MHz, DMSO-d$_6$): δ [ppm] = 0.42-0.50 (m, 2H), 0.63-0.71 (m, 2H), 2.57-2.65 (m, 1H), 3.64-3.71 (m, 2H), 3.95-4.06 (m, 5H), 4.90 (t, 1H), 5.68 (s, 2H), 6.78-6.88 (m, 2H), 7.18-7.28 (m, 1H), 7.44-7.53 (m, 1H), 7.57 (s, 1H), 7.83 (d, 1H), 8.05 (d, 1H), 8.07-8.13 (m, 1H), 8.33 (s, 1H), 8.45 (d, 2H), 8.98 (s, 1H), 9.43 (s, 1H). |
| 2-1-18 SM = 1-9-22 | 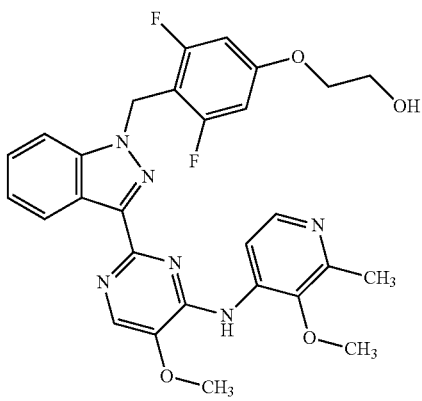 [SMILES: COc1cnc(-c2nn(Cc3c(F)cc(OCCO)cc3F)c3ccccc23)nc1Nc1ccnc(C)c1OC] | 2-{3(5-difluoro-4-[(3-{5-methoxy-4-[(3-methoxy-2-methylpyridin-4-yl)amino]pyrimidin-2-yl}-1H-indazol-1-yl)methyl]phenoxy}-ethanol | $^1$H-NMR (400 MHz, DMSO-d$_6$): δ [ppm] = 2.47 (s, 3H), 3.68 (t, 2H), 3.82 (s, 3H), 4.01 (t, 2H), 4.07 (s, 3H), 4.99 (br. s, 1H), 5.69 (s, 2H), 6.77-6.89 (m, 2H), 7.27 (t, 1H), 7.50 (t, 1H), 7.86 (d, 1H), 8.09-8.21 (m, 2H), 8.37 (br. s, 1H), 8.46 (d, 1H), 8.77 (br. s, 1H). |
| 2-1-19 SM = 1-9-27 Reaction time: 30 min. | 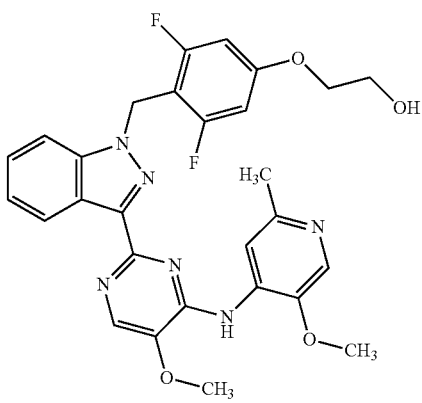 [SMILES: COc1cnc(C)cc1Nc1nc(-c2nn(Cc3c(F)cc(OCCO)cc3F)c3ccccc23)ncc1OC] | 2-{3(5-difluoro-4-[(3-{5-methoxy-4-[(5-methoxy-2-methylpyridin-4-yl)amino]pyrimidin-2-yl}-1H-indazol-1-yl)methyl]phenoxy}-ethanol | $^1$H-NMR (400 MHz, DMSO-d$_6$): δ [ppm] = 2.60 (s, 3H), 3.61-3.71 (m, 2H), 3.97-4.03 (m, 2H), 4.07 (s, 3H), 4.09 (s, 3H), 4.89 (br. s, 1H), 5.74 (s, 2H), 6.74-6.83 (m, 2H), 7.29-7.35 (m, 1H), 7.49-7.57 (m, 1H), 7.88 (d, 1H), 8.34 (s, 1H), 8.37-8.43 (m, 1H), 8.51 (d, 1H), 8.55 (s, 1H), 9.09 (s, 1H). |

Example 2-2-1

Preparation of 4-[(2-{1-[2,6-difluoro-4-(2-hydroxy-ethoxy)benzyl]-1 H-indazol-3-yl}-5-methoxypyrimidin-4-yl)amino]pyridine-3-carboxamide

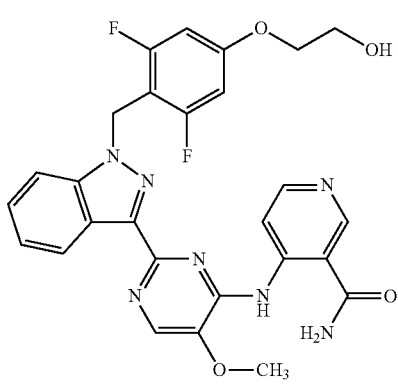 [SMILES: COc1cnc(-c2nn(Cc3c(F)cc(OCCO)cc3F)c3ccccc23)nc1Nc1ccncc1C(N)=O]

34 mg of 4-[(2-{1-[4-(2-{[tert-butyl(dimethyl)silyl]oxy}ethoxy)-2,6-difluorobenzyl]-1 H-indazol-3-yl}-5-methoxypyrimidin-4-yl)amino]pyridine-3-carboxamide 1-10-1 (0.049 mmol, 1.0 eq.) was dissolved in 0.5 mL dioxane. 49 µL Hydrochloric acid in dioxane (4 M, 0.19 mmol, 4.0 eq.) was added and the mixture was stirred at room temperature over night. The reaction mixture was diluted with ethyl acetate and saturated sodiumhydrogencarbonate-solution, and a white precipitation was filtered off under vacuo, washed with methanol and dried at the rotary evaporator (FC). The layers of the filtrate were separated and the aqueous layer was extracted with ethyl acetate twice. The combined organic layers were dried in use of a water resistant filter and the filtrate was evaporated under reduced pressure. The crude product was purified by flash chromatography (F1). FC and F1 were united to provide the 94% pure target compound: 23 mg, 0.04 mmol, 80%.

$^1$H-NMR (400 MHz, DMSO-$d_6$): δ [ppm]=3.66 (q, 2H), 3.94-4.08 (m, 5H), 4.86 (t, 1H), 5.69 (s, 2H), 6.77-6.88 (m, 2H), 7.22-7.32 (m, 1H), 7.45-7.54 (m, 1H), 7.78-7.91 (m, 2H), 8.36-8.50 (m, 3H), 8.52 (d, 1H), 8.94 (s, 1H), 9.31 (d, 1H), 12.19 (s, 1H).

Example 2-3-1

Preparation of 3-{4-[(3-{4-[(2,5-dimethylpyridin-4-yl)amino]-5-methoxypyrimidin-2-yl}-1 H-indazol-1-yl)methyl]-3,5-difluorophenoxy}propan-1-ol

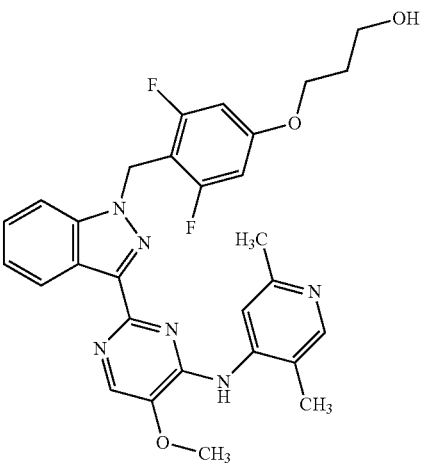 [SMILES: COc1cnc(-c2nn(Cc3c(F)cc(OCCCO)cc3F)c3ccccc23)nc1Nc1cc(C)ncc1C]

160 mg 1-9-16 2-[1-(2,6-difluoro-4-{3-[(2S)-tetrahydro-2H-pyran-2-yloxy]propoxy}-benzyl)-1H-indazol-3-yl]-N-(2,5-dimethylpyridin-4-yl)-5-methoxypyrimidin-4-amine (0.25 mmol, 1.0 eq.) was dissolved in 4.8 mL methanol and treated with the 19 mg p-Toluenesulfonic acid monohydrate (0.10 mmol, 0.4 eq.). It was stirred under argon atmosphere over night. 19 mg p-Toluenesulfonic acid monohydrate (0.10 mmol, 0.4 eq.) was added and it was stirred at room temperature for three hours. The reaction mixture was dried under reduced pressure. The crude product was dissolved in methanol and treated with ethyl acetate and a resin was formed. The solvent was pipetted off and the resin dried under reduced pressure to provide the 91% pure target compound, which was further purified by HPLC: 76 mg, 95% pure, 0.13 mmol, 52%.

15 $^1$H-NMR (400 MHz, DMSO-$d_6$): δ [ppm]=1.82 (quint, 2H), 2.23 (s, 3H), 2.46 (s, 3H), 3.51 (q, 2H), 4.00-4.08 (m, 5H), 4.58 (t, 1H), 5.67 (s, 2H), 6.72-6.82 (m, 2H), 7.18 (t, 1H), 7.42-7.50 (m, 1H), 7.81 (d, 1H), 8.14 (s, 1H), 8.19 (s, 1H), 8.27 (s, 1H), 8.29-8.35 (m, 2H).

The following examples were prepared according to the same procedure from the indicated starting materials (SM=starting material):

| | | | |
|---|---|---|---|
| 2-3-2 SM = 1-9-17 | 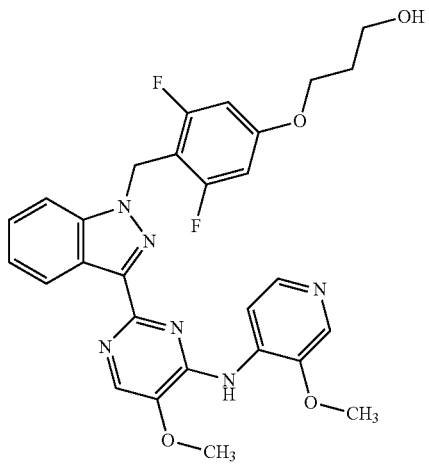 [SMILES: COc1cnccc1Nc1nc(-c2nn(Cc3c(F)cc(OCCCO)cc3F)c3ccccc23)ncc1OC] | 3-{3,5-difluoro-4-[(3-{5-methoxy-4-[(3-methoxy-pyridin-4-yl)-amino]pyrimidin-2-yl}-1H-indazol-1-yl)methyl]-phenoxy}propan-1-ol | $^1$H-NMR (400 MHz, DMSO-d$_6$): δ [ppm] = 1.83 (quint, 2H), 3.52 (q, 2H), 4.01-4.10 (m, 8H), 4.62 (t, 1H), 5.70 (s, 2H), 6.78-6.87 (m, 2H), 7.24-7.33 (m, 1H), 7.46-7.55 (m, 1H), 7.87 (d, 1H), 8.09 (s, 1H), 8.20 (d, 1H), 8.37 (s, 1H), 8.40 (s, 1H), 8.47 (d, 1H), 8.95 (d, 1H). |
| 2-3-3 SM = 1-9-18 | 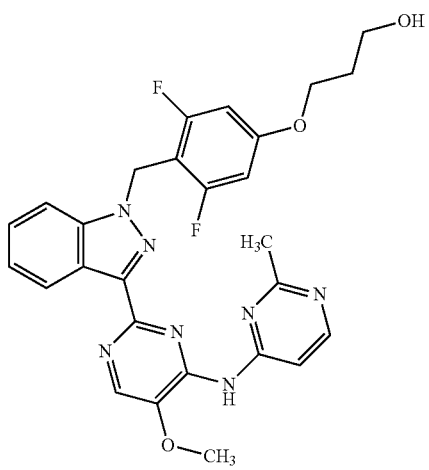 [SMILES: COc1cnc(-c2nn(Cc3c(F)cc(OCCCO)cc3F)c3ccccc23)nc1Nc1ccnc(C)n1] | 3-{3,5-difluoro-4-[(3-{5-methoxy-4-[(2-methyl-pyrimidin-4-yl)-amino]pyrimidin-2-yl}-1H-indazol-1-yl)methyl]-phenoxy}propan-1-ol | $^1$H-NMR (400 MHz, DMSO-d$_6$): δ [ppm] = 1.82 (quin, 2H), 2.56 (s, 3H), 3.51 (q, 2H), 4.02 (s, 3H), 4.05 (t, 2H), 4.58 (t, 1H), 5.70 (s, 2H), 6.80-6.88 (m, 2H), 7.30 (t, 1H), 7.51 (t, 1H), 7.87 (d, 1H), 8.44 (s, 1H), 8.49 (d, 1H), 8.54 (d, 1H), 8.57 (d, 1H), 8.95 (s, 1H). |
| 2-3-4 SM = 1-9-23 | 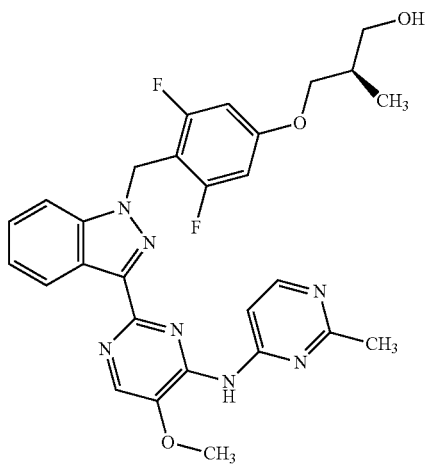 [SMILES: COc1cnc(-c2nn(Cc3c(F)cc(OC[C@H](C)CO)cc3F)c3ccccc23)nc1Nc1ccnc(C)n1] | (2R)-3-{3,5-difluoro-4-[(3-{5-methoxy-4-[(2-methylpyrimidin-4-yl)amino]-pyrimidin-2-yl}-1H-indazol-1-yl)methyl]phenoxy}-2-methyl-propan-1-ol | $^1$H-NMR (400 MHz, DMSO-d$_6$): δ [ppm] = 0.92 (d, 3H), 1.88-2.02 (m, 1H), 2.56 (s, 3H), 3.35-3.40 (m, 2H), 3.79-3.87 (m, 1H), 3.92-3.98 (m, 1H), 4.02 (s, 3H), 4.60 (t, 1H), 5.70 (s, 2H), 6.78-6.87 (m, 2H), 7.26-7.33 (m, 1H), 7.47-7.55 (m, 1H), 7.86 (d, 1H), 8.45 (s, 1H), 8.49 (d, 1H), 8.52-8.60 (m, 2H), 8.95 (br. s, 1H). |

| | | | |
|---|---|---|---|
| 2-3-5 SM = 1-9-24 | 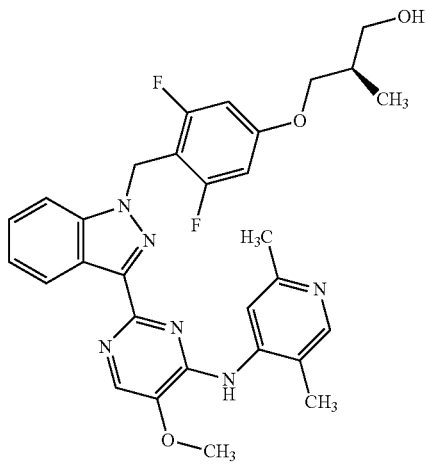 [SMILES: COc1cnc(-c2nn(Cc3c(F)cc(OC[C@H](C)CO)cc3F)c3ccccc23)nc1Nc1cc(C)ncc1C] | (2R)-3-{4-[(3-{4-[(2,5-dimethyl-pyridin-4-yl)-amino]-5-methoxypyrimidin-2-yl}-1H-indazol-1-yl)methyl]-3,5-difluorophenoxy}-2-methylpropan-1-ol | $^1$H-NMR (400 MHz, DMSO-d$_6$): δ [ppm] = 0.92 (d, 3H), 1.90-2.01 (m, 1H), 2.23 (s, 3H), 2.46 (s, 3H), 3.35-3.42 (m, 2H), 3.79-3.86 (m, 1H), 3.91-3.98 (m, 1H), 4.05 (s, 3H), 4.60 (t, 1H), 5.67 (s, 2H), 6.72-6.81 (m, 2H), 7.19 (t, 1H), 7.43-7.51 (m, 1H), 7.81 (d, 1H), 8.14 (s, 1H), 8.19 (s, 1H), 8.27 (s, 1H), 8.30-8.35 (m, 2H). |
| 2-3-6 SM = 1-9-25 | 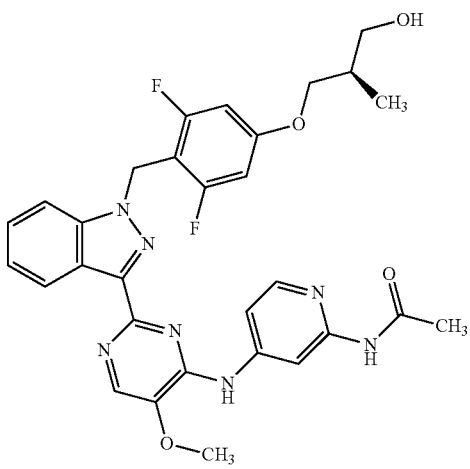 [SMILES: COc1cnc(-c2nn(Cc3c(F)cc(OC[C@H](C)CO)cc3F)c3ccccc23)nc1Nc1ccnc(NC(C)=O)c1] | N-[4-({2-[1-(2,6-difluoro-4-{[(2R)-3-hydroxy-2-methylpropyl]oxy}benzyl)-1H-indazol-3-yl]-5-methoxypyrimidin-4-yl}amino)-pyridin-2-yl]acetamide | $^1$H-NMR (400 MHz, DMSO-d$_6$): δ [ppm] = 0.91 (d, 3H), 1.89-2.00 (m, 1H), 2.09 (s, 3H), 3.35-3.40 (m, 2H), 3.80-3.86 (m, 1H), 3.91-3.98 (m, 1H), 4.02 (s, 3H), 4.58 (t, 1H), 5.69 (s, 2H), 6.75-6.84 (m, 2H), 7.20-7.27 (m, 1H), 7.45-7.53 (m, 1H), 7.82 (d, 1H), 8.17 (d, 1H), 8.29-8.34 (m, 2H), 8.37 (dd, 1H), 8.45 (d, 1H), 9.51 (s, 1H), 10.32 (s, 1H). |
| 2-3-7 SM = 1-9-26 | 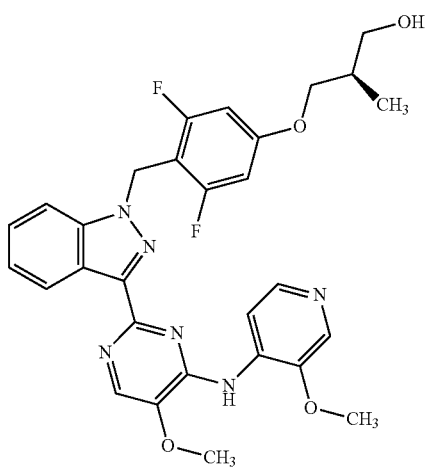 [SMILES: COc1cnccc1Nc1nc(-c2nn(Cc3c(F)cc(OC[C@H](C)CO)cc3F)c3ccccc23)ncc1OC] | (2R)-3-{3,5-difluoro-4-[(3-{5-methoxy-4-[(3-methoxypyridin-4-yl)amino]pyrimidin-2-yl}-1H-indazol-1-yl)methyl]phenoxy}-2-methylpropan-1-ol | $^1$H-NMR (400 MHz, DMSO-d$_6$): δ [ppm] = 0.92 (d, 3H), 1.88-2.02 (m, 1H), 3.35-3.41 (m, 2H), 3.84 (dd, 1H), 3.95 (dd, 1H), 4.03 (s, 3H), 4.06 (s, 3H), 4.64 (t, 1H), 5.70 (s, 2H), 6.78-6.87 (m, 2H), 7.29 (t, 1H), 7.46-7.56 (m, 1H), 7.87 (d, 1H), 8.09 (s, 1H), 8.20 (d, 1H), 8.36 (s, 1H), 8.40 (s, 1H), 8.47 (d, 1H), 8.95 (d, 1H). |

| | | | |
|---|---|---|---|
| 2-3-8<br>SM =<br>1-9-28 | 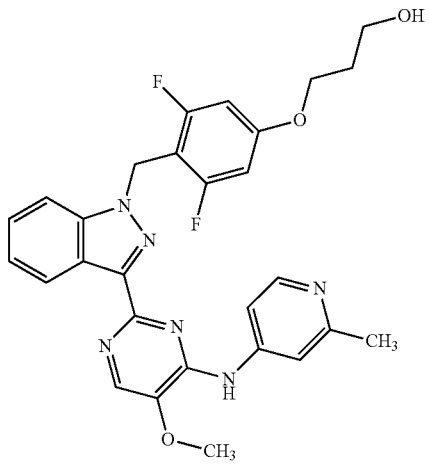 [SMILES: COc1cnc(-c2nn(Cc3c(F)cc(OCCCO)cc3F)c3ccccc23)nc1Nc1ccnc(C)c1] | 3-{3,5-difluoro-4-[(3-{5-methoxy-4-[(2-methylpyridin-4-yl)amino]-pyrimidin-2-yl}-1H-indazol-1-yl)-methyl]phenoxy}-propan-1-ol | ¹H-NMR (400 MHz, DMSO-d₆): δ [ppm] = 1.82 (quin, 2H), 2.45 (s, 3H), 3.51 (q, 2H), 4.01-4.08 (m, 5H), 4.62 (t, 1H), 5.70 (s, 2H), 6.76-6.83 (m, 2H), 7.27 (t, 1H), 7.50 (t, 1H), 7.84 (d, 1H), 7.89-7.93 (m, 1H), 8.13 (s, 1H), 8.27 (d, 1H), 8.35 (s, 1H), 8.49 (d, 1H), 9.32 (s, 1H). |

Example 2-4-1

Preparation of 2-{4-[(3-{4-[(2,6-dimethylpyrimidin-4-yl)amino]-5-methoxypyrimidin-2-yl}-1H-indazol-1-yl)methyl]-3,5-difluorophenoxy}ethanol

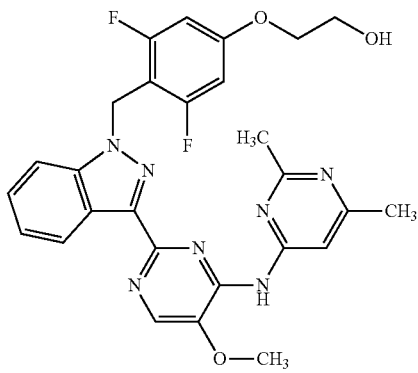 [SMILES: COc1cnc(-c2nn(Cc3c(F)cc(OCCO)cc3F)c3ccccc23)nc1Nc1cc(C)nc(C)n1]

As side product of the reaction to 1-9-29 the desired target compound was isolated: 11.3 mg, 0.02 mmol, 3%.

¹H-NMR (400 MHz, DMSO-d6): δ [ppm]=2.43 (s, 3H), 3.27 (s, 3H), 3.58-3.66 (m, 2H), 4.08-4.18 (m, 2H), 5.70 (s, 2H), 6.75-6.85 (m, 2H), 7.27 (t, 1H), 7.44-7.54 (m, 1H), 7.83 (d, 1H), 8.17-8.23 (m, 1H), 8.26 (s, 1H), 8.53 (d, 1H), 8.89 (br. s, 1H), 11.79 (br. s, 1H).—one CH₃ under DMSO signal.

Synthetic Intermediates of Prodrugs

Intermediate 3-1-1

Preparation of 2-{3,5-difluoro-4-[(3-{5-methoxy-4-[(2-methylpyridin-4-yl)amino]pyrimidin-2-yl}-1H-indazol-1-yl)methyl]phenoxy}ethyl N-(tert-butoxycarbonyl)-L-alaninate

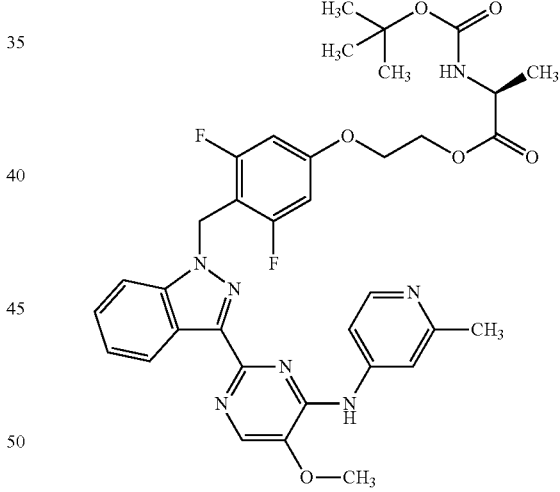

214 mg 2-{3,5-Difluoro-4-[(3-{5-methoxy-4-[(2-methylpyridin-4-yl)amino]pyrimidin-2-yl}-1 H-indazol-1-yl) methyl]phenoxy}ethanol 2-1-2 (0.41 mmol, 1.0 eq.) was dissolved in 6.8 mL DMF and 6.6 mL dichloromethane. Then 234 mg N-(tert-butoxycarbonyl)-L-alanine (1.24 mmol, 3.0 eq.), 42 mg 4-dimethylaminopyridine (0.41 mmol, 1.0 eq.), 0.10 mL N,N-diisopropylethylamine (1.24 mmol, 3.0 eq.) and 103 mg 1-(3-dimethylaminopropyl)-3-ethylcarbodiimidhydrochloride (0.54 mmol, 1.3 eq.) were added. The reaction mixture was put in an ultrasonic bath for 15 min. 234 mg N-(tert-butoxycarbonyl)-L-alanine (1.24 mmol, 3.0 eq.), 42 mg 4-dimethylaminopyridine (0.41 mmol, 1.0 eq.), 0.10 mL N,N-diisopropylethylamine (1.24 mmol, 3.0 eq.) and 103 mg 1-(3-dimethylaminopropyl)-3- ethylcarbodiimidhydrochloride (0.54 mmol, 1.3 eq.) were added again and sonication was continued for another 60 min. The reaction mixture was evaporated. The residue was dissolved in 25 ml dichloromethane and the organic layer was washed with 5%-aqueous citric acid. This mixture was stirred over night. The layers were separated. The organic layer was washed with saturated sodiumhydrogencarbonate-solution, dried using a water resistant filter and concentrated in vacuo. The crude product was purified by flash chromatography to provide the target compound in 90% purity: 133 mg, 0.17 mmol, 42%.

$^1$H-NMR (400 MHz, DMSO-d$_6$): δ [ppm]=1.20 (d, 3H), 1.29 (s, 9H), 2.45 (s, 3H), 3.92-4.02 (m, 1H), 4.03 (s, 3H), 4.20 (d, 2H), 4.26-4.44 (m, 2H), 5.71 (s, 2H), 6.75-6.87 (m, 2H), 7.22-7.32 (m, 2H), 7.50 (t, 1H), 7.85 (d, 1H), 7.90 (dd, 1H), 8.15 (d, 1H), 8.29 (d, 1H), 8.35 (s, 1H), 8.49 (d, 1H), 9.29 (s, 1H).

The following intermediates were prepared according to the same procedure from the indicated starting materials (SM=starting material):

| | | | |
|---|---|---|---|
| 3-1-2<br>SM =<br>2-1-3 | 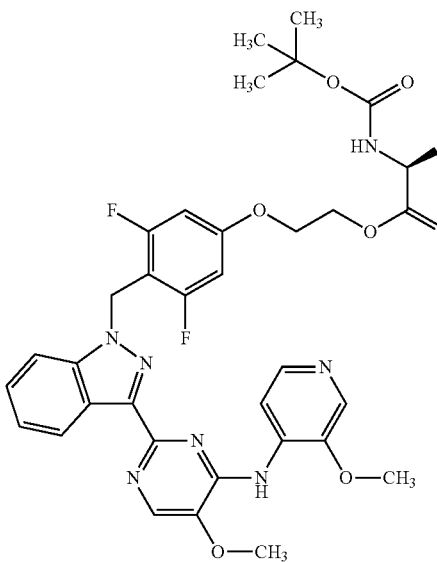 | 2-{3,5-difluoro-4-[(3-{5-methoxy-4-[(3-methoxypyridin-4-yl)amino]pyrimidin-2-yl}-1H-indazol-1-yl)methyl]phenoxy}ethyl N-(tert-butoxycarbonyl)-L-alaninate | $^1$H-NMR (400 MHz, DMSO-d$_6$): δ [ppm]= 1.18 (d, 3H), 1.27 (s, 9H), 3.97 (t, 1H), 4.02 (s, 3H), 4.05 (s, 3H), 4.19 (d, 2H), 4.24-4.42 (m, 2H), 5.69 (s, 2H), 6.78-6.88 (m, 2H), 7.22-7.30 (m, 2H), 7.46-7.52 (m, 1H), 7.85 (d, 1H), 8.08 (s, 1H), 8.20 (d, 1H), 8.35 (s, 1H), 8.38 (s, 1H), 8.45 (d, 1H), 8.95 (d, 1H). |
| 3-1-3<br>SM =<br>2-1-11 | 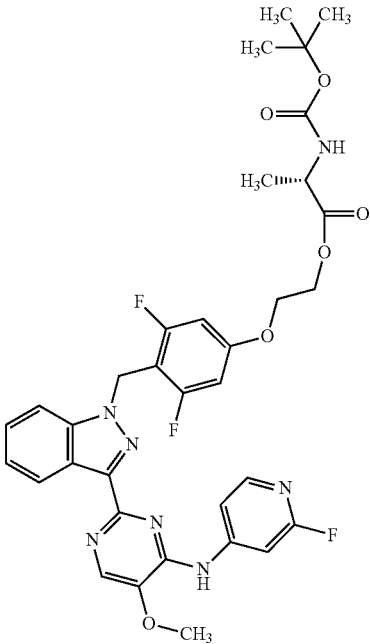 [SMILES: COc1cnc(-c2nn(Cc3c(F)cc(OCCOC(=O)[C@H](C)NC(=O)OC(C)(C)C)cc3F)c3ccccc23)nc1Nc1ccnc(F)c1] | 2-{3,5-difluoro-4-[(3-{4-[(2-fluoropyridin-4-yl)-amino]-5-methoxypyrimidin-2-yl}-1H-indazol-1-yl)methyl]-phenoxy}ethyl N-(tert-butoxycarbonyl)-L-alaninate | $^1$H-NMR (400 MHz, DMSO-d$_6$): δ [ppm] = 1.19 (d, 3H), 1.28 (s, 9H), 3.92-4.02 (m, 1H), 4.06 (s, 3H), 4.15-4.25 (m, 2H), 4.26-4.43 (m, 2H), 5.71 (s, 2H), 6.76-6.86 (m, 2H), 7.24-7.32 (m, 2H), 7.46-7.54 (m, 1H), 7.86 (d, 1H), 8.02-8.10 (m, 2H), 8.12 (d, 1H), 8.43 (s, 1H), 8.48 (d, 1H), 9.77 (s, 1H). |

Intermediate 3-2-1

Preparation of 2-{3,5-difluoro-4-[(3-{5-methoxy-4-[(2-methylpyridin-4-yl)amino]pyrimidin-2-yl}-1H-indazol-1-yl)methyl]phenoxy}ethyl L-alaninate, salt with trifluoroacetic acid

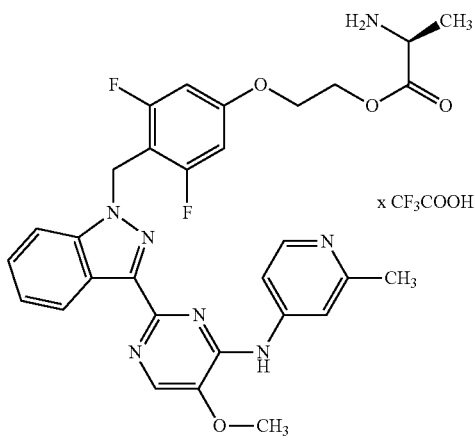 [SMILES: COc1cnc(-c2nn(Cc3c(F)cc(OCCOC(=O)[C@H](C)N)cc3F)c3ccccc23)nc1Nc1ccnc(C)c1]

125 mg 2-{3,5-Difluoro-4-[(3-{5-methoxy-4-[(2-methylpyridin-4-yl)amino]pyrimidin-2-yl}-1H-indazol-1-yl)methyl]phenoxy}ethyl N-(tert-butoxycarbonyl)-L-alaninate 3-1-1 (0.16 mmol, 1.0 eq.) was dissolved in 1.3 mL dichloromethane. 0.31 mL trifluoracetic acid (4.08 mmol, 25.0 eq.) was added and the mixture was stirred at room temperature for 1 hour. The reaction mixture was concentrated in vacuo. The crude product was lyophilized from water to provide the crude product in 92% purity which was used without further purification: 203 mg, 0.26 mmol, 162%.

$^1$H-NMR (400 MHz, DMSO-$d_6$): δ [ppm]=1.34 (d, 3H), 2.65 (s, 3H), 4.04-4.15 (m, 4H), 4.19-4.30 (m, 2H), 4.38-4.54 (m, 2H), 5.74 (s, 2H), 6.77-6.88 (m, 2H), 7.31 (t, 1H), 7.51 (t, 1H), 7.84 (d, 1H), 8.20-8.39 (m, 3H), 8.46 (d, 1H), 8.52 (d, 1H), 8.60 (s, 1H), 8.79-8.87 (m, 1H), 10.54 (s, 1H).

The following intermediates were prepared according to the same procedure from the indicated starting materials (SM=starting material):

| | | | |
|---|---|---|---|
| 3-2-2<br>SM =<br>3-1-2 | 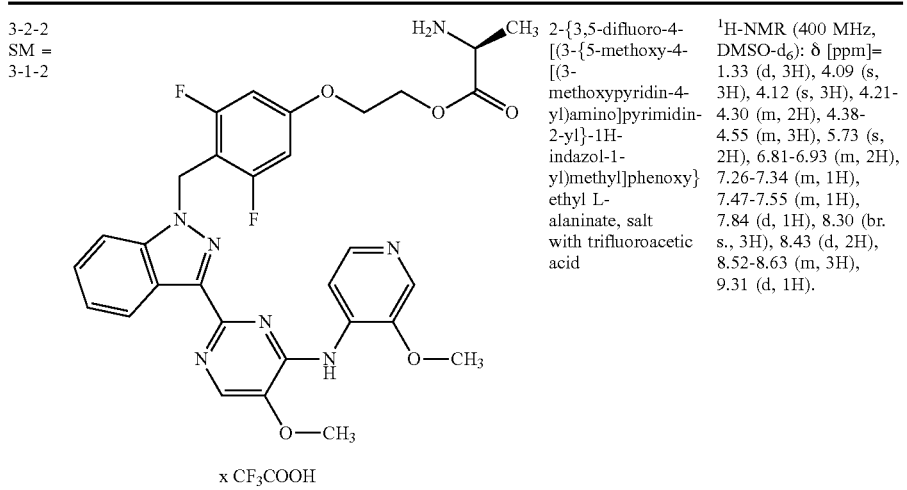 | 2-{3,5-difluoro-4-[(3-{5-methoxy-4-[(3-methoxypyridin-4-yl)amino]pyrimidin-2-yl}-1H-indazol-1-yl)methyl]phenoxy}ethyl L-alaninate, salt with trifluoroacetic acid | $^1$H-NMR (400 MHz, DMSO-$d_6$): δ [ppm]= 1.33 (d, 3H), 4.09 (s, 3H), 4.12 (s, 3H), 4.21-4.30 (m, 2H), 4.38-4.55 (m, 3H), 5.73 (s, 2H), 6.81-6.93 (m, 2H), 7.26-7.34 (m, 1H), 7.47-7.55 (m, 1H), 7.84 (d, 1H), 8.30 (br. s., 3H), 8.43 (d, 2H), 8.52-8.63 (m, 3H), 9.31 (d, 1H). |
| 3-2-3<br>SM =<br>3-1-3 | 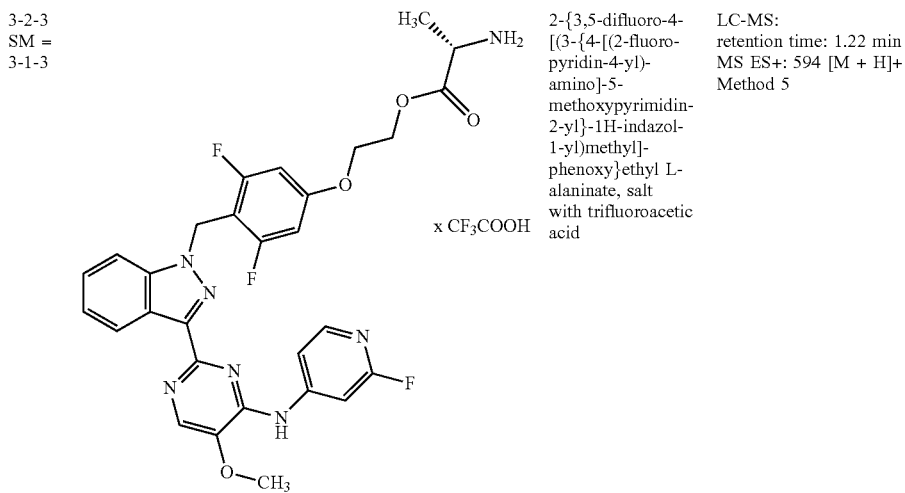 | 2-{3,5-difluoro-4-[(3-{4-[(2-fluoropyridin-4-yl)amino]-5-methoxypyrimidin-2-yl}-1H-indazol-1-yl)methyl]phenoxy}ethyl L-alaninate, salt with trifluoroacetic acid | LC-MS:<br>retention time: 1.22 min<br>MS ES+: 594 [M + H]+<br>Method 5 |

Intermediate 3-3-1

Preparation of 2-{3,5-difluoro-4-[(3-{5-methoxy-4-[(2-methylpyridin-4-yl)amino]pyrimidin-2-yl}-1H-indazol-1-yl)methyl]phenoxy}ethyl $N^2,N^6$-bis(tert-butoxycarbonyl)-L-lysyl-L-alaninate

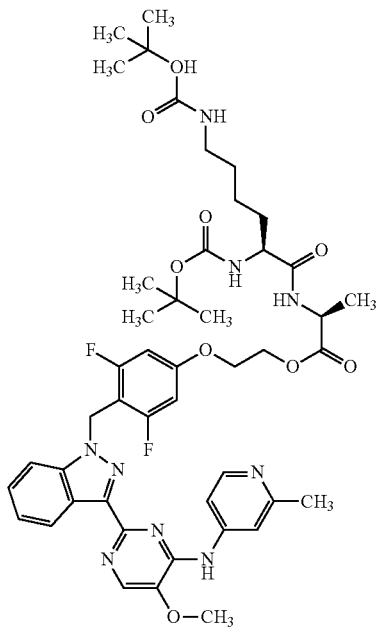 [SMILES: COc1cnc(-c2nn(Cc3c(F)cc(OCCOC(=O)[C@H](C)NC(=O)[C@H](CCCCNC(=O)OC(C)(C)C)NC(=O)OC(C)(C)C)cc3F)c3ccccc23)nc1Nc1ccnc(C)c1]

85 mg $N^2,N^6$-Bis(tert-butoxycarbonyl)-L-lysine (0.24 mmol, 1.5 eq.), 50 mg 1-hydroxy-1 H-benzotriazole hydrat (0.33 mmol, 2.0 eq.) and 0.11 mL N,N-diisopropylethylamine (0.65 mmol, 4.0 eq.) were dissolved in 2.5 mL DMF. Afterwards 56 mg 1-(3-dimethylaminopropyl)-3-ethylcarbodiimidhydrochlorid (0.29 mmol, 1.8 eq.) was added. After 30 min. 115 mg 2-{3,5-difluoro-4-[(3-{5-methoxy-4-[(2-methylpyridin-4-yl)amino]pyrimidin-2-yl}-1 H-indazol-1-yl)methyl]phenoxy}ethyl L-alaninate trifluoroacetate 3-2-1 (1:1) (0.16 mmol, 1.0 eq.) dissolved in 2.5 mL DMF was given into the reaction mixture. It was stirred over night at room temperature. The DMF was evaporated under vacuo. The residue was dissolved in ethyl acetate and the organic layer was washed with 5%-aqueous citric acid twice and also was washed with saturated sodiumhydrogencarbonate-solution. The organic layer was dried using a water resistant filter and the filtrate was evaporated under reduced pressure. The crude product was purified by flash chromatography and HPLC to provide the target compound in 98% purity: 64 mg, 0.07 mmol, 42%.

$^1$H-NMR (300 MHz, DMSO-$d_6$): δ [ppm]=1.13-1-54 (m, 27H), 2.43 (s, 3H), 2.77-2.86 (m, 2H), 3.79-3.92 (m, 1H), 4.02 (s, 3H), 4.19 (d, 5H), 5.69 (s, 2H), 6.66-6.89 (m, 4H), 7.25 (t, 1H), 7.48 (t, 1H), 7.78-7.91 (m, 2H), 8.13 (d, 1H), 8.21 (d, 1H), 8.26 (s, 1H), 8.33 (s, 1H), 8.48 (d, 1H), 9.29 (s, 1H).

The following intermediate was prepared according to the same procedure from the indicated starting materials (SM=starting material):

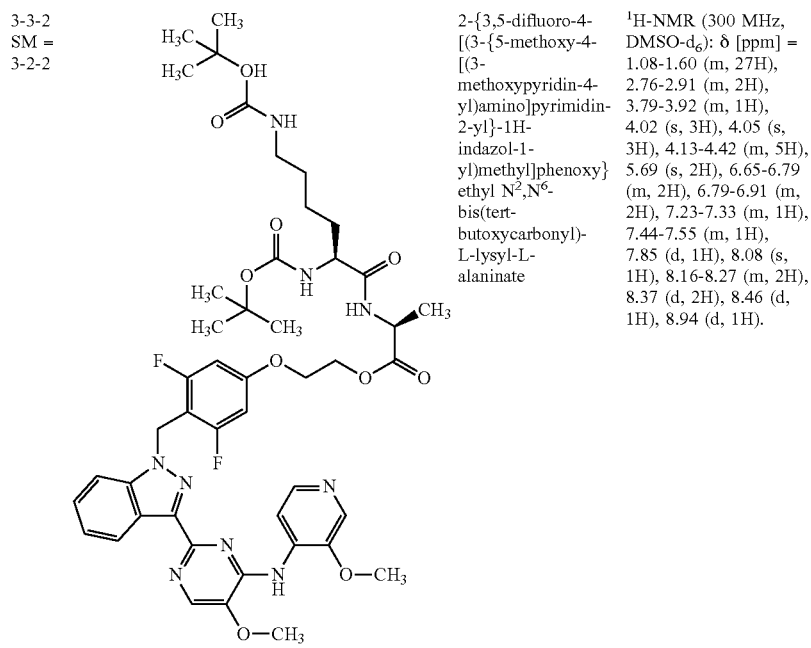

| | | | |
|---|---|---|---|
| 3-3-2 SM = 3-2-2 | | 2-{3,5-difluoro-4-[(3-{5-methoxy-4-[(3-methoxypyridin-4-yl)amino]pyrimidin-2-yl}-1H-indazol-1-yl)methyl]phenoxy}ethyl $N^2,N^6$-bis(tert-butoxycarbonyl)-L-lysyl-L-alaninate | $^1$H-NMR (300 MHz, DMSO-$d_6$): δ [ppm] = 1.08-1.60 (m, 27H), 2.76-2.91 (m, 2H), 3.79-3.92 (m, 1H), 4.02 (s, 3H), 4.05 (s, 3H), 4.13-4.42 (m, 5H), 5.69 (s, 2H), 6.65-6.79 (m, 2H), 6.79-6.91 (m, 2H), 7.23-7.33 (m, 1H), 7.44-7.55 (m, 1H), 7.85 (d, 1H), 8.08 (s, 1H), 8.16-8.27 (m, 2H), 8.37 (d, 2H), 8.46 (d, 1H), 8.94 (d, 1H). |

Intermediate 3-4-1

Preparation of 2-{3,5-difluoro-4-[(3-{4-[(2-fluoropyridin-4-yl)amino]-5-methoxypyrimidin-2-yl}-1H-indazol-1-yl)methyl]phenoxy}ethyl $N^2,N^6$-bis(tert-butoxycarbonyl)-D-lysyl-L-alaninate

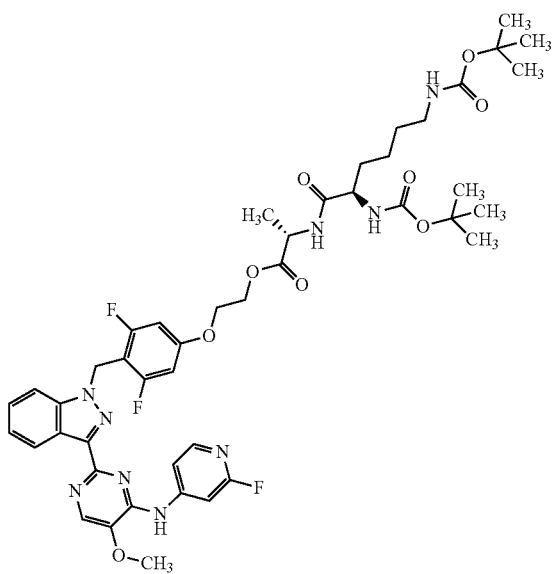 [SMILES: COc1cnc(-c2nn(Cc3c(F)cc(OCCOC(=O)[C@H](C)NC(=O)[C@@H](CCCCNC(=O)OC(C)(C)C)NC(=O)OC(C)(C)C)cc3F)c3ccccc23)nc1Nc1ccnc(F)c1]

399 mg 3-2-3 2-{3,5-difluoro-4-[(3-{4-[(2-fluoropyridin-4-yl)amino]-5-methoxypyrimidin-2-yl}-1H-indazol-1-yl)methyl]phenoxy}ethyl L-alaninate trifluoroacetate (1:1) (0.56 mmol, 1.0 eq.), 391 mg $N^2,N^6$-bis(tert-butoxycarbonyl)-D-lysine (1.13 mmol, 2.0 eq.), 515 mg 1-[Bis(dimethylamino)methylene]-1H-1,2,3-triazolo[4,5-b]pyridinium 3-oxid hexafluorophosphate (1.35 mmol, 2.4 eq.) and 490 µL N,Ndiisopropylethyl amine (2.8 mmol, 5.0 eq.) were combined in 87 mL DMF. The reaction mixture was stirred under Argon atmosphere for two days. The reaction mixture was evaporated and the crude product (3.3 g) was purified by flash chromatography and afterwards treated with ethyl acetate. The undissolved precipitate was filtered off to provide the 98% pure target compound: 310 mg, 0.33 mmol, 58%.

$^1$H-NMR (400 MHz, DMSO-$d_6$): δ [ppm]=1.11-1.20 (m, 2H), 1.23 (d, 3H), 1.26-1.31 (m, 2H), 1.32 (s, 9H), 1.35 (s, 9H), 1.40-1.58 (m, 2H), 2.79-2.91 (m, 2H), 3.84-3.94 (m, 1H), 4.06 (s, 3H), 4.17-4.25 (m, 2H), 4.25-4.42 (m, 2H), 5.71 (s, 2H), 6.67-6.77 (m, 2H), 6.78-6.84 (m, 2H), 7.25-7.31 (m, 1H), 7.47-7.55 (m, 1H), 7.87 (d, 1H), 8.00-8.10 (m, 2H), 8.12 (d, 1H), 8.19 (d, 1H), 8.42 (s, 1H), 8.48 (d, 1H), 9.77 (s, 1H).

The following intermediate was prepared according to the same procedure from the indicated starting materials (SM=starting material):

| | | | |
|---|---|---|---|
| 3-4-2<br>SM =<br>3-2-3 | 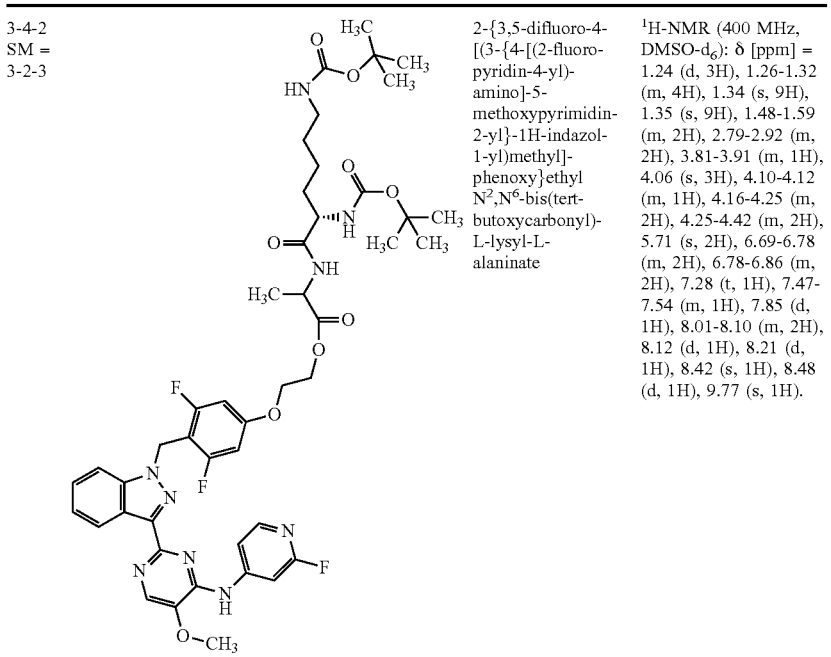 | 2-{3,5-difluoro-4-[(3-{4-[(2-fluoropyridin-4-yl)-amino]-5-methoxypyrimidin-2-yl}-1H-indazol-1-yl)methyl]-phenoxy}ethyl $N^2,N^6$-bis(tert-butoxycarbonyl)-L-lysyl-L-alaninate | $^1$H-NMR (400 MHz, DMSO-$d_6$): δ [ppm] = 1.24 (d, 3H), 1.26-1.32 (m, 4H), 1.34 (s, 9H), 1.35 (s, 9H), 1.48-1.59 (m, 2H), 2.79-2.92 (m, 2H), 3.81-3.91 (m, 1H), 4.06 (s, 3H), 4.10-4.12 (m, 1H), 4.16-4.25 (m, 2H), 4.25-4.42 (m, 2H), 5.71 (s, 2H), 6.69-6.78 (m, 2H), 6.78-6.86 (m, 2H), 7.28 (t, 1H), 7.47-7.54 (m, 1H), 7.85 (d, 1H), 8.01-8.10 (m, 2H), 8.12 (d, 1H), 8.21 (d, 1H), 8.42 (s, 1H), 8.48 (d, 1H), 9.77 (s, 1H). |

143

EXAMPLE COMPOUNDS OF PRODRUGS

Example 4-1-1

Preparation of 2-{3,5-difluoro-4-[(3-{5-methoxy-4-[(2-methylpyridin-4-yl)amino]pyrimidin-2-yl}-1H-indazol-1-yl)methyl]phenoxy}ethyl L-lysyl-L-alaninate, salt with trifluoroacetic acid

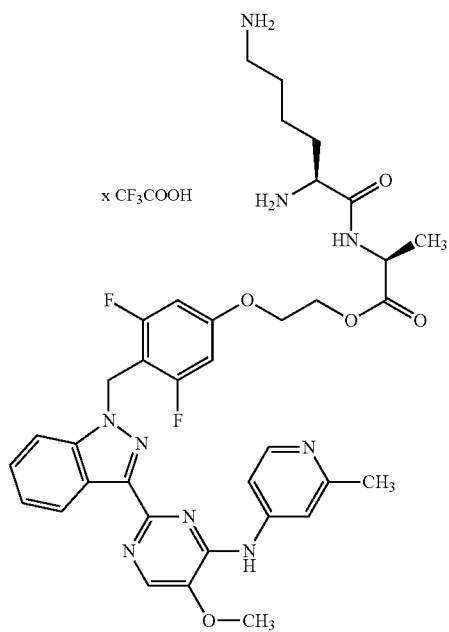 [SMILES: COc1cnc(-c2nn(Cc3c(F)cc(OCCOC(=O)[C@H](C)NC(=O)[C@@H](N)CCCCN)cc3F)c3ccccc23)nc1Nc1ccnc(C)c1]

58.00 mg 2-{3,5-Difluoro-4-[(3-{5-methoxy-4-[(2-methylpyridin-4-yl)amino]pyrimidin-2-yl}-1H-indazol-1-yl)methyl]phenoxy}ethyl $N^2,N^6$ bis(tert-butoxycarbonyl)-L-lysyl-L-alaninate 3-3-1 (0.06 mmol, 1.0 eq.) was dissolved in 1.8 mL dichloromethane. 0.49 mL trifluoracetic acid (6.32 mmol, 100.0 eq.) was added and the mixture was stirred at room temperature for 30 min. The reaction mixture was concentrated in vacuo at room temperature. The residue was treated with diethylether. Immediately there was a beige precipitate. It was filtered off under vacuo and washed with diethylether. Because the solid in the filter cake was very hygroscopic and changed immediately to an oily solid, the filter cake was dissolved in water and lyophilized: 95% purity, 50 mg, 0.05 mmol, 79%.

$^1$H-NMR (400 MHz, DMSO-$d_6$): δ [ppm]=1.29 (d, 3H), 1.31-1.41 (m, 2H), 1.43-1.58 (m, 2H), 1.63-1.74 (m, 2H), 2.65 (s, 3H), 2.68-2.78 (m, 2H), 3.75 (br.s., 1H), 4.09 (s, 3H), 4.18-4.25 (m, 2H), 4.28-4.44 (m, 3H), 5.74 (s, 2H), 6.76-6.89 (m, 2H), 7.25-7.36 (m, 1H), 7.47-7.55 (m, 1H), 7.70 (br. s, 3H), 7.83 (d, 1H), 8.11 (br. s, 3H), 8.21-8.29 (m, 1H), 8.46 (d, 1H), 8.52 (d, 1H), 8.60 (s, 1H), 8.77-8.89 (m, 2H), 10.51 (s, 1H).

The following examples were prepared according to the same procedure from the indicated starting materials (SM=starting material):

| | | | |
|---|---|---|---|
| 4-1-2<br>SM =<br>3-3-2 | 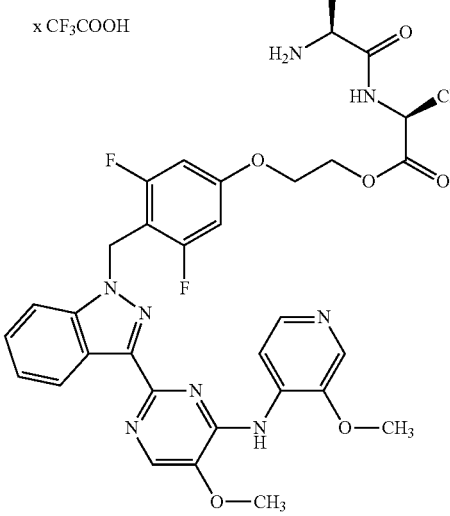 | 2-{3,5-difluoro-4-[(3-{5-methoxy-4-[(3-methoxypyridin-4-yl)amino]pyrimidin-2-yl}-1H-indazol-1-yl)methyl]phenoxy}ethyl L-lysyl-L-alaninate, salt with trifluoroacetic acid | $^1$H-NMR (300 MHz, DMSO-$d_6$): δ [ppm] = 1.28 (d, 3H), 1.31-1.43 (m, 2H), 1.44-1.58 (m, 2H), 1.63-1.76 (m, 2H), 2.65-2.80 (m, 2H), 3.69-3.82 (m, 1H), 4.10 (s, 3H), 4.14 (s, 3H), 4.18-4.44 (m, 5H), 5.73 (s, 2H), 6.78-6.95 (m, 2H), 7.23-7.38 (m, 1H), 7.47-7.57 (m, 1H), 7.75 (br. s., 3H), 7.84 (d, 1H), 8.15 (br. s., 3H), 8.38-8.53 (m, 2H), 8.57-8.70 (m, 3H), 8.87 (d, 1H), 9.38 (d, 1H). |

| | | | |
|---|---|---|---|
| 4-1-3 SM = 3-4-1 | 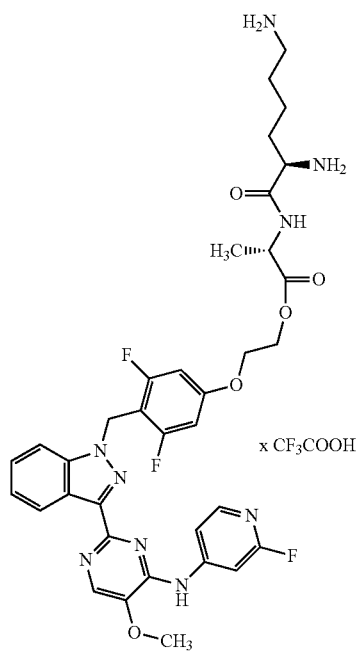 [SMILES: COc1cnc(-c2nn(Cc3c(F)cc(OCCOC(=O)[C@H](C)NC(=O)[C@H](N)CCCCN)cc3F)c3ccccc23)nc1Nc1ccnc(F)c1] | 2-{3,5-difluoro-4-[(3-{4-[(2-fluoro-pyridin-4-yl)-amino]-5-methoxypyrimidin-2-yl}-1H-indazol-1-yl)methyl]-phenoxy}ethyl D-lysyl-L-alaninate, salt with trifluoroacetic acid | ¹H-NMR (400 MHz, DMSO-d₆): δ [ppm] = 1.24-1.38 (m, 5H), 1.45-1.57 (m, 2H), 1.64-1.76 (m, 2H), 2.68-2.81 (m, 2H), 3.72-3.83 (m, 1H), 4.07 (s, 3H), 4.19-4.28 (m, 2H), 4.30-4.46 (m, 3H), 5.72 (s, 2H), 6.78-6.88 (m, 2H), 7.29 (t, 1H), 7.51 (t, 1H), 7.74 (br. s., 3H), 7.87 (d, 1H), 8.01-8.06 (m, 1H), 8.06-8.10 (m, 1H), 8.14 (br. s., 4H), 8.43 (s, 1H), 8.48 (d, 1H), 8.92 (d, 1H), 9.81 (s, 1H). |
| 4-1-4 SM = 3-4-2 | 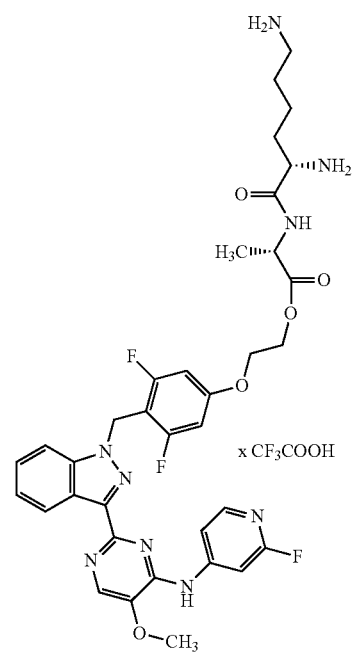 [SMILES: COc1cnc(-c2nn(Cc3c(F)cc(OCCOC(=O)[C@H](C)NC(=O)[C@@H](N)CCCCN)cc3F)c3ccccc23)nc1Nc1ccnc(F)c1] | 2-{3,5-difluoro-4-[(3-{4-[(2-fluoro-pyridin-4-yl)-amino]-5-methoxypyrimidin-2-yl}-1H-indazol-1-yl)methyl]-phenoxy}ethyl L-lysyl-L-alaninate, salt with trifluoroacetic acid | ¹H-NMR (400 MHz, DMSO-d₆): δ [ppm] = 1.27-1.42 (m, 5H), 1.48-1.58 (m, 2H), 1.64-1.77 (m, 2H), 2.69-2.81 (m, 2H), 3.71-3.81 (m, 1H), 4.07 (s, 3H), 4.19-4.27 (m, 2H), 4.29-4.46 (m, 3H), 5.72 (s, 2H), 6.78-6.87 (m, 2H), 7.25-7.33 (m, 1H), 7.47-7.55 (m, 1H), 7.75 (br. s., 3H), 7.87 (d, 1H), 8.01-8.05 (m, 1H), 8.06-8.09 (m, 1H), 8.10-8.23 (m, 4H), 8.43 (s, 1H), 8.48 (d, 1H), 8.88 (d, 1H), 9.81 (s, 1H). |

Synthetic Intermediates of Reference Compounds

Intermediate 5-1-1

Preparation of 2-[3,5-difluoro-4-({3-[5-methoxy-4-(pyridin-4-ylamino)pyrimidin-2-yl]-1 H-indazol-1-yl}methyl)phenoxy]ethyl N-(tert-butoxycarbonyl)-L-alaninate

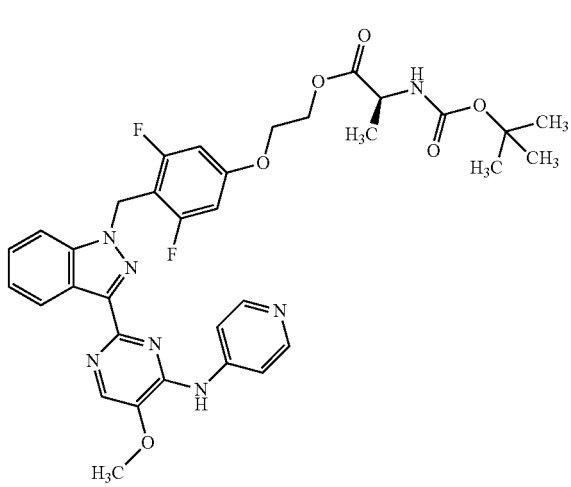 [SMILES: COc1cnc(-c2nn(Cc3c(F)cc(OCCOC(=O)[C@H](C)NC(=O)OC(C)(C)C)cc3F)c3ccccc23)nc1Nc1ccncc1]

178 mg 2-[3,5-Difluoro-4-({3-[5-methoxy-4-(pyridin-4-ylamino)pyrimidin-2-yl]-1 H-indazol-1-yl}methyl)phenoxy]ethanol Example 6-1-1 (0.353 mmol, 1.0 eq.) was dissolved in 6 mL DMF and 6 mL dichloromethane. Then 200 mg N-(tert-butoxycarbonyl)-L-alanine (1.1 mmol, 3.0 eq.), 43 mg 4-dimethylaminopyridine (0.35 mmol, 1.0 eq.), 0.0.37 mL N,N-diisopropylethylamine (2.1 mmol, 6.0 eq.) and 88 mg 1-(3-dimethylaminopropyl)-3-ethylcarbodiimidhydrochloride (0.46 mmol, 1.3 eq.) were added. The reaction mixture was put in an ultrasonic bath for 15 min. 200 mg N-(tert-butoxycarbonyl)-LI-alanine (1.1 mmol, 3.0 eq.), 43 mg 4-dimethylaminopyridine (0.35 mmol, 1.0 eq.) and 88 mg 1-(3-dimethylaminopropyl)-3-ethylcarbodiimidhydrochloride (0.46 mmol, 1.3 eq.) were added again and sonication was continued for another 15 min. The reaction mixture was evaporated. The residue was dissolved in 300 ml dichloromethane and the organic layer was washed with 5%-aqueous citric acid. The layers were separated. The organic layer was washed with saturated sodiumhydrogencarbonate-solution, dried using a water resistant filter and evaporated under vacuo. The crude product was used without further purification.
LC-MS:
retention time: 0.91 min MS ES+: 676 [M+H]+
Method 7

Intermediate 5-2-1

Preparation of 2-[3,5-difluoro-4-({3-[5-methoxy-4-(pyridin-4-ylamino)pyrimidin-2-yl]-1 H-indazol-1-yl}methyl)phenoxy]ethyl L-alaninate, salt with trifluoroacetic acid

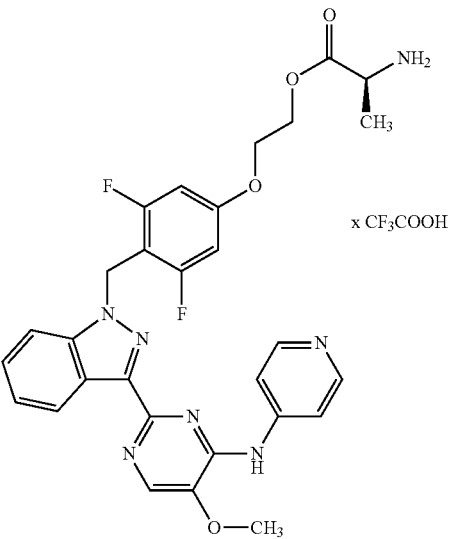 [SMILES: COc1cnc(-c2nn(Cc3c(F)cc(OCCOC(=O)[C@H](C)N)cc3F)c3ccccc23)nc1Nc1ccncc1]

63.80 mg 2-[3,5-Difluoro-4-({3-[5-methoxy-4-(pyridin-4-ylamino)pyrimidin-2-yl]-1 H-indazol-1-yl}methyl)phenoxy]ethyl N-(tert-butoxycarbonyl)-L-alaninate 5-1-1 (0.09 mmol, 1.0 eq.) was dissolved in 5.0 mL dichloromethane. 1.0 mL trifluoracetic acid was added and the mixture was stirred at room temperature for 30 min. The reaction mixture was evaporated under vacuo. The crude product was dissolved in acetonitrile and evaporated under vacuo. The crude product was dissolved in dichloromethane and methanol. By addition of diethylether the target compound precipitated. It was filtered off, dried under vacuum and used without further purification: 97% pure, 56 mg, 0.08 mmol, 84%.
LC-MS:
retention time: 0.63 min
MS ES+: 576 [M+H]+
Method 7

Intermediate 5-3-1

Preparation of 2-[3,5-difluoro-4-({3-[5-methoxy-4-(pyridin-4-ylamino)pyrimidin-2-yl]-1 H-indazol-1-yl}methyl)phenoxy]ethyl $N^2,N^6$-bis(tert-butoxycarbonyl)-L-lysyl-L-alaninate

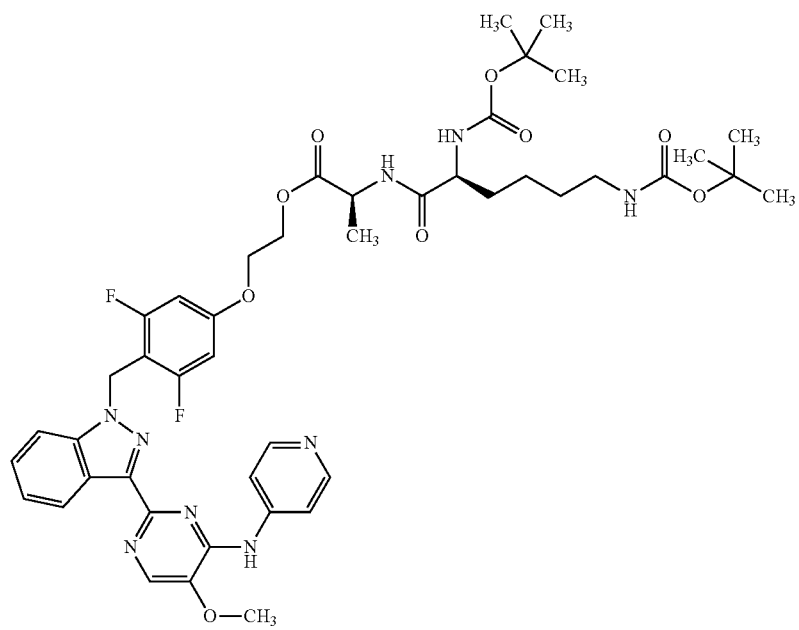 [SMILES: COc1cnc(-c2nn(Cc3c(F)cc(OCCOC(=O)[C@H](C)NC(=O)[C@H](CCCCNC(=O)OC(C)(C)C)NC(=O)OC(C)(C)C)cc3F)c3ccccc23)nc1Nc1ccncc1]

397 mg N²,N⁶-Bis(tert-butoxycarbonyl)-L-lysine (1.15 mmol, 2.0 eq.) and 0.4 mL N,N-diisopropylethylamine (2.29 mmol, 4.0 eq.) were dissolved in 6 mL DMF. Afterwards 242 mg 1-(3-dimethylaminopropyl)-3-ethylcarbodiimidhydrochloride (1.26 mmol, 2.2 eq.) was added. After 30 min. 395.00 mg 2-[3,5-difluoro-4-({3-[5-methoxy-4-(pyridin-4-ylamino)pyrimidin-2-yl]-1 H-indazol-1-yl}methyl)phenoxy]ethyl L-alaninate trifluoroacetate (1:1) 5-2-1 (0.57 mmol, 1.0 eq.) dissolved in 6 mL DMF was given into the reaction mixture. It was stirred 30 min at room temperature. The DMF was evaporated under vacuo. The residue was dissolved in 500 mL ethyl acetate and the organic layer was washed with 5%-aqueous citric acid twice. The organic layer was dried using a water resistant filter and the filtrate was evaporated under reduced pressure. The crude product was purified by flash chromatography to provide the target compound in 99% purity: 320 mg, 0.35 mmol, 61%.

LC-MS:

retention time: 1.01 min

MS ES+: 904 [M+H]⁺

Method 7

Example 5-4-1

Preparation of 2-[1-(4-ethoxy-2,6-difluorobenzyl)-1H-indazol-3-yl]-4-(pyridin-4-ylamino)pyrimidin-5-ol

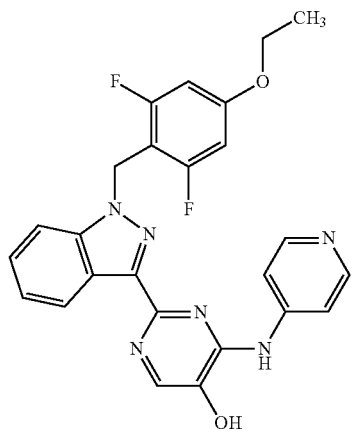 [SMILES: CCOc1cc(F)c(Cn2nc(-c3ncc(O)c(Nc4ccncc4)n3)c3ccccc32)c(F)c1]

Example 6-5-1 was prepared as described in WO 2013050438—Example 3-1

Example 5-5-1

Preparation of tert-butyl [2-(2-bromoethoxy)ethyl]carbamate

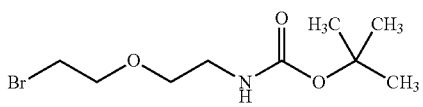

200 mg tert-butyl [2-(2-hydroxyethoxy)ethyl]carbamate (0.97 mmol, 1.0 eq.) and 388 mg tetrabromomethane (1.17 mmol, 1.2 eq.) were dissolved in 1.2 mL THF and cooled to 0° C. 307 mg triphenylphosphane (1.17 mmol, 1.2 eq.) were added. The reaction mixture was stirred at room temperature for 3 d. Hexane was added to form a white precipitate which was filtered off. The filtrate was evaporated under vacuo to provide the crude target compound, which was used without further purification: 381 mg, 1.42 mmol, 145%.

$^1$H-NMR (400 MHz, DMSO-d6): δ [ppm]=1.34 (s, 9H), 3.04 (q, 2H), 3.38 (t, 2H), 3.54 (t, 2H), 3.66 (t, 2H), 6.76 (t, 1H).

Example 5-6-1

Preparation of tert-butyl (2-{2-[{5-(2-{2-[(tert-butoxycarbonyl)amino]ethoxy}ethoxy)-2-[1-(4-ethoxy-2,6-difluorobenzyl)-1H-indazol-3-yl]pyrimidin-4-yl}(pyridin-4-yl)amino]ethoxy}-ethyl)carbamate

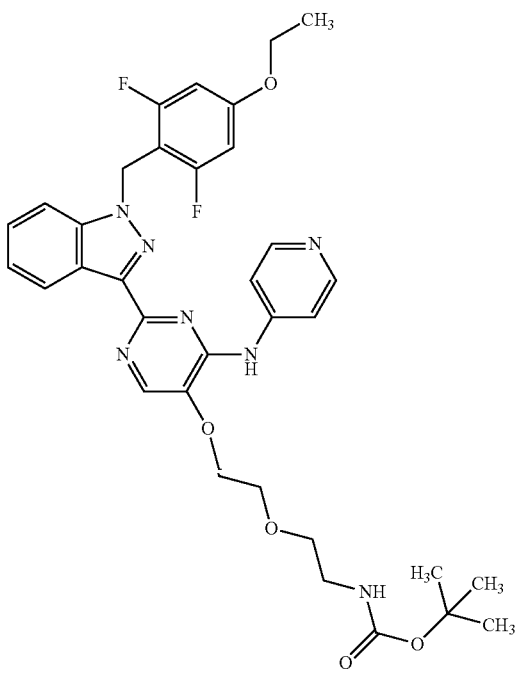 [SMILES: CCOc1cc(F)c(Cn2nc(-c3ncc(OCCOCCNC(=O)OC(C)(C)C)c(Nc4ccncc4)n3)c3ccccc32)c(F)c1]

35 mg 2-[1-(4-ethoxy-2,6-difluorobenzyl)-1H-indazol-3-yl]-4-(pyridin-4-ylamino)-pyrimidin-5-ol 5-4-1 (0.074 mmol, 1.0 eq.) was dissolved in 0.6 mL DMF. 31 mg potassium carbonate (0.22 mmol, 3.0 eq.) and 20 mg tert-butyl [2-(2-bromoethoxy)ethyl]carbamate 5-5-1 (0.074 mmol, 1.0 eq.) were added. The reaction mixture was stirred at room temperature over night. 20 mg tert-butyl [2-(2-bromoethoxy)ethyl]carbamate 5-5-1 (0.074 mmol, 1.0 eq.) was added and the reaction mixture was stirred for 2.5 h at room temperature. Butanone was added and the organic layer was washed with brine. The aqueous layer was extracted with butanone. The combined organic layers were dried with a waterresitent filter and concentrated in vacuo. The crude product was purified by flash chromatography to provide the 85% pure target compound: 20 mg, 0.03 mmol, 34%.

retention time: 1.20 min

MS ES+: 662.3 [M+H]+

Method 1

Example 5-7-1

Preparation of 5-[2-(2-aminoethoxy)ethoxy]-2-[1-(4-ethoxy-2,6-difluorobenzyl)-1H-indazol-3-yl]-N-(pyridin-4-yl)pyrimidin-4-amine, salt with hydrochloric acid

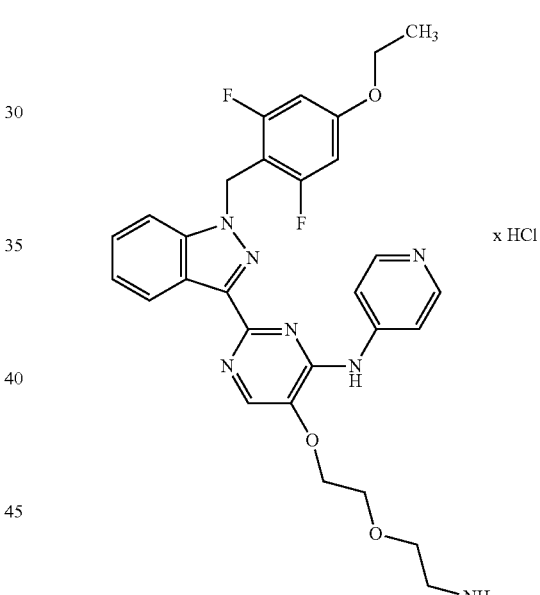

20 mg tert-butyl {2-[2-({2-[1-(4-ethoxy-2,6-difluorobenzyl)-1H-indazol-3-yl]-4-(pyridin-4-ylamino)pyrimidin-5-yl}oxy)ethoxy]ethyl}carbamate 5-6-1 (0.03 mmol, 1.0 eq.) was dissolved in 0.1 mL dioxane. 0.03 mL hydrochlorid acid (4 M in dioxane, 0.12 mmol, 4.0 eq.) were added and the reaction mixture was stirred 2 h at room temperature. The solvents were evaporated and the 90% pure crude product was used without further purification: 20 mg, 0.03 mmol, 100%.

$^1$H-NMR (400 MHz, DMSO-d6): δ [ppm]=1.25 (t, 3H), 2.91-3.03 (m, 2H), 3.67-3.77 (m, 2H), 3.88-3.95 (m, 2H), 4.01 (q, 2H), 4.42-4.46 (m, 2H), 5.68 (s, 2H), 6.75-6.82 (m, 2H), 7.18-7.34 (m, 1H), 7.42-7.53 (m, 1H), 7.83 (d, 1H), 8.15 (br. s, 3H), 8.39 (d, 1H), 8.53-8.65 (m, 3H), 8.81 (d, 2H), 10.62 (s, 1H), 14.98 (br. s, 1H).

REFERENCE COMPOUNDS

Example 6-1-1

Preparation of 2-[3,5-difluoro-4-({3-[5-methoxy-4-(pyridin-4-ylamino)pyrimidin-2-yl]-1H-indazol-1-yl}methyl)phenoxy]ethanol

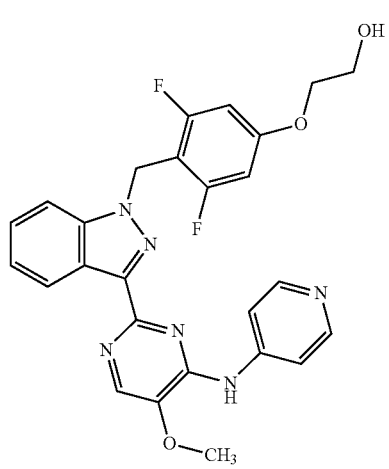 [SMILES: COc1cnc(-c2nn(Cc3c(F)cc(OCCO)cc3F)c3ccccc23)nc1Nc1ccncc1]

990 mg of 2-[3,5-difluoro-4-({3-[5-methoxy-4-(pyridin-4-ylamino)pyrimidin-2-yl]-1H-indazol-1-yl}methyl)phenoxy]ethyl acetate 6-3-1 (1.8 mmol, 1.0 eq.) was dissolved in 5.1 mL methanole. 803 mg lithiumhydroxide (34 mmol, 18.5 eq.) was dissolved in 6.5 mL water and added to the reaction mixture. The reaction mixture was stirred at rt over night. Saturated ammonium chlorid solution was added to neutrolize the reaction mixture. The precipitate was filtered off and dried under vacuum at 50° C. The crude product was purified by flash chromatography to provide the analytically pure target compound: 650 mg, 1.29 mmol, 71%.

$^1$H-NMR (300 MHz, DMSO-d$_6$): δ [ppm]=3.60-3.67 (m, 2H), 3.92-4.07 (m, 5H), 4.80-4.94 (t, 1H), 5.65 (s, 2H), 6.74-6.83 (m, 2H), 7.23 (t, 1H), 7.46 (t, 1H), 7.81 (d, 1H), 8.17 (d, 2H), 8.32 (s, 1H), 8.35-8.49 (m, 3H), 9.41 (s, 1H).

Example 6-2-1

Preparation of 2-[3,5-difluoro-4-({3-[5-methoxy-4-(pyridin-4-ylamino)pyrimidin-2-yl]-1 H-indazol-1-yl}methyl)phenoxy]ethyl L-lysyl-L-alaninate, salt with trifluoroacetic acid

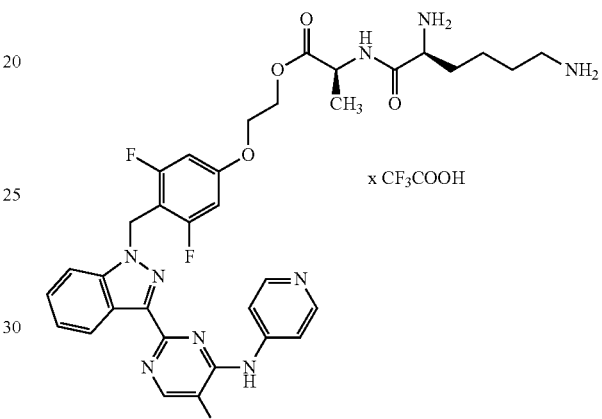

320.00 mg 2-[3,5-Difluoro-4-({3-[5-methoxy-4-(pyridin-4-ylamino)pyrimidin-2-yl]-1 H-indazol-1-yl}methyl)phenoxy]ethyl M, NM-bis(tert-butoxycarbonyl)-L-lysyl-L-alaninate 5-3-1 (0.34 mmol, 1.0 eq.) was dissolved in 22 mL dichloromethane. 5.5 mL trifluoracetic acid was added and the mixture was stirred at room temperature for 15 min. The reaction mixture was evaporated under vacuo at room temperature. The residue was treated with 100 mL diethylether and decanted off. Again it was digested with 100 mL diethylether and decanted off. The crude product was dried under high-vacuum and lyophilized: 312 mg, 0.33 mmol, 100% purity, 99%.

$^1$H-NMR (600 MHz, DMSO-d6): δ [ppm]=8.9 (d, 1H), 8.62 (m, 3H), 8.59 (s, 1H), 8.44 (d, 1H), 8.12 (s, 3H), 7.87 (d, 1H), 7.7 (s, 3H), 7.52 (t, 1H), 7.31 (t, 1H), 6.87 (d, 2H), 5.74 (s, 2H), 4.4 (m, 1H), 4.35-4.3 (m, 2H), 4.22 (m, 2H), 4.1 (s, 3H), 3.75, (m, 1H), 2.73 (m, 2H), 1.70 (q, 2H), 1.51 (q, 2H), 1.35 (m, 2H), 1.30 (d, 3H).

Example 6-3-1

Preparation of 2-[3,5-difluoro-4-({3-[5-methoxy-4-(pyridin-4-ylamino)pyrimidin-2-yl]-1H-indazol-1-yl}methyl)phenoxy]ethyl acetate

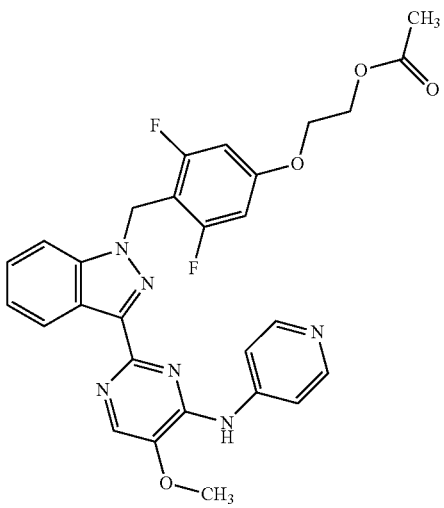 [SMILES: COc1cnc(-c2nn(Cc3c(F)cc(OCCOC(C)=O)cc3F)c3ccccc23)nc1Nc1ccncc1]

Example 6-3-1 was prepared as described in WO 2013050438—Example 2-51-1

Example 6-4-1

Preparation of 2-[1-(4-ethoxy-2,6-difluorobenzyl)-1H-indazol-3-yl]-5-methoxy-N-(pyridin-4-yl)pyrimidin-4-amine

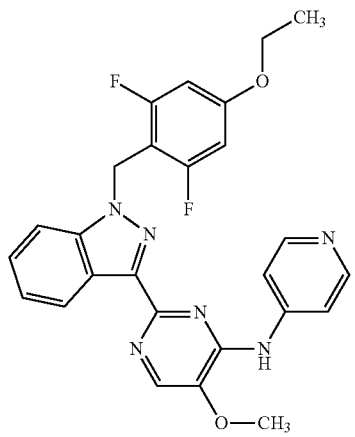 [SMILES: CCOc1cc(F)c(Cn2nc(-c3ncc(OC)c(Nc4ccncc4)n3)c3ccccc32)c(F)c1]

Example 6-4-1 was prepared as described in WO 2013050438—Example 2-5-1

Example 6-5-1

Preparation of 5-[({2-[2-({2-[1-(4-ethoxy-2,6-difluorobenzyl)-1H-indazol-3-yl]-4-(pyridin-4-ylamino)pyrimidin-5-yl}oxy)ethoxy]ethyl}carbamothioyl)amino]-2-(6-hydroxy-3-oxo-3H-xanthen-9-yl)benzoic acid

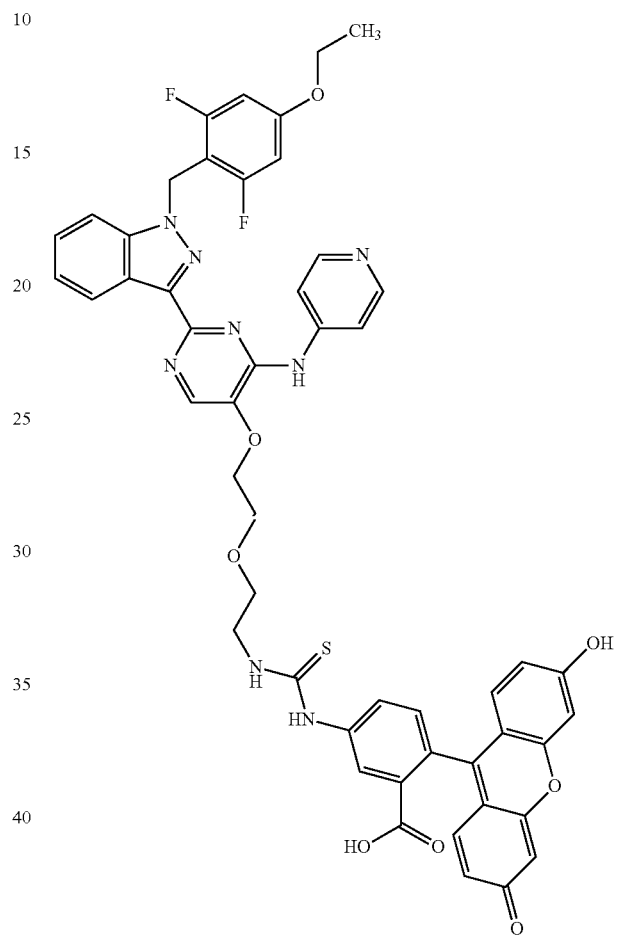

14 mg 5-[2-(2-aminoethoxy)ethoxy]-2-[1-(4-ethoxy-2,6-difluorobenzyl)-1H-indazol-3-yl]-N-(pyridin-4-yl)pyrimidin-4-amine dihydrochloride 6-8-1 (0.022 mmol, 1.0 eq.), 8.5 mg 3',6'-dihydroxy-5-isothiocyanato-3H-spiro[2-benzofuran-1,9'-xanthen]-3-one (0.022 mmol, 1.0 eq.) and 11 µL diisopropylethylamine (0.065 mmol, 3.0 eq.) were dissolved in 91 µL dichloromethane. The reaction mixture was stirred at room temperature for 72 h. Ethyl acetate and aqueous acidic acid were added. It was stirred at room temperature over night. The aqueous layer was extracted with ethyl acetate twice. The combined organic layers were washed with brine, dried over a water resistant filter and concentrated in vacuo. The crude product was purified by flash chromatography to provide the 97% pure target compound: 7.5 mg, 0.01 mmol, 35%.
retention time: 1.13 min
MS ES+: 951.3 [M+H]+
Method 1
Biological Investigations The following assays can be used to illustrate the commercial utility of the compounds according to the present invention.

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

The half-life of prodrugs (Table 3) poses a challenge for the verification of their biological activity. The Bub1 enzymatic activity assay (as per Biological Assay 1.0 infra) requires a minimum reaction time of 60 minutes in order to be able to assess the inhibitory activity of the compounds. During this time typically 20% to 60% of the prodrugs have been already converted to their corresponding drugs at the pH of 7.5 at which the assay is performed. Ideally one would perform the biological assay at a pH at which the prodrug is stable (e.g. pH 4). This is not viable in the case of Bub1, because the kinase is inactive this pH. Alternatively, an assay requiring shorter incubation times would better estimate the binding affinities of the prodrugs. In the present invention we have developed a biological assay (5.0) which allows quantifying the affinity of the prodrugs starting from 15 minutes of compound-enzyme incubation in aqueous buffer. Extrapolating the stability data from Tables 3 and 4, one would expect at this time point most of the compound present in the test solution to be the prodrug.

Figure 2:
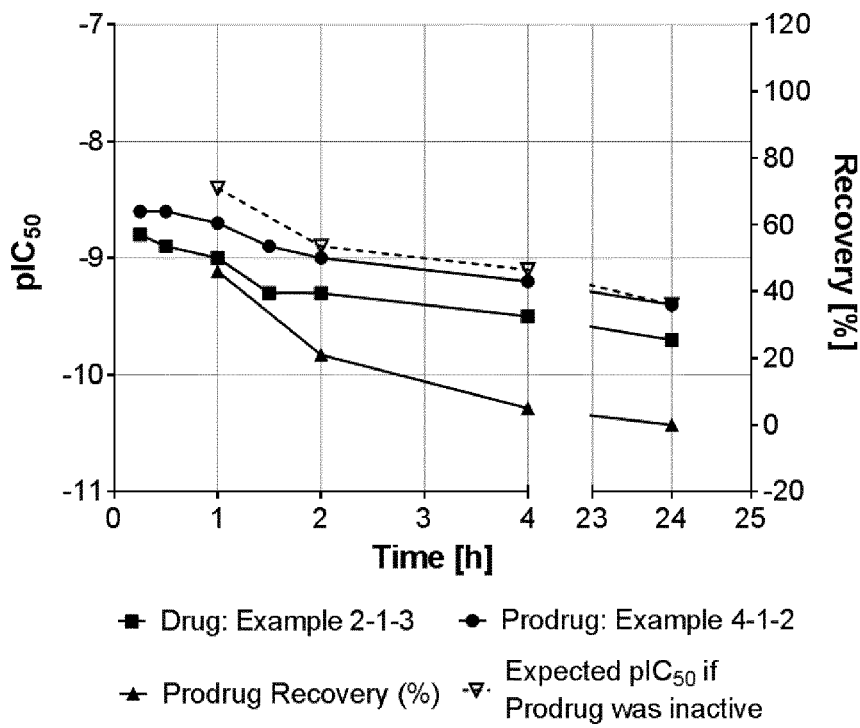
FIG. 2: binding affinities over time of example 2-1-3 and example 4-1-2 (prodrug), 5 together with the prodrug stability and $pIC_{50}$ to be expected if only the drug present.

FIGS. 1 and 2 combine the results from Biological Assay 5 with those from Biological Assay 6. The binding affinities over time of drug and prodrug pairs are shown as $pIC_{50}$ together with the prodrug stability, and the $pIC_{50}$ to be expected if only the drug present in the sample was responsible for the activity in the assay. Extrapolating the $pIC_{50}$ from these graphs to time 0 (at which 100% of prodrug is present in the sample), the actual affinity of the drug and prodrug can be inferred. Secondly, looking at the differences between expected and real $pIC_{50}$ an estimate can be made about the contribution of the prodrug to the observed activity.

These data demonstrate that the prodrugs are inhibitors of Bub1 kinase activity and therefore they contribute to the biological activities reported by the assays 1.0, 2.0, 3.0 and 4.0.

Biological Assay 1.0:
Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG (SEQ ID No. 1) (C-terminus in amide form), purchased from e.g. Biosyntan (Berlin, Germany) by the (recombinant) catalytic domain of human Bub1 (amino acids 704-1085), expressed in Hi5 insect cells with an N-terminal His6-tag and purified by affinity—(Ni-NTA) and size exclusion chromatography.

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nL of compounds were transferred into a black low volume test microtiter plate from the same supplier. Subsequently, 2 µL of Bub1 (the final concentration of Bub1 was adjusted depending on the activity of the enzyme lot in order to be within the linear dynamic range of the assay: typically ~200 ng/mL were used) in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1x Complete EDTA-free protease inhibitor mixture (Roche)] were added to the compounds in the test plate and the mixture was incubated for 15 min at 22° C. to allow pre-equilibration of the putative enzyme-inhibitor complexes before the start of the kinase reaction, which was initiated by the addition of 3 µL 1.67-fold concentrated solution (in assay buffer) of adenosine-tri-phosphate (ATP, 10 µM final concentration) and peptide substrate (1 µM final concentration). The resulting mixture (5 µL final volume) was incubated at 22° during 60 min., and the reaction was stopped by the addition of 5 µL of an aqueous EDTA-solution (50 mM EDTA, in 100 mM HEPES pH 7.5 and 0.2% (w/v) bovine serum albumin) which also contained the TR-FRET detection reagents (0.2 µM streptavidin-XL665 [Cisbio Bioassays, Codolet, France] and 1 nM anti-phosho-Serine antibody [Merck Millipore, cat. #35-001] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antibody complex recognizing the Phospho-serine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of (typically 32-) control wells for high- (=enzyme reaction without inhibitor=0%=Minimum inhibition) and low- (=all assay components without enzyme=100%=Maximum inhibition) Bub1 activity. $IC_{50}$ values were calculated by fitting the normalized inhibition data to a 4-parameter logistic equation (Minimum, Maximum, $IC_{50}$, Hill; $Y=Max+(Min-Max)/(1+(X/IC_{50})Hill)$).

Biological Assay 2.0:
Proliferation Assay:

Human tumour cells were originally obtained from the American Type Culture Collection (ATCC), the Deutsche Sammlung von Mikroorganismen und Zellkulturen (DSMZ, German Collection of Microorganisms and Cell Cultures), or Epo GmbH Berlin. Cultivated HeLa human cervical tumor cells (DSMZ ACC-57) were plated at a density of 3000 cells/well in a 96-well multititer plate in 200 µL of growth medium supplemented 10% fetal calf serum. After 24 hours, the cells of one plate (zero-point plate) were stained with crystal violet (see below), while the medium of the other plates was supplemented with the test substances in various concentrations (0 µM, as well as in the range of 0.001-10 µM; the final concentration of the solvent dimethyl sulfoxide was adjusted to 0.1%) using a Hewlett-Packard HP D300 Digital Dispenser. The cells were incubated for 4 days in the presence of test substances. Cell proliferation was determined by staining the cells with crystal violet: the cells were fixed by adding 20 µL/measuring point of an 11% glutaric aldehyde solution for 15 minutes at room temperature. After three washing cycles of the fixed cells with water, the plates were dried at room temperature. The cells were stained by adding 100 µL/measuring point of a 0.1% crystal violet solution (pH 3.0). After three washing cycles of the stained cells with water, the plates were dried at room temperature. The dye was dissolved by adding 100 µL/measuring point of a 10% acetic acid solution. Absorption was determined by photometry at a wavelength of 595 nm. The change of cell number, in percent, was calculated by normalization of the measured values to the absorption values of the zero-point plate (=0%) and the absorption of the untreated (0 µm) cells (=100%). The $IC_{50}$ values were determined by means of a 4 parameter fit.

Tab. 1. Compounds had been evaluated in the HeLa human cervical cancer cell line to demonstrate antiproliferative activity.

The following table gives the data for the examples of the present invention for the biological assays 1 and 2:

Biological Assay 3.0:
Proliferation Assay (HeLa+Paclitaxel):

Cultivated HeLa human cervical tumor cells (DSMZ ACC-57) were plated at a density of 3000 cells/well in a 96-well multititer plate in 200 µL of growth medium supplemented 10% fetal calf serum. After 24 hours, the cells of one plate (zero-point plate) were stained with crystal violet (see below). The medium of the other plates was supplemented with 3 nM of paclitaxel (Sigma-Aldrich) and the cells were incubated at 37° C. After 4 hours the test substances were added in various concentrations (0 µM, as well as in the range of 0.001-10 µM; the final concentration of the solvent dimethyl sulfoxide was adjusted to 0.1%) using a Hewlett-Packard HP D300 Digital Dispenser. The cells were incubated for another 92 hours at 37° C. in the presence of test substances. Cell proliferation was determined by staining the cells with crystal violet: the cells were fixed by adding 20 µL/measuring point of an 11% glutaric aldehyde solution for 15 minutes at room temperature. After three washing cycles of the fixed cells with water, the plates were dried at room temperature. The cells were stained by adding 100 µL/measuring point of a 0.1% crystal violet solution (pH 3.0). After three washing cycles of the stained cells with water, the plates were dried at room temperature. The dye was dissolved by adding 100 µL/measuring point of a 10% acetic acid solution. Absorption was determined by photometry at a wavelength of 595 nm. The change of cell number, in percent, was calculated by normalization of the measured values to the absorption values of the zero-point plate (=0%) and the 5 absorption of the untreated (0 µm) cells (=100%). The $IC_{50}$ values were determined by means of a 4 parameter fit.

Biological Assay 4.1: Formation-Assay
Cell-Based Mechanistic Assay: Changes of Phosphorylation Status of Histone 2A by Inhibition of Kinase Activity of Bub1

This assay determines the suppression of histone 2A phosphorylation by a Bub1 kinase inhibitor during co-treatment with Nocodazole. 25000 cells (cells were ordered from ATCC) were seeded in 96 well plate for 5 h at 37° C. Cells were treated with Nocodazole (1 µg/ml) and varying concentrations (between 3 nM and 10 µM) of test compounds for 16h. Cells were fixed (20 min, Fixing solution R&D), washed three times with PBS and blocked with Odyssey blocking buffer before incubating with the primary antibody against phosphorylated H2A (5 µg/ml ABIN482721) overnight at 2-80. After washing, secondary IRDye-labeled antibody mix with cell stains was added for 1h and washed again with PBS. Plates were scanned with LiCor Odyssey Infrared Imager CLx at 800 nm for P-H2A and at 700 nm for cell stains Draq5/Sapphire. The quotient of 800 nm and 700 nm for Nocodazole only treated cells was set as 100% and the quotient of 800 nm and 700 nm of untreated cells was set as 0%. The results given as % reflecting the inhibition of Bub1 kinase activity compared to control and normalized according to cell number. The $IC_{50}$ values were determined by means of a 4 parameter fit.

Biological Assay 4.2: Abrogation-Assay
Cell-Based Mechanistic Assay: Changes of Phosphorylation Status of Pre-Induced Phospho-Histone 2A by Inhibition of Kinase Activity of Bub1

This assay measures the inhibition of histone 2A phosphorylation, which was induced by pre-treatment of the cells with Nocodazole, by a Bub1 kinase inhibitor. 25000 cells (cells were ordered from ATCC) were seeded in 96 well plate for 5 h at 37° C. Cells were treated with Nocodazole (1 µg/ml). After 16h varying concentrations (between 3 nM and 10 µM) of test compounds were added and the cells were incubated for another 1h. Cells were fixed (20 min, Fixing solution R&D), washed three times with PBS and blocked with Odyssey blocking buffer before incubating with the primary antibody against phosphorylated H2A (5 µg/ml ABIN482721) overnight at 2-8° C. After washing, secondary IRDye-labeled antibody mix with cell stains was added for 1h and washed again with PBS. Plates were scanned with LiCor Odyssey Infrared Imager CLx at 800 nm for P-H2A and at 700 nm for cell stains Draq5/Sapphire. The quotient of 800 nm and 700 nm for Nocodazole only treated cells was set as 100% and the quotient of 800 nm and 700 nm of untreated cells was set as 0%. The results given as % reflecting the inhibition of Bub1 kinase activity compared to control and normalized according to cell number. The $IC_{50}$ values were determined by means of a 4 parameter fit.

Histone H2A is an immediate intracellular substrate of Bub1 kinase. Determination of the phosphorylation status of Histone H2A provides a direct measure of the intracellular activity of Bub1 kinase. The compounds according to the invention inhibit Bub1 kinase activity in with $IC_{50}$ values in the nanomolar range in biochemical assays similar as it was described for compounds from WO 2013050438. Surprisingly, it was now found that the compounds according to the invention inhibit intracellular Bub1 kinase activity, in terms of inhibition of Histone H2A phosphorylation, much more potently as compared to compounds from WO 2013050438.

Compounds according to the invention provide additional surprising benefits, such as:
more potent inhibition of HeLa human tumor cells, when used in combination with paclitaxel, and/or
reduced drug-drug interaction when used in combination with paclitaxel.

Biological Assay 5.0:
Equilibrium Probe Competition Assay:

Bub1 binding affinity of compounds described in the present invention were quantified using a time-resolved fluorescence energy transfer (TR-FRET) kinase binding assay which measures displacement of the synthetic fluorescent probe 5-[({2-[2-({2-[1-(4-ethoxy-2,6-difluorobenzyl)-1H-indazol-3-yl]-4-(pyridin-4-ylamino)pyrimidin-5- yl}oxy)ethoxy]ethyl}carbamothioyl)amino]-2-(6-hydroxy-3-oxo-3H-xanthen-9-yl)benzoic acid (6-5-1) by the (recombinant) catalytic domain of human Bub1 (amino acids 704-1085). The enzyme was expressed in Hi5 insect cells with N-terminal 6×His/AviTag® sequences, purified by affinity- (Ni-NTA) and size exclusion chromatography and site-specific biotinylated ex-vivo using a commercially available kit (Avidity). The probe 6-5-1 itself inhibits the kinase activity of Bub1 with an $IC_{50}$ of 20.8 nM.

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were made by serial dilution (1:3.4) of freshly prepared 2 mM stocks in a clear low volume 384-well source microtiter plate (Greiner Bio-One, Frickenhausen, Germany), from which 50 nl of compounds were transferred into a black low volume test microtiter plate from the same supplier. Subsequently 2 µL of a solution containing biotinylated Bub1 (the final concentration of Bub1 was adjusted depending on the activity of the enzyme lot in order to be within the linear dynamic range of the assay: typically ~200 µM were used) and 1 nM Streptavidin Terbium Cryptate (Cisbio, No. 610SATLB) in aqueous assay buffer [50 mM Tris/HCl pH 7.5, 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Triton X-100 (Sigma), were added to the compounds in the test plate and the mixture was incubated for 15 min at 22° C. to allow pre-equilibration of the putative enzyme-inhibitor complexes before the start of the probe competition reaction, which was initiated by the addition of 3 µL 1.67-fold concentrated solution (in assay buffer) of 6-5-1 (final concentration: 1.5 nM). The resulting mixture (5 µL final volume) was incubated at 22° C. during 0, 15, 30, 60, 120, 240 and 1440 min. After each time point the resonance energy transfer from the Streptavidin Tb cryptate to the 3',6'-dihydroxy-3H-spiro[2-benzofuran-1,9'-xanthen]-3-one moiety of 6-5-1 was measured in order to quantify the amount of fluorescent probe displaced by the test compounds. To this end, the fluorescence emissions at 520 nm and 490 nm after excitation at 330-350 nm were measured in a Pherastar FS TR-FRET plate reader, (BMG Lab technologies, Offenburg, Germany) and the ratio of the emissions (520 nm/490 nm) was taken as indicator for the amount of Bub1/6-5-1 equilibrium complexes. The data were normalized using two sets of control wells for high- (=enzyme reaction without inhibitor=0%=Minimum inhibition) and low- (=all assay components without enzyme=100%=Maximum inhibition) Bub1 activity. $IC_{50}$ values were calculated by fitting the normalized inhibition data to a 4-parameter logistic equation (Minimum, Maximum, $IC_{50}$, Hill; Y=Max+(Min−Max)/(1+(X/IC50)Hill)).

Biological Assay 6.0:
Stability in Buffer at Various pH Values (HPLC Detection)
 0.3 mg of the test compound was solved in 0.1 ml dimethylsulfoxide and 0.4 ml acetonitrile. For complete dissolution the HPLC vial with the sample solution was sonified for about 20 seconds. Then 1.0 ml of the respective buffer solution was added and the sample was again treated in the ultrasonic bath.
Buffer Solutions Used:
pH 4.0: Fluka buffer, Order No. 33643 (11.76 g citric acid, 2.57 g sodium chloride and 2.72 g sodium hydroxide)
pH 7.4: 90 g of sodium chloride, 13.61 g of potassium dihydrogen phosphate and 83.35 g of 1 M sodium hydroxide solution were made up to 1 L with Millipore water and then diluted 1:10.
10 µl portions of the sample solution were analysed by HPLC at different times (0 h, 1 h, 2h, 4h and 24h) at 37° C. The peak areas in percentage were used for quantification.

HPLC Method:
Agilent 1100 with DAD (G1315B), binary pump (G1312A), autosampler (G1329A), column oven (G1316A), thermostat (G1330B); column: Kromasil 100 C18, 250 mm×4 mm, 5 µm; column temperature: 37° C.; eluent A: water+5 ml of perchloric acid/litre, eluent B: acetonitrile.

Gradient:
0 min 98% A, 2% B→0-3.0 min 85% A, 15% B→3.0-8.0 min 50% A, 50% B→8.0-16.0 min 50% A, 50% B→16.0-20.0 min 10% A, 90% B→20.0-21.0 10% A, 90% B→21.0-24.0 min 98% A, 2% B→24.0-25.0 min 98% A, 2% B; flow rate: 1.5 ml/min; UV detection: 210 nm.

The ratios of the peak area (F) at different times in relation to the peak area at the starting point are shown in Table 3 for representative examples:

Biological Assay 7.0:
Evaluation of Drug-Drug Interaction Potential with Paclitaxel To evaluate the drug-drug interaction potential of test compounds with paclitaxel in vivo 8 mg/kg of paclitaxel were injected once intravenously into the tail vein of NMRI nude mice. Immediately thereafter 50 mg/kg of the test compound was administered by gavage to mice. Blood was taken from mice following decapitation 1, 3, 7 and 24 hours after injection of Paclitaxel. Plasma concentrations of test compound and of paclitaxel, respectively, were determined by LC/MSMS. The data from the paclitaxel mono treatment group, the test compound mono treatment group, and the combination treatment group were compared for evaluation of the drug-drug interaction potential.

TABLE 1

| Example Nr. | Biological Assay 1: Bub1 kinase assay median $IC_{50}$ [mol/L] | Biological Assay 2: Proliferation assay (HeLa cell line) median $IC_{50}$ [mol/L] |
| --- | --- | --- |
| 2-1-1 | 1.3E−8 | 4.1E−6 |
| 2-1-2 | 2.4E−8 | 1.3E−6 |
| 2-1-3 | 7.1E−9 | 1.7E−6 |
| 2-1-4 | 8.3E−9 | >1.0E−5 |
| 2-1-5 | 1.0E−8 | 3.1E−6 |
| 2-1-6 | 7.7E−9 | 8.5E−6 |
| 2-1-7 | 2.3E−8 | 9.1E−6 |
| 2-1-8 | 3.1E−8 | >1.0E−5 |
| 2-1-9 | 1.3E−8 | nd |
| 2-1-10 | 2.9E−8 | >1.0E−5 |
| 2-1-11 | 1.9E−8 | 5.1E−6 |
| 2-1-12 | 3.3E−8 | >1.0E−5 |
| 2-1-13 | 5.0E−9 | >1.0E−5 |
| 2-1-14 | 4.2E−7 | 1.5E−6 |
| 2-1-15 | 9.8E−9 | >1.0E−5 |
| 2-1-16 | 1.7E−8 | 3.1E−6 |
| 2-1-18 | 1.4E−8 | 1.4E−6 |
| 2-1-19 | 9.5E−8 | >1.0E−5 |
| 2-3-1 | 1.5E−8 | >1.0E−5 |
| 2-3-2 | 1.0E−8 | 1.0E−6 |
| 2-3-3 | 5.5E−8 | >1.0E−5 |
| 2-3-4 | 4.3E−8 | >1.0E−5 |
| 2-3-5 | 5.8E−8 | 3.3E−6 |
| 2-3-6 | 1.9E−8 | >1.0E−5 |

TABLE 1-continued

| | Biological Assay 1: Bub1 kinase assay median IC$_{50}$ [mol/L] | Biological Assay 2: Proliferation assay (HeLa cell line) median IC$_{50}$ [mol/L] |
|---|---|---|
| 2-3-7 | 2.8E−8 | 6.9E−6 |
| 2-3-8 | 1.7E−8 | 2.6E−6 |
| 2-4-1 | 3.7E−8 | nd |
| Reference Compounds: | | |
| 6-1-1 | 6.2E−9 | 3.2E−6 |
| 6-3-1 | 1.0E−8 | 3.3E−6 |
| 6-4-1 | 5.2E−8 | 2.4E−6 |
| 6-5-1 | 2.1E−8 | nd |

TABLE 2

| | Biological Assay 4.1: H2A Formation IC$_{50}$ [mol/L] | Biological Assay 4.2: H2A Abrogation IC$_{50}$ [mol/L] | Biological Assay 3: Proliferation Assay (HeLa + Paclitaxel) IC$_{50}$ [mol/L] |
|---|---|---|---|
| Example Nr. | | | |
| 2-1-1 | 9.4E−8 | 1.0E−8 | 2.4E−7 |
| 2-1-2 | 8.7E−9 | 1.1E−8 | 3.5E−7 |
| 2-1-3 | 4.3E−8 | 2.9E−8 | 6.3E−8 |
| 2-1-4 | 8.2E−9 | 1.5E−7 | 1.0E−7 |
| 2-1-5 | 6.9E−9 | 6.0E−7 | 1.5E−7 |
| 2-1-6 | 5.6E−8 | 8.9E−7 | 3.7E−7 |
| 2-1-7 | 2.7E−8 | >3.0E−6 2.8E−7 | 4.8E−7 |
| 2-1-8 | nd | nd | 1.2E−7 |
| 2-1-9 | nd | nd | nd |
| 2-1-10 | 4.6E−8 | 1.6E−8 | 2.9E−7 |
| 2-1-11 | 4.9E−9 | 5.2E−9 | 1.1E−7 |
| 2-1-12 | 6.0E−9 | 1.1E−8 | 4.2E−7 |
| 2-1-13 | 1.8E−8 | 2.7E−9 | 5.1E−7 |
| 2-1-14 | 3.9E−8 | 1.1E−8 | 1.1E−6 |
| 2-1-15 | 2.4E−8 | 1.2E−9 | 3.6E−7 |
| 2-1-16 | 8.7E−8 | 7.4E−8 | 3.0E−7 |
| 2-1-18 | 3.5E−8 | 2.1E−9 | 5.1E−8 |
| 2-1-19 | nd | nd | 1.4E−7 |
| 2-3-1 | 3.8E−8 | 7.2E−10 | 7.2E−8 |
| 2-3-2 | >1.0E−6, 2.3E−8 | 9.8E−9 | 5.5E−8 |
| 2-3-3 | 2.1E−7 | 3.1E−7 | 2.0E−7 |
| 2-3-4 | 2.4E−9 | 1.9E−9 | 1.5E−7 |
| 2-3-5 | 2.0E−9 | >1.0E−6 | 6.9E−8 |
| 2-3-6 | 5.3E−8 | 2.7E−10 | 1.2E−7 |
| 2-3-7 | 6.3E−8 | 3.1E−10 | 1.1E−7 |
| 2-3-8 | >1.0E−6 | >1.0E−6 | 1.6E−7 |
| 2-4-1 | nd | nd | nd |
| Reference Compounds: | | | |
| 6-1-1 | 2.0E−7 | 5.4E−6 | 4.3E−7 |
| 6-3-1 | 1.7E−6 | 3.6E−6 | 6.5E−7 |
| 6-4-1 | 7.4E−8 | 9.2E−7 | 6.6E−7 |
| 6-5-1 | nd | nd | nd |

TABLE 3

| | Biological Assay 6: Stability pH 4: % Test Compound/Parent compound after 4 h [F(t = 4 h) × 100/F(t = 0 h)] | Biological Assay 6: Stability pH 7.4: % Test Compound/Parent compound after 4 h [F(t = 4 h) × 100/F(t = 0 h)] |
|---|---|---|
| Prodrug No./ Parents compound No. | | |
| 4-1-1/2-1-2 | 100%/0% | 4%/96% |
| 4-1-2/2-1-3 | 100%/13% | 5%/107% |
| 4-1-3/2-1-11 | 100%/2% | 0%/97% |
| 4-1-4/2-1-11 | 100%/1% | 9%/92% |
| Reference Compounds: | | |
| 6-2-1/6-1-1 | 100%/2% | 3%/103% |

TABLE 4

Assay 5

| Compound | Type | Time (min.) | IC$_{50}$ (M) | Recovery (%) |
|---|---|---|---|---|
| 2-1-2 | Drug | 0 | | |
| 2-1-2 | Drug | 15 | 1.6E−09 | |
| 2-1-2 | Drug | 30 | 3.5E−09 | |
| 2-1-2 | Drug | 60 | 2.2E−09 | |
| 2-1-2 | Drug | 90 | 3.2E−09 | |
| 2-1-2 | Drug | 120 | 2.9E−09 | |
| 2-1-2 | Drug | 240 | 4.0E−09 | |
| 2-1-2 | Drug | 1440 | 2.4E−09 | |
| 4-1-1 | Prodrug | 0 | | |
| 4-1-1 | Prodrug | 15 | 1.7E−08 | |
| 4-1-1 | Prodrug | 30 | 1.0E−08 | |
| 4-1-1 | Prodrug | 60 | 1.2E−08 | 44 |
| 4-1-1 | Prodrug | 90 | 1.0E−08 | |
| 4-1-1 | Prodrug | 120 | 7.2E−09 | 19 |
| 4-1-1 | Prodrug | 240 | 5.8E−09 | 4 |
| 4-1-1 | Prodrug | 1440 | 2.7E−09 | 0 |
| 2-1-3 | Drug | 0 | | |
| 2-1-3 | Drug | 15 | 1.7E−09 | |
| 2-1-3 | Drug | 30 | 1.3E−09 | |
| 2-1-3 | Drug | 60 | 9.0E−10 | |
| 2-1-3 | Drug | 90 | 5.4E−10 | |
| 2-1-3 | Drug | 120 | 4.9E−10 | |
| 2-1-3 | Drug | 240 | 3.1E−10 | |
| 2-1-3 | Drug | 1440 | 2.0E−10 | |
| 4-1-2 | Prodrug | 0 | | |
| 4-1-2 | Prodrug | 15 | 2.7E−09 | |
| 4-1-2 | Prodrug | 30 | 2.3E−09 | |
| 4-1-2 | Prodrug | 60 | 2.2E−09 | 46 |
| 4-1-2 | Prodrug | 90 | 1.3E−09 | |
| 4-1-2 | Prodrug | 120 | 1.0E−09 | 21 |
| 4-1-2 | Prodrug | 240 | 6.9E−10 | 5 |
| 4-1-2 | Prodrug | 1440 | 3.6E−10 | 0 |

The invention claimed is:
1. A compound of formula (I)

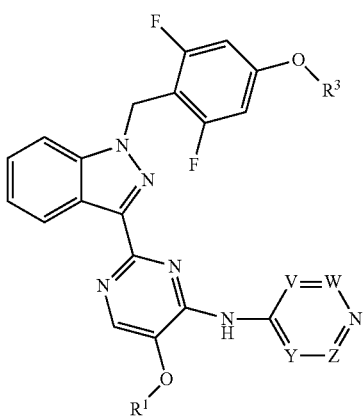

(I)

wherein:
V, W, Y and Z are independently CH or $CR^2$, wherein one of V, W, Y and Z is $CR^2$;
or
V is N, and W, Y and Z are independently CH or $CR^2$;
or
V and Y are N, and W and Z are independently CH or $CR^2$;
$R^1$ is a group selected from the group consisting of:
  $C_1$-$C_6$-alkyl, $C_1$-$C_6$-haloalkyl, $C_3$-$C_6$-cycloalkyl, ($C_1$-$C_3$-alkoxy)-($C_2$-$C_3$-alkyl)-, and ($C_3$-$C_6$-cycloalkyl)-($C_1$-$C_3$-alkyl)-,
$R^2$ is independently halogen or a group selected from the group consisting of:
  $C_1$-$C_3$-alkyl, $C_3$-$C_4$-cycloalkyl, $C_1$-$C_3$-haloalkyl, $C_1$-$C_3$-alkoxy,
  $C_1$-$C_3$-haloalkoxy, —N(H)C(=O)—($C_1$-$C_3$-alkyl),
  —N(H)C(=O)H,
  —N(H)C(=O)—($C_1$-$C_3$-hydroxyalkyl),
  —N(H)C(=O)—($C_1$-$C_3$-alkyl)-($C_1$-$C_3$-alkoxy),
  —N(H)C(=O)-phenyl,
  —N(H)C(=O)—($C_3$-$C_4$-cycloalkyl),
  —N(H)C(=O)—($C_1$-$C_3$-alkyl)-($C_3$-$C_4$-cycloalkyl),
  and —N(H)C(=O)N(H)$R^8$,
    wherein said —N(H)C(=O)-phenyl being optionally substituted at the phenyl ring one, two or three times, identically or differently, with a substituent selected from the group consisting of:
    halogen, hydroxy, cyano, $C_1$-$C_4$-alkyl, $C_1$-$C_4$-haloalkyl,
    $C_1$-$C_4$-alkoxy, $C_1$-$C_4$-haloalkoxy, $C_3$-$C_4$-cycloalkyl, and
    $C_3$-$C_4$-cycloalkyloxy, and
    wherein said —N(H)C(=O)—($C_3$-$C_4$-cycloalkyl) is optionally substituted at the $C_3$-$C_4$-cycloalkyl ring with a substituent selected from the group consisting of:
    fluorine, chlorine, trifluoromethyl, and methoxy,
$R^3$ is a group selected from the group consisting of:
  $C_2$-$C_6$-hydroxyalkyl, and $R^4$,
    wherein said $C_2$-$C_6$-hydroxyalkyl groups being optionally substituted with one, two or three halogen atoms selected from the group consisting of:
    fluorine, and chlorine,
$R^4$ is —($C_2$-$C_6$-alkyl)-OC(=O)—C(H)($R^5$)—N(H)C(=O)—C(H)($R^7$)—$NH_2$,
  wherein said $C_2$-$C_6$-alkyl group is optionally substituted with one, two or three halogen atoms selected from the group consisting of:
  fluorine, and chlorine,
$R^5$ and $R^7$ are independently hydrogen (glycine) or a group selected from the group consisting of:
  —$CH_3$ (alanine), —C(H)($CH_3$)$_2$ (valine), —($CH_2$)$_2$$CH_3$ (norvaline), —$CH_2$C(H)($CH_3$)$_2$ (leucine),
  —C(H)($CH_3$)$CH_2$$CH_3$ (isoleucine), —($CH_2$)$_3$$CH_3$ (norleucine), —C($CH_3$)$_3$ (2-tert-butylglycine),
  benzyl (phenylalanine), 4-hydroxybenzyl (tyrosine),
  —($CH_2$)$_3$$NH_2$ (ornithine),
  —($CH_2$)$_4$$NH_2$ (lysine), —($CH_2$)$_2$C(H)(OH)$CH_2$$NH_2$ (hydroxylysine), —$CH_2$OH (serine),
  —($CH_2$)$_2$OH (homoserine), —C(H)(OH)$CH_3$ (threonine), —($CH_2$)$_3$N(H)C(=NH)$NH_2$ (arginine),
  —($CH_2$)$_3$N(H)C(=O)$NH_2$ (citrulline), —$CH_2$C(=O)$NH_2$ (asparagine), —$CH_2$C(=O)OH (aspartic acid),
  —($CH_2$)$_2$C(=O)OH (glutamic acid), —($CH_2$)$_2$C(=O)$NH_2$ (glutamine), —$CH_2$SH (cysteine),
  —($CH_2$)$_2$SH (homocysteine), —($CH_2$)$_2$$SCH_3$ (methionine), —$CH_2$$SCH_3$ (S-methylcysteine),
  (1H-imidazol-4-yl)methyl-(histidine), (1H-indol-3-yl)methyl-(tryptophan),
  —$CH_2$$NH_2$ (2,3-diaminopropanoic acid), and
  —($CH_2$)$_2$$NH_2$ (2,4-diaminobutanoic acid); and
$R^8$ is hydrogen or a group selected from the group consisting of:
  $C_1$-$C_3$-alkyl, $C_1$-$C_3$-haloalkyl, $C_2$-$C_3$-hydroxyalkyl, $C_3$-$C_4$-cycloalkyl, ($C_3$-$C_4$-cycloalkyl)-($C_1$-$C_3$-alkyl)-, and ($C_1$-$C_3$-alkoxy)-($C_2$-$C_3$-alkyl)-, or an N-oxide, a salt, a tautomer or a stereoisomer of said compound, or a salt of said N-oxide, tautomer or stereoisomer.

2. The compound of formula (I) according to claim 1, wherein:

V, W, Y and Z are independently CH or $CR^2$, wherein one of V, W, Y and Z is $CR^2$;

or,

V is N, and W, Y and Z are independently CH or $CR^2$;

$R^1$ is a group selected from the group consisting of:
$C_1$-$C_3$-alkyl, $C_1$-$C_3$-haloalkyl, $C_3$-$C_4$-cycloalkyl, ($C_1$-$C_3$-alkoxy)-($C_2$-$C_3$-alkyl)-, and ($C_3$-$C_4$-cycloalkyl)-($C_1$-$C_3$-alkyl)-, $R^2$ is halogen or a group selected from the group consisting of:
$C_1$-$C_3$-alkyl, $C_3$-$C_4$-cycloalkyl, $C_1$-$C_3$-haloalkyl, $C_1$-$C_3$-alkoxy,
$C_1$-$C_3$-haloalkoxy, —N(H)C(=O)—($C_1$-$C_3$-alkyl),
—N(H)C(=O)H,
—N(H)C(=O)—($C_1$-$C_3$-hydroxyalkyl),
—N(H)C(=O)—($C_1$-$C_3$-alkyl)-($C_1$-$C_3$-alkoxy),
—N(H)C(=O)-phenyl,
—N(H)C(=O)—($C_3$-$C_4$-cycloalkyl),
—N(H)C(=O)—($C_1$-$C_3$-alkyl)-($C_3$-$C_4$-cycloalkyl),
and —N(H)C(=O)N(H)$R^8$,
wherein said —N(H)C(=O)-phenyl being optionally substituted at the phenyl ring one, two or three times, identically or differently, with a substituent selected from the group consisting of:
halogen, hydroxy, cyano, $C_1$-$C_4$-alkyl, $C_1$-$C_4$-haloalkyl,
$C_1$-$C_4$-alkoxy, $C_1$-$C_4$-haloalkoxy, $C_3$-$C_4$-cycloalkyl, and
$C_3$-$C_4$-cycloalkyloxy, and
wherein said —N(H)C(=O)—($C_3$-$C_4$-cycloalkyl) being optionally substituted at the $C_3$-$C_4$-cycloalkyl ring with a substituent selected from the group consisting of:
fluorine, chlorine, trifluoromethyl, and methoxy;

$R^3$ is a group selected from the group consisting of:
$C_2$-$C_6$-hydroxyalkyl, and $R^4$,
wherein said $C_2$-$C_6$-hydroxyalkyl groups being optionally substituted with one, two or three halogen atoms selected from the group consisting of:
fluorine, and chlorine;

$R^4$ is —($C_2$-$C_6$-alkyl)-OC(=O)—C(H)($R^5$)—N(H)C(=O)—C(H)($R^7$)—$NH_2$,
wherein said $C_2$-$C_6$-alkyl is optionally substituted with one, two or three halogen atoms selected from the group consisting of:
fluorine, and chlorine;

$R^5$ and $R^7$ are independently hydrogen(glycine) or a group selected from the group consisting of:
—$CH_3$ (alanine), —C(H)($CH_3$)$_2$ (valine), —($CH_2$)$_2$$CH_3$ (norvaline), —$CH_2$C(H)($CH_3$)$_2$ (leucine),
—C(H)($CH_3$)$CH_2$$CH_3$ (isoleucine), —($CH_2$)$_3$$CH_3$ (norleucine), —C($CH_3$)$_3$ (2-tert-butylglycine), benzyl (phenylalanine), 4-hydroxybenzyl (tyrosine),
—($CH_2$)$_3$$NH_2$ (ornithine),
—($CH_2$)$_4$$NH_2$ (lysine), —($CH_2$)$_2$C(H)(OH)$CH_2$$NH_2$ (hydroxylysine), —$CH_2$OH (serine),
—($CH_2$)$_2$OH (homoserine), —C(H)(OH)$CH_3$ (threonine), —($CH_2$)$_3$N(H)C(=NH)$NH_2$ (arginine),
—($CH_2$)$_3$N(H)C(=O)$NH_2$ (citrulline), —$CH_2$C(=O)$NH_2$ (asparagine), —$CH_2$C(=O)OH (aspartic acid), —($CH_2$)$_2$C(=O)OH (glutamic acid), —($CH_2$)$_2$C(=O)$NH_2$ (glutamine), —$CH_2$SH (cysteine),
—($CH_2$)$_2$SH (homocysteine), —($CH_2$)$_2$$SCH_3$ (methionine), —$CH_2$$SCH_3$ (S-methylcysteine),
(1H-imidazol-4-yl)methyl-(histidine), (1H-indol-3-yl)methyl-(thryptophan),
—$CH_2$$NH_2$ (2,3-diaminopropanoic acid), and —($CH_2$)$_2$$NH_2$ (2,4-diaminobutanoic acid); and $R^8$ is hydrogen or a group selected from the group of:
$C_1$-$C_3$-alkyl, $C_1$-$C_3$-haloalkyl, $C_2$-$C_3$-hydroxyalkyl, $C_3$-$C_4$-cycloalkyl,
($C_3$-$C_4$-cycloalkyl)-($C_1$-$C_3$-alkyl)-, and ($C_1$-$C_3$-alkoxy)-($C_2$-$C_3$-alkyl)-, or an N-oxide, a salt, a tautomer or a stereoisomer of said compound, or a salt of said N-oxide, tautomer or stereoisomer.

3. The compound of formula (I) according to claim 1, wherein:

V, W, Y and Z are independently CH or $CR^2$, wherein one of V, W, Y and Z is $CR^2$;

or,

V is N, and W, Y and Z are independently CH or $CR^2$;

$R^1$ is a group selected from the group of consisting of:
$C_1$-$C_3$-alkyl, $C_1$-$C_3$-haloalkyl, and $C_3$-$C_4$-cycloalkyl;

$R^2$ is independently halogen or a group selected from the group consisting of:
$C_1$-$C_3$-alkyl, $C_3$-$C_4$-cycloalkyl, $C_1$-$C_3$-haloalkyl, $C_1$-$C_3$-alkoxy,
$C_1$-$C_3$-haloalkoxy, —N(H)C(=O)—($C_1$-$C_3$-alkyl),
—N(H)C(=O)H,
—N(H)C(=O)—($C_1$-$C_3$-hydroxyalkyl),
—N(H)C(=O)—($C_1$-$C_3$-alkyl)-($C_1$-$C_3$-alkoxy),
—N(H)C(=O)-phenyl,
—N(H)C(=O)—($C_3$-$C_4$-cycloalkyl),
—N(H)C(=O)—($C_1$-$C_3$-alkyl)-($C_3$-$C_4$-cycloalkyl),
and —N(H)C(=O)N(H)$R^8$,
wherein said —N(H)C(=O)-phenyl being optionally substituted at the phenyl ring one, two or three times, identically or differently, with a substituent selected from the group consisting of:
halogen, hydroxy, cyano, $C_1$-$C_4$-alkyl, $C_1$-$C_4$-haloalkyl,
$C_1$-$C_4$-alkoxy, $C_1$-$C_4$-haloalkoxy, $C_3$-$C_4$-cycloalkyl, and
$C_3$-$C_4$-cycloalkyloxy, and
wherein said —N(H)C(=O)—($C_3$-$C_4$-cycloalkyl) being optionally substituted at the $C_3$-$C_4$-cycloalkyl ring with a substituent selected from the group consisting of:
fluorine, chlorine, trifluoromethyl, and methoxy;

$R^3$ is a group selected from the group consisting of:
$C_2$-$C_6$-hydroxyalkyl, and $R^4$,
wherein said $C_2$-$C_6$-hydroxyalkyl group being optionally substituted with one, two or three halogen atoms selected from group consisting of:
fluorine, and chlorine;

$R^4$ is —($C_2$-$C_6$-alkyl)-OC(=O)—C(H)($R^5$)—N(H)C(=O)—C(H)($R^7$)—$NH_2$,
wherein said $C_2$-$C_6$-alkyl group is optionally substituted with one, two or three halogen atoms selected from the group consisting of:
fluorine, and chlorine;

$R^5$ and $R^7$ are independently a group selected from the group consisting of:
—$CH_3$ (alanine), —C(H)($CH_3$)$_2$ (valine),
—($CH_2$)$_2$$CH_3$ (norvaline), —($CH_2$)$_3$$NH_2$ (ornithine), —(CH$_2$)$_4$NH$_2$ (lysine), and —(CH$_2$)$_3$N(H)C(═NH)NH$_2$ (arginine); and R$^8$ is hydrogen or a group selected from the group consisting of:
C$_1$-C$_3$-alkyl, C$_1$-C$_3$-haloalkyl, C$_2$-C$_3$-hydroxyalkyl, C$_3$-C$_4$-cycloalkyl,
(C$_3$-C$_4$-cycloalkyl)-(C$_1$-C$_3$-alkyl)-, and (C$_1$-C$_3$-alkoxy)-(C$_2$-C$_3$-alkyl)-, or an N-oxide, a salt, a tautomer or a stereoisomer of said compound, or a salt of said N-oxide, tautomer or stereoisomer.

4. The compound of formula (I) according to claim 1, wherein

V, W, Y and Z are independently CH or CR$^2$, wherein one of V, W, Y and Z is CR$^2$;
or
V is N, and W, Y and Z are independently CH or CR$^2$;
R$^1$ is a C$_1$-C$_3$-alkyl group;
R$^2$ are independently halogen or a group selected from the group consisting of:
C$_1$-C$_3$-alkyl, C$_3$-C$_4$-cycloalkyl, C$_1$-C$_3$-haloalkyl, C$_1$-C$_3$-alkoxy,
and —N(H)C(═O)—(C$_1$-C$_3$-alkyl);
R$^3$ is a group selected from the group consisting of: C$_2$-C$_6$-hydroxyalkyl, and R$^4$;
R$^4$ is —(C$_2$-C$_6$-alkyl)-OC(═O)—C(H)(R$^5$)—N(H)C(═O)—C(H)(R$^7$)—NH$_2$; and
R$^5$ and R$^7$ are independently a group selected from the group consisting of:
—CH$_3$ (alanine), and —(CH$_2$)$_4$NH$_2$ (lysine), or an N-oxide, a salt, a tautomer or a stereoisomer of said compound, or a salt of said N-oxide, tautomer or stereoisomer.

5. The compound of formula (I) according to claim 1, wherein:

V, W, Y and Z are independently CH or CR$^2$, wherein one of V, W, Y and Z is CR$^2$;
or
V is N, and W, Y and Z are independently CH or CR$^2$;
R$^1$ is a methyl group;
R$^2$ is independently fluorine or chlorine, or a group selected from the group consisting of:
methyl, cyclopropyl, difluoromethyl, methoxy, and —N(H)C(═O)—CH$_3$;
R$^3$ is a group selected from the group consisting of: —(CH$_2$)$_2$OH, and R$^4$;
R$^4$ is —(CH$_2$)$_2$—OC(═O)—C(H)(R$^5$)—N(H)C(═O)—C(H)(R$^7$)—NH$_2$;
R$^5$ is —CH$_3$ (alanine); and
R$^7$ is —(CH$_2$)$_4$NH$_2$ (lysine), or an N-oxide, a salt, a tautomer or a stereoisomer of said compound, or a salt of said N-oxide, tautomer or stereoisomer.

6. The compound of formula (I) according to claim 1, wherein:

V, W, Y and Z are independently CH or CR$^2$, wherein one of V, W, Y and Z is CR$^2$;
or
V is N, and W, Y and Z are independently CH or CR$^2$;
R$^1$ is a methyl group;
R$^2$ is independently fluorine or chlorine, or a group selected from the group consisting of:
methyl, cyclopropyl, difluoromethyl, methoxy, —N(H)C(═O)—CH$_3$,
—N(H)C(═O)-cyclopropyl, and —N(H)C(═O)N(H)-cyclopropyl; and
R$^3$ is a —(CH$_2$)$_2$OH group, or an N-oxide, a salt, a tautomer or a stereoisomer of said compound, or a salt of said N-oxide, tautomer or stereoisomer.

7. The compound of formula (I) according to claim 1, which is selected from the group consisting of:

2-{4-[(3-{4-[(3-chloropyridin-4-yl)amino]-5-methoxypyrimidin-2-yl}-1H-indazol-1-yl)methyl]-3,5-difluorophenoxy}ethanol;

2-{3,5-difluoro-4-[(3-{5-methoxy-4-[(2-methylpyridin-4-yl)amino]pyrimidin-2-yl}-1H-indazol-1-yl)methyl]phenoxy}ethanol;

2-{3,5-difluoro-4-[(3-{5-methoxy-4-[(3-methoxypyridin-4-yl)amino]pyrimidin-2-yl}-1H-indazol-1-yl)methyl]phenoxy}ethanol;

N-{4-[(2-{1-[2,6-difluoro-4-(2-hydroxyethoxy)benzyl]-1H-indazol-3-yl}-5-methoxypyrimidin-4-yl)amino]pyridin-2-yl}acetamide;

2-{3,5-difluoro-4-[(3-{5-methoxy-4-[(3-methylpyridin-4-yl)amino]pyrimidin-2-yl}-1H-indazol-1-yl)methyl]phenoxy}ethanol;

2-{3,5-difluoro-4-[(3-{4-[(3-fluoropyridin-4-yl)amino]-5-methoxypyrimidin-2-yl}-1H-indazol-1-yl)methyl]phenoxy}ethanol;

2-(4-{[3-(4-{[2-(difluoromethyl)pyridin-4-yl]amino}-5-methoxypyrimidin-2-yl)-1H-indazol-1-yl]methyl}-3,5-difluorophenoxy)ethanol;

2-{4-[(3-{4-[(2,5-dimethylpyridin-4-yl)amino]-5-methoxypyrimidin-2-yl}-1H-indazol-1-yl)methyl]-3,5-difluorophenoxy}ethanol;

2-{4-[(3-{4-[(3-cyclopropylpyridin-4-yl)amino]-5-methoxypyrimidin-2-yl}-1H-indazol-1-yl)methyl]-3,5-difluorophenoxy}ethanol;

2-{1-[2,6-difluoro-4-(2-hydroxyethoxy)benzyl]-1H-indazol-3-yl}-4-[(2-methylpyrimidin-4-yl)amino]pyrimidin-5-ol;

2-{3,5-difluoro-4-[(3-{4-[(2-fluoropyridin-4-yl)amino]-5-methoxypyrimidin-2-yl}-1H-indazol-1-yl)methyl]phenoxy}ethanol;

2-{3,5-difluoro-4-[(3-{4-[(5-fluoro-2-methylpyridin-4-yl)amino]-5-methoxypyrimidin-2-yl}-1H-indazol-1-yl)methyl]phenoxy}ethanol;

2-[3,5-difluoro-4-({3-[5-methoxy-4-(pyrimidin-4-ylamino)pyrimidin-2-yl]-1H-indazol-1-yl}methyl)phenoxy]ethanol;

N-{4-[(2-{1-[2,6-difluoro-4-(2-hydroxyethoxy)benzyl]-1H-indazol-3-yl}-5-methoxypyrimidin-4-yl)amino]-5-methylpyridin-2-yl}acetamide;

2-{3,5-difluoro-4-[(3-{5-methoxy-4-[(2-methylpyridin-4-yl)amino]pyrimidin-2-yl}-1H-indazol-1-yl)methyl]phenoxy}ethyl L-lysyl-L-alaninate, salt with trifluoroacetic acid;

2-{3,5-difluoro-4-[(3-{5-methoxy-4-[(2-methylpyridin-4-yl)amino]pyrimidin-2-yl}-1H-indazol-1-yl)methyl]phenoxy}ethyl L-lysyl-L-alaninate;

2-{3,5-difluoro-4-[(3-{5-methoxy-4-[(3-methoxypyridin-4-yl)amino]pyrimidin-2-yl}-1H-indazol-1-yl)methyl]phenoxy}ethyl L-lysyl-L-alaninate, salt with trifluoroacetic acid;

2-{3,5-difluoro-4-[(3-{5-methoxy-4-[(3-methoxypyridin-4-yl)amino]pyrimidin-2-yl}-1H-indazol-1-yl)methyl]phenoxy}ethyl L-lysyl-L-alaninate;

N-{4-[(2-{1-[2,6-difluoro-4-(2-hydroxyethoxy)benzyl]-1H-indazol-3-yl}-5-methoxypyrimidin-4-yl)amino]pyridin-2-yl}cyclopropanecarboxamide;

1-cyclopropyl-3-{4-[(2-{1-[2,6-difluoro-4-(2-hydroxyethoxy)benzyl]-1H-indazol-3-yl}-5-methoxypyrimidin-4-yl)amino]pyridin-2-yl}urea;

2-{3,5-difluoro-4-[(3-{5-methoxy-4-[(3-methoxy-2-methylpyridin-4-yl)amino]pyrimidin-2-yl}-1H-indazol-1-yl)methyl]phenoxy}ethanol;

2-{3,5-difluoro-4-[(3-{5-methoxy-4-[(5-methoxy-2-methylpyridin-4-yl)amino]pyrimidin-2-yl}-1H-indazol-1-yl)methyl]phenoxy}ethanol;

3-{4-[(3-{4-[(2,5-dimethylpyridin-4-yl)amino]-5-methoxypyrimidin-2-yl}-1H-indazol-1-yl)methyl]-3,5-difluorophenoxy}propan-1-ol;

3-{3,5-difluoro-4-[(3-{5-methoxy-4-[(3-methoxypyridin-4-yl)amino]pyrimidin-2-yl}-1H-indazol-1-yl)methyl]phenoxy}propan-1-ol;

3-{3,5-difluoro-4-[(3-{5-methoxy-4-[(2-methylpyrimidin-4-yl)amino]pyrimidin-2-yl}-1H-indazol-1-yl)methyl]phenoxy}propan-1-ol;

(2R)-3-{3,5-difluoro-4-[(3-{5-methoxy-4-[(2-methylpyrimidin-4-yl)amino]pyrimidin-2-yl}-1H-indazol-1-yl)methyl]phenoxy}-2-methylpropan-1-ol;

(2R)-3-{4-[(3-{4-[(2,5-dimethylpyridin-4-yl)amino]-5-methoxypyrimidin-2-yl}-1H-indazol-1-yl)methyl]-3,5-difluorophenoxy}-2-methylpropan-1-ol;

N-[4-({2-[1-(2,6-difluoro-4-{[(2R)-3-hydroxy-2-methylpropyl]oxy}benzyl)-1H-indazol-3-yl]-5-methoxypyrimidin-4-yl}amino)pyridin-2-yl]acetamide;

(2R)-3-{3,5-difluoro-4-[(3-{5-methoxy-4-[(3-methoxypyridin-4-yl)amino]pyrimidin-2-yl}-1H-indazol-1-yl)methyl]phenoxy}-2-methylpropan-1-ol;

3-{3,5-difluoro-4-[(3-{5-methoxy-4-[(2-methylpyridin-4-yl)amino]pyrimidin-2-yl}-1H-indazol-1-yl)methyl]phenoxy}propan-1-ol;

2-{4-[(3-{4-[(2,6-dimethylpyrimidin-4-yl)amino]-5-methoxypyrimidin-2-yl}-1H-indazol-1-yl)methyl]-3,5-difluorophenoxy}ethanol;

2-{3,5-difluoro-4-[(3-{4-[(2-fluoropyridin-4-yl)amino]-5-methoxypyrimidin-2-yl}-1H-indazol-1-yl)methyl]phenoxy}ethyl D-lysyl-L-alaninate, salt with trifluoroacetic acid;

2-{3,5-difluoro-4-[(3-{4-[(2-fluoropyridin-4-yl)amino]-5-methoxypyrimidin-2-yl}-1H-indazol-1-yl)methyl]phenoxy}ethyl D-lysyl-L-alaninate;

2-{3,5-difluoro-4-[(3-{4-[(2-fluoropyridin-4-yl)amino]-5-methoxypyrimidin-2-yl}-1H-indazol-1-yl)methyl]phenoxy}ethyl L-lysyl-L-alaninate, salt with trifluoroacetic acid;
and 2-{3,5-difluoro-4-[(3-{4-[(2-fluoropyridin-4-yl)amino]-5-methoxypyrimidin-2-yl}-1H-indazol-1-yl)methyl]phenoxy}ethyl L-lysyl-L-alaninate, or an N-oxide, a salt, a tautomer or a stereoisomer of said compound, or a salt of said N-oxide, tautomer or stereoisomer.

8. The compound of formula (I) according to claim 1, which is selected from the group consisting of:

2-{4-[(3-{4-[(3-chloropyridin-4-yl)amino]-5-methoxypyrimidin-2-yl}-1H-indazol-1-yl)methyl]-3,5-difluorophenoxy}ethanol;

2-{3,5-difluoro-4-[(3-{5-methoxy-4-[(2-methylpyridin-4-yl)amino]pyrimidin-2-yl}-1H-indazol-1-yl)methyl]phenoxy}ethanol;

2-{3,5-difluoro-4-[(3-{5-methoxy-4-[(3-methoxypyridin-4-yl)amino]pyrimidin-2-yl}-1H-indazol-1-yl)methyl]phenoxy}ethanol;

N-{4-[(2-{1-[2,6-difluoro-4-(2-hydroxyethoxy)benzyl]-1H-indazol-3-yl}-5-methoxypyrimidin-4-yl)amino]pyridin-2-yl}acetamide;

2-{3,5-difluoro-4-[(3-{5-methoxy-4-[(3-methylpyridin-4-yl)amino]pyrimidin-2-yl}-1H-indazol-1-yl)methyl]phenoxy}ethanol;

2-{3,5-difluoro-4-[(3-{4-[(3-fluoropyridin-4-yl)amino]-5-methoxypyrimidin-2-yl}-1H-indazol-1-yl)methyl]phenoxy}ethanol;

2-(4-{[3-(4-{[2-(difluoromethyl)pyridin-4-yl]amino}-5-methoxypyrimidin-2-yl)-1H-indazol-1-yl]methyl}-3,5-difluorophenoxy)ethanol;

2-{4-[(3-{4-[(2,5-dimethylpyridin-4-yl)amino]-5-methoxypyrimidin-2-yl}-1H-indazol-1-yl)methyl]-3,5-difluorophenoxy}ethanol;

2-{4-[(3-{4-[(3-cyclopropylpyridin-4-yl)amino]-5-methoxypyrimidin-2-yl}-1H-indazol-1-yl)methyl]-3,5-difluorophenoxy}ethanol;

2-{1-[2,6-difluoro-4-(2-hydroxyethoxy)benzyl]-1H-indazol-3-yl}-4-[(2-methyl-pyrimidin-4-yl)amino]pyrimidin-5-ol;

2-{3,5-difluoro-4-[(3-{4-[(2-fluoropyridin-4-yl)amino]-5-methoxypyrimidin-2-yl}-1H-indazol-1-yl)methyl]phenoxy}ethanol;

2-{3,5-difluoro-4-[(3-{4-[(5-fluoro-2-methylpyridin-4-yl)amino]-5-methoxypyrimidin-2-yl}-1H-indazol-1-yl)methyl]phenoxy}ethanol;

2-[3,5-difluoro-4-({3-[5-methoxy-4-(pyrimidin-4-ylamino)pyrimidin-2-yl]-1H-indazol-1-yl}methyl)phenoxy]ethanol;

N-{4-[(2-{1-[2,6-difluoro-4-(2-hydroxyethoxy)benzyl]-1H-indazol-3-yl}-5-methoxypyrimidin-4-yl)amino]-5-methylpyridin-2-yl}acetamide;

2-{3,5-difluoro-4-[(3-{5-methoxy-4-[(2-methylpyridin-4-yl)amino]pyrimidin-2-yl}-1H-indazol-1-yl)methyl]phenoxy}ethyl L-lysyl-L-alaninate, salt with trifluoroacetic acid;

2-{3,5-difluoro-4-[(3-{5-methoxy-4-[(3-methoxypyridin-4-yl)amino]pyrimidin-2-yl}-1H-indazol-1-yl)methyl]phenoxy}ethyl L-lysyl-L-alaninate, salt with trifluoroacetic acid;

N-{4-[(2-{1-[2,6-difluoro-4-(2-hydroxyethoxy)benzyl]-1H-indazol-3-yl}-5-methoxypyrimidin-4-yl)amino]pyridin-2-yl}cyclopropanecarboxamide;

1-cyclopropyl-3-{4-[(2-{1-[2,6-difluoro-4-(2-hydroxyethoxy)benzyl]-1H-indazol-3-yl}-5-methoxypyrimidin-4-yl)amino]pyridin-2-yl}urea;

2-{3,5-difluoro-4-[(3-{5-methoxy-4-[(3-methoxy-2-methylpyridin-4-yl)amino]pyrimidin-2-yl}-1H-indazol-1-yl)methyl]phenoxy}ethanol;

2-{3,5-difluoro-4-[(3-{5-methoxy-4-[(5-methoxy-2-methylpyridin-4-yl)amino]pyrimidin-2-yl}-1H-indazol-1-yl)methyl]phenoxy}ethanol;

3-{4-[(3-{4-[(2,5-dimethylpyridin-4-yl)amino]-5-methoxypyrimidin-2-yl}-1H-indazol-1-yl)methyl]-3,5-difluorophenoxy}propan-1-ol;

3-{3,5-difluoro-4-[(3-{5-methoxy-4-[(3-methoxypyridin-4-yl)amino]pyrimidin-2-yl}-1H-indazol-1-yl)methyl]phenoxy}propan-1-ol;

3-{3,5-difluoro-4-[(3-{5-methoxy-4-[(2-methylpyrimidin-4-yl)amino]pyrimidin-2-yl}-1H-indazol-1-yl)methyl]phenoxy}propan-1-ol;

(2R)-3-{3,5-difluoro-4-[(3-{5-methoxy-4-[(2-methylpyrimidin-4-yl)amino]pyrimidin-2-yl}-1H-indazol-1-yl)methyl]phenoxy}-2-methylpropan-1-ol;

(2R)-3-{4-[(3-{4-[(2,5-dimethylpyridin-4-yl)amino]-5-methoxypyrimidin-2-yl}-1H-indazol-1-yl)methyl]-3,5-difluorophenoxy}-2-methylpropan-1-ol;

N-[4-({2-[1-(2,6-difluoro-4-{[(2R)-3-hydroxy-2-methyl-propyl]oxy}benzyl)-1H-indazol-3-yl]-5-methoxypyrimidin-4-yl}amino)pyridin-2-yl]acetamide;

(2R)-3-{3,5-difluoro-4-[(3-{5-methoxy-4-[(3-methoxy-pyridin-4-yl)amino]pyrimidin-2-yl}-1H-indazol-1-yl)methyl]phenoxy}-2-methylpropan-1-ol;

3-{3,5-difluoro-4-[(3-{5-methoxy-4-[(2-methylpyridin-4-yl)amino]pyrimidin-2-yl}-1H-indazol-1-yl)methyl]phenoxy}propan-1-ol;

2-{4-[(3-{4-[(2,6-dimethylpyrimidin-4-yl)amino]-5-methoxypyrimidin-2-yl}-1H-indazol-1-yl)methyl]-3,5-difluorophenoxy}ethanol;

2-{3,5-difluoro-4-[(3-{4-[(2-fluoropyridin-4-yl)amino]-5-methoxypyrimidin-2-yl}-1H-indazol-1-yl)methyl]phenoxy}ethyl D-lysyl-L-alaninate, salt with trifluoroacetic acid;

and

2-{3,5-difluoro-4-[(3-{4-[(2-fluoropyridin-4-yl)amino]-5-methoxypyrimidin-2-yl}-1H-indazol-1-yl)methyl]phenoxy}ethyl L-lysyl-L-alaninate, salt with trifluoroacetic acid, or an N-oxide, a salt, a tautomer or a stereoisomer of said compound, or a salt of said N-oxide, tautomer or stereoisomer.

9. A method of preparing a compound of formula (Ia), comprising reacting an intermediate compound of formula (1-9):

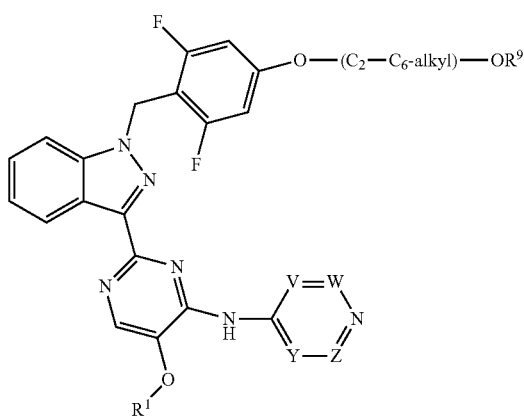

(1-9)

wherein $R^1$, V, W, Y and Z are as defined in claim 1, and $R^9$ is a methyl or an ethyl group or an alcohol protecting group, with a deprotection agent, to form the compound of formula (Ia):

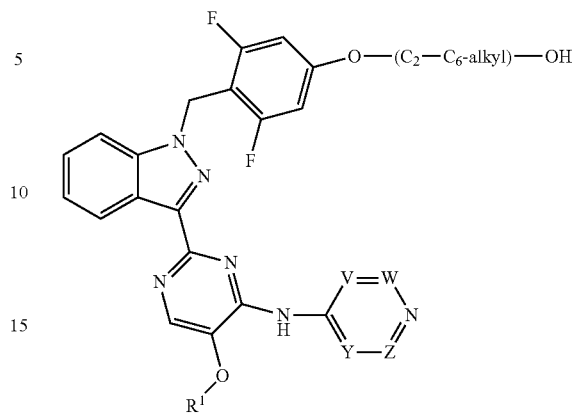

(Ia)

wherein $R^1$, V, W, Y and Z are as defined in claim 1.

10. A method of preparing a compound of formula (Ib), comprising reacting an intermediate compound of formula (1-20):

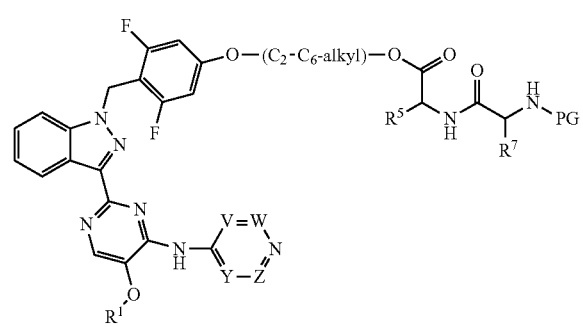

1-20 wherein $R^1$, $R^5$, $R^7$, V, W, Y and Z are as defined in claim 1, and PG is an amino protecting group, with a Brønsted acid, to form the compound of formula (Ib):

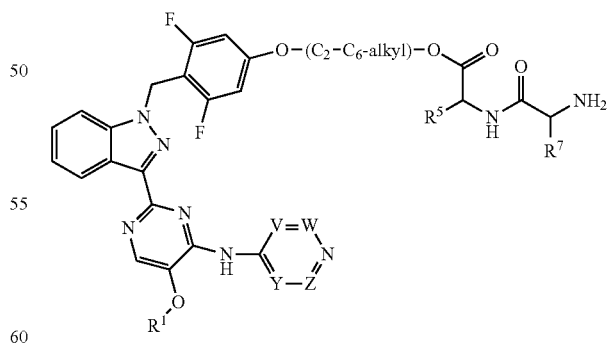

(Ib)

wherin $R^1$, $R^5$, $R^7$, V, W, Y and Z are as defined in claim 1.

11. A method for treatment of a disease, comprising administering to a patient in need thereof an effective amount of a compound of formula (I) according to claim 1, or an N-oxide, a salt, a tautomer or a stereoisomer of said compound, or a salt of said N-oxide, tautomer or stereoisomer, wherein the disease is a hyperproliferative disease and/or a disorder responsive to induction of cell death.

12. The method according to claim 11, wherein the hyperproliferative disease and/or disorder responsive to induction of cell death is a haematological tumour, a solid tumours and/or metastases thereof.

13. The method according to according to claim 11, wherein the disease is a hyperproliferative disease, and wherein the hyperproliferative disease is cervical cancer.

14. A pharmaceutical composition comprising at least one compound of formula (I) according to claim 1, or an N-oxide, a salt, a tautomer or a stereoisomer of said compound, or a salt of said N-oxide, tautomer or stereoisomer, together with at least one pharmaceutically acceptable carrier or auxiliary.

15. A method for treatment of a haematological tumour, a solid tumour and/or metastases thereof, comprising administering to a patient in need thereof the composition according to claim 14.

16. A combination comprising one or more first active ingredients selected from a compound of formula (I) according to claim 1, or an N-oxide, a salt, a tautomer or a stereoisomer of said compound, or a salt of said N-oxide, tautomer or stereoisomer, and one or more second active ingredients selected from the group consisting of chemotherapeutic anti-cancer agents and target-specific anti-cancer agents.

17. A compound of formula (1-9):

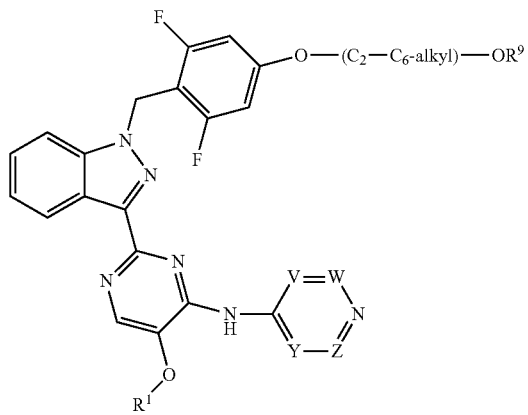

1-9 wherein $R^1$, V, W, Y and Z are as defined in claim 1, and $R^9$ is a methyl or an ethyl group or an alcohol protecting group.

18. A compound of formula (1-20):

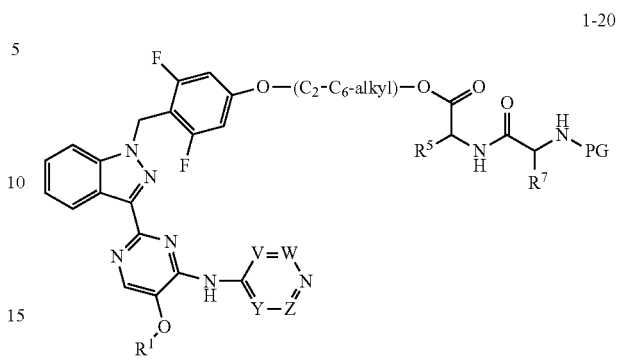

1-20 wherein $R^1$, $R^5$, $R^7$, V, W, Y and Z are as defined in claim 1, and PG is an amino protecting group.

19. The compound according to claim 1, or a pharmaceutically acceptable salt thereof.

20. The compound according to claim 7, or a pharmaceutically acceptable salt thereof.

21. The compound according to claim 8, or a pharmaceutically acceptable salt thereof.

22. The method according to claim 11, comprising administering to the patient in need thereof an effective amount of the compound of formula (I), or a pharmaceutically acceptable salt thereof.

23. A compound, which is 2-{3,5-difluro-4-[(3-{5-methoxy-4-[(3-methoxypyridin-4-yl)amino]pyrimidin-2-yl}-1H-indazol-1-yl)methyl]phenoxy}ethanol, or an N-oxide, a salt, or a salt of the N-oxide thereof.

24. The compound according to claim 23, or a pharmaceutically acceptable salt thereof.

25. The compound according to claim 23, which is 2-{3,5-difluro-4-[(3-{5-methoxy-4-[(3-methoxypyridin-4-yl)amino]pyrimidin-2-yl}-1H-indazol-1-yl)methyl]phenoxy}ethanol.

26. A pharmaceutical composition comprising the compound according to claim 23, or an N-oxide, a pharmaceutically acceptable salt, or a pharmaceutically acceptable salt of the N-oxide thereof, together with at least one pharmaceutically acceptable carrier or auxiliary.

27. A pharmaceutical composition comprising the compound according to claim 24, or pharmaceutically acceptable salt thereof, together with at least one pharmaceutically acceptable carrier or auxiliary.

28. A pharmaceutical composition comprising the compound according to claim 25, together with at least on pharmaceutically acceptable carrier or auxiliary.

* * * * *